(12) United States Patent
Johnston et al.

(10) Patent No.: US 10,889,553 B2
(45) Date of Patent: *Jan. 12, 2021

(54) ASYMMETRIC TRIAZOLE BENZAMIDE DERIVATIVES AND THE COMPOSITIONS AND METHODS OF TREATMENT REGARDING THE SAME

(71) Applicant: NysnoBio Ireland DAC, Dundrum (IE)

(72) Inventors: Jennifer Johnston, Mill Valley, CA (US); Paul Ross Fatheree, San Francisco, CA (US)

(73) Assignee: NysnoBio Ireland DAC, Dundrum (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/208,277

(22) Filed: Dec. 3, 2018

(65) Prior Publication Data
US 2020/0172497 A1   Jun. 4, 2020

Related U.S. Application Data

(60) Provisional application No. 62/593,582, filed on Dec. 1, 2017.

(51) Int. Cl.
| | |
|---|---|
| *C07D 249/14* | (2006.01) |
| *C07D 401/14* | (2006.01) |
| *C07D 401/12* | (2006.01) |
| *C07D 403/10* | (2006.01) |
| *A61P 25/16* | (2006.01) |
| *C07D 409/12* | (2006.01) |
| *C07D 405/10* | (2006.01) |
| *A61P 35/00* | (2006.01) |
| *C07D 403/14* | (2006.01) |

(52) U.S. Cl.
CPC ............ *C07D 249/14* (2013.01); *A61P 25/16* (2018.01); *A61P 35/00* (2018.01); *C07D 401/12* (2013.01); *C07D 401/14* (2013.01); *C07D 403/10* (2013.01); *C07D 403/14* (2013.01); *C07D 405/10* (2013.01); *C07D 409/12* (2013.01)

(58) Field of Classification Search
CPC .............................. C07D 249/14; A61P 25/16
See application file for complete search history.

(56) References Cited

U.S. PATENT DOCUMENTS

| | | | |
|---|---|---|---|
| 4,323,566 | A | 4/1982 | Clitherow et al. |
| 5,817,675 | A | 10/1998 | Whitefield |
| 8,362,020 | B2 | 1/2013 | Lopez et al. |
| 8,592,584 | B2 | 11/2013 | Hergenrother et al. |
| 8,778,945 | B2 | 7/2014 | Hergenrother et al. |
| 8,916,705 | B2 | 12/2014 | Hergenrother |
| 9,102,661 | B2 | 8/2015 | Hergenrother et al. |
| 10,155,936 | B2 | 12/2018 | Johnston |
| 10,308,617 | B2 * | 6/2019 | Johnston .................. A61P 35/00 |
| 2010/0184765 | A1 | 7/2010 | Huang et al. |
| 2012/0083003 | A1 | 4/2012 | Johnston et al. |
| 2012/0149744 | A1 | 6/2012 | Welsh et al. |
| 2012/0295891 | A1 | 11/2012 | Van Brandt et al. |
| 2014/0073609 | A1 | 3/2014 | Hergenrother et al. |
| 2015/0017264 | A1 | 1/2015 | Hergenrother et al. |
| 2015/0099759 | A1 | 4/2015 | Hergenrother et al. |
| 2015/0210659 | A1 | 7/2015 | Chen et al. |
| 2015/0210717 | A1 | 7/2015 | Gunes et al. |
| 2015/0231132 | A1 | 8/2015 | Hergenrother |
| 2016/0160205 | A1 | 6/2016 | Johnston |
| 2018/0118697 | A1 | 5/2018 | Johnston et al. |
| 2019/0359578 | A1 | 11/2019 | Johnston et al. |

FOREIGN PATENT DOCUMENTS

| | | |
|---|---|---|
| KR | 20100015088 A | 2/2010 |
| WO | WO 2010/091382 A1 | 8/2010 |
| WO | WO 2013/124407 A1 | 8/2013 |
| WO | WO 2013/131089 A2 | 9/2013 |

(Continued)

OTHER PUBLICATIONS

Akif et al., "High-resolution crystal structures of *Drosophila melanogaster* angiotensin-converting enzyme in complex with novel inhibitors and antihypertensive drugs." Journal of Molecular Biology (2010); 400(3): 502-517.

Anwander et al., "Volatile Donor-Functionalized Alkoxy Derivatives of Lutetium and Their Structural Characterizationl." Inorg. Chem. (1997); 36(16): 3545-3552.

Boriack-Sjodin et al., "Structural analysis of inhibitor binding to human carbonic anhydrase II." Protein Science (1998); 7(12): 2483-2489.

Bottomley et al., "Structural and functional analysis of the human HDAC4 catalytic domain reveals a regulatory structural zinc-binding domain." Journal of Biological Chemistry (2008); 283(39): 26694-26704.

(Continued)

*Primary Examiner* — Golam M Shameem
(74) *Attorney, Agent, or Firm* — Cooley LLP; Andrew S. Keith

(57) ABSTRACT

The present disclosure is directed to asymmetric triazole benzamide compounds of formula (I) and formula (II), pharmaceutical compositions thereof and methods for modulating or activating a Parkin ligase The present disclosure is also directed to methods of treating and/or reducing the incidence of diseases or conditions related to the activation of Parkin ligase. $R^1$, $R^2$, $R^3$, $M^1$, $M^2$, $M^3$, $L^1$, $L^2$, and $L^3$ are as defined herein.

(I)

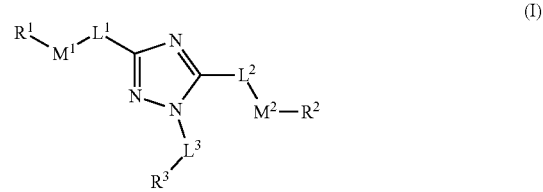

13 Claims, 3 Drawing Sheets

(56) References Cited

FOREIGN PATENT DOCUMENTS

| WO | WO 2014/022858 A1 | 2/2014 |
|---|---|---|
| WO | WO 2014/041125 A1 | 3/2014 |
| WO | WO 2016/033285 | 3/2016 |
| WO | WO 2016/090371 A2 | 6/2016 |
| WO | WO 2017/210694 A1 | 12/2017 |

OTHER PUBLICATIONS

Bourguet et al., "Pharmacomodulation of Broad Spectrum Matrix Metalloproteinase Inhibitors Towards Regulation of Gelatinases." Intech Open Access Publisher, 2012; 29 pages.

Brandstetter et al., "The 1.8-Å crystal structure of a matrix metalloproteinase 8-barbiturate inhibitor complex reveals a previously unobserved mechanism for collagenase substrate recognition." Journal of Biological Chemistry (2001); 276(20): 17405-17412.

Bressi et al., "Exploration of the HDAC2 foot pocket: Synthesis and SAR of substituted N-(2-aminophenyl) benzamides." Bioorganic & Medicinal Chemistry Letters (2010); 20(10): 3142-3145.

Briganti et al., "Carbonic anhydrase activators: X-ray crystallographic and spectroscopic investigations for the interaction of isozymes I and II with histamine." Biochemistry (1997); 36(34): 10384-10392.

Browner et al., "Matrilysin-inhibitor complexes: common themes among metalloproteases." Biochemistry (1995); 34(20): 6602-6610. (Abstract).

Cappalonga et al., "Structural comparison of sulfodiimine and sulfonamide inhibitors in their complexes with zinc enzymes." Journal of Biological Chemistry (1992); 267(27): 19192-19197.

Carta et al., "Dithiocarbamates strongly inhibit carbonic anhydrases and show antiglaucoma action in vivo." Journal of Medicinal Chemistry (2012); 55(4): 1721-1730.

Chernyshev et al., "Acyl and sulfonyl derivatives of 3, 5-diamino-1-R-1, 2, 4-triazoles." Chemistry of Heterocyclic Compounds (2005); 41.9: 1139-1146.

Database Caplus [Online], chemical Abstracts Service, Columbus, OH, Feb. 22, 2010, Ryu, et al., "Pharmaceutical composition containing ERK2 inhibitor, triazolyl benzamide derivatives, for preventing and treating cancers and cardiovascular diseases", XP002782613, retrieved from STN Database accession No. 2010:218046.

Database Registry Chemical Abstracts Service, Columbus, Ohio, Accession No. RN 384352-93-6, Entered STN: Jan. 19, 2002.

Dunten et al., "X-ray structure of a novel matrix metalloproteinase inhibitor complexed to stromelysin." Protein Science (2001); 10(5): 923-926.

Everett, T.R., et al., "S-Nitrosoglutathione improves haemodynamics in early-onset pre-eclampsia." Br J Clin Pharmacol. (Sep. 2014); 78(3): 660-669.

Extended European Search Report in European Patent Application No. 15865563.9, dated Jul. 20, 2018, 14 pages.

Fernandez et al., "The X-Ray Structure of Carboxypeptidase a Inhibited by a Thiirane Mechanism-Based Inhibitor." Chemical Biology & Drug Design (2010); 75(1): 29-34.

Finzel et al., "Structural characterizations of nonpeptidic thiadiazole inhibitors of matrix metalloproteinases reveal the basis for stromelysin selectivity." Protein Science (1998); 7(10): 2118-2126.

Hajduk et al., "NMR-based modification of matrix metalloproteinase inhibitors with improved bioavailability." Journal of Medicinal Chemistry (2002); 45(26): 5628-5639.

Ikeuchi et al., "Attenuation of proteolysis-mediated cyclin E regulation by alternatively spliced Parkin in human colorectal cancers." Int. J. Cancer (2009); 125(9): 2029-2035.

Kim and Lipscomb, "Comparison of the structures of three carboxypeptidase A-phosphonate complexes determined by X-ray crystallography." Biochemistry (1991); 30(33): 8171-8180.

Kitada et al., "Mutations in the parkin gene cause autosomal recessive juvenile parkinsonism." Nature (1998); 392(6676): 605-608.

Lloyd et al., "Crystal structure of human carbonic anhydrase II at 1.95 Å resolution in complex with 667-coumate, a novel anti-cancer agent." Biochemical Journal (2005); 385(3): 715-720.

Matsumine et al., "A microdeletion of D6S305 in a family of autosomal recessive juvenile parkinsonism (PARK2)." Genomics (1998); 49(1): 143-146.

Monzingo and Matthews, "Binding of N-carboxymethyl dipeptide inhibitors to thermolysin determined by X-ray crystallography: a novel class of transition-state analogs for zinc peptidases." Biochemistry (1984); 23(24): 5724-5729.

Nogrady, Thomas, Medicinal Chemistry a Biochemical Approach, Medicinal Chemistry a Biochemical Approach, Oxford University Press, New York (1985); pp. 388-394, 9 pages.

Ozawa, K., et al., "S-nitrosylation regulates mitochondrial quality control via activation of parkin." Scientific Reports (2013); vol. 3, Article No. 2202.

Park et al., "Identification of novel inhibitors of extracellular signal-regulated kinase 2 based on the structure-based virtual screening." Bioorganic & Medicinal Chemistry Letters (2008); 18(20): 5372-5376.

Park et al., "Sulfamide-based inhibitors for carboxypeptidase A. Novel type transition state analogue inhibitors for zinc proteases." Journal of Medicinal Chemistry (2002); 45(24): 5295-5302.

Pavlovsky et al., "X-ray structure of human stromelysin catalytic domain complexed with nonpeptide inhibitors: implications for inhibitor selectivity." Protein Science (1999); 8(07): 1455-1462.

PCT/US2015/064305, International Preliminary Report on Patentability dated Jun. 6, 2017, 7 pages.

PCT/US2015/064305, International Search Report and Written Opinion dated May 27, 2016, 11 pages.

PCT/US2017/035994, International Search Report and Written Opinion dated Oct. 20, 2017, 16 pages.

PCT/US2018/063678, Invitation to Pay Additional Fees, dated Mar. 4, 2019, 2 pages.

Popovic et al., "Ubiquitination in disease pathogenesis and treatment." Nature Medicine (2014); 20(11): 1242-1253.

Prachayasittikul et al., "8-Hydroxyquinolines: a review of their metal chelating properties and medicinal applications." Drug Design, Development and Therapy (2013); 7: 1157-1178.

PubChem Compound Database; CID=13008745, National Center for Biotechnology Information, https://pubchem.ncbi.nlm.nih.gov/compound/13008745 (accessed Mar. 15, 2019).

Puerta and Cohen, "Examination of novel zinc-binding groups for use in matrix metalloproteinase inhibitors." Inorganic Chemistry (2003); 42(11): 3423-3430.

Puerta et al., "Heterocyclic zinc-binding groups for use in next-generation matrix metalloproteinase inhibitors: potency, toxicity, and reactivity." JBIC Journal of Biological Inorganic Chemistry (2006); 11(2): 131-138.

Rao, B.G., "Recent developments in the design of specific matrix metalloproteinase inhibitors aided by structural and computational studies." Current Pharmaceutical Design (2005); 11(3): 295-322.

Registry No. 850242-99-8, Entered May 11, 2005, 1 page.

Regnström, Karin, et al. "Label Free Fragment Screening Using Surface Plasmon Resonance as a Tool for Fragment Finding-Analyzing Parkin, a Difficult CNS Target." PLOS One (2013); 8(7): e66879, 1-12.

Rice et al., "Evaluation of selected chemotypes in coupled cellular and molecular target-based screens identifies novel HIV-1 zinc finger inhibitors." Journal of Medicinal Chemistry (1996); 39(19): 3606-3616.

Riley et al., "Structure and function of Parkin E3 ubiquitin ligase reveals aspects of RING and HECT ligases." Nat Commun. (2013); 4: 1982, pp. 1-9.

Schröder et al., "Structure-based design and synthesis of potent matrix metalloproteinase inhibitors derived from a 6 H-1, 3, 4-thiadiazine scaffold." Journal of Medicinal Chemistry (2001); 44(20): 3231-3243.

Scozzafava and Supuran, "Carbonic Anhydrase and Matrix Metalloproteinase Inhibitors: Sulfonated Amino Acid Hydroxamates with MMP Inhibitory Properties Act as Efficient inhibitors of CA Isozymes

(56) References Cited

OTHER PUBLICATIONS

I, II, and IV, and N-Hydroxysulfonamides Inhibit Both These Zinc Enzymes 1." Journal of Medicinal Chemistry (2000); 43(20): 3677-3687.
Shimura et al., "Familial Parkinson disease gene product, parkin, is a ubiquitin-protein ligase." Nature Genetics (2000); 25(3): 302-305.
Tronrud et al., "Crystallographic structural analysis of phosphoramidates as inhibitors and transition-state analogs of thermolysin." European Journal of Biochemistry (1986); 157(2): 261-268.
Veeriah et al., "Somatic mutations of the Parkinson's disease-associated gene PARK2 in glioblastoma and other human malignancies." Nature Genetics (2010); 42(1): 77-82.
Wang and Maldonado, "The ubiquitin-proteasome system and its role in inflammatory and autoimmune diseases." Cell Mol Immunol (2006); 3(4): 255-261.
Wang et al., "Characterization of alpha-nitromethyl ketone as a new zinc-binding group based on structural analysis of its complex with carboxypeptidase A." Bioorg Med Chem Lett (2009); 19(17): 5009-5011.
Wang et al., "Design and synthesis of novel inhibitors of gelatinase B." Bioorganic & Medicinal Chemistry Letters (2002); 12(16): 2201-2204.
Wang et al., "ERK-mediated phosphorylation of TFAM downregulates mitochondrial transcription: Implications for Parkinson's disease." Mitochondrion (2014), 17: 132-140.
Wang et al., "Optical 2-benzyl-5-hydroxy-4-oxopentanoic acids against carboxypeptidase A: Synthesis, kinetic evaluation and X-ray crystallographic study." Chinese Chemical Letters (2010); 21: 159-162.
Wang et al., "Suppression of breast cancer by chemical modulation of vulnerable zinc fingers in estrogen receptor." Nature Medicine (2004); 10(1): 40-47.
Watermeyer et al., "Probing the Basis of Domain-Dependent Inhibition Using Novel Ketone Inhibitors of Angiotensin-Converting Enzyme." Biochemistry (2008); 47(22): 5942-5950.
Yu et al., "Clioquinol targets zinc to lysosomes in human cancer cells." Biochemical Journal (2009); 417(1): 133-139.
Bagal, et al., "Heterocyclic nitro compounds." Chemistry of Heterocyclic Compounds (Feb. 1970); 6(2): 249-253.
PCT/US2018/063678, International Search Report and Written Opinion dated May 1, 2019, 11 pages.
Pubmed Compound Summary for CID 130741852, 'JSSNUYBUPFERQS-UHFFFAOYSA-N', U.S. National Library of Medicine, Oct. 9, 2017 (Oct. 9, 2017), p. 1-9; p. 3 (https://pubchem.ncbi.nlm.nih.gov/compound/130741852).
Pubmed Compound Summary for CID 332816, 'N-[3-(Propanoylamino)-1H-1,2,4-triazol-5-yl]propanamide', U.S. National Library of Medicine, Mar. 26, 2005 (Mar. 26, 2005), p. 1-13; p. 4 (https://pubchem.ncbi.nlm.nih.gov/compound/332816).
Pubmed Compound Summary for CID 130008745, 'GYBCPUTUQAVKHMUHFFFAOYSA-N', U.S. National Library of Medicine, Oct. 7, 2017 (Oct. 7, 2017), p. 1-9; p. 3 (https://pubchem.ncbi.nlm.nih.gov/compound/130008745).
Database Registry Chemical Abstracts Service, Columbus, Ohio, Accession No. RN 1075703-21-7, Entered STN: Nov. 25, 2008.
Yerande et al. (2014). "Mercury(II) Chloride-Mediated Desulphurization of Amidinothioureas: Synthesis and Antimicrobial Activity of 3-Amino-1,2,4-triazole Derivatives." Journal of Heterocyclic Chemistry. 51(6): 1883-1887.

* cited by examiner

ASYMMETRIC TRIAZOLE BENZAMIDE DERIVATIVES AND THE COMPOSITIONS AND METHODS OF TREATMENT REGARDING THE SAME

CROSS-REFERENCE TO RELATED APPLICATIONS

This application claims priority to U.S. Provisional Application No. 62/593,582, filed Dec. 1, 2017, the disclosures of which are hereby incorporated by reference in their entireties for all purposes.

FIELD OF THE INVENTION

The present invention relates to asymmetric triazole benzamide compounds and their derivatives as well as methods of modulating Parkin ligase or methods of treating various diseases and conditions with the triazole benzamide compounds and their derivatives.

BACKGROUND OF THE INVENTION

Ubiquitin-Proteasome Pathway System (UPS) is a critical pathway that regulates key regulator proteins and degrades misfolded or abnormal proteins. UPS is central to multiple cellular processes, and if defective or imbalanced, it leads to pathogenesis of a variety of diseases. Posttranslational modification of proteins by ubiquitin is a fundamental cellular mechanism that regulates protein stability and activity and underlies a multitude of functions, from almost every aspect of biology. The covalent attachment of ubiquitin to specific protein substrates is achieved through the action of E3 ubiquitin ligases. These ligases comprise over 500 different proteins and are categorized into multiple classes defined by the structural element of their E3 functional activity. Specifically, both HECT and RING ligases transfer an activated ubiquitin from a thioester to the e-amino acid group of a lysine residue on a substrate; however, HECT ligases have an active site cysteine that forms an intermediate thioester bond with ubiquitin, while RING ligases function as a scaffold to allow direct ubiquitin transfer from the E2 to substrate. Recent evidence suggests that a subfamily of RING ligases, the RING-between-RING (RBR) family, may contain a catalytic cysteine residue 1,2 in addition to a canonical RING domain. (Riley et al. 2013. *Nat Commun.* 4:1982, "Riley et al."), which is herein incorporated by reference in its entirety.

Deubiquitinating proteins and ubiquitin-specific proteases (DUBs and USPs) and E3 Ligases play a vital role in the UPS. These proteins are supported by flexible Zinc Finger (ZnF) domains which stabilize the binding of ubiquitin (Ub) for specialized functions.

Parkin is a RING-between-RING E3 ligase that functions in the covalent attachment of ubiquitin to specific substrates, and mutations in Parkin are linked to Parkinson's disease, cancer and mycobacterial infection. The individual RING domains for Parkin have been the subject of much debate, in regards to the specific residues that coordinate Zn ions, as well as their relationship to canonical RING crossbrace structures defining classical E2-binding domains. R0 is a novel domain structure, but is more similar to Zn-finger domains than to E3 RING domains (Riley et al. 2013. *Nat Commun.* 4:1982)

While many drug discovery programs focus on the UPS, few have been successful due to the lack of selectivity and direct access to enzymatic protein active sites. The present invention is directed towards a novel approach of disrupting Zn-finger domains that provide a therapeutic benefit for various diseases and disorders, including oncology and neurology disorders.

SUMMARY OF THE INVENTION

The compounds of the present disclosure can modulate or active Parkin ligase and may be useful in treating various diseases and conditions as disclosed herein. In one embodiment, the present disclosure provides compounds comprising the structure of formula (I)

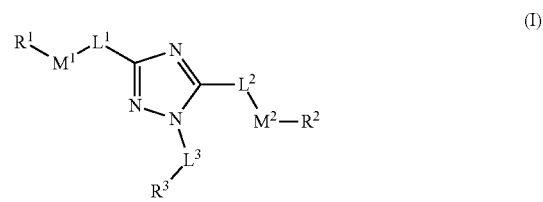

or a pharmaceutically acceptable salt or solvate thereof, wherein:

$L^1$, $L^2$ and $L^3$ are each independently selected from a bond, alkylene, or alkenylene;

$M^1$ and $M^2$ are each independently selected from —$NR^4$—, —$NR^4C(O)$—, —$N(C(O)R^1)$—, —$C(O)NR^4$—, —$NR^4C(O)NR^4$—, —$C(O)$—, —$C(=NR^4)$—, —$C(=NOR^4)$—, —$OC(O)$—, —$C(O)O$—, —$OC(O)O$—, —$OC(O)NR^4$—, —$NR^4C(O)O$—, —$S(O)_m$—, —$S(O)_mNR^4$—, or —$NR^4S(O)_m$—, provided that $M^1$ and $M^2$ are not both —$NR^4$—;

$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H, or alkyl, wherein each alkyl is optionally substituted with one or more $R^5$;

$R^5$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, or —$SR^6$;

$R^6$ is each independently alkyl, alkenyl, alkynyl, haloalkyl, haloalkenyl, haloalkynyl; or alternatively two $R^6$ on the same N atom can together form a 3-6 membered N-heterocyclyl;

$R^7$ is each independently I, Br, Cl, F, —$CH_2F$, —$CHF_2$, —$CF_3$, —$OCF_3$, —CN, -alkyl-CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, —$SR^6$, cycloalkyl, heterocyclyl, aryl, or heteroaryl, wherein each cycloalkyl, heterocyclyl, aryl, and heteroaryl is optionally substituted with one or more $R^5$;

m is 0, 1, or 2; and wherein the compound is not N,N'-(1-phenyl-1H-1,2,4-triazole-3,5-diyl)dibenzamide, N-(3-benzamido-1-phenyl-1H-1,2,4-triazol-5-yl)furan-2-carboxamide, N-(5-cinnamamido-1-phenyl-1H-1,2,4-triazol-3-yl)benzamide, N-(1-phenyl-5-(phenylamino)-1H-1,2,4-triazol-3-yl)benzamide, 4-fluoro-N-(5-(4-methoxybenzamido)-1-phenyl-1H-1,2,4-triazol-3-yl)benzamide, N,N'-(1-phenyl-1H-1,2,4-triazole-3,5-diyl)bis(4-methylbenzamide), N-(5-((2-chlorobenzyl)amino)-1-phenyl-1H-1,2,4-triazol-3-yl)-2-fluorobenzamide, N-(3-benzamido-1-phenyl-1H-1,2,4-triazol-5-yl)-4-fluorobenzamide, N-(3-benzamido-1-phenyl-1H-1,2,4-triazol-5-yl)-4-nitrobenzamide, N-(3-benzamido-1-phenyl-1H-1,2,4-triazol-5-yl)-3-nitrobenzamide, and 4-((3-benzamido-1-phenyl-1H-1,2,4-triazol-5-yl)carbamoyl)benzoic acid.

In one embodiment of the compound of formula (I), $L^1$, $L^2$ and $L^3$ are each independently a bond.

In one embodiment of the compound of formula (I), $M^1$ and $M^2$ are each independently selected from $-NR^4-$, $-NR^4C(O)-$, $-C(O)NR^4-$, $-N(C(O)R^1)-$, or $-NR^4S(O)_m-$. In one embodiment, $M^1$ and $M^2$ are each independently selected from $-NR^4-$, $-NR^4C(O)-$ or $-C(O)NR^4-$.

In one embodiment of the compound of formula (I), $R^4$ at each occurrence is independently H or $C_1$-$C_3$ alkyl.

In one embodiment of the compound of formula (I), $L^3$ is a bond and $R^3$ is an aryl or a heteroaryl, optionally substituted with one or more $R^7$.

In one embodiment of the compound of formula (I), $R^3$ is a phenyl or phenyl fused bicycle, optionally substituted with one or more IV. In another embodiment, $R^3$ is heteroaryl selected from imidazolyl or pyrazolyl, optionally substituted with one or more $R^7$.

In one embodiment of the compound of formula (I), $R^7$ is each independently I, Br, Cl, F, $-CH_2F$, $-CHF$, $-CF$, $-OCF_3$, $-CN$, $-NH_2$, $-NMe_2$, $-NO_2$, $-N_3$, $-OH$, $OR^6$, $-SH$, cycloalkyl, heterocyclyl, aryl, or heteroaryl, wherein each cycloalkyl, heterocyclyl, aryl, and heteroaryl is optionally substituted with one or more $R^5$.

In one embodiment of the compound of formula (I), $R^3$ is a phenyl substituted with a 4-6 membered heterocyclyl, which is optionally substituted with one or more $R^7$.

In one embodiment of the compound of formula (I), $R^1$ and $R^2$ are each independently selected from phenyl, 6-10 membered aryl, 5-10 membered heteroaryl, 4-10 membered heterocyclyl, phenyl-($C_1$-$C_3$ alkyl)-, phenyl-($C_2$-$C_3$ alkenyl)-, 5-6 membered heteroaryl-($C_1$-$C_3$ alkyl)-, or heteroaryl-($C_2$-$C_3$ alkenyl)-, wherein each cycloalkyl, aryl, heteroaryl portion is optionally substituted with one or more $R^5$. In some embodiments, the 6-10 membered aryl or 5-10 membered heteroaryl is a bicyclic ring.

In one embodiment of the compound of formula (I), $R^5$ is selected from I, Br, Cl, F, $C_1$-$C_6$ alkyl, alkynyl, $-CN$, $-(C_1$-$C_3$ alkylene)-CN, $-NH_2$, $-NO_2$, $-N_3$, $-OH$, $-OCF_3$, $-OMe$, $-NMe_2$, or $-NEt_2$.

In one embodiment of the compound of formula (I), at least one of $R^1$, $R^2$, and $R^3$ is phenyl and substituted with at least one of methyl, ethyl, $-C\equiv CH$, I, Br, Cl, F, $-CF_3$, $-CN$, $-CH_2CN$, $-CH_2CH_2CN$, $-NH_2$, $-NO_2$, $-N_3$, $-OH$, $-OCF_3$, $-OMe$ or $-NMe_2$. In some embodiments, at least two of $R^1$, $R^2$, and $R^3$ is phenyl and substituted with at least one of methyl, ethyl, $-C\equiv CH$, I, Br, Cl, F, $-CF_3$, $-CN$, $-CH_2CN$, $-CH_2CH_2CN$, $-NH_2$, $-NO_2$, $-N_3$, $-OH$, $-OCF_3$, $-OMe$ or $-NMe_2$. In another embodiment, at least one of $R^1$, $R^2$, and $R^3$ is pyridyl, optionally substituted with one or more of methyl, ethyl, $-C\equiv CH$, I, Br, Cl, F, $-CF_3$, $-CN$, $-CH_2CN$, $-CH_2CH_2CN$, $-NH_2$, $-NO_2$, $-N_3$, $-OH$, $-OCF_3$, $-OMe$ or $-NMe_2$.

In one embodiment, the compound of formula (I) has the structure of formula (I')

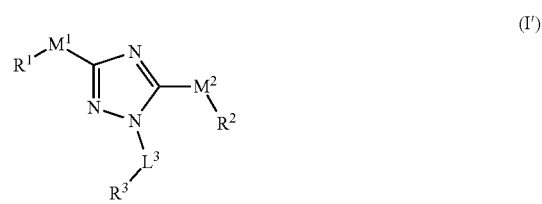

(I')

or a pharmaceutically acceptable salt or solvate thereof, wherein $L^3$, $M^1$, $M^2$, $R^1$, $R^2$, and $R^3$ are as defined for formula (I).

In one embodiment of the compound of formula (I'), $M^1$ and $M^2$ are each independently selected from $-NR^4-$, $-NR^4C(O)-$, $-C(O)NR^4-$, $-N(C(O)R^1)-$, or $-NR^4S(O)_m-$.

In one embodiment of the compound of formula (I'). $R^1$ and $R^2$ are each independently selected from phenyl, 6-10 membered amyl, 5-10 membered heteroaryl, 4-10 membered heterocyclyl, phenyl-($C_1$-$C_3$ phenyl-($C_2$-$C_3$ alkenyl)-, 5-6 membered heteroaryl-($C_1$-$C_3$ alkyl)-, or heteroaryl-($C_2$-$C_3$ alkenyl)-, wherein each cycloalkyl, aryl, heteroaryl portion is optionally substituted with one or more $R^5$; and $R^3$ is an aryl or a heteroaryl, optionally substituted with one or more $R^7$.

In one embodiment, the compound of formula (I) has the structure of formula (IA):

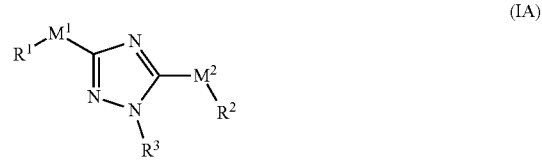

(IA)

or a pharmaceutically acceptable salt or solvate thereof, wherein:

$M^1$ and $M^2$ are each independently selected from $-NR^4C(O)-$ or $-C(O)NR^4-$;

$R^1$ and $R^2$ are each independently

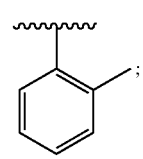

$R^3$ is selected from

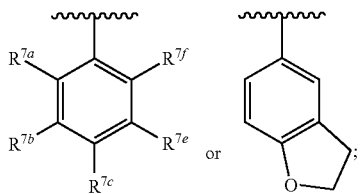

$R^4$ is each independently H or $C_1$-$C_3$ alkyl; and
$R^{7a}$, $R^{7b}$, $R^{7e}$, and $R^{7e}$ is each independently H, I, Br, Cl, F, —$CH_2F$, —$CHF_2$, —$CHF_2$, —$CF_3$, —$OCF_3$, —$N_3$, —CN, —OH, methyl, ethyl, propyl, $C_1$-$C_3$ haloalkyl, $C_1$-$C_3$ alkoxy, or $C_1$-$C_3$ haloalkoxy;

$R^{7c}$ is H, I, Br, Cl, F, —$CH_2F$, —$CHF_2$, —$CF_3$, —$OCF_3$, —$N_3$, —CN, —OH, $C_1$-$C_3$ alkyl $C_1$-$C_3$ haloalkyl, $C_1$-$C_3$ alkoxy, $C_1$-$C_3$ haloalkoxy, 4-6 membered heterocyclyl, or 5-6 membered heteroaryl, wherein the heterocyclyl and heteroaryl is optionally substituted with one or more $R^5$;

$R^5$ is I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —C(O)O($C_1$-$C_6$ alkyl);

wherein at least one of $R^{7a}$, $R^{7b}$, $R^{7c}$, $R^{7e}$, and $R^{7e}$ is not H.

In one embodiment of the compound of formula (IA), $R^3$ is selected from $R^3$ is

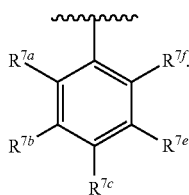

In one embodiment of the compound of formula (IA), four of $R^{7a}$, $R^{7b}$, $R^{7c}$, $R^{7e}$ and $R^{7e}$ is H. In another embodiment, three of $R^{7a}$, $R^{7b}$, $R^{7c}$, $R^{7e}$, and $R^{7e}$ is H. In some embodiments, $R^{7a}$, $R^{7b}$, $R^{7c}$; $R^{7e}$, and $R^{7e}$ is each independently H, I, Br, Cl, F, —$CH_2F$, —$CHF_2$, —$CHF_2$, —$CF_3$, —$OCF_3$, —$N_3$, —CN, —OH, methyl, ethyl, propyl, —C≡CH; —CN, —$NH_2$, —$NO_2$, —$N_3$, —OH, —$OCF_3$, —OMe, —$NMe_2$, or —$NEt_2$.

In one embodiment of the compound of formula (IA), $R^3$ is

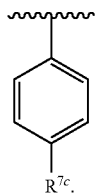

In some embodiments, $R^{7c}$ is I, Br, —$CH_2F$, —$CHF_2$, —$CF_3$, methyl, ethyl, propyl, —C≡CH; —CN, —$NH_2$, —$NO_2$, —$N_3$, —OH, —$OCF_3$, —OMe, —$NMe_2$, —$NEt_2$, in other embodiments, $R^{7c}$ is I, Br, —$CH_2F$, —$CHF_2$, —$CF_3$, —$OCF_3$, or —OMe. In one embodiment, $R^{7c}$ is azetidinyl, pyrrolidinyl, piperidinyl, morpholinyl, piperazinyl, or pyrazolyl, each optionally substituted with one or more $R^5$.

In one embodiment, the compound of formula (I) has the structure of formula (IB):

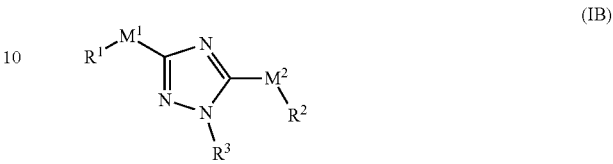

(IB)

or a pharmaceutically acceptable salt or solvate thereof, wherein:

$M^1$ and $M^2$ are each independently selected from —$NR^4$—, —$NR^4C(O)$— or —$C(O)NR^4$—;

$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

wherein one of -$M^1$-$R^1$ and -$M^2$-$R^2$ is —$NR^4$-(cycloalkylalkyl), —$NR^4$-(heterocyclylalkyl), —$NR^4$-(arylalkyl), or —$NR^4$-(heteroarylalkyl), wherein cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H or $C_1$-$C_3$ alkyl;

$R^5$ is I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —C(O)O($C_1$-$C_6$ alkyl); and $R^7$ is each independently I, Br, Cl, F, —$CH_2F$, —$CHF_2$, —$CF_3$, —$OCF_3$, —CN, -alkyl-CN, —$CONH_2$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, —$SR^6$, cycloalkyl, heterocyclyl, aryl, or heteroaryl, wherein each cycloalkyl, heterocyclyl, and heteroaryl is optionally substituted with one or more $R^5$.

In one embodiment of the compound of formula. (IB), one of -$M^1$-$R^1$ and -$M^2$-$R^2$ is —$NR^4$—($C_1$-$C_3$ alkylene)-cycloalkyl, —$NR^4$—($C_1$-$C_3$ alkylene)-heterocycyl, —$NR^4$—($C_1$-$C_3$ alkylene)-aryl, or —$NR^4$—($C_1$-$C_3$ alkylene)-heteroaryl; wherein cycloalkyl, aryl, heteroaryl, and heterocyclyl is each optionally substituted with one or more $R^5$. In some embodiments, one of -$M^1$-$R^1$ and -$M^2$-$R^2$ is —$NR^4$—($C_1$-$C_3$ alkylene)-phenyl, or —$NR^4$—($C_1$-$C_3$ alkylene)-pyridyl, wherein phenyl and pyridyl is each optionally substituted with one or more $R^5$. In other embodiments, one of -$M^1$-$R^1$ and -$M^2$-$R^2$ is —$NR^4$—$CH_2$-phenyl, —$NR^4$—$CH_2CH_2$-phenyl, —$NR^4$—$CH_2$-pyridyl, —$NR^4$—$CH_2CH_2$-pyridyl,

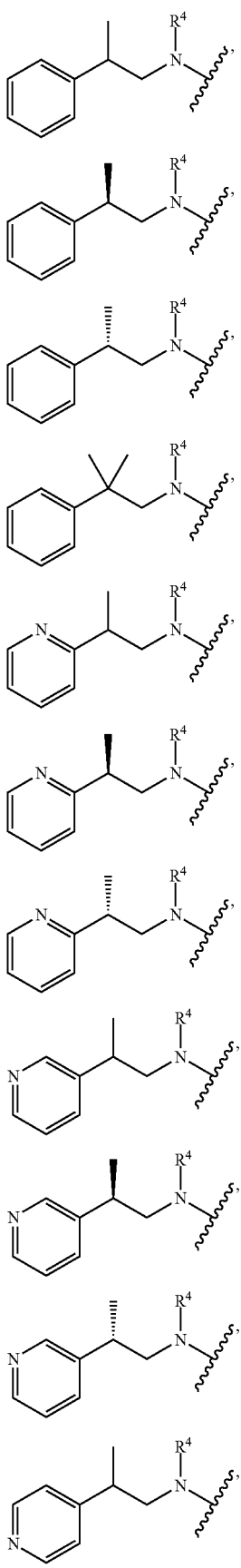

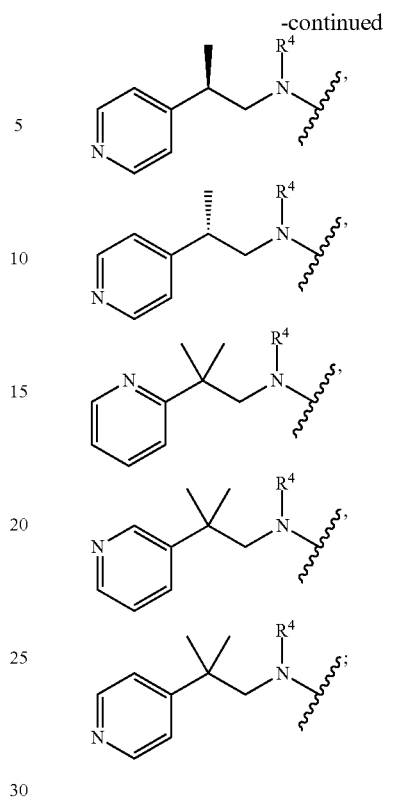

wherein phenyl and pyridyl is each optionally substituted with one or more $R^5$.

In one embodiment of the compound of formula (IB), $R^1$ and $R^2$ are each independently selected from phenyl or pyridyl, each optionally substituted with one or more $R^5$.

In one embodiment of the compound of formula (IB), one of -$M^1$-$R^1$ and -$M^2$-$R^2$ is —$NR^4$—($C_1$-$C_3$ alkylene)-phenyl, or —$NR^4$—($C_1$-$C_3$ alkylene)-pyridyl, and the other one of -$M^1$-$R^1$ and -$M^2$-$R^2$ is —$NR^4$C(O)-phenyl, —$NR^4$C(O)-pyridyl, —C(O)$NR^4$-phenyl, or —C(O)$NR^4$-pyridyl; wherein each phenyl and pyridyl is optionally substituted with one or more $R^5$. In some embodiments, one of -$M^1$-$R^1$ and -$M^2$-$R^2$ is —$NR^4$—($C_1$-$C_{13}$ alkylene)-phenyl, or —$NR^4$—($C_1$-$C_3$ alkylene)-pyridyl, wherein each phenyl and pyridyl is optionally substituted with one or more $R^5$, and the other one of -$M^1$-$R^1$ and -$M^2$-$R^2$ is

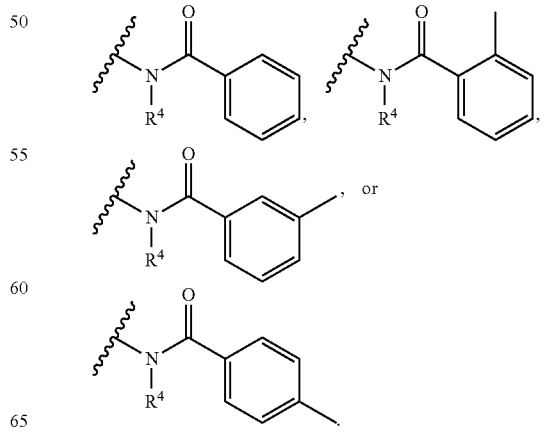

In other embodiments, one of -M¹-R¹ and -M²-R² is —NR⁴—(C₁-C₃ alkylene)-phenyl, or —NR⁴—(C₁-C₃ alkylene)-pyridyl, wherein each phenyl and pyridyl is optionally substituted with one or more R⁵, and the other one of -M¹-R¹ and -M²-R² is

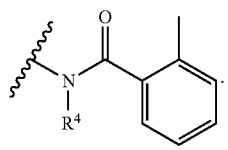

In one embodiment of the compound of formula (IB), R³ is phenyl, optionally substituted with one or more R⁷; and R⁷ is each independently I, Br, Cl, F, —CH₂F, —CHF₂, —CF₃, —CN, —N₃, —OH, methyl, ethyl, propyl, —CH; —CN, —NH₂, —NO₂, —N₃, —OH, —OCF₃, —OMe, —NMe₂, or —NEt₂.

In one embodiment of the compound of formula (IB), R⁵ is selected from I, Br, Cl, F, —CH₂F, —CHF₂, —CF₃, —OCF₃, —N₃, —CN, —OH, methyl, ethyl, propyl, —C≡CH; —CN, —NH₂, —NO₂, —N₃, —OH, —OCF₃, —OMe, —NMe₂, or —NEt₂.

In one embodiment of the compound of formula (IB), the compound is not

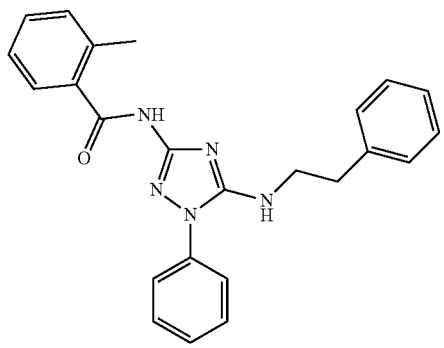

In one embodiment, the compound of formula (I) has the structure of formula (IB'):

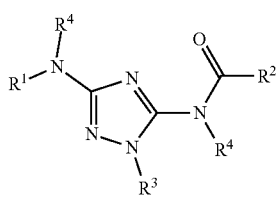

(IB')

or a pharmaceutically acceptable salt or solvate thereof, wherein:
R¹ is cycloalkylalkyl, heterocyclylalkyl, arylalkyl, or heteroarylalkyl, wherein cycloalkyl, aryl, heteroaryl, and heterocyclyl portion is optionally substituted with one or more R⁵;
R² is selected from cycloalkyl, aryl, biphenyl, heterocyclyl, or heteroaryl, wherein each optionally substituted with one or more R⁵;
R³ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more R⁷;
R⁴ is each independently H or C₁-C₁₃ alkyl;
R⁵ is I, Br, Cl, F, —CH₂F, —CHF₂, —CF₃, alkyl, alkynyl, —CN, —(C₁-C₃ alkylene)-CN, —NH₂, —NO₂, —N₃, —OH, —OCF₃, —OMe, —NMe₂, —NEt₂, or —C(O)O(C₁-C₆ alkyl); and
R⁷ is each independently I, Br, Cl, F, —CH₂F, —CHF₂, —CF₃, —CN, -alkyl-CN, —CONH₂, —CONHR⁶, —CONR⁶R⁶, —COOH, —NHR⁶, —NO₂, —NR⁶R⁶, —N₃, —OH, OR⁶, —COOR⁶, —OSO₃R⁶, oxo, R⁶, —SH, —SO₂R⁶, —SO₃H, —SO₃R⁶, —SR⁶, cycloalkyl, heterocyclyl, aryl, or heteroaryl, wherein each cycloalkyl, heterocyclyl, aryl, and heteroaryl is optionally substituted with one or more R⁵.

In one embodiment of the compound of formula (IB'), R¹ is —C₁-C₃ alkylene-cycloalkyl, —C₁-C₃ alkylene-heterocyclyl, —C₁-C₃ alkylene-aryl, or —C₁-C₃ alkylene-heteroaryl; wherein cycloalkyl, aryl, heteroaryl, and heterocyclyl is each optionally substituted with one or more R⁵. In some embodiments, R¹ is —C₁-C₃ alkylene-phenyl or —C₁-C₃ alkylene-pyridyl, wherein phenyl and pyridyl is each optionally substituted with one or more R⁵. In another embodiment, R¹ is —CH₂-phenyl, —CH₂CH₂-phenyl, —CH₂-pyridyl, —CH₂CH₂-pyridyl,

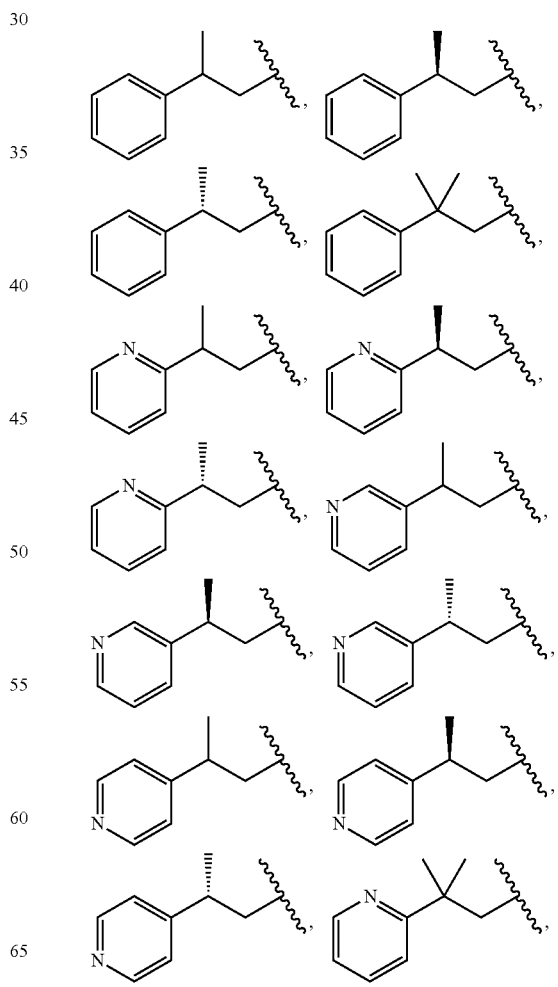

-continued

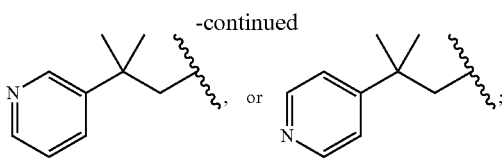

wherein phenyl and pyridyl is each optionally substituted with one or more $R^5$.

In one embodiment of the compound of formula (IB'), $R^2$ is aryl or 5-6 membered heteroaryl, each optionally substituted with one or more $R^5$. In another embodiment, $R^2$ is phenyl optionally substituted with one or more $R^5$. In some embodiments, $R^2$ is

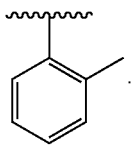

In one embodiment of the compound of formula (IB'), $R^3$ is phenyl, optionally substituted with one or more $R^7$; and $R^7$ is each independently I, Br, Cl, F, —CH$_2$F, —CHF$_2$, —CF$_3$, —OCF$_3$, —CN, —N$_3$, —OH, methyl, ethyl, propyl, —C≡CH, —CN, —NH$_2$, —NO$_2$, —N$_3$, —OH, —OCF$_3$, —OMe, —NMe$_2$, or —NEt$_2$.

In one embodiment of the compound of formula (IB'), 5 is selected from I, Br, Cl, F, —CH$_2$F, —CHF$_2$, —CF$_3$, —OCF$_3$, —N$_3$, —CN, —OH, methyl, ethyl, propyl, —C≡CH; —CN, —NH$_2$, —NO$_2$, —N$_3$, —OH, —OCF$_3$, —OMe, —NMe$_2$, or —NEt$_2$.

In one embodiment, the compound of formula (I) has the structure of formula (IC):

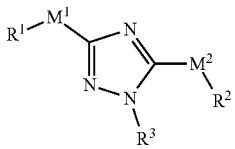

(IC)

or a pharmaceutically acceptable salt or solvate thereof, wherein:

$M^1$ and $M^2$ are each independently selected from —NR$^4$—, —NR$^4$C(O)— or —C(O)NR$^4$—;

$R^1$ and $R^2$ are each independently selected from an alkyl, alkenyl, cycloalkyl, aryl; biphenyl, heterocyclyl heterocycloalkyl, 5-6 membered heteroaryl, cycloalkylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

wherein at least one of -M$^1$-R$^1$ and -M$^2$-R$^2$ is —NR$^4$-(4-6 membered heterocyclyl), —NR$^4$-(5-6 membered heteroaryl), or —NR$^4$-napthalenyl, wherein 4-6 membered heterocyclyl, 5-6 membered heteroaryl, and naphthalenyl is each optionally substituted with one or more $R^5$;

$R^3$ is selected phenyl, optionally substituted with one or more $R^7$;

$R^4$ is each independently H or C$_1$-C$_3$ alkyl; and $R^5$ and $R^7$ are each independently selected from I, Br, Cl, F, —CH$_2$F, —CHF$_2$, —CF$_3$, —C$_1$-C$_6$ alkyl, alkynyl, —CN, (—C$_1$-C$_3$ alkylene)-CN, —NH$_2$, —NO$_2$, —N$_3$, —OH, —OCF$_3$, —OMe, —NMe$_2$, —NEt$_2$, or —C(O)O(C$_1$-C$_6$ alkyl).

In one embodiment of the compound of formula (IC), at least one of -M$^1$-R$^1$ and -M$^2$-R$^2$ is —NR$^4$-azetidinyl, —NR$^4$-pyrrolidinol, —NR$^4$-isoxazolyl, —NR$^4$-oxazolyl, —NR$^4$-thiazolyl, —NR$^4$-thiophenyl, —NR$^4$-pyridyl, —NR$^4$-pyridazinyl, —NR$^4$-pyrazinyl, —NR$^4$-pyrimidinyl, or —NR$^4$-pyridinone, wherein each of azetidinyl, pyrrolidinyl piperidinyl imidazolyl, isoxazolyl, oxazolyl, thiazolyl, pyridyl, pyridazinyl, pyrazinyl, pyrimidinyl, or pyridinone is optionally substituted with one or more $R^5$. In other embodiments, at least one of -M$^1$-R$^1$ and -M$^2$-R$^2$ is —NR$^4$-pyridyl, wherein pyridyl is optionally substituted with one or more $R^5$. In some embodiments, -M$^1$-R$^1$ and -M$^2$-R$^2$ are each —NR$^4$-pyridyl, wherein pyridyl is optionally substituted with one or more $R^5$. In other embodiments, one of -M$^1$-R$^1$ and -M$^2$-R$^2$ is —NR$^4$-azetidinyl, —NR$^4$-pyrrolidinyl, —NR$^4$-piperidinyl, —NR$^4$-imidazolyl, —NR$^4$-oxazolyl, —NR$^4$-thiazolyl, —NR$^4$-thiophenyl, —NR$^4$-pyridyl, —NR$^4$-pyridazinyl, —NR$^4$-pyrazinyl, —NR$^4$-pyrimidinyl, or —NR$^4$-pyridinone, wherein each of azetidinyl, pyrrolidinyl, piperidinyl, imidazolyl, isoxazolyl, oxazolyl, thiazolyl, pyridyl, pyridazinyl, pyrazinyl, pyrimidinyl, or pyridinone is optionally substituted with one or more $R^5$, and the other one of -M$^1$-R$^1$ and -M$^2$-R$^2$ is

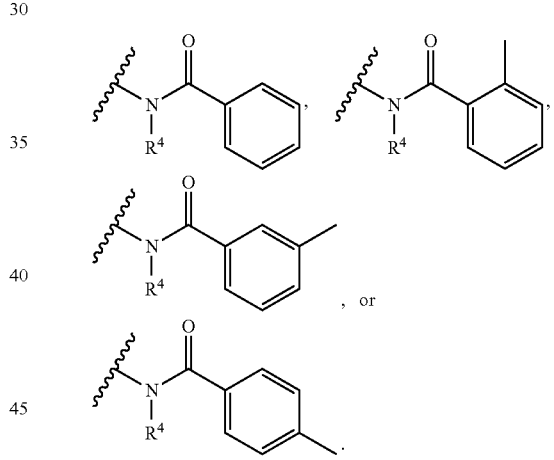

In one embodiment of the compound of formula (IC), one of -M$^1$-R$^1$ and -M$^2$-R$^2$ is —NR$^4$-azetidinyl, —NR$^4$-pyrrolidinyl, —NR$^4$-piperidinyl, —NR$^4$-imidazolyl, —NR$^4$-isoxazolyl, —NR$^4$-oxazolyl, —NR$^4$-thiazolyl, —NR$^4$-thiophenyl, —NR$^4$-pyridyl, —NR$^4$-pyridazinyl, pyrazinyl, —NR$^4$-pyrimidinyl, or —NR$^4$-pyridinone, wherein each of azetidinyl, pyrrolidinyl, piperidinyl, imidazolyl, isoxazolyl, oxazolyl, thiazolyl, pyridyl, pyridazinyl, pyrazinyl, pyrimidinyl, or pyridinone is optionally substituted with one or more $R^5$, and the other one of -M$^1$-R$^1$ and -M$^2$-R$^2$ is

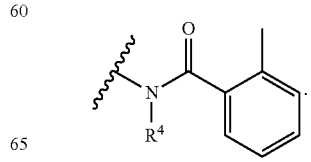

In one embodiment of the compound of formula (IC), $R^5$ and $R^7$ is each selected from I, Br, Cl, F, —$CH_2F$, —$CHF_2$, —$CF_3$, —$N_3$, —CN, —OH, methyl, ethyl, propyl, —C≡CH, —CN, —$NH_2$, —$NO_2$, —$N_3$, —OH, —$OCF_3$, —OMe, —$NMe_2$, or —$NEt_2$.

In one embodiment of the compound of formula (IC), the compound is not

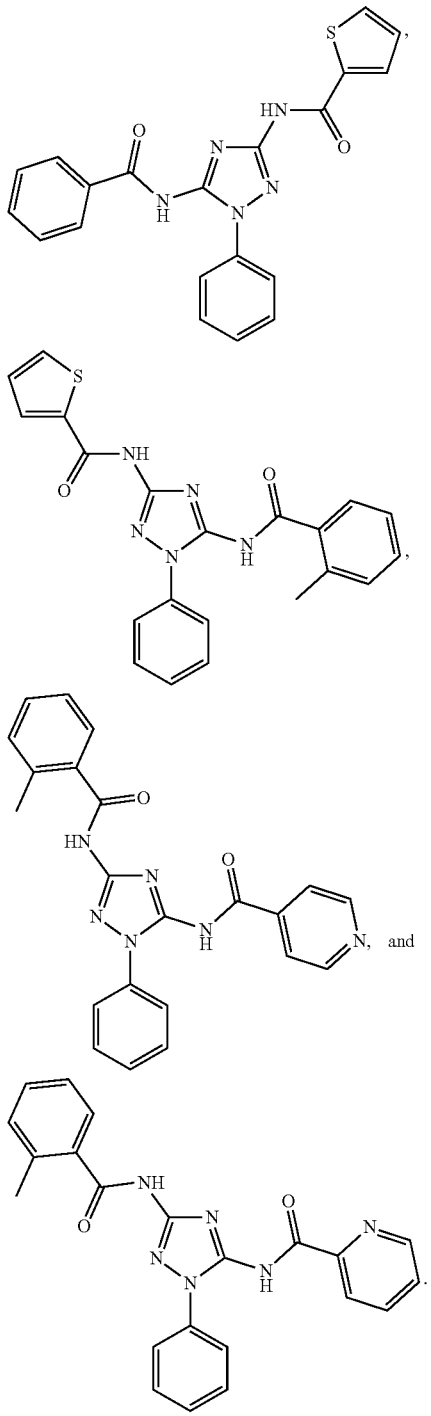

In one embodiment, the compound of formula (I) has the structure of formula (ID):

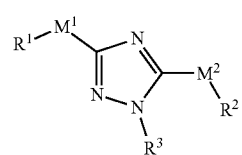

(ID)

or a pharmaceutically acceptable salt or solvate thereof, wherein:

$M^1$ and $M^2$ are each independently selected from —$NR^4$—, —$NR^4C(O)$— or —$C(O)NR^4$—;

$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H or $C_1$-$C_3$ alkyl; and $R^5$ and $R^7$ are each independently selected from I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —$C(O)O(C_1$-$C_6$ alkyl);

wherein at least one of $R^1$ and $R^2$ is a phenyl substituted with at least one of —C≡CH or —$N_3$.

In one embodiment of the compound of formula (ID), $M^1$ and $M^2$ are each —$NR^4C(O)$—.

In one embodiment of the compound of formula (ID), at least one of $R^1$ and $R^2$ is a phenyl substituted with at least one of —C≡CH or —$N_3$ and the other one of $R^1$ and $R^2$ is a phenyl or pyridyl, optionally substituted with one or more $R^5$.

In one embodiment of the compound of formula (ID), $R^3$ is phenyl optionally substituted with one or more $R^7$.

In one embodiment of the compound of formula (ID), $R^5$ and $R^7$ is each selected from I, Br, Cl, F, —$CH_2F$, —$CHF_2$, —$CF_3$, —$N_3$, —CN, —OH, methyl, ethyl, propyl, —C≡CH, —CN, —$NH_2$, —$NO_2$, —$N_3$, —OH, —$OCF_3$, —OMe, —$NMe_2$, or —$NEt_2$.

In one embodiment, the compound of formula (I) has the structure of formula (IE):

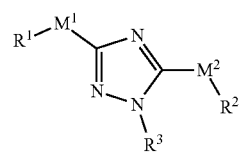

(IE)

or a pharmaceutically acceptable salt or solvate thereof, wherein:

M¹ and M² are each independently selected from —NR⁴—, —NR⁴C(O)—, —C(O)NR⁴—, or —S(O)$_m$NR⁴—;

R¹ and R² are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more R⁵;

R³ is selected from an aryl or heteroaryl, wherein aryl and heteroaryl is optionally substituted with one or more R⁷;

R⁴ is each independently H or $C_1$-$C_3$ alkyl; and

R⁵ and R⁷ are each independently selected from I, Br, Cl, F, —CH₂F, —CHF₂, —CF₃, —$C_1$-$C_6$ alkyl, alkynyl, —CN, —($C_1$-$C_3$ alkylene)-CN, —NH₂, —NO₂, —N₃, —OH, —OCF₃, —OMe, —NMe₂, —NEt₂, or —C(O)O($C_1$-$C_6$ alkyl);

wherein when M¹ and M² are both —NR⁴C(O)—, at least one of R¹ and R² is selected from

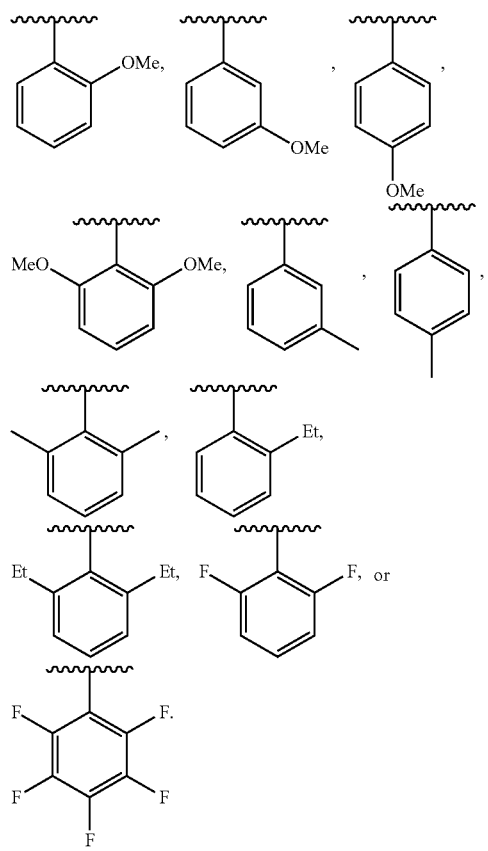

In one embodiment of the compound of formula. (IE), M¹ and M² are both —S(O)$_m$NR⁴—. In another embodiment, M¹ and M² are both —C(O)NR⁴—.

In one embodiment of the compound of formula (IE), at least one of R¹ and R² is a phenyl or pyridyl, optionally substituted with one or more R⁵. In some embodiments, R¹ and R² is phenyl, optionally substituted with one or more R⁵. In other embodiments, at least one of R¹ and R² is selected from In one embodiment of the compound of formula (IE), at least one of R³ is a phenyl or pyridyl, optionally substituted with one or more R⁷.

In one embodiment of the compound of formula (IE), R⁵ and R⁷ is each selected from I, Br, Cl, F, —CH₂F, —CHF₂, —CF₃, —OCF₃, —N₃, —CN, —OH, methyl, ethyl, propyl, —C≡CH, —CN, —NH₂, —NO₂, —N₃, —OH, —OCF₃, —OMe, —NMe₂, or —NEt₂.

In one embodiment of the compound of formula (IE), the compound is not and

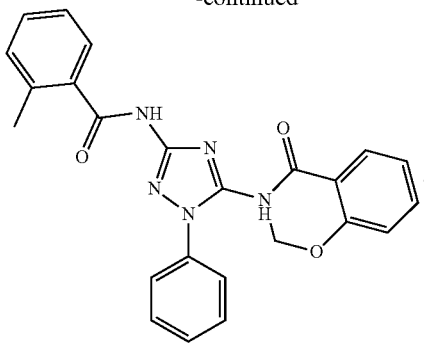

In one embodiment, the compound of formula (I) has the structure of formula (IF):

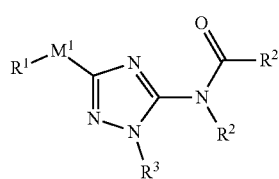

or a pharmaceutically acceptable salt or solvate thereof, wherein:

$M^1$ is selected from —$NR^4$—, —$NR^4C(O)$— or —$C(O)NR^4$—;

$R^1$ and $R^2$ are each independently selected from an alkyl, alkenyl, cycloalkyl, aryl, biphenyl, heterocyclyl heterocycloalkyl, 5-6 membered heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H or $C_1$-$C_3$ alkyl; and $R^5$ and $R^7$ are each independently selected from I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —OMe, —$NMe_2$, —$NEt_2$, or —C(O)O($C_1$-$C_6$ alkyl).

In one embodiment of the compound of formula (IF), $R^1$ and $R^2$ are each independently selected from aryl or 5-6 membered heteroaryl, each optionally substituted with one or more $R^5$.

In one embodiment of the compound of formula (IF), $R^2$ is phenyl optionally substituted with one or more $R^5$. In another embodiment, $R^2$ is

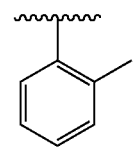

In one embodiment of the compound of formula (IF), $R^3$ is cycloalkyl, aryl, heterocyclyl, or heteroaryl, each optionally substituted with one or more $R^7$. In another embodiment, $R^3$ is phenyl optionally substituted with one or more $R^7$.

In one embodiment of the compound of formula (I), (I'), (IA), (IB), (IB'), (IC), (ID), (IE), or (IF) the compound is selected from Table 1. In one embodiment, the compound of formula (I) or (IA) is

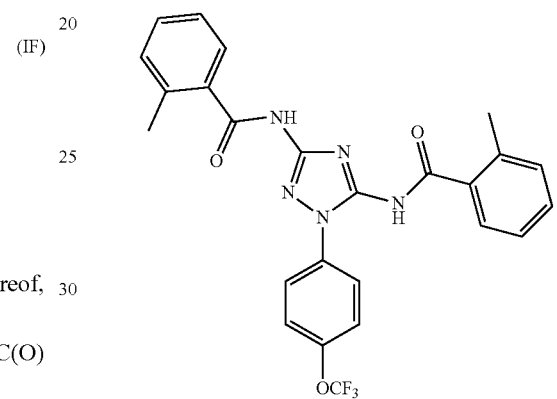

or a pharmaceutically acceptable salt thereof. In other embodiments, the compound of formula (I) or (IB) is

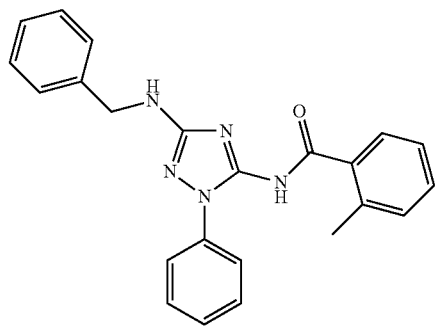

or a pharmaceutically acceptable salt thereof.

In one embodiment, the compound of the present disclosure is selected from Table 2.

In one embodiment, the compound of formula (I), excludes compounds of Table A. In one embodiment, the compound of formula. (I), (I'), (IA), (IB), (IB'), (IC), (ID), (IE), or (IF) excludes compounds of Table A.

In one embodiment, the present disclosure provides a pharmaceutical composition comprising a pharmaceutically acceptable carrier or a pharmaceutically acceptable excipient and a compound of any one of formula (I), (I'), (IA), (IB), (IB'), (IC), (ID), (IE), or (IF). In one embodiment, the pharmaceutical composition comprises

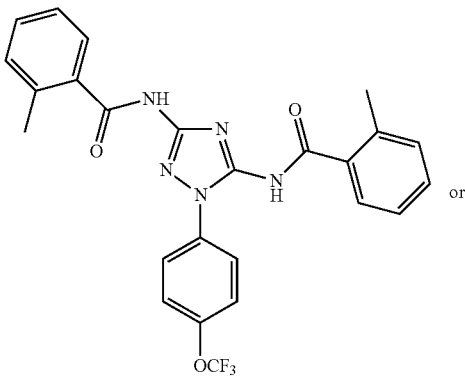

or

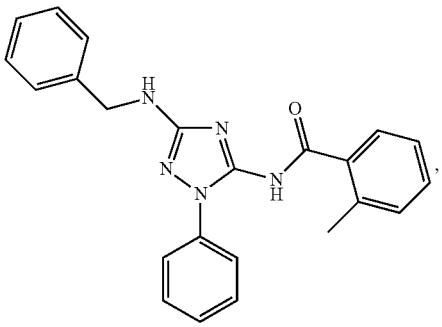

or a pharmaceutically acceptable salt thereof.

In one embodiment, the present disclosure provides a pharmaceutical composition comprising a pharmaceutically acceptable carrier or a pharmaceutically acceptable excipient and a compound of Table 1. In one embodiment, the present disclosure provides a pharmaceutical composition comprising a pharmaceutically acceptable carrier or a pharmaceutically acceptable excipient and a compound of Table 2. In one embodiment, the present disclosure provides a pharmaceutical composition comprising a pharmaceutically acceptable carrier or a pharmaceutically acceptable excipient and

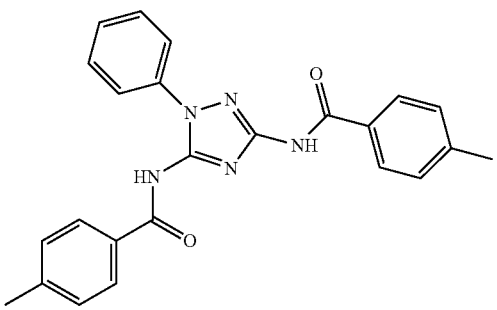

or a pharmaceutically acceptable salt thereof. In one embodiment of the pharmaceutical composition, the compounds of Table A are excluded.

In one embodiment, the present disclosure provides a pharmaceutical composition as disclosed herein comprises one additional therapeutically active agent.

In one embodiment, the present disclosure provides compounds comprising the structure of formula (II):

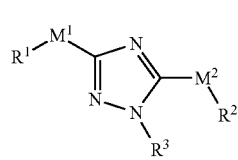

(II)

or a pharmaceutically acceptable salt or solvate thereof, wherein:

$M^1$ and $M^2$ are each independently selected from a bond, —$NR^4$—, or —$NR^4C(O)$—, —$C(O)NR^4$—;

$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

wherein at least one of $M^1$ and $M^2$ is a bond or —$NR^4$—;

wherein when $M^1$ is —$NR^4$—, then $R^1$ is cycloalkylalkyl, heterocyclylalkyl, arylalkyl, or heteroarylalkyl, wherein cycloalkyl, aryl, heteroaryl, and heterocyclyl portion is optionally substituted with one or more $R^5$;

wherein when $M^2$ is —$NR^4$—, then $R^2$ is cycloalkylalkyl, heterocyclylalkyl, arylalkyl, or heteroarylalkyl, wherein cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H, alkyl, wherein each alkyl is optionally substituted with one or more $R^5$;

$R^5$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —OH, $OR^6$, —$COOR^6$, —$OSO_3R^6$, oxo, $R^6$, —SH, —$SO_2R^6$, —$SO_3H$, —$SO_3R^6$, or —$SR^6$;

$R^6$ is each independently alkyl, alkenyl, alkynyl, haloalkyl, haloalkenyl, haloalkynyl; or alternatively two $R^6$ on the same N atom can together form a 3-6 membered N-heterocyclyl; and $R^7$ is each independently I, Br, Cl, F, —$CH_2F$, —$CHF_2$, —$CHF_2$, —$OCF_3$, —CN, -alkyl-CN, —$CONH_2$, —$CONHR^6$, —$CONR^6R^6$, —COOH, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, —$SR^6$, cycloalkyl, heterocyclyl, aryl, or heteroaryl, wherein each cycloalkyl, heterocyclyl, aryl, and heteroaryl is optionally substituted with one or more $R^5$;

wherein the compound is not N-benzyl-N-(5-(benzylamino)-1-phenyl-1H-1,2,4-triazol-3-yl)acetamide, N-(5-((2-chlorobenzyl)amino)-1-phenyl-1H-1,2,4-triazol-3-yl)-2-fluorobenzamide and $N^3,N^5$-bis(4-methylbenzyl)-1-phenyl-1H-1,2,4-triazole-3,5-diamine.

In one embodiment of the compound of formula (II), at least one of -$M^1$-$R^1$ and -$M^2$-$R^2$ is —$NR^4$—($C_1$-$C_3$ alkylene)-cycloalkyl, —NR⁴—(C₁-C₃ alkylene)-heterocyclyl, —NR⁴—(C₁-C₃ alkylene)-aryl, or —NR⁴—(C₁-C₃ alkylene)-heteroaryl; wherein cycloalkyl, aryl, heteroaryl, and heterocyclyl is each optionally substituted with one or more R⁵.

In one embodiment of the compound of formula (II), at least one of -M¹-R¹ and -M²-R² is —NR⁴—(C₁-C₃ alkylene)-phenyl, or —NR⁴—(C₁-C₃ alkylene)-pyridyl, wherein phenyl and pyridyl is each optionally substituted with one or more R⁵. In other embodiments, at least one of -M¹-R¹ and -M²-R² is —NR⁴—CH₂-phenyl, —NR⁴—CH₂CH₂-phenyl, —NR⁴—CH₂-pyridyl, —NR⁴—CH₂CH₂-pyridyl,

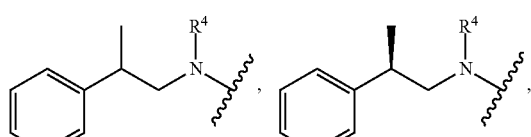

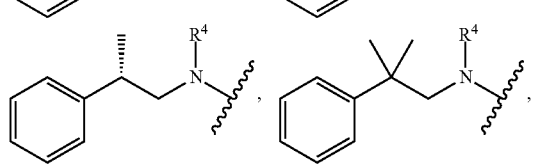

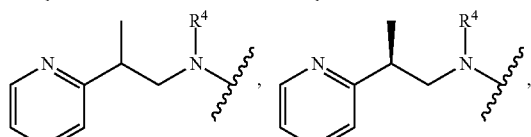

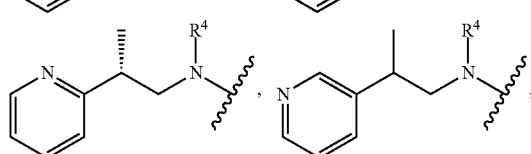

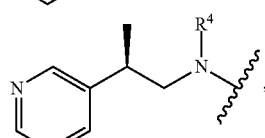

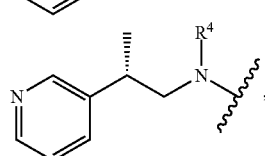

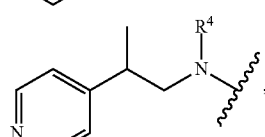

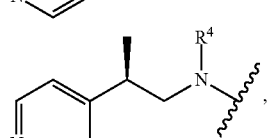

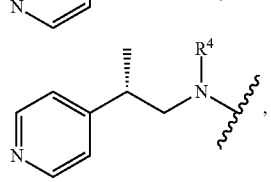

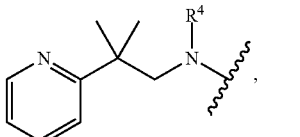

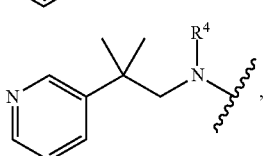

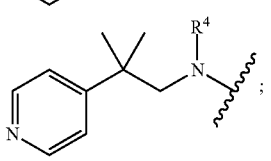

wherein phenyl and pyridyl is each optionally substituted with one or more R⁵. In some embodiments, -M¹-R¹ and -M²-R² are each selected from —NR⁴—CH₂-phenyl, —NR⁴—CH₂CH₂-phenyl, —NR⁴—CH₂-pyridyl, —NR⁴—CH₂CH₂-pyridyl,

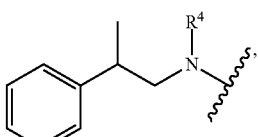

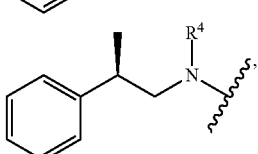

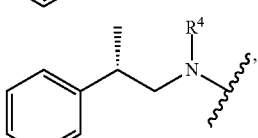

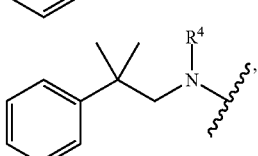

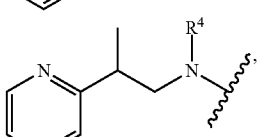

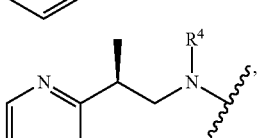

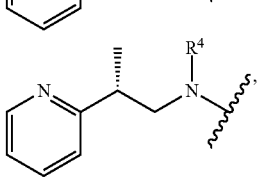

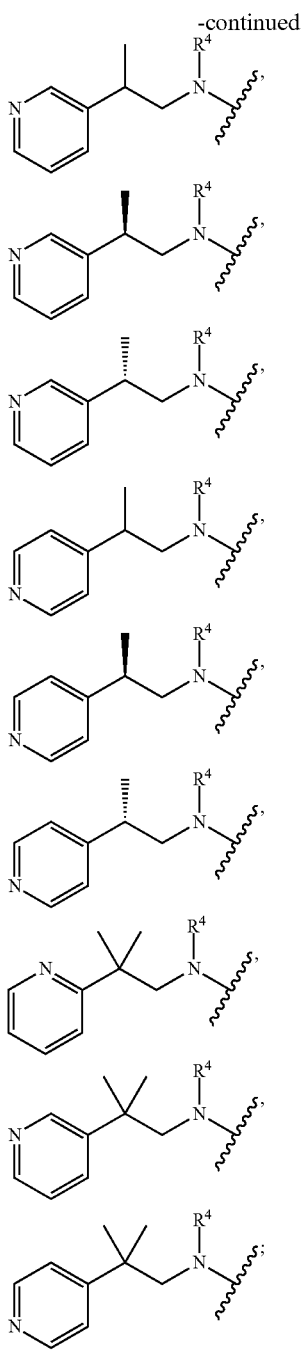

wherein phenyl and pyridyl is each optionally substituted with one or more $R^5$.

In one embodiment of the compound of formula (II), $R^1$ and $R^2$ are each independently selected from phenyl or pyridyl, each optionally substituted with one or more $R^5$.

In one embodiment of the compound of formula (II), one of $M^1$ and $M^2$ is a bond.

In one embodiment of the compound of formula (II), $R^1$ and $R^2$ are each independently selected from phenyl or 5-6 membered heteroaryl, each optionally substituted with one or more $R^5$. In other embodiments, $R^1$ and $R^2$ are each independently selected from phenyl, azetidinyl, pyrrolidinyl, piperidinyl, imidazolyl, isoxazolyl, oxazolyl, thiazolyl, pyridyl, pyridazinyl, pyrazinyl, pyrimidinyl pyridinoneor, or pyridine N-oxide, each optionally substituted with one or more $R^5$.

In one embodiment of the compound of formula (II), $M^1$ is a bond and $R^1$ is pyridyl, optionally substituted with one or more $R^5$.

In one embodiment of the compound of formula (II), $M^2$ is a bond and $R^2$ is pyridyl, optionally substituted with one or more $R^5$.

In one embodiment of the compound of formula (II), is a bond and $M^2$ is —$NR^4$— or —$NR^4C(O)$—.

In one embodiment of the compound of formula (II), $M^2$ is a bond and $M^1$ is —$NR^4$— or —$NR^4C(O)$—.

In one embodiment of the compound of formula (II), $R^3$ is phenyl, optionally substituted with one or more $R^7$; and $R^7$ is each independently I, Br, Cl, F, —$CH_2F$, —$CHF_2$, —$CF_3$, —$OCF_3$, —$CN$, —$N_3$, —OH, methyl, ethyl, propyl, —C≡CH; —CN, —$NH_2$, —$NO_2$, —$N_3$, —OH, —$OCF_3$, —OMe, —$NMe_2$, or —$NEt_2$.

In one embodiment of the compound of formula (II), $R^5$ and $R^7$ are each independently selected from I, Br, Cl, F, —$CH_2F$, —$CHF_2$, —$CF_3$, —$OCF_3$, —$N_3$, —CN, —OH, methyl, ethyl, propyl, —C≡CH; —CN, —$NH_2$, —$NO_2$, —$N_3$, —OH, —$OCF_3$, —OMe, —$NMe_2$, or —$NEt_2$.

In one embodiment of the compound of formula (II), $R^4$ is each independently H or $C_1$-$C_3$ alkyl.

In one embodiment, the compound of formula (II) has the structure of formula (IIA):

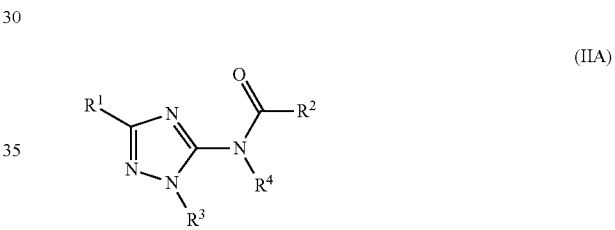

(IIA)

or a pharmaceutically acceptable salt or solvate thereof, wherein:

$R^1$ and $R^2$ are each independently selected from an cycloalkyl, aryl, biphenyl, heterocyclyl, or heteroaryl, each optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H, alkyl, wherein each alkyl is optionally substituted with one or more $R^5$;

$R^5$ is each independently I, Br, Cl, F, —$CH_2F$, —$CHF_2$, —$CF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, or —$SR^6$;

$R^6$ is each independently alkyl, alkenyl, alkynyl, haloalkyl, haloalkenyl, haloalkynyl; or alternatively two $R^6$ on the same N atom can together form a 3-6 membered N-heterocyclyl;

$R^7$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —COOR⁶, —OSO₃R⁶, oxo, R⁶, —SH, —SO₂R⁶, —SO₃H, —SO₃R⁶, cycloalkyl, heterocyclyl, aryl, or heteroaryl, wherein each cycloalkyl, heterocyclyl, acyl, and heteroaryl is optionally substituted with one or more R⁵.

In one embodiment of the compound of formula (IIA), R¹ is aryl, optionally substituted with one or more R⁵. In another embodiment, R¹ is phenyl, optionally substituted with one or more R⁵. In some embodiments, R¹ is 5-6 membered heteroaryl, optionally substituted with one or more R⁵. In other embodiments, R¹ is pyridyl, optionally substituted with one or more R⁵.

In one embodiment of the compound of formula (IIA), R² is phenyl optionally substituted with one or more R⁵. In some embodiments, R² is

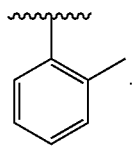

In one embodiment of the compound of formula (IIA), R³ is cycloalkyl, aryl, heterocyclyl, or heteroaryl, each optionally substituted with one or more R⁷. In some embodiments, R³ is phenyl optionally substituted with one or more R⁷.

In one embodiment of the compound of formula (IIA), R⁵ is I, Br, Cl, F, —CH₂F, —CHF₂, —CF₃, —C₁-C₆ alkyl, alkynyl, —CN, —(C₁-C₃ alkylene)-CN, —NH₂, —NO₂, —N₃, —OH, —OCF₃, —OMe, —NMe₂, —NEt₂, or —C(O)O(C₁-C₆ alkyl).

In one embodiment of the compound of formula (IIA), R⁵ and R⁷ are each independently selected from I, Br, Cl, F, —CH₂F, —CHF₂, —OCF₃, —N₃, —CN, —OH, methyl, ethyl, propyl, —C≡CH; —CN, —NH₂, —NO₂, —N₃, —OH, —OCF₃, —OMe, —NMe₂, or —NEt₂.

In one embodiment, the compound of formula (II) or (IIA) excludes the compounds of Table C.

In one embodiment of the compound of formula (II) or the compound is selected from Table 3A.

In one embodiment, the present disclosure provides a pharmaceutical composition comprising a pharmaceutically acceptable carrier or a pharmaceutically acceptable excipient and a compound of formula (II) or (IIA). In other embodiments, the pharmaceutical composition further comprising one additional therapeutically active agent. In one embodiment of the pharmaceutical composition, the compounds of Table C are excluded.

In one embodiment, the present disclosure provides compounds comprising the structure of formula (III):

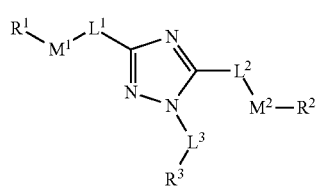

or a pharmaceutically acceptable salt or solvate thereof, wherein:

L¹, L² and L³ are each independently selected from a bond, alkylene, or alkenylene;

M¹ and M² are each independently selected from —NR⁴—, —NR⁴C(O)—, —N(C(O)R¹)—, —C(O)NR⁴—, —NR⁴C(O)NR⁴—, —C(O)—, —C(=NR)—, —C(=NOR⁴)—, —OC(O)—, —C(O)O—, —OC(O)O—, —OC(O)NR⁴—, —NR⁴C(O)O—, —S(O)ₘ—, —S(O)ₘNR⁴—, or —NR⁴S(O)ₘ—, provided that M¹ and M² are not both —NR⁴—;

R¹ and R² are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocycloalkyl, heteroarylalkyl, heteroarylalkenyl, or heteroarylalkynyl, wherein each cycloalkyl, aryl, heteroaryl, and heterocyclyl portion is optionally substituted with one or more R⁵;

R³ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more R⁷;

R⁴ is each independently H, alkyl, wherein each alkyl is optionally substituted with one or more R⁵;

R⁵ is each independently I, Br, Cl, F, —CH₂F, —CHF₂, —CF₃, —OCF₃, —CN, -alkyl-CN, —CONH₂, —CONHR⁶, —CONR⁶R⁶, —COR⁶, —COOH, —NH₂, —NHR⁶, —NO₂, —NR⁶R⁶, —NR⁶COR⁶, -(alkylene)NR⁶COR⁶, —N₃, —OH, OR⁶, —COOR⁶, —OSO₃R⁶, oxo, R⁶, —SH, —SO₂R⁶, —SO₃H, —SO₃R⁶, or —SR⁶;

R⁶ is each independently alkyl, alkenyl, alkynyl, haloalkyl, haloalkenyl, haloalkynyl; or alternatively two R⁶ on the same N atom can together form a 3-6 membered N-heterocyclyl;

R⁷ is each independently I, Br, Cl, F, —CH₂F, —CHF₂, —CF₃, —CN, -alkyl-CN, —CONH₂, —CONHR⁶, —CONR⁶R⁶, —COOH, —NH₂, —NHR⁶, —NO₂, —NR⁶R⁶, —N₃, —OH, OR⁶, —COOR⁶, —OSO₃R⁶, oxo, R⁶, —SH, —SO₂R⁶, —SO₃H, —SO₃R⁶, —SR⁶, cycloalkyl, heterocyclyl, aryl, or heteroaryl, wherein each cycloalkyl, heterocyclyl, aryl, and heteroaryl is optionally substituted with one or more R⁵;

m is 0, 1, or 2; and wherein the compound is not N,N'-(1-phenyl-1H-1,2,4-triazole-3,5-diyl)dibenzamide, N-(3-benzamido-1-phenyl-1H-1,2,4-triazol-5-yl)furan-2-carboxamide, N-(5-cinnamamido-1-phenyl-1H-1,2,4-triazol-3-yl) benzamide, N-(1-phenyl-5-(phenylamino)-1H-1,2,4-triazol-3-yl)benzamide, 4-fluoro-N-(5-(4-methoxybenzamido)-1-phenyl-1H-1,2,4-triazol-3-yl) benzamide, N,N'-(1-phenyl-1H-1,2,4-triazole-3,5-diyl) bis(4-methylbenzamide), N-(5-((2-chlorobenzyl)amino)-1-phenyl-1H-1,2,4-triazol-3-yl)-2-fluorobenzamide, N-(3-benzamido-1-phenyl-1H-1,2,4-triazol-5-yl)-4-fluorobenzamide, N-(3-benzamido-1-phenyl-1H-1,2,4-triazol-5-yl)-4-nitrobenzamide, N-(3-benzamido-1-phenyl-1H-1,2,4-triazol-5-yl)-3-nitrobenzamide, and 4-((3-benzamido-1-phenyl-1H-1,2,4-triazol-5-yl)carbamoyl)benzoic acid.

In one embodiment, the compound of formula (III) has the structure of formula (IIIA):

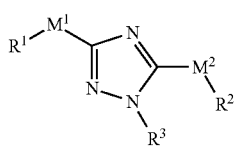
(IIIA)

or a pharmaceutically acceptable salt or solvate thereof, wherein:
M$^1$ and M$^2$ are each independently selected from —NR$^4$—, —NR$^4$C(O)— or —C(O)NR$^4$—, provided that -M$^1$-R$^1$ and M$^2$ are not both —NR$^4$—;
R$^1$ and R$^2$ are each independently phenyl, optionally substituted with one or more R$^5$;
wherein at least one of R$^1$ or R$^2$ is substituted with —(C$_1$-C$_6$ alkylene)NHCO(C$_1$-C$_{10}$ alkyl) or —(C$_1$-C$_6$ alkylene)N(C$_1$-C$_3$ alkyl)CO(C$_1$-C$_{10}$ alkyl);
R$^3$ is

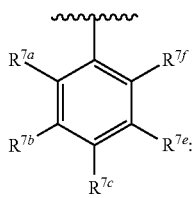

R$^4$ is each independently H or C$_1$-C$_3$ alkyl;
R$^5$ is each independently I, Br, Cl, F, —CH$_2$F, —CHF$_2$, —CF$_3$, —C$_1$-C$_6$ alkyl, alkynyl, —CN, —(C$_1$-C$_6$ alkylene)-CN, —NH$_2$, —NO$_2$, —N$_3$, —OH, —OCF$_3$, —OMe, —NMe$_2$, —NEt$_2$, —C(O)O(C$_1$-C$_6$ alkyl), —CO(C$_1$-C$_{10}$ alkyl), —NHCO(C$_1$-C$_{10}$ alkyl), —N(C$_1$-C$_3$ alkyl)CO(C$_1$-C$_{10}$ alkyl), —(C$_1$-C$_6$ alkylene)NHCO(C$_1$-C$_{10}$ alkyl), or —(C$_1$-C$_6$ alkylene)N(C$_1$-C$_3$ alkyl)CO(C$_1$-C$_{10}$ alkyl);
R$^{7a}$, R$^{7b}$, R$^{7e}$, and R$^{7c}$ is each independently H, I, Br, Cl, F, —CH$_2$F, —CHF$_2$, —CF$_3$, —OCF$_3$, —N$_3$, —CN, —OH, methyl, ethyl, propyl, C$_1$-C$_3$ haloalkyl, C$_1$-C$_3$ alkoxy, or C$_1$-C$_3$ haloalkoxy; and
R$^{7c}$ is H, I, Br, Cl, F, —CH$_2$F, —CHF$_2$, —CF$_3$, —OCF$_3$, —N$_3$, —CN, —OH, C$_1$-C$_3$ alkyl, C$_1$-C$_3$ haloalkyl, C$_1$-C$_3$ alkoxy, C$_1$-C$_3$ haloalkoxy, 4-6 membered heterocyclyl, or 5-6 membered heteroaryl, wherein the heterocyclyl and heteroaryl is optionally substituted with one or more R$^5$.

In some embodiment of the compounds of formula (III) and/or (IIIA), R$^1$ is phenyl substituted with —(C$_1$-C$_3$ alkylene)NHCO(C$_1$-C$_8$ alkyl) or —(C$_1$-C$_3$ alkylene)N(C$_1$-C$_3$ alkyl)CO(C$_1$-C$_8$ alkyl). In some embodiments, R$^1$ is phenyl substituted with —CH$_2$NHCO(C$_1$-C$_8$ alkyl) or —CH$_2$N(C$_1$-C$_3$ alkyl)CO(C$_1$-C$_8$ alkyl).

In some embodiment of the compounds of formula (III) and/or (IIIA), R$^{7a}$, R$^{7b}$, R$^{7c}$, R$^{7e}$, and R$^{7e}$ is each independently H, I, Br, Cl, F, Cl, F, —CH$_2$F, —CHF$_2$, —CF$_3$, —OCF$_3$, —CN, —OH, methyl, ethyl, propyl, —C≡CH, —CN, —NH$_2$, —NO$_2$, —N$_3$, —OH, —OCF$_3$, —OMe, —NMe$_2$, or —NEt$_2$. In some embodiments, R$^{7a}$, R$^{7b}$, R$^{7e}$, and R$^{7e}$ is each independently H.

In one embodiment, the compound of formula (III) and/or (IIIA), is

or

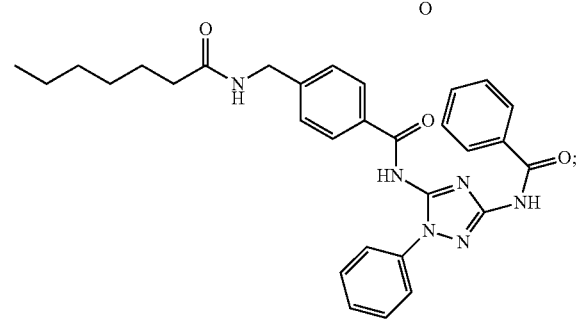

or a pharmaceutically acceptable salt thereof.

In one embodiment, the compound of formula (III) has the structure of formula (IIIB):

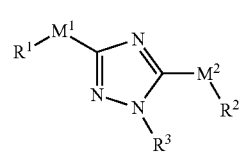
(IIIB)

or a pharmaceutically acceptable salt or solvate thereof, wherein:
M$^1$ and M$^2$ are each independently selected from —NR$^4$—, —NR$^4$C(O)— or —C(O)NR$^4$—, provided that M$^1$ and M$^2$ are not both —NR$^4$—;
R$^1$ and R$^2$ are each independently phenyl, optionally substituted with one or more R$^5$;
R$^3$ is phenyl, substituted with one or more R$^7$;
R$^4$ is each independently H or C$_1$-C$_3$ alkyl;
R$^5$ is each independently I, Br, Cl, F, —CH$_2$F, —CHF$_2$, —CF$_3$, —C$_1$-C$_6$ alkyl, alkynyl, —CN, —(C$_1$-C$_3$ alkylene)-CN, —NH$_2$; —NO$_2$, —N$_3$, —OH, —OCF$_3$, —OMe, —NMe$_2$, —NEt$_2$, —C(O)O(C$_1$-C$_6$ alkyl), —CO(C$_1$-C$_{10}$ alkyl); —NHCO(C$_1$-C$_{10}$ alkyl), —N(C$_1$-C$_3$ alkyl)(CO(C$_1$-C$_{10}$ alkyl), —(C$_1$-C$_6$ alkylene)NHCO (C$_1$-C$_{10}$ alkyl), or —(C$_1$-C$_6$ alkylene)N(C$_1$-C$_3$ alkyl)CO(C$_1$-C$_{10}$ alkyl); and
wherein at least one R$^7$ is heterocyclyl substituted with —C(C$_1$-C$_{10}$ alkyl), which is optionally further substituted with one or more R$^5$.

In some embodiment of the compounds of formula (III) and/or (IIIB), R$^3$ is phenyl, substituted with 6-membered heterocyclyl and wherein the 6-membered heterocyclyl is substituted with —CO(C$_1$-C$_{10}$ alkyl). In some embodiment of the compounds of formula (III) and/or (IIIB), R$^3$ is phenyl substituted with a piperidine or a piperazine, wherein the piperidine or the piperazine is substituted with —CO(C$_1$-C$_{10}$ alkyl).

In some embodiment of the compounds of formula (III) and/or (IIIB), $R^1$ and $R^2$ are each independently phenyl, optionally substituted with one or more substitutent selected from I, Br, Cl, F, —CH$_2$F, —CHF$_2$, —CF$_3$, —OCF$_3$, —N$_3$, —CN, —OH, methyl, ethyl, propyl, —C≡CH; —CN, —NH$_2$, —NO$_2$, —N$_3$, —OH, —OCF$_3$, —OMe, —NMe$_2$, or —NEt$_2$.

In some embodiment of the compounds of formula (III) and/or the compound is

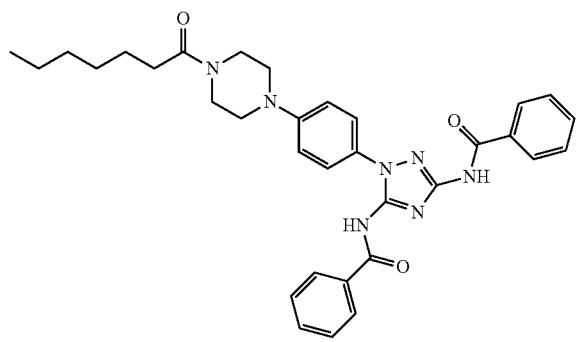

or a pharmaceutically acceptable salt thereof.

In one embodiment, the compound of formula (III), excludes compounds of Table A. In one embodiment, the compound of formula (III), excludes compounds of Table B.

In one embodiment of the present disclosure, a method of modulating a Parkin ligase is provided comprising administering to a subject in need thereof an effective amount of a compound of (I), (I'), (IA), (IB), (IB'), (IC), (ID), (IE), (IF), (III), (IIIA), (IIIB), (II) and/or (IIA), or a pharmaceutically acceptable salt thereof.

In one embodiment of the present disclosure, a method of treating a disease or a condition comprising administering to a subject in need thereof a therapeutically effective amount of a compound of (I), (I'), (IA), (IB), (IB), (IC), (ID), (IE), (IF), (III), (IIIA), (IIIB), (II) and/or (IIA), or a pharmaceutically acceptable salt thereof. is provided. In some embodiments, the disease or the condition is cancer. In some embodiments, the cancer is colon cancer, lung cancer, or ovarian cancer.

In one embodiment of the present disclosure, a method of treating Parkinson's Disease is provided, comprising administering to a subject in need thereof a therapeutically effective amount of a compound of (I), (I'), (IA), (IB), (IB'), (IC), (ID), (IE), (IF), (III), (IIIA), (IIIB), (II) and/or (IIA), or a pharmaceutically acceptable salt thereof.

In one embodiment of the present disclosure, a method of slowing the progression of Parkinson's Disease is provided, comprising administering to a subject in need thereof a therapeutically effective amount of a compound of (I), (I'), (IA), (IB), (IB'), (IC), (ID), (IE), (IF), (III), (IIIA), (IIIB), (II) and/or (IIA), or a pharmaceutically acceptable salt thereof.

In one embodiment of the present disclosure, a method of restoring dopamine neuronal balance in a subject in need thereof is provided, comprising administering to a subject in need thereof a therapeutically effective amount of a compound of (I), (I'), (IA), (IB), (IB'), (IC), (ID), (IE), (IF), (III), (IIIA), (IIIB), (II) and/or (IIA), or a pharmaceutically acceptable salt thereof.

In one embodiment of the present disclosure, a method of delaying or preventing dopamine neuron loss in a subject in need thereof is provided, comprising administering to a subject in need thereof a therapeutically effective amount of a compound of (I), (I'), (IA), (IB), (IB'), (IC), (ID), (IE), (IF), (III), (IIIA), (IIIB), (II) and/or (IIA), or a pharmaceutically acceptable salt thereof.

In one embodiment of the present disclosure, a method of increasing mitophagy of damaged mitochondria in a subject in need thereof is provided, comprising administering to a subject in need thereof a therapeutically effective amount of a compound of (I), (I'), (IA), (IB), (IB'), (IC), (ID), (IE), (IF'), (III), (IIIA), (IIIB), (II) and/or (IIA), or a pharmaceutically acceptable salt thereof.

In one embodiment of any one of the methods disclosed herein, the compound is Compound 42 or a pharmaceutically acceptable salt thereof. In one embodiment of any one of the methods disclosed herein, In one embodiment of any one of the methods disclosed herein, a compound selected from Table 1, 2, 3A and/or 3B is administered to a subject in need thereof. In another embodiment of the methods disclosed herein,

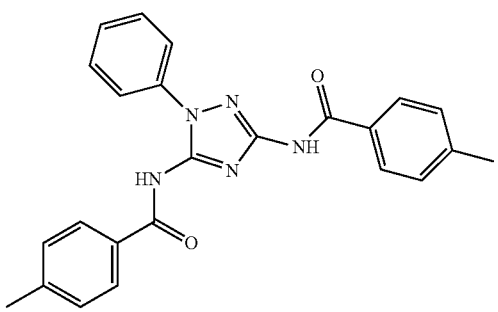

or a pharmaceutically acceptable salt thereof is administered to a subject in need thereof.

In some embodiments of any one of the methods disclosed herein, a compound selected from Tables A and C are excluded.

DETAILED DESCRIPTION

Figure 1:
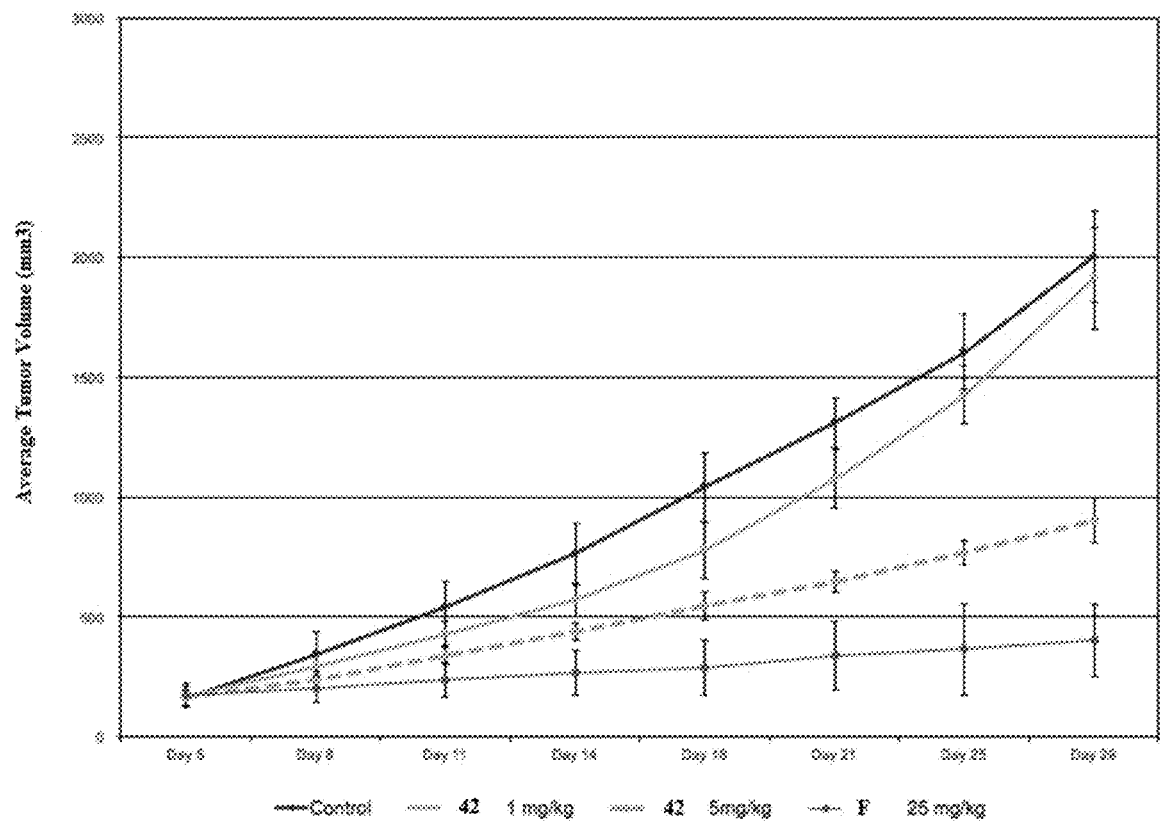
FIG. 1 shows a Xenograft study testing Compound 42 efficacy to delay subcutaneous HCT-116 tumor growth. Compound 42, Compound F or control were administered daily (IP). Group 1=Vehicle Control, Group 2=Compound F (25 mg/kg), Group 3=Compound 42 (1 mg/kg), Group 4=Compound 42 (5 mg/kg)

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range from "50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a kinase inhibitor" refers to one or more kinase inhibitors or at least one kinase inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "treating" means one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

As used herein, the "alignment" of two or more protein/amino acid sequences may be performed using the alignment program Clustat W2, available at www.ebi.ac.uk/Tools/msa/clustalw2/. The following default parameters may be used for Pairwise alignment: Protein Weight Matrix Gonnet; Gap Open 10; Gap Extension 0.1.

"Ubiquitin Proteasome Pathway System (UPS)" as used herein relates to the ubiquitin proteasome pathway, conserved from yeast to mammals, and is required for the targeted degradation of most short-lived proteins in the eukaryotic cell. Targets include cell cycle regulatory proteins, whose timely destruction is vital for controlled cell division, as well as proteins unable to fold properly within the endoplasmic reticulum. Ubiquitin modification is an ATP-dependent process carried out by three classes of enzymes. An "ubiquitin activating enzyme" (E1) forms a thio-ester bond with ubiquitin, a highly conserved 76-amino acid protein. This reaction allows subsequent binding of ubiquitin to a "ubiquitin conjugating enzyme" (E2), followed by the formation of an isopeptide bond between the carboxy-terminus of ubiquitin and a lysine residue on the substrate protein. The latter reaction requires a "ubiquitin ligase" (E3). E3 ligases can be single- or multi-subunit enzymes, in some cases, the ubiquitin-binding and substrate binding domains reside on separate polypeptides brought together by adaptor proteins or culling. Numerous E3 ligases provide specificity in that each can modify only a subset of substrate proteins. Further specificity is achieved by post-translational modification of substrate proteins, including, but not limited to, phosphorylation. Effects of monoubiquitination include changes in subcellular localization. However, multiple ubiquitination cycles resulting in a polyubiquitin chain are required for targeting a protein to the proteasome for degradation. The multisubunit 26S proteasome recognizes, unfolds, and degrades polyubiquitinated substrates into small peptides. The reaction occurs within the cylindrical core of the proteasome complex, and peptide bond hydrolysis employs a core threonine residue as the catalytic nucleophile. It has been shown that an additional layer of complexity, in the form of multiubiquitin chain receptors, may lie between the polyubiquitination and degradation steps. These receptors react with a subset of polyubiquitinated substrates, aiding in their recognition by the 26S proteasome, and thereby promoting their degradation. This pathway is not only important in cellular homeostasis, but also in human disease. Because ubiquitin/proteasome-dependent degradation is often employed in control of the cell division cycle and cell growth, researchers have found that proteasome inhibitors hold some promise of being developed into potential cancer therapeutic agents.

Protein degradation through the ubiquitin-proteasome system is the major pathway of non-lysosomal proteolysis of intracellular proteins. It plays important roles in a variety of fundamental cellular processes such as regulation of cell cycle progression, division, development and differentiation, apoptosis, cell trafficking, and modulation of the immune and inflammatory responses. The central element of this system is the covalent linkage of ubiquitin to targeted proteins, which are then recognized by the 26S proteasome, an adenosine triphosphate-dependent, multi-catalytic protease. Damaged, oxidized, or misfolded proteins as well as regulatory proteins that control many critical cellular functions are among the targets of this degradation process. Aberration of this system leads to the dysregulation of cellular homeostasis and the development of multiple diseases (Wang et al. *Cell Mol Immunol.* 2006 August; 3(4): 255-61).

"Parkin ligase" or "Parkin" as used herein relates to a protein which in humans is encoded by the PARK2 gene. (Kitada T, Asakawa S. Hattori N, Matsumine H, Yamamura Y, Minoshima S, Yokochi M, Mizuno Y, Shimizu N (April 1998). "Mutations in the parkin gene cause autosomal recessive juvenile parkinsonism". *Nature* 392 (6676): 605-608. doi:10.1038/33416. PMID 9560156, Matsumine H, Yamamura Y, Hattori N, Kobayashi T, Kitada T, Yoritaka A, Mizuno Y (April 1998). "A microdeletion of D65305 in a family of autosomal recessive juvenile parkinsonism (PARK2)". *Genomics* 49 (1): 143-146. doi:10.1006/geno.1997.5196. PMID 9570960. The protein is a component of a multiprotein E3 ubiquitin ligase complex which in turn is part of the ubiquitin-proteasome system that mediates the targeting of proteins for degradation. Mutations in the PARK2 gene are known to cause a familial form of Parkinson's disease known as autosomal recessive juvenile Parkinson's disease (AR-JP).

"Ligase" as used herein, is an enzyme that can catalyze the joining of two or more compounds or biomolecules by bonding them together with a new chemical bond. The "ligation" of the two usually with accompanying hydrolysis of a small chemical group dependent to one of the larger compounds or biomolecules, or the enzyme catalyzing the linking together of two compounds, e.g., enzymes that catalyze joining of groups C—O, C—S, C—N, etc. Ubiquitin-protein (E3) ligases are a large family of highly diverse enzymes selecting proteins for ubiquitination.

"Ub Ligases" are involved in disease pathogenesis for oncology, inflammation & infectious disease. E3 ligase belonging to the RING-between-RING (RBR) family of E3 ligases containing both canonical RING domains and a catalytic cysteine residue usually restricted to HECT E3 ligases; termed 'RING/HECT hybrid' enzymes. Mutations in Parkin linked to Parkinson's disease, cancer and mycobacterial infection. Parkin is recognized as a neuroprotective protein with a role in mitochondrial integrity. Human genetic data implicate loss of Parkin activity as a mechanism for pathogenesis of Parkinson's disease (PD).

"Zinc Finger (ZnF) Domain" as used herein relates to a protein structure characterized by coordinating zinc ions to stabilize the functional activity. ZnF stabilize the binding of Ub, Deubiquitinating Enzymes (DUBS), and Ligases (E3) in the UPS.

"Ligands" as used herein bind to metal via one or more atoms in the ligand, and are often termed as chelating ligands. A ligand that binds through two sites is classified as bidentate, and three sites as tridentate. The "bite angle" refers to the angle between the two bonds of a bidentate chelate. Chelating ligands are commonly formed by linking donor groups via organic linkers. A classic bidentate ligand is ethylenediamine, which is derived by the linking of two ammonia groups with an ethylene (—CH2CH2-) linker. A classic example of a polydentate ligand is the hexadentate chelating agent EDTA, which is able to bond through six sites, completely surrounding some metals. The binding affinity of a chelating system depends on the chelating angle or bite angle. Many ligands are capable of binding metal ions through multiple sites, usually because the ligands have lone pairs on more than one atom. Some ligands can bond to a metal center through the same atom but with a different number of lone pairs. The bond order of the metal ligand bond can be in part distinguished through the metal ligand bond angle (M-X—R). This bond angle is often referred to as being linear or bent with further discussion concerning the degree to which the angle is bent. For example, an imido ligand in the ionic form has three lone pairs. One lone pair is used as a sigma X donor, the other two lone pairs are available as L type pi donors. If both lone pairs are used in pi bonds then the M-N—R geometry is linear. However, if one or both of these lone pairs are non-bonding then the M-N—R bond is bent and the extent of the bend speaks to how much pi bonding there may be. It was found that few heteroatoms, such as nitrogen, oxygen, and sulfur atoms, interacted with zinc, ideal distances between the zinc and these heteroatoms were identified. Whereas carboxylates bound to the zinc via both monodentate and bidentate interactions, the hydroxamates bound dominantly in a bidentate manner. These results aid in the design of new inhibitors with the potential to interact with zinc in the target protein. Virtually every molecule and every ion can serve as a ligand for (or "coordinate to") metals. Monodentate ligands include virtually all anions and all simple Lewis bases. Thus, the halides and pseudohalides are important anionic ligands whereas ammonia, carbon monoxide, and water are particularly common charge-neutral ligands. Simple organic species are also very common, be they anionic ($RO^-$ and $RCO_2^-$) or neutral ($R_2O$, $R_2S$, $R_{3-x}NH_x$, and $R_3P$). Complexes of polydentate ligands are called chelate complexes. They tend to be more stable than complexes derived from monodentate ligands. This enhanced stability, the chelate effect, is usually attributed to effects of entropy, which favors the displacement of many ligands by one poly dentate ligand. When the chelating ligand forms a large ring that at least partially surrounds the central atom and bonds to it, leaving the central atom at the center of a large ring. The more rigid and the higher its denticity, the more inert will be the macrocyclic complex.

"Chelator" as used herein relates to a binding agent that suppresses chemical activity by forming a chelate (a coordination compound in which a metal atom or ion is bound to a ligand at two or more points on the ligand, so as to form, for example, a heterocyclic ring containing a metal atom).

"Chelation" as used herein relates to a particular way that ions and molecules bind metal ions. According to the International Union of Pure and Applied Chemistry (IUPAC), chelation involves the formation or presence of two or more separate coordinate bonds between a polydentate (multiple bonded) ligand and a single central atom. Usually these ligands are organic compounds, and are called chelants, chelators, chelating agents, or sequestering agents.

"Electrophile" as used herein relates to species that is attracted to an electron rich center. In chemistry, an electrophile is a reagent attracted to electrons. It participates in a chemical reaction by accepting an electron pair in order to bond to a nucleophile. Because electrophiles accept electrons, they are Lewis acids. Most electrophiles are positively charged, have an atom that carries a partial positive charge, or have an atom that does not have an octet of electrons.

The terms below, as used herein, have the following meanings, unless indicated otherwise:

"Amino" refers to the —$NH_2$ radical.

"Cyano" refers to the —CN radical.

"Halo" or "halogen" refers to bromo, chloro, fluoro or iodo radical.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_{10}$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-dodecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or brandied divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkenyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes CO alkynyls, A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —OR$_a$ where R$_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —NHR$_a$ or —NR$_a$R$_a$ where each R$_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)R$_a$ moiety, wherein R$_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in R$_a$, as defined above. For example, "C1-$C_{10}$ acyl" refers to alkylcarbonyl group as defined above, where R$_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —R$_b$—R$_c$ where R$_b$ is an alkylene group as defined above and R$_c$ is one or more aryl radicals as defined above, for example, benzyl, diphenylmethyl and the like. Unless stated otherwise specifically in the specification, an aralkyl group can be optionally substituted.

"Aralkenyl" or "arylalkenyl" refers to a radical of the formula —R$_b$—R$_c$ where R$_b$ is an alkenylene o group as defined above and R$_c$ is one or more aryl radicals as defined above. Unless stated otherwise specifically in the specification, an aralkenyl group can be optionally substituted.

"Aralkynyl" or "arylalkynyl" refers to a radical of the formula —R$_b$—R$_c$ where R$_b$ is an alkynylene group as defined above and R$_c$ is one or more aryl radicals as defined above. Unless stated otherwise specifically in the specification, an aralkynyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cycloetenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —R$_b$—R$_d$ where R$_b$ is an alkylene, alkenylene, or alkynylene group as defined above and R$_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above. e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic, partially aromatic, or aromatic ring radical which consists of two to twelve carbon atoms and from one to six heteroatoms selected from the group consisting of nitrogen, oxygen and sulfur. Heterocyclyl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heterocyclylalkyl" refers to a radical of the formula —$R_b$—$R_e$ where $R_b$ is an alkylene group as defined above and $R_e$ is a heterocyclyl radical as defined above. Unless stated otherwise specifically in the specification, a heterocycloalkylalkyl group can be optionally substituted.

"Heterocyclylalkenyl" refers to a radical of the formula —$R_b$—$R_e$ where $R_b$ is an alkenylene group as defined above and $R_e$ is a heterocyclyl radical as defined above. Unless stated otherwise specifically in the specification, a heterocycloalkylalkenyl group can be optionally substituted.

"Heterocyclylalkynyl" refers to a radical of the formula —$R_b$—$R_e$ where $R_b$ is an alkynylene group as defined above and $R_e$ is a heterocyclyl radical as defined above. Unless stated otherwise specifically in the specification, a heterocycloalkylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula —$R_b$—$R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula —$R_b$—$R_f$ where $R_b$ is an alkynylene chain as defined above and $R_f$ is a heteroaryl radical as defined above. Unless stated otherwise specifically in the specification, a heteroarylalkynyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitrites. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SO_2R_h$, —$SO_2R_g$, —$OSO_2R_g$, —$SO_3R_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_h$, —$CH_2SO_2NR_gR_h$. In the foregoing, and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

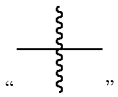

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

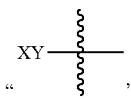

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

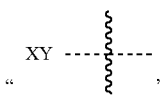

infers that when $R^3$ is "XY", the point of attachment bond is the same bond as the bond by which $R^3$ is depicted as being bonded to $CH_3$.

The following description includes information that may be useful in understanding the present invention. It is not an admission that any of the information provided herein is prior art or relevant to the presently claimed inventions, or that any publication specifically or implicitly referenced is prior art.

Compounds of the Present Disclosure

The compound of the present disclosure can be useful for modulating Parkin ligase. Further, the compound of the present disclosure can be useful for treating various diseases and conditions including, but not limited to, cancer, neurological disease, a disorder characterized by abnormal accumulation of α-synuclein, a disorder of an aging process, cardiovascular disease, bacterial infection, viral infection, mitochondrial related disease, mental retardation, deafness, blindness, diabetes, obesity, autoimmune disease, glaucoma, Leber's Hereditary Optic Neuropathy, and rheumatoid arthritis.

In one embodiment, the present disclosure provides compounds comprising the structure of formula (I):

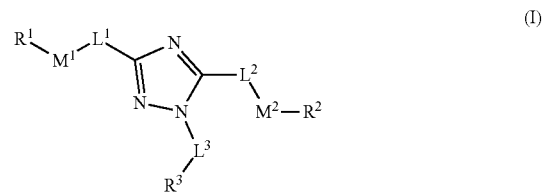

(I)

or a pharmaceutically acceptable salt or solvate thereof, wherein:

$L^1$, $L^2$ and $L^3$ are each independently selected from a bond, alkylene, or alkenylene;

$M^1$ and $M^2$ are each independently selected from —$NR^4$—, —$NR^4C(O)$—, —$N(C(O)R^1)$—, —$C(O)NR^4$—, —$NR^4C(O)NR^4$—, —$C(O)$—, —$C(=NR^4)$—, —$C(=NOR^4)$—, —$OC(O)$—, —$C(O)O$—, —$OC(O)O$—, —$OC(O)NR^4$—, —$NR^4C(O)O$—, —$S(O)_m$—, —$S(O)_mNR^4$—, or —$NR^4S(O)_m$—, provided that $M^1$ and $M^2$ are not both —$NR^4$—;

$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H, or alkyl, wherein each alkyl is optionally substituted with one or more $R^5$;

$R^5$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, or —$SR^6$;

$R^6$ is each independently alkyl, alkenyl, alkynyl, haloalkyl, haloalkenyl, haloalkynyl; or alternatively two $R^6$ on the same N atom can together form a 3-6 membered N-heterocyclyl;

$R^7$ is each independently I, Br, Cl, F, —$CH_2F$, —$CHF_2$, —$CF_3$, —$OCF_3$, —CN, -alkyl-CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —SO$_3$H, —SO$_3$R$^6$, —SR$^6$, cycloalkyl, heterocyclyl, aryl, or heteroaryl, wherein each cycloalkyl, heterocyclyl, aryl, and heteroaryl is optionally substituted with one or more R$^5$;

m is 0, 1, or 2; and wherein the compound is not N,N'-(1-phenyl-1H-1,2,4-triazole-3,5-diyl)dibenzamide, N-(3-benzamido-1-phenyl-1H-1,2,4-triazol-5-yl)furan-2-carboxamide, N-(5-cinnamamido-1-phenyl-1H-1,2,4-triazol-3-yl) benzamide, N-(1-phenyl-5-(phenylamino)-1H-1,2,4-triazol-3-yl)benzamide, 4-fluoro-N-(5-(4-methoxybenzamido)-1-phenyl-1H-1,2,4-triazol-3-yl) benzamide, N,N'-(1-phenyl-1H-1,2,4-triazole-3,5-diyl) bis(4-methylbenzamide), N-(5-((2-chlorobenzyl) amino)-1-phenyl-1H-1,2,4-triazol-3-yl)-2-fluorobenzamide, N-(3-benzamido-1-phenyl-1H-1,2,4-triazol-5-yl)-4-fluorobenzamide, N-(3-benzamido-1-phenyl-1H-1,2,4-triazol-5-yl)-4-nitrobenzamide, N-(3-benzamido-1-phenyl-1H-1,2,4-triazol-5-yl)-3-nitrobenzamide, and 4-((3-benzamido-1-phenyl-1H-1,2,4-triazol-5-yl)carbamoyl)benzoic acid.

In one embodiment of the compound of formula (I), L$^1$, L$^2$ and L$^3$ are each independently a bond.

In one embodiment of the compound of formula (I), M$^1$ and M$^2$ are each independently selected from —NR$^4$—, —NR$^4$C(O)—, —C(O)NR$^4$—, —N(C(O)R$^1$)—, or —NR$^4$S(O)$_m$—. In one embodiment, M$^1$ and M$^2$ are each independently selected from —NR$^4$—, —NR$^4$C(O)— or —C(O)NR$^4$—.

In one embodiment of the compound of formula (I), -M$^1$-R$^1$ is —NR$^4$C(O)R$^1$. In one embodiment of the compound of formula (I), -M$^2$-R$^2$ is —NR$^4$C(O)R$^2$. In one embodiment of the compound of formula (I), -M$^1$-R$^1$ is —NR$^4$C(O)R$^1$ and -M$^2$-R$^2$ is —NR$^4$C(O)R$^2$.

In one embodiment of the compound of formula (I), R$^4$ at each occurrence is independently H or C$_1$-C$_3$ alkyl.

In one embodiment of the compound of formula (I), L$^3$ is a bond and R$^3$ is an aryl or a heteroaryl, optionally substituted with one or more R$^7$.

In one embodiment of the compound of formula (I), R$^3$ is a phenyl or phenyl fused bicycle, optionally substituted with one or more R$^7$. In another embodiment, R$^3$ is heteroaryl selected from imidazolyl or pyrazolyl, optionally substituted with one or more R$^7$.

In one embodiment of the compound of formula (I), R$^7$ is each independently I, Br, Cl, —CH$_2$F, —CHF, —CF, —CN, —NH$_2$, —NMe$_2$, —NO$_2$, —N$_3$, —OH, OR$^6$, R$^6$, —SH, cycloalkyl, heterocyclyl, aryl, or heteroaryl, wherein each cycloalkyl, heterocyclyl, aryl, and heteroaryl is optionally substituted with one or more R$^5$.

In one embodiment of the compound of formula (I), R$^3$ is a phenyl substituted with a 4-6 membered heterocyclyl, which is optionally substituted with one or more R$^7$.

In one embodiment of the compound of formula (I), R$^1$ and R$^2$ are each independently selected from phenyl, 6-10 membered aryl, 5-10 membered heteroaryl, 4-10 membered heterocyclyl, phenyl-(C$_1$-C$_3$ alkyl)-, phenyl-(C$_2$-C$_3$ alkenyl)-, 5-6 membered heteroaryl-(C$_1$-C$_3$ alkyl)-, or heteroaryl-(C$_2$-C$_3$ alkenyl)-, wherein each cycloalkyl, aryl, heteroaryl portion is optionally substituted with one or more R$^5$. In some embodiments, the 6-10 membered aryl or 5-10 membered heteroaryl is a bicyclic ring.

In one embodiment of the compound of formula (I), R$^5$ is selected from I, Br, Cl, F, C$_1$-C$_6$ alkyl, alkynyl, —CN, —(C$_1$-C$_3$ alkylene)-CN, —NH$_2$, —NO$_2$, —N$_3$, —OH, —OCF$_3$, —OMe, —NMe$_2$, or —NEt$_2$.

In one embodiment of the compound of formula (I), at least one of R$^1$, R$^2$, and R$^3$ is phenyl and substituted with at least one of methyl, ethyl, —C≡CH, I, Br, Cl, F, —CF$_3$, —CN, —CH$_2$CN, —CH$_2$CH$_2$CN, —NH$_2$, —NO$_2$, —N$_3$, —OH, —OCF$_3$, —OMe or —NMe$_2$. In some embodiments, at least two of R$^1$, R$^2$, and R$^3$ is phenyl and substituted with at least one of methyl, ethyl, —C≡CH, I, Br, Cl, F, —CF$_3$, —CN, —CH$_2$CN, —CH$_2$CH$_2$CN, —NH$_2$, —NO$_2$, —N$_3$, —OH, —OCF$_3$, —OMe or —NMe$_2$. In another embodiment, at least one of R$^1$, R$^2$, and R$^3$ is pyridyl, optionally substituted with one or more of methyl, ethyl, —C≡CH, I, Br, Cl, F, —CF$_3$, —CN, —CH$_2$CN, —CH$_2$CH$_2$CN, —NH$_2$, —NO$_2$, —N$_3$, —OH, —OCF$_3$, —OMe or —NMe$_2$.

In one embodiment, the compound of formula (I) has the structure of formula (I'):

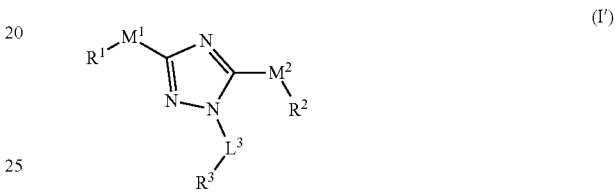

or a pharmaceutically acceptable salt or solvate thereof, wherein L$^3$, M$^1$, M$^2$, R$^1$, R$^2$, and R$^3$ are as defined for formula (I).

In one embodiment of the compound of formula (I'), M$^1$ and M$^2$ are each independently selected from —NR$^4$—, —NR$^4$C(O)—, —C(O)NR$^4$—, —N(C(O)R$^1$)—, or —NR$^4$S(O)$_m$—.

In one embodiment of the compound of formula (I'), -M$^1$-R$^1$ is —NR$^4$C(O)R$^1$. In one embodiment of the compound of formula (I'), -M$^2$-R$^2$ is —NR$^4$C(O)R$^2$. In one embodiment of the compound of formula (I'), -M$^1$-R$^1$ is —NR$^4$C(O)R$^1$ and -M$^2$-R$^2$ is —NR$^4$C(O)R$^2$.

In one embodiment of the compound of formula (I'). R$^1$ and R$^2$ are each independently selected from phenyl, 6-10 membered acyl, 5-10 membered heteroaryl, 4-10 membered heterocyclyl, phenyl-(C$_1$-C$_3$ alkyl)-, phenyl-(C$_2$-C$_3$ alkenyl)-, 5-6 membered heteroaryl-(C$_1$-C$_3$ alkyl)-, or heteroaryl-(C$_2$-C$_3$ alkenyl)-, wherein each cycloalkyl, aryl, heteroaryl portion is optionally substituted with one or more R$^5$; and R$^3$ is an aryl or a heteroaryl, optionally substituted with one or more R$^7$.

In one embodiment, the compound of formula (I) has the structure of formula (IA):

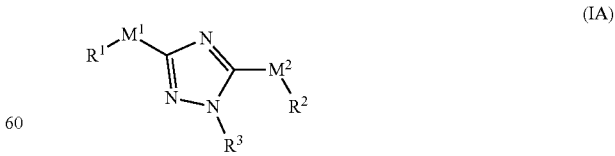

or a pharmaceutically acceptable salt or solvate thereof, wherein:

M$^1$ and M$^2$ are each independently selected from —NR$^4$C(O)— or —C(O)NR$^4$—;

$R^1$ and $R^2$ are each independently

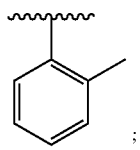

;

$R^3$ is selected from

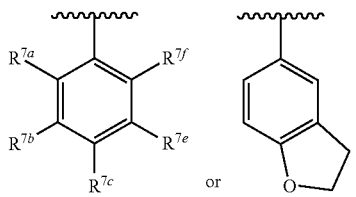

$R^4$ is each independently H or $C_1$-$C_3$ alkyl; and $R^{7a}$, $R^{7b}$, $R^{7e}$, and $R^{7e}$ is each independently H, I, Br, Cl, F, —$CH_2F$, —$CHF_2$, —$CHF_2$, —$CF_3$, —$OCF_3$, —$N_3$, —CN, —OH, methyl, ethyl, propyl, $C_1$-$C_3$ haloalkyl, $C_1$-$C_3$ alkoxy, or $C_1$-$C_3$ haloalkoxy;

$R^{7c}$ is H, I, Br, Cl, F, —$CH_2F$, —$CHF_2$, —$CF_3$, —$OCF_3$, —$N_3$, —CN, —OH, $C_1$-$C_3$ alkyl $C_1$-$C_3$ haloalkyl, $C_1$-$C_3$ alkoxy, $C_1$-$C_3$ haloalkoxy, 4-6 membered heterocyclyl, or 5-6 membered heteroaryl, wherein the heterocyclyl and heteroaryl is optionally substituted with one or more $R^5$;

$R^5$ is I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —$C(O)O(C_1$-$C_6$ alkyl);

wherein at least one of $R^{7a}$, $R^{7b}$, $R^{7c}$, $R^{7e}$, and $R^{7e}$ is not H.

In one embodiment of the compound of formula (IA), -$M^1$-$R^1$ is —$NR^4C(O)R^1$. In one embodiment of the compound of formula (IA), -$M^2$-$R^2$ is —$NR^4C(O)R^2$. In one embodiment of the compound of formula (IA), -$M^1$-$R^1$ is —$NR^4C(O)R^1$ and -$M^2$-$R^2$ is —$NR^4C(O)R^2$.

In one embodiment of the compound of formula (IA), $R^3$ is selected from $R^3$ is

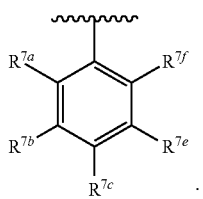

In one embodiment of the compound of formula (IA), four of $R^{7a}$, $R^{7b}$, $R^{7c}$, $R^{7e}$, and $R^{7e}$ is H. In another embodiment, three of $R^{7a}$, $R^{7b}$, $R^{7c}$, $R^{7e}$, and $R^{7e}$ is H. In some embodiments, $R^{7a}$, $R^{7b}$, $R^{7c}$, $R^{7e}$, and $R^{7e}$ is each independently H, I, Br, Cl, F, —$CH_2F$, —$CHF_2$, —$CF_3$, —$OCF_3$, —$N_3$, —CN, —OH, methyl, ethyl, propyl, —C≡CH; —CN, —$NH_2$, —$NO_2$, —$N_3$, —OH, —$OCF_3$, —OMe, —$NMe_2$, or —$NEt_2$.

In one embodiment of the compound of formula (IA), $R^3$ is

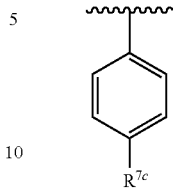

In some embodiments, $R^{7c}$ is I, Br, —$CH_2F$, —$CHF_2$, —$CF_3$, methyl, ethyl, propyl, —C≡CH; —CN, —$NH_2$, —$NO_2$, —$N_3$, —OH, —$OCF_3$, —OMe, —$NMe_2$, or —$NEt_2$. In other embodiments, $R^{7c}$ is I, Br, —$CH_2F$, —$CHF_2$, —$CF_3$, —$OCF_3$, or In one embodiment, $R^{7c}$ is azetidinyl, pyrrolidinyl, piperidinyl, morpholinyl, piperazinyl, or pyrazolyl, each optionally substituted with one or more $R^5$.

In one embodiment, the compound of formula (I) has the structure of formula (IB):

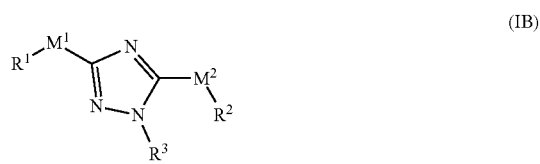

(IB)

or a pharmaceutically acceptable salt or solvate thereof, wherein:

$M^1$ and $M^2$ are each independently selected from —$NR^4$—, —$NR^4$—, —$NR^4C(O)$— or —$C(O)NR^4$—;

$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

wherein one of -$M^1$-$R^1$ and -$M^2$-$R^2$ is —$NR^4$-(cycloalkylalkyl), —$NR^4$-(heterocyclylalkyl), —$NR^4$-(arylalkyl), or —$NR^4$-(heteroarylalkyl), wherein cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H or $C_1$-$C_3$ alkyl;

$R^5$ is I, Br, Cl, F, —$CH_2F$, —$CHF_2$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —$C(O)O(C_1$-$C_6$ alkyl); and $R^7$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, —$SR^6$, cycloalkyl, heterocyclyl, aryl, or heteroaryl, wherein each cycloalkyl, heterocyclyl, and heteroaryl is optionally substituted with one or more $R^5$.

In one embodiment of the compound of formula (IB), one of -M$^1$-R$^1$ and -M$^2$-R$^2$ is —NR$^4$—(C$_1$-C$_3$ alkylene)-cycloalkyl, —NR$^4$—(C$_1$-C$_3$ alkylene)-heterocyclyl, —NR$^4$—(C$_1$-C$_3$ alkylene)-aryl, or —NR$^4$—(C$_1$-C$_3$ alkylene)-heteroaryl; wherein cycloalkyl, aryl, heteroaryl, and heterocyclyl is each optionally substituted with one or more R$^5$. In some embodiments, one of -M$^1$-R$^1$ and -M$^2$-R$^2$ is —NR$^4$—(C$_1$-C$_3$ alkylene)-phenyl, or —NR$^4$—(C$_1$-C$_3$ alkylene)-pyridyl, wherein phenyl and pyridyl is each optionally substituted with one or more R$^5$. In other embodiments, one of -M$^1$-R$^1$ and -M$^2$-R$^2$ is —NR$^4$—CH$_2$-phenyl, —NR$^4$—CH$_2$CH$_2$-phenyl, —NR$^4$—CH$_2$-pyridyl, —NR$^4$—CH$_2$CH$_2$-pyridyl,

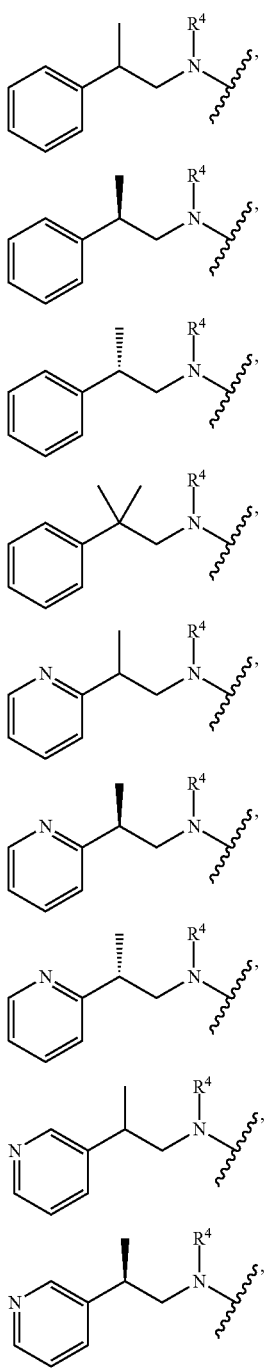

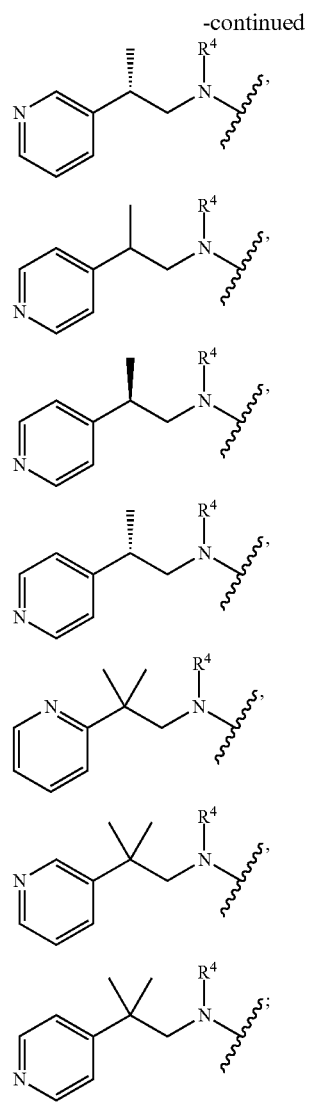

wherein phenyl and pyridyl is each optionally substituted with one or more R$^5$.

In one embodiment of the compound of formula (IB), is -M$^1$-R$^1$ is —NR$^4$C(O)R$^1$. In one embodiment of the compound of formula (IB), -M$^2$-R$^2$ is —NR$^4$C(O)R$^2$.

In one embodiment of the compound of formula (IB), R$^1$ and R$^2$ are each independently selected from phenyl or pyridyl, each optionally substituted with one or more R$^5$.

In one embodiment of the compound of formula (IB), one of -M$^1$-R$^1$ and -M$^2$-R$^2$ is —NR$^4$—(C$_1$-C$_3$ alkylene)-phenyl, or —NR$^4$—(C$_1$-C$_3$ alkylene)-pyridyl, and the other one of -M$^1$-R$^1$ and -M$^2$-R$^2$ is —NR$^4$C(O)-phenyl, —NR$^4$C(O)-pyridyl, —C(O)NR$^4$-phenyl, or —C(O)NR$^4$-pyridyl; wherein each phenyl and pyridyl is optionally substituted with one or more R$^5$. In some embodiments, one of -M$^1$-R$^1$ and -M$^2$-R$^2$ is —NR$^4$—(C$_1$-C$_3$ alkylene)-phenyl, or —NR$^4$—(C$_1$-C$_3$ alkylene)-pyridyl, wherein each phenyl and pyridyl is optionally substituted with one or more R$^5$, and the other one of -M$^1$-R$^1$ and -M$^2$-R$^2$ is

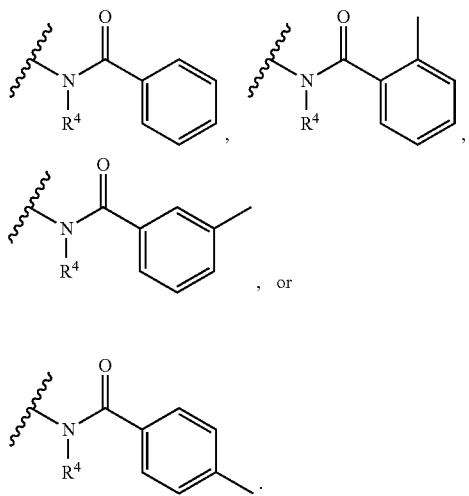

In other embodiments, one of -M¹-R¹ and -M²-R² is —NR⁴—($C_1$-$C_3$ alkylene)-phenyl, or —NR⁴—($C_1$-$C_3$ alkylene)-pyridyl, wherein each phenyl and pyridyl is optionally substituted with one or more $R^5$, and the other one of -M¹-R¹ and -M²-R² is

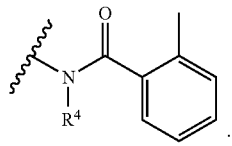

In one embodiment of the compound of formula (IB), $R^3$ is phenyl, optionally substituted with one or more $R^7$; and $R^7$ is each independently I, Br, Cl, F, —$CH_2$F, —$CHF_2$, —$CF_3$, —$OCF_3$, —CN, —$N_3$, —OH, methyl, ethyl, propyl, —C≡CH; —CN, —$NO_2$, —$N_3$, —OH, —$OCF_3$, —OMe, —$NMe_2$, or —$NEt_2$.

In one embodiment of the compound of formula (IB), $R^5$ is selected from I, Br, Cl, F, —$CH_2$F, —$CHF_2$, —$CF_3$, —$OCF_3$, —$N_3$, —CN, —OH, methyl, ethyl, propyl, —C≡CH; —CN, —$NH_2$, —$NO_2$, —$N_3$, —OH, —$OCF_3$, —OMe, —$NMe_2$, or —$NEt_2$.

In one embodiment of the compound of formula (IB), the compound is not

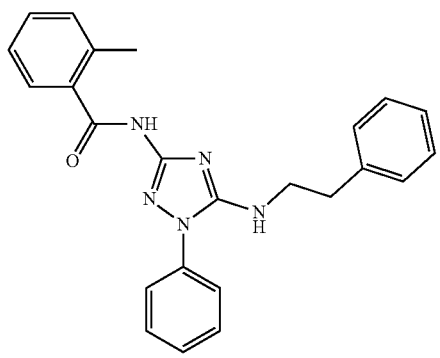

In one embodiment, the compound of formula (I) has the structure of formula (IB'):

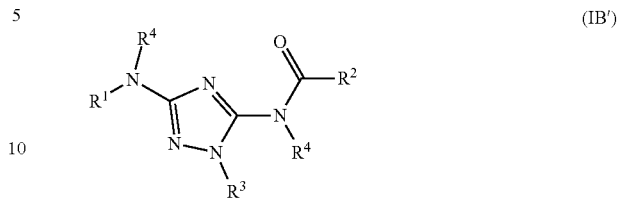

(IB')

or a pharmaceutically acceptable salt or solvate thereof, wherein:

$R^1$ is cycloalkylalkyl, heterocyclylalkyl, arylalkyl, or heteroarylalkyl, wherein cycloalkyl, aryl, heteroaryl, and heterocyclyl portion is optionally substituted with one or more $R^5$;

$R^2$ is selected from cycloalkyl, aryl, biphenyl, heterocyclyl, or heteroaryl, wherein each optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H or $C_1$-$C_3$ alkyl;

$R^5$ is I, Br, Cl, F, —$CH_2$F, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —C(O)O($C_1$-$C_6$ alkyl); and $R^7$ is each independently I, Br, Cl, F, —$CH_2$F, —$CHF_2$, —$CF_3$, —$OCF_3$, —CN, -alkyl-CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3$H, —$SO_3R^6$, —$SR^6$, cycloalkyl, heterocyclyl, aryl, or heteroaryl, wherein each cycloalkyl, heterocyclyl, aryl, and heteroaryl is optionally substituted with one or more $R^5$.

In one embodiment of the compound of formula (IB'), $R^1$ is —$C_1$-$C_3$ alkylene-cycloalkyl, alkylene-heterocyclyl, alkylene-aryl, or —$C_1$-$C_3$ alkylene-heteroaryl, wherein cycloalkyl, aryl, heteroaryl, and heterocyclyl is each optionally substituted with one or more $R^5$. In some embodiments, $R^1$ is —$C_1$-$C_3$ alkylene-phenyl or —$C_1$-$C_3$ alkylene-pyridyl, wherein phenyl and pyridyl is each optionally substituted with one or more $R^5$. In another embodiment, $R^1$ is —$CH_2$-phenyl, —$CH_2CH_2$-phenyl, —$CH_2CH_2$-pyridyl,

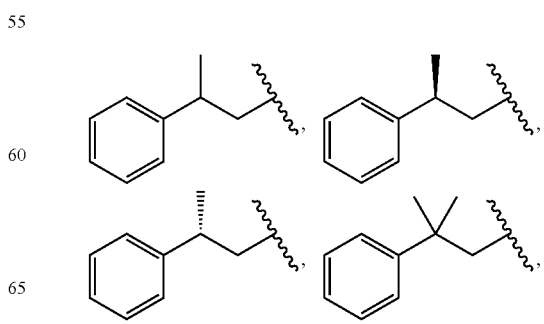

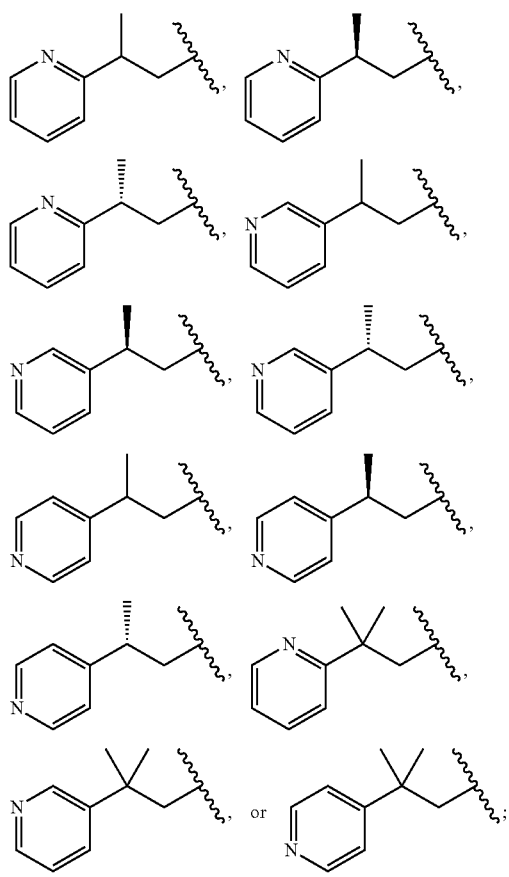

wherein phenyl and pyridyl s each optionally substituted with one or more $R^5$.

In one embodiment of the compound of formula (IB'), $R^2$ is aryl or 5-6 membered heteroaryl, each optionally substituted with one or more $R^5$. In another embodiment, $R^2$ is phenyl optionally substituted with one or more $R^5$. In some embodiments, $R^2$ is

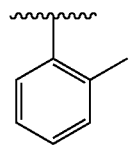

In one embodiment of the compound of formula (IB'), $R^3$ is phenyl, optionally substituted with one or more $R^7$; and $R^7$ is each independently I, Br, Cl, F, —$CH_2F$, —$CHF_2$, —$CF_3$, —$OCF_3$, —CN, —$N_3$, —OH, methyl, ethyl, propyl, —C≡CH; —CN, —$NH_2$, —$NO_2$, —$N_3$, —OH, —$OCF_3$, —OMe, —$NMe_2$, or —$NEt_2$.

In one embodiment of the compound of formula (IB'), $R^5$ is selected from I, Br, Cl, F, —$CH_2F$, —$CHF_2$, —$CF_3$, —$OCF_3$, —CN, —OH, methyl, ethyl, propyl, —C≡CH; —CN, —$NH_2$, —$NO_2$, —$N_3$, —OH, —$OCF_3$, —OMe, —$NMe_2$, or —$NEt_2$. In one embodiment, the compound of formula (I) has the structure of formula (IC):

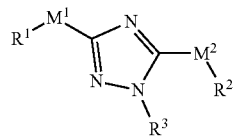

(IC)

or a pharmaceutically acceptable salt or solvate thereof, wherein:

$M^1$ and $M^2$ are each independently selected from —$NR^4C(O)$— or —$C(O)NR^4$—;

$R^1$ and $R^2$ are each independently selected from an alkyl, alkenyl, cycloalkyl, aryl, biphenyl, heterocyclyl heterocycloalkyl, 5-6 membered heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

wherein at least one of -$M^1$-$R^1$ and -$M^2$-$R^2$ is —$NR^4$-(4-6 membered heterocyclyl), —$NR^4$-(5-6 membered heteroaryl), or —$NR^4$-naphthalenyl, wherein 4-6 membered heterocyclyl, 5-6 membered heteroaryl, and naphthalenyl is each optionally substituted with one or more $R^5$;

$R^3$ is selected phenyl, optionally substituted with one or more $R^7$;

$R^4$ is each independently H or $C_1$-$C_3$ alkyl; and $R^5$ and $R^7$ are each independently selected from I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —C(O)O($C_1$-$C_6$ alkyl).

In one embodiment of the compound of formula (IC), at least one of -$M^1$-$R^1$ and -$M^2$-$R^2$ is —$NR^4$-azetidinyl, —$NR^4$-pyrrolidinyl, —$NR^4$-piperidinyl, —$NR^4$-imidazolyl, —$NR^4$-isoxazolyl, —$NR^4$-oxazolyl, —$NR^4$-thiazolyl, —$NR^4$-thiophenyl, —$NR^4$-pyridyl, —$NR^4$-pyridazinyl, —$NR^4$-pyrazinyl, —$NR^4$-pyrimidinyl, or —$NR^4$-pyridinone, wherein each of azetidinyl, pyrrolidinyl, piperidinyl imidazolyl, isoxazolyl, oxazolyl, thiazolyl, pyridyl, pyridazinyl, pyrazinyl, pyrimidinyl, or pyridinone is optionally substituted with one or more $R^5$. In other embodiments, at least one of -$M^1$-$R^1$ and -$M^2$-$R^2$ is —$NR^4$-pyridyl, wherein pyridyl is optionally substituted with one or more $R^5$. In some embodiments, -$M^1$-$R^1$ and -$M^2$-$R^2$ are each —$NR^4$-pyridyl, wherein pyridyl is optionally substituted with one or more $R^5$. In other embodiments, one of -$M^1$-$R^1$ and -$M^2$-$R^2$ is —$NR^4$-azetidinyl, —$NR^4$-pyrrolidinyl, —$NR^4$-piperidinyl, —$NR^4$-imidazolyl, —$NR^4$-isoxazolyl, —$NR^4$-oxazolyl, —$NR^4$-thiazolyl, —$NR^4$-thiophenyl, —$NR^4$-pyridyl, —$NR^4$-pyridazinyl, —$NR^4$-pyrazinyl, —$NR^4$-pyrimidinyl, or —$NR^4$-pyridinone, wherein each of azetidinyl, pyrrolidinyl, piperidinyl, imidazolyl, isoxazolyl, oxazolyl, thiazolyl, pyridyl, pyridazinyl, pyrazinyl, pyrimidinyl, or pyridinone is optionally substituted with one or more $R^5$, and the other one of -$M^1$-$R^1$ and -$M^2$-$R^2$ is

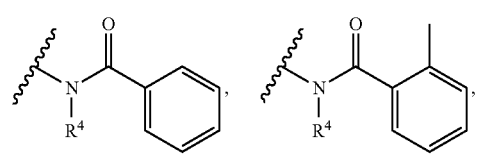

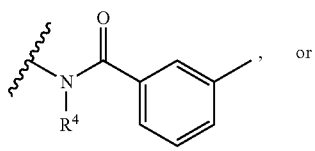, or

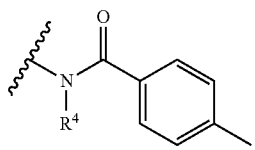.

In one embodiment of the compound of formula (IC), -M¹-R¹ and -M²-R² is —NR⁴-azetidinyl, —NR⁴-pyrrolidinyl, —NR⁴-piperidinyl, —NR⁴-imidazolyl, —NR⁴-isoxazolyl, —NR⁴-oxazolyl, —NR⁴-thiazolyl, —NR⁴-thiophenyl, —NR⁴-pyridyl, —NR⁴-pyridazinyl, —NR⁴-pyrazinyl, —NR⁴-pyrimidinyl, or —NR⁴-pyridinone, wherein each of azetidinyl, pyrrolidinyl, piperidinyl, imidazolyl, isoxazolyl, oxazolyl, thiazolyl, pyridyl, pyridazinyl, pyrazinyl, pyrimidinyl, or pyridinone is optionally substituted with one or more R⁵, and the other one of -M¹-R¹ and -M²-R² is

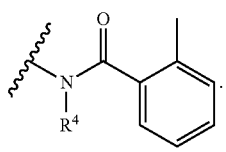.

In one embodiment of the compound of formula (IC), -M¹-R¹ is —NR⁴C(O)R¹. In one embodiment of the compound of formula (IC), -M²-R² is —NR⁴C(O)R².

In one embodiment of the compound of formula (IC), R⁵ and R⁷ is each selected from I, Br, Cl, F, —CH₂F, —CHF₂, —CF₃, —OCF₃, —N₃, —CN, —OH, methyl, ethyl, propyl, —C≡CH; —CN, —NH₂, —NO₂, —N₃, —OH, —OCF₃, —OMe, —NMe₂, or —NEt₂.

In one embodiment of the compound of formula (IC), the compound is not

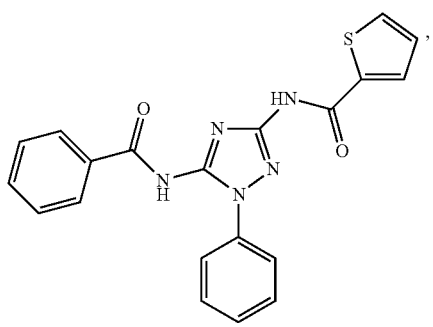,

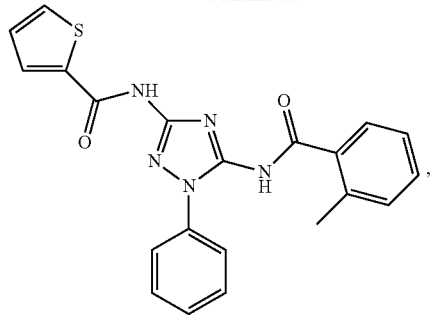,

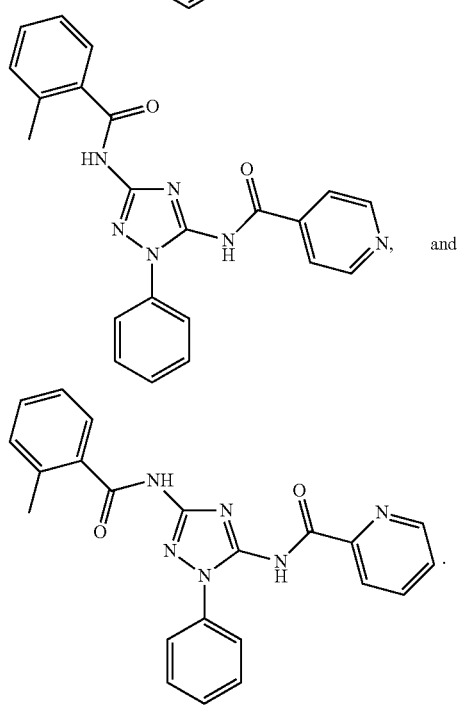

In one embodiment, the compound of formula (I) has the structure of formula (ID):

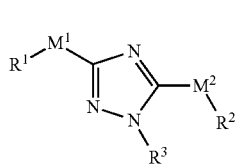 (ID)

or a pharmaceutically acceptable salt or solvate thereof, wherein:
M¹ and M² are each independently selected from —NR⁴C(O)— or —C(O)NR⁴—;
R¹ and R² are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more R⁵;
R³ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H or $C_1$-$C_3$ alkyl; and $R^5$ and $R^7$ are each independently selected from I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —C(O)O($C_1$-$C_6$ alkyl);

wherein at least one of $R^1$ and $R^2$ is a phenyl substituted with at least one of C≡CH or —$N_3$.

In one embodiment of the compound of formula (ID), $M^1$ and $M^2$ are each —$NR^4C(O)$—. In one embodiment of the compound of formula (ID), -$M^1$-$R^1$ is —$NR^4C(O)R^1$. In one embodiment of the compound of formula (ID), -$M^2$-$R^2$ is —$NR^4C(O)R^2$. In one embodiment of the compound of formula (ID), -$M^1R^1$ is —$NR^4C(O)R^1$ and -$M^2$-$R^2$ is —$NR^4C(O)R^2$.

In one embodiment of the compound of formula (ID), at least one of $R^1$ and $R^2$ is a phenyl substituted with at least one of —C≡CH or —$N_3$ and the other one of $R^1$ and $R^2$ is a phenyl or pyridyl, optionally substituted with one or more $R^5$.

In one embodiment of the compound of formula (ID), $R^3$ is phenyl optionally substituted with one or more $R^7$.

In one embodiment of the compound of formula (ID), $R^5$ and $R^7$ is each selected from I, Br, Cl, F, —$CH_2F$, —$CHF_2$, —CH, —$OCF_3$, —$N_3$, —CN, —OH, methyl, ethyl, propyl, —C≡CH, —CN, —$NH_2$, —$NO_2$, —$N_3$, —OH, —$OCF_3$, —OMe, —$NMe_2$, or —$NEt_2$.

In one embodiment, the compound of formula (I) has the structure of formula (IE):

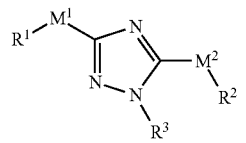

(IE)

or a pharmaceutically acceptable salt or solvate thereof, wherein:

$M^1$ and $M^2$ are each independently selected from —$NR^4$—, —$NR^4C(O)$—, —$C(O)NR^4$—, or —$S(O)_mNR^4$—;

$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heroalyl, and heterocyclyl portion is optionally substituted with one or more $R^5$;

$R^3$ is selected from an aryl or heteroaryl, wherein aryl and heteroaryl is optionally substituted with one or more $R^7$;

$R^4$ is each independently H or $C_1$-$C_3$ alkyl; and $R^5$ and $R^7$ are each independently selected from I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —C(O)O($C_1$-$C_6$ alkyl);

wherein when $M^1$ and $M^2$ are both —$NR^4C(O)$—, at least one of $R^1$ and $R^2$ is selected from

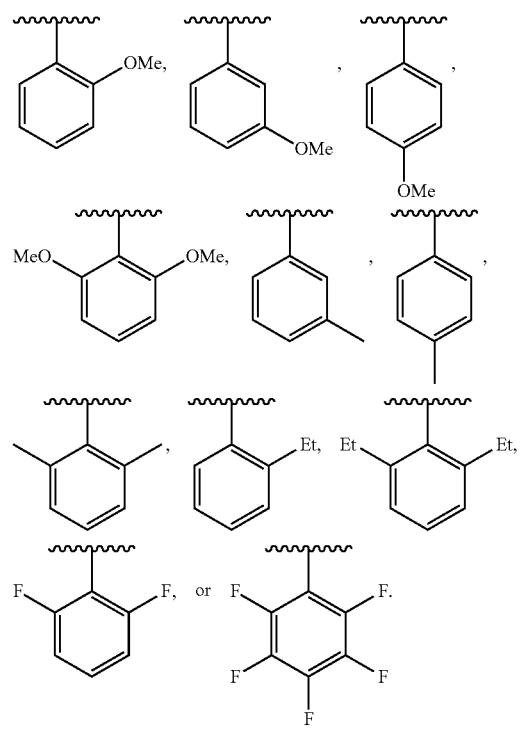

In one embodiment of the compound of formula (IE), $M^1$ and $M^2$ are both —$S(O)_mNR^4$—. In another embodiment, $M^1$ and $M^2$ are both —$C(O)NR^4$—. In one embodiment of the compound of formula (IE), -$M^1$-$R^1$ is —$NR^4C(O)R^1$. In one embodiment of the compound of formula (IE), -$M^2$-$R^2$ is —$NR^4C(O)R^2$. In one embodiment of the compound of formula (IE), -$M^1$-$R^1$ is —$NR^4C(O)R^1$ and -$M^2$-$R^2$ is —$NR^4C(O)R^2$.

In one embodiment of the compound of formula (IE), at least one of $R^1$ and $R^2$ is a phenyl or pyridyl, optionally substituted with one or more $R^5$. In some embodiments, $R^1$ and $R^2$ is phenyl, optionally substituted with one or more $R^5$. In other embodiments, at least one of $R^1$ and $R^2$ is selected from

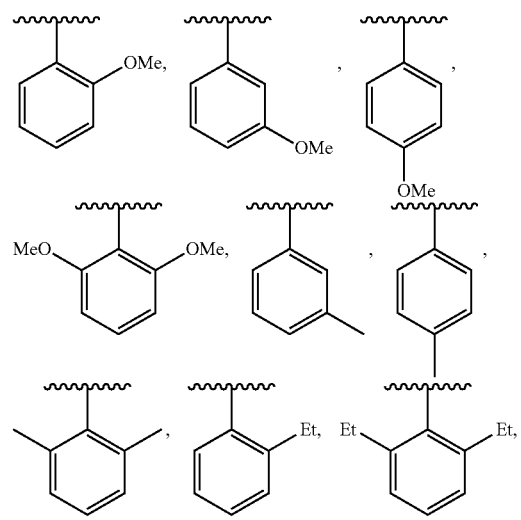

-continued

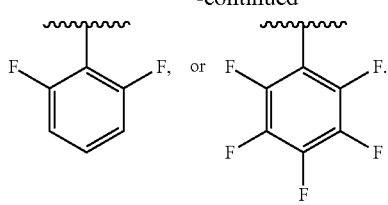

In one embodiment of the compound of formula (IE), at least one of $R^3$ is a phenyl or pyridyl, optionally substituted with one or more $R^7$.

In one embodiment of the compound of formula (IE), $R^5$ and $R^7$ is each selected from I, Br, Cl, F, —$CH_2F$, —$CHF_2$, —$CF_3$, —$OCF_3$, —$N_3$, —CN, —OH, methyl, ethyl, propyl, —C≡CH, —CN, —$NH_2$, —$NO_2$, —$N_3$, —OH, —$OCF_3$, —OMe, —$NMe_2$, or —$NEt_2$.

In one embodiment of the compound of formula (IE), the compound is not

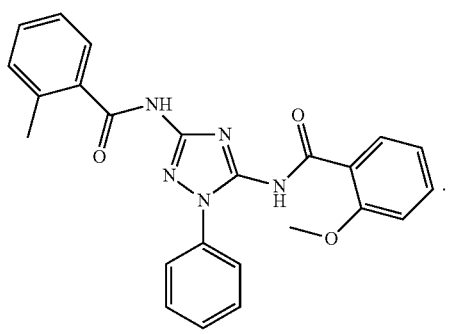

and

In one embodiment, the compound of formula (I) has the structure of formula (IF):

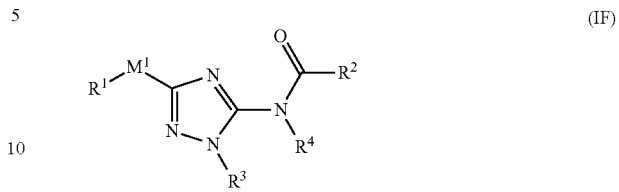

(IF)

or a pharmaceutically acceptable salt or solvate thereof, wherein:

$M^1$ is selected from —$NR^4$—, —$NR^4C(O)$— or —$C(O)NR^4$—;

$R^1$ and $R^2$ are each independently selected from an alkyl, alkenyl, cycloalkyl, aryl, biphenyl, heterocyclyl heterocycloalkyl, 5-6 membered heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently H or $C_1$-$C_3$ alkyl; and $R^5$ and $R^7$ are each independently selected from I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, or —C(O)O($C_1$-$C_6$ alkyl).

In one embodiment of the compound of formula (IF), -$M^1$-$R^1$ is —$NR^4C(O)R^1$.

In one embodiment of the compound of formula (if), $R^1$ and $R^2$ are each independently selected from aryl or 5-6 membered heteroaryl, each optionally substituted with one or more $R^5$.

In one embodiment of the compound of formula (IF), $R^2$ is phenyl optionally substituted with one or more $R^5$. In another embodiment, $R^2$ is

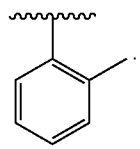

In one embodiment of the compound of formula (IF), $R^3$ is cycloalkyl, aryl, heterocyclyl, or heteroaryl, each optionally substituted with one or more $R^7$. In another embodiment, $R^3$ is phenyl optionally substituted with one or more $R^7$.

In one embodiment of the compound of formula (I), (I'), (IA), (IB), (IT), (IC), (ID), (IE), or (IF), the compound is selected from Table 1 below, or a pharmaceutically acceptable salt or solvate thereof.

TABLE 1

| Compd ID | Structure |
|---|---|
| 1 | 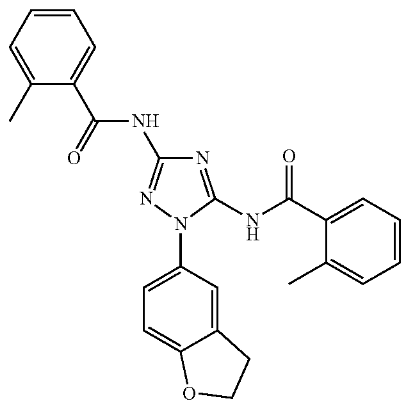 |
| 2 | 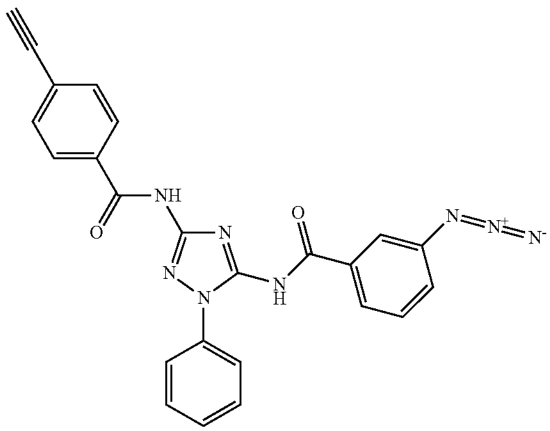 |
| 3 | 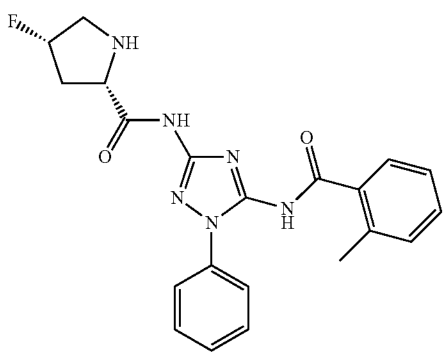 |
| 4 | 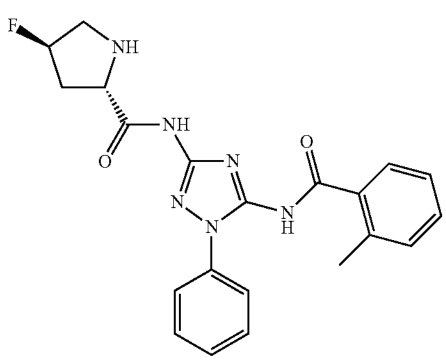 |

TABLE 1-continued
| Compd ID | Structure |
|---|---|
| 5 | 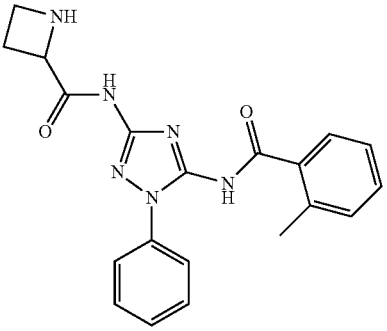 |
| 6 | 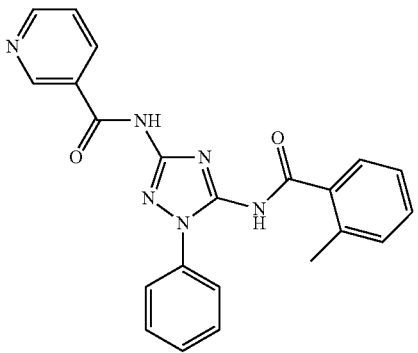 |
| 7 | 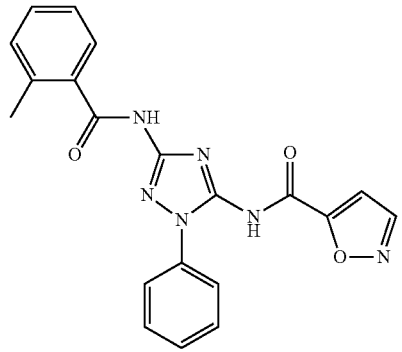 |
| 8 | 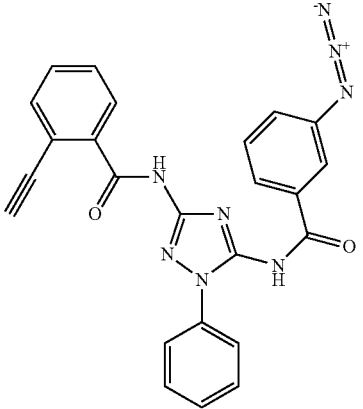 |

TABLE 1-continued

| Compd ID | Structure |
|---|---|
| 9 | *(2-methylbenzamide linked to 1-phenyl-1H-1,2,4-triazole-3,5-diamine with oxazole-4-carboxamide)* |
| 10 | *(2-methylbenzamide linked to 1-phenyl-1H-1,2,4-triazole-3,5-diamine with oxazole-2-carboxamide)* |
| 11 | *(3-ethynylbenzamide linked to 1-phenyl-1H-1,2,4-triazole-3,5-diamine with 3-azidobenzamide)* |
| 12 | *(4-azidobenzamide linked to 1-phenyl-1H-1,2,4-triazole-3,5-diamine with 3-ethynylbenzamide)* |

TABLE 1-continued

| Compd ID | Structure |
|---|---|
| 13 | 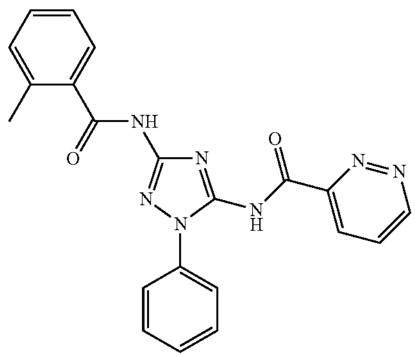 |
| 14 | 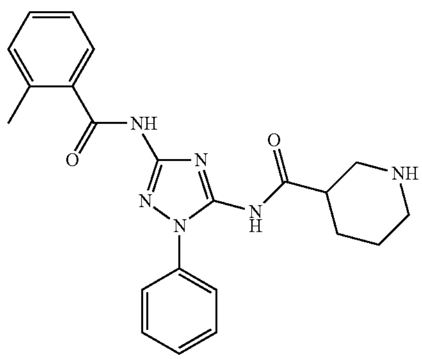 |
| 15 | 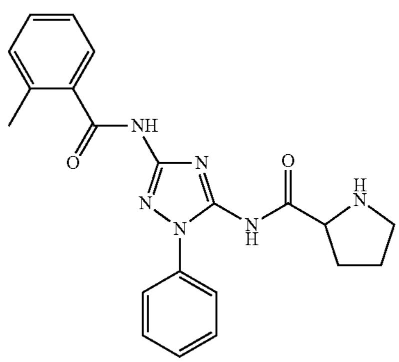 |
| 16 | 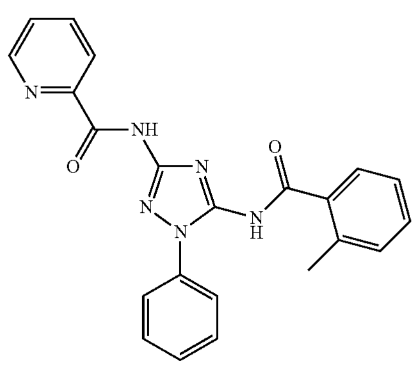 |

TABLE 1-continued

| Compd ID | Structure |
|---|---|
| 17 | 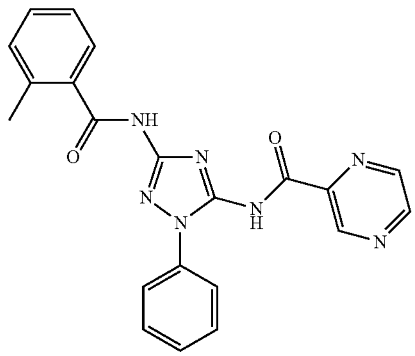 |
| 18 | 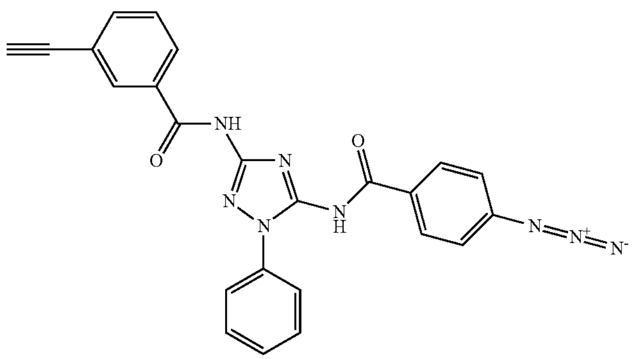 |
| 19 | 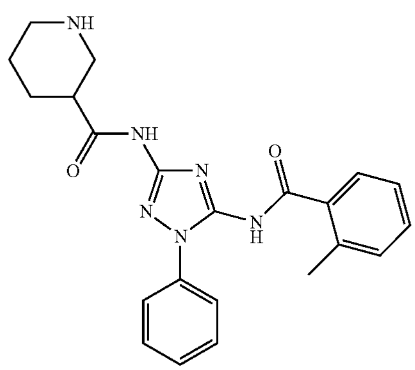 |
| 20 | 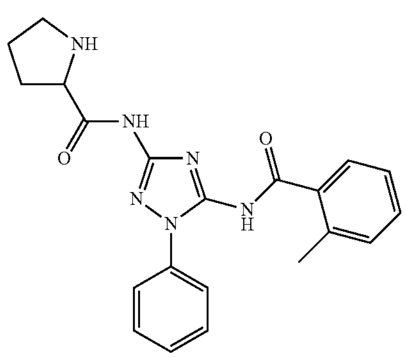 |

TABLE 1-continued

| Compd ID | Structure |
|---|---|
| 21 | 4-methyl-N-(1-phenyl-5-(4-methylbenzamido)-1H-1,2,4-triazol-3-yl)benzamide |
| 22 | 2-methyl-N-(1-phenyl-5-(1-methyl-1H-imidazole-4-carboxamido)-1H-1,2,4-triazol-3-yl)benzamide |
| 23 | 2-methoxy-N-(1-phenyl-5-(2-methoxybenzamido)-1H-1,2,4-triazol-3-yl)benzamide |
| 24 | 2-methyl-N-(1-(3,4-difluorophenyl)-5-(2-methylbenzamido)-1H-1,2,4-triazol-3-yl)benzamide |

TABLE 1-continued

| Compd ID | Structure |
|---|---|
| 25 | *[chemical structure: 1-(4-trifluoromethylphenyl)-3,5-bis(2-methylbenzamido)-1H-1,2,4-triazole]* |
| 26 | *[chemical structure: 1-(2-chlorophenyl)-3,5-bis(2-methylbenzamido)-1H-1,2,4-triazole]* |
| 27 | *[chemical structure: 1-phenyl-3,5-bis(3-methoxybenzamido)-1H-1,2,4-triazole]* |
| 28 | *[chemical structure: 1-phenyl-3-(2-methylbenzamido)-5-(pyrimidine-2-carboxamido)-1H-1,2,4-triazole]* |

TABLE 1-continued

| Compd ID | Structure |
|---|---|
| 29 | 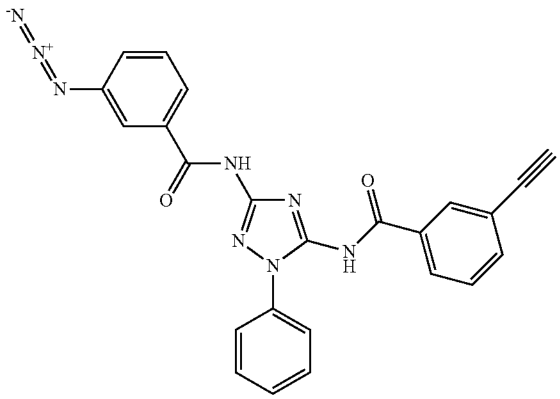 |
| 30 | 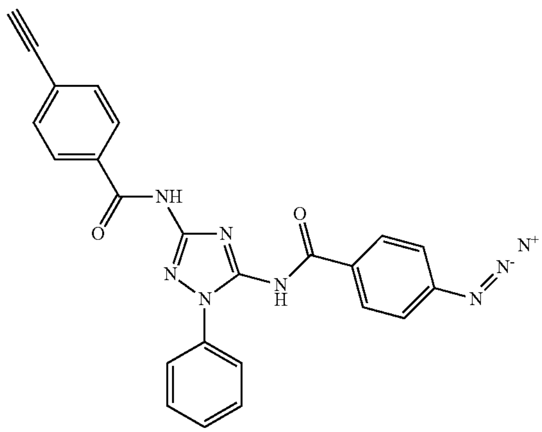 |
| 31 | 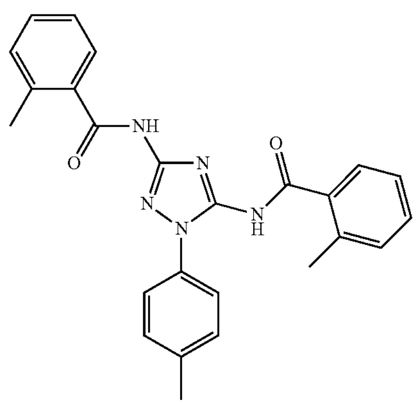 |
| 32 | 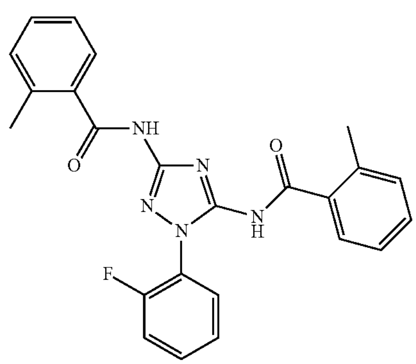 |

TABLE 1-continued
| Compd ID | Structure |
|---|---|
| 33 | 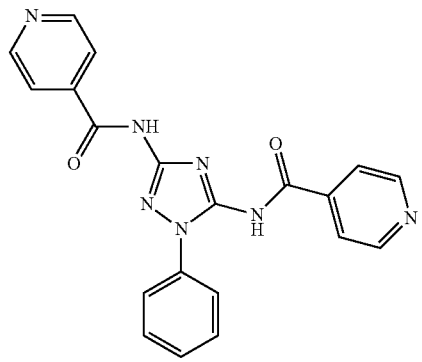 |
| 34 | 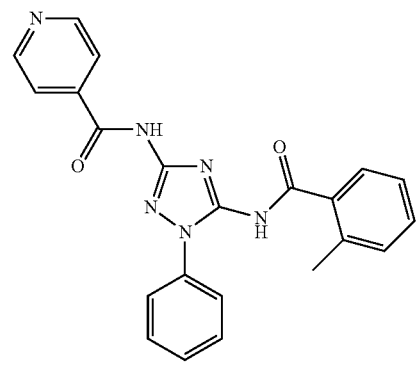 |
| 35 | 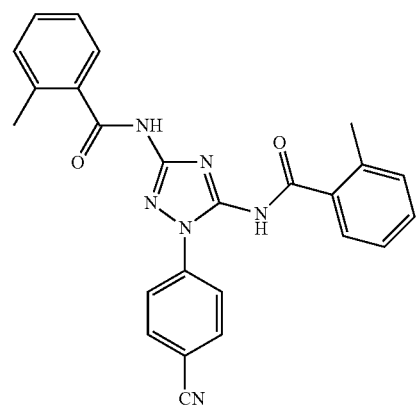 |
| 36 | 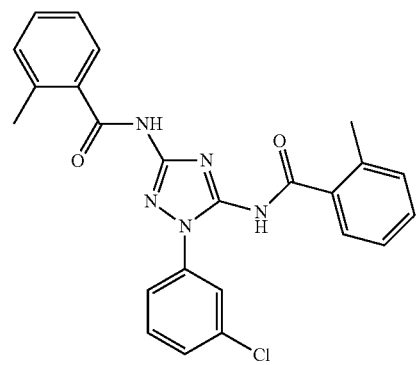 |

TABLE 1-continued

| Compd ID | Structure |
|---|---|
| 37 | 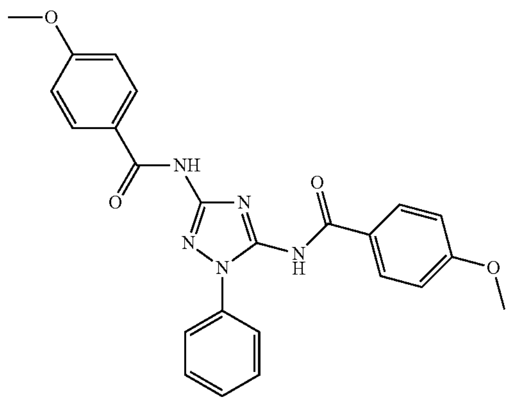 |
| 38 | 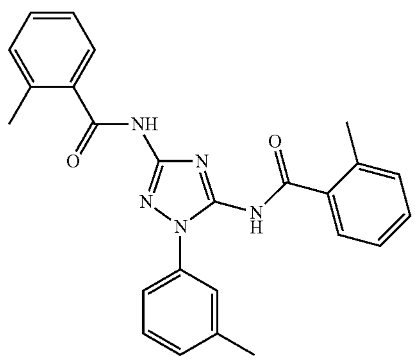 |
| 39 | 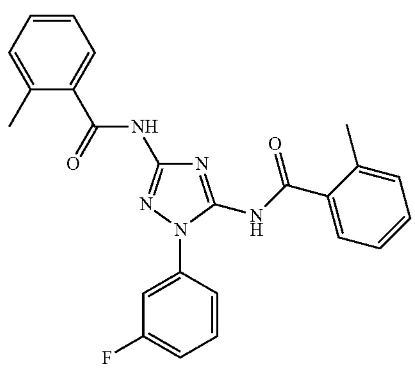 |
| 40 | 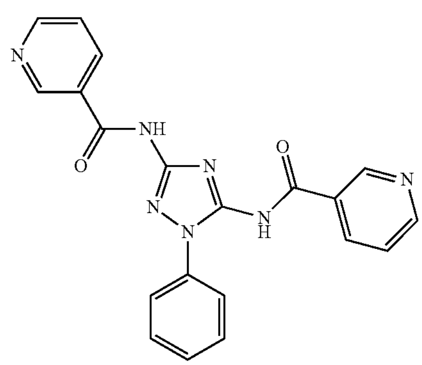 |

TABLE 1-continued
| Compd ID | Structure |
|---|---|
| 41 | 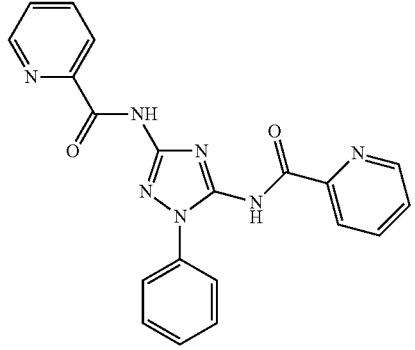 |
| 42 | 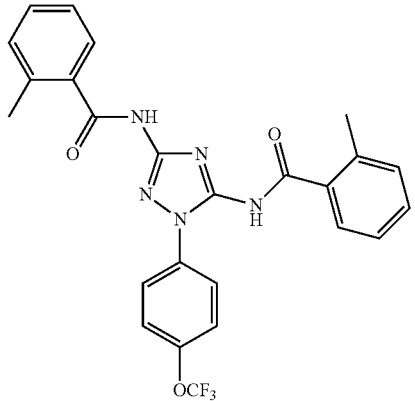 |
| 43 | 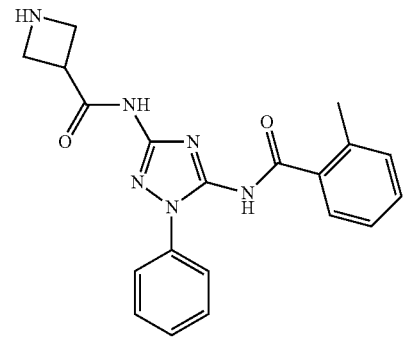 |
| 44 | 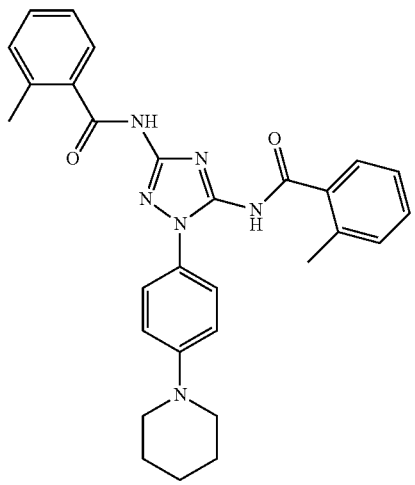 |

TABLE 1-continued
| Compd ID | Structure |
|---|---|
| 45 | 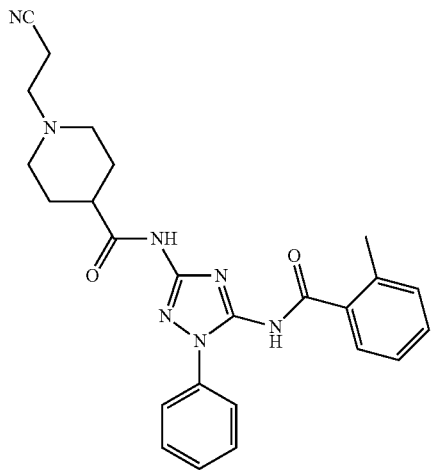 |
| 46 | 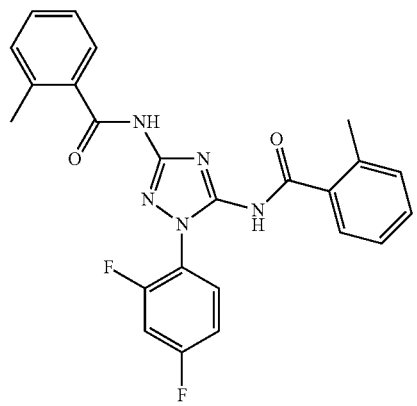 |
| 47 | 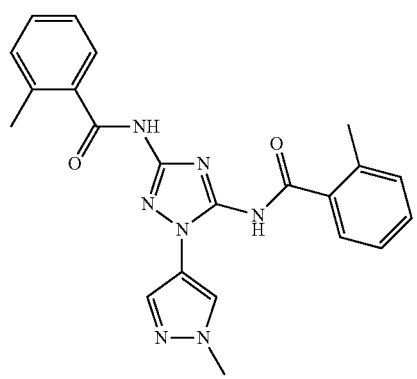 |

TABLE 1-continued
| Compd ID | Structure |
|---|---|
| 48 | 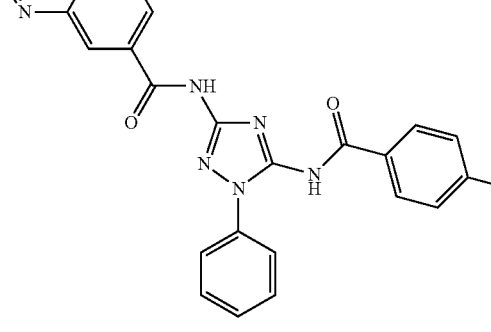 |
| 49 | 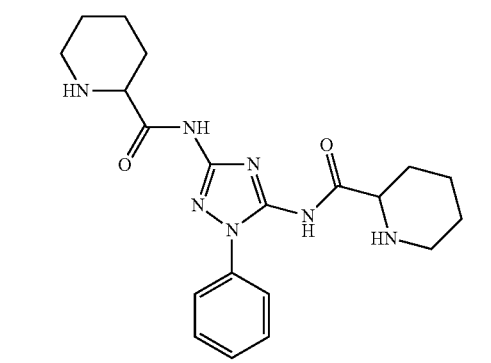 |
| 50 | 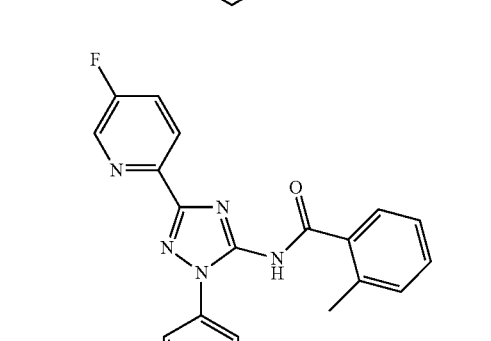 |
| 51 | 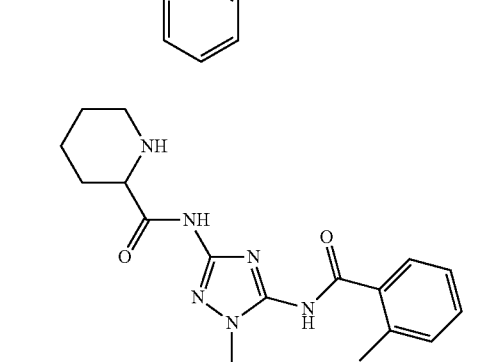 |

TABLE 1-continued

| Compd ID | Structure |
|---|---|
| 52 | 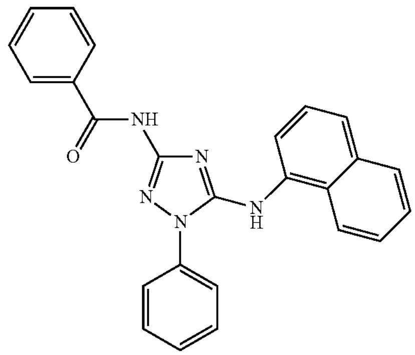 |
| 53 | 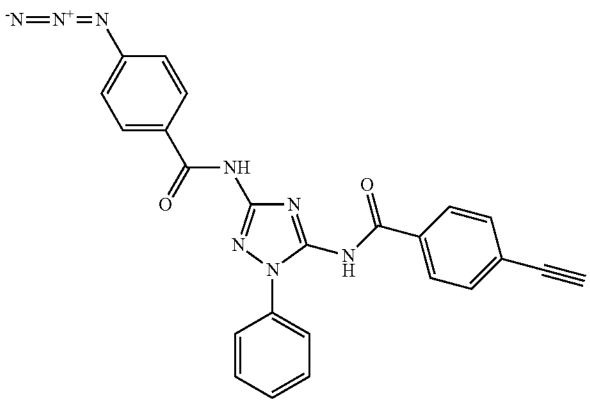 |
| 54 | 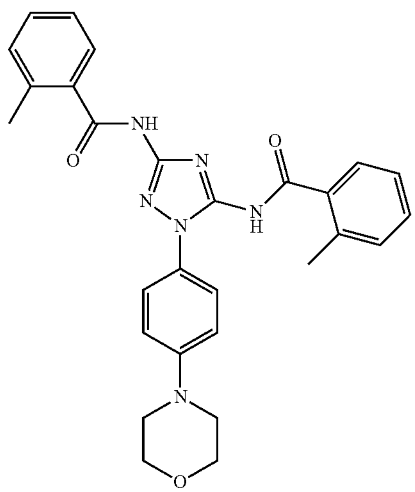 |
| 55 | 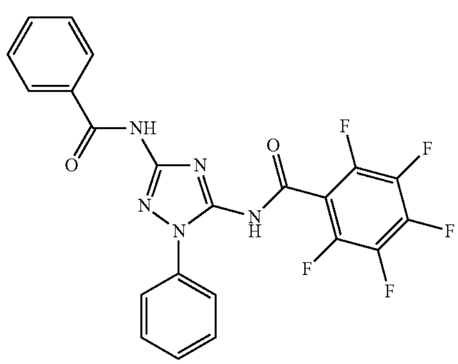 |

TABLE 1-continued
| Compd ID | Structure |
|---|---|
| 56 | 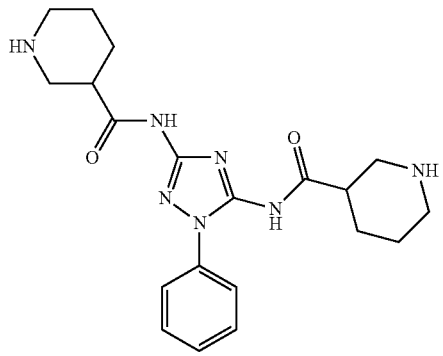 |
| 57 | 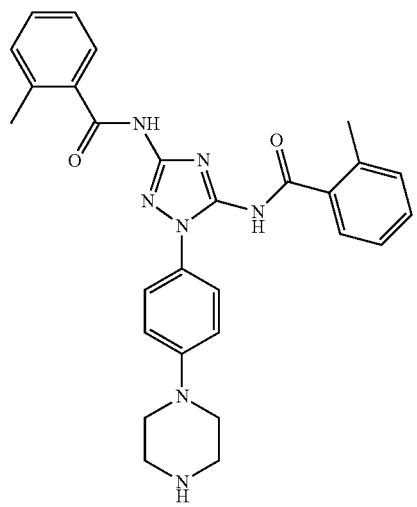 |
| 58 | 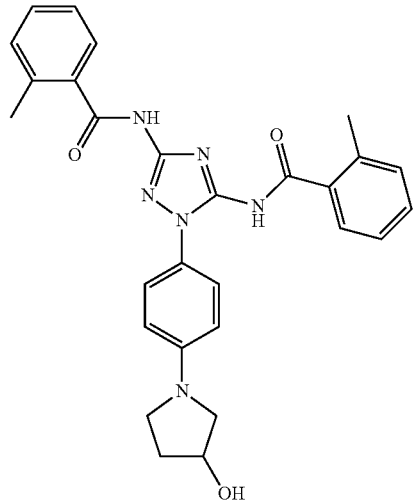 |

TABLE 1-continued

| Compd ID | Structure |
|---|---|
| 59 | 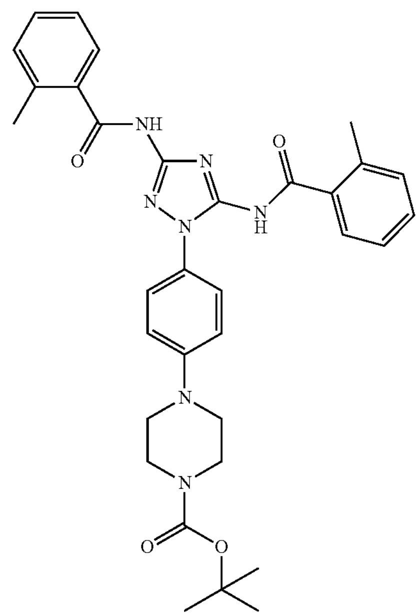 |
| 60 | 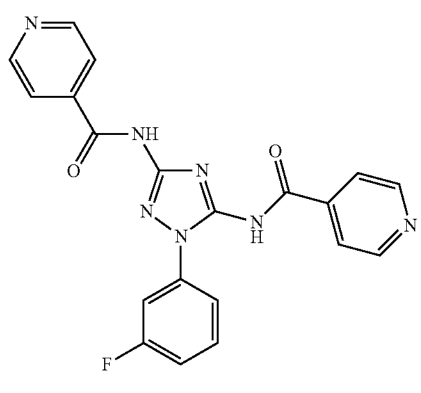 |
| 61 | 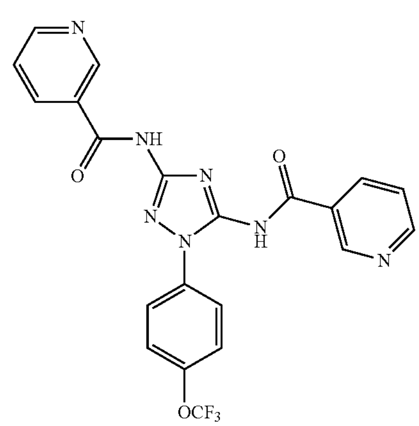 |

TABLE 1-continued

| Compd ID | Structure |
|---|---|
| 62 | 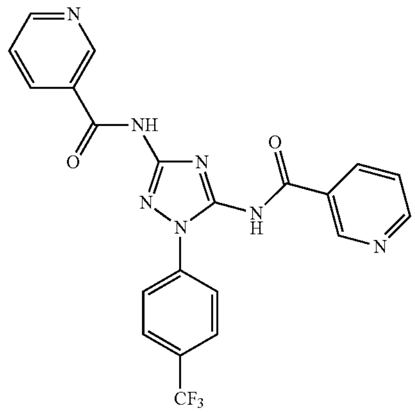 |
| 63 | 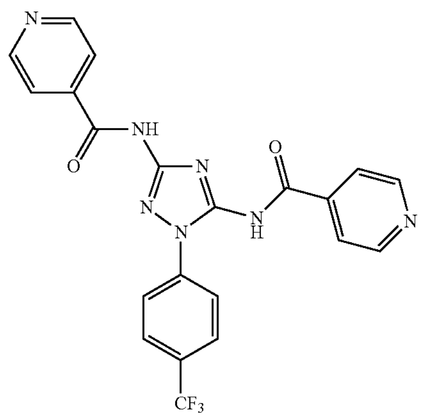 |
| 64 | 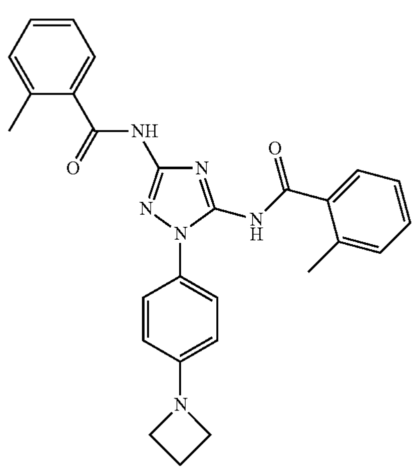 |

TABLE 1-continued

| Compd ID | Structure |
|---|---|
| 65 | *(chemical structure: 1-(4-trifluoromethoxyphenyl)-3,5-bis(isonicotinamido)-1H-1,2,4-triazole)* |
| 66 | *(chemical structure: N-[5-(3-azidobenzamido)-1-phenyl-1H-1,2,4-triazol-3-yl]-2-methylbenzamide)* |
| 67 | *(chemical structure: N-[5-(4-azidobenzamido)-1-phenyl-1H-1,2,4-triazol-3-yl]-2-methylbenzamide)* |

TABLE 1-continued
| Compd ID | Structure |
|---|---|
| 68 | 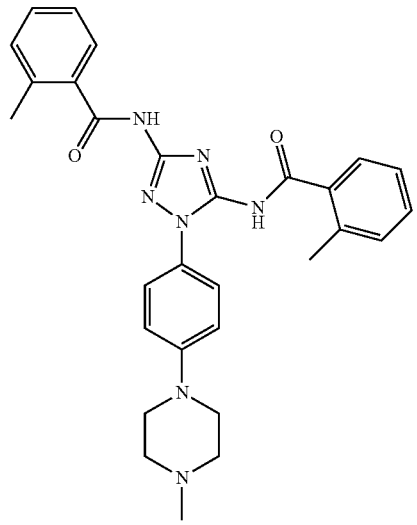 |
| 69 | 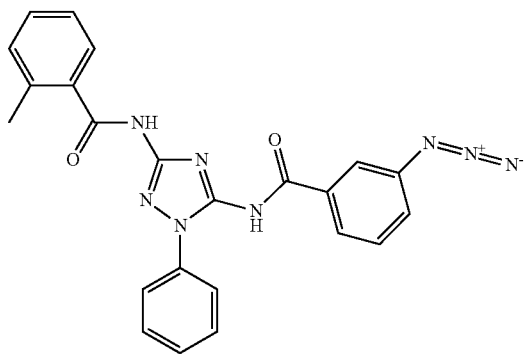 |
| 70 | 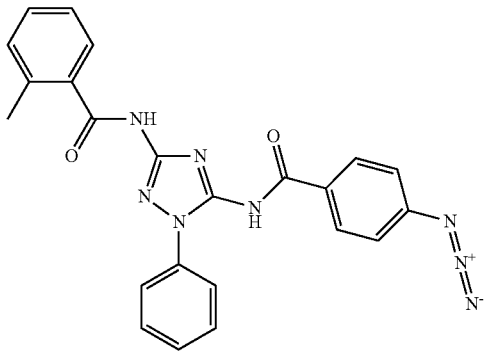 |

TABLE 1-continued
| Compd ID | Structure |
|---|---|
| 71 | 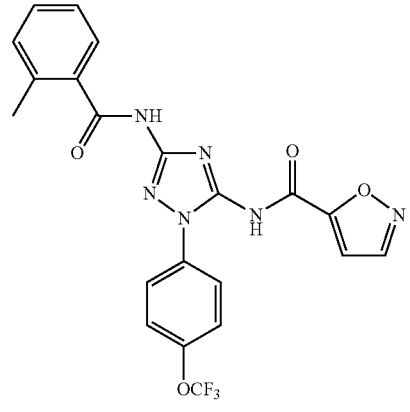 |
| 72 | 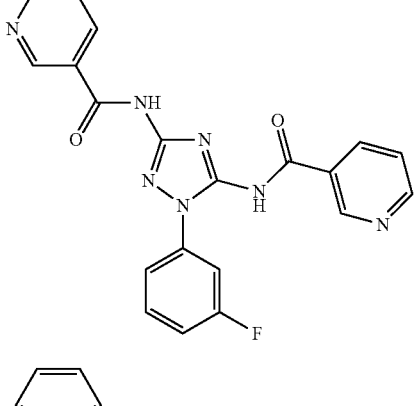 |
| 73 | 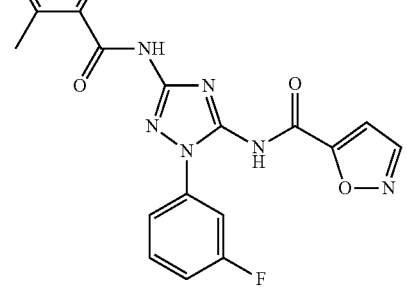 |
| 74 | 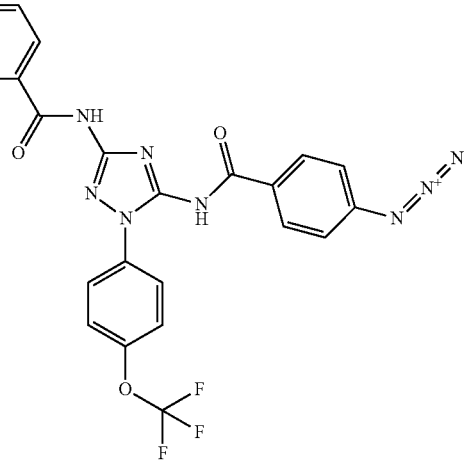 |

TABLE 1-continued
| Compd ID | Structure |
|---|---|
| 75 | 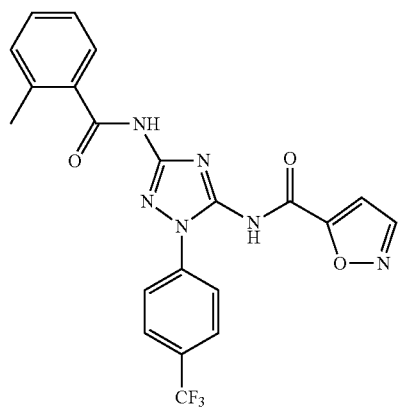 |
| 76 | 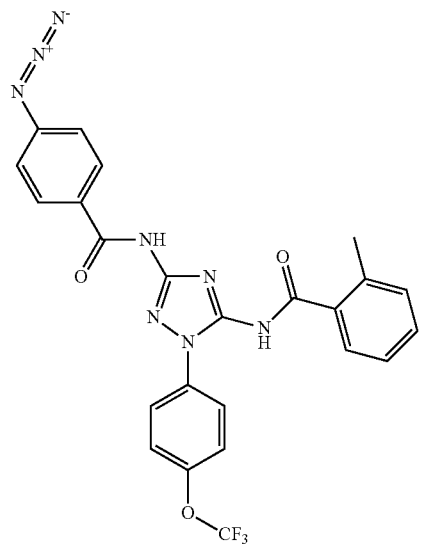 |
| 77 | 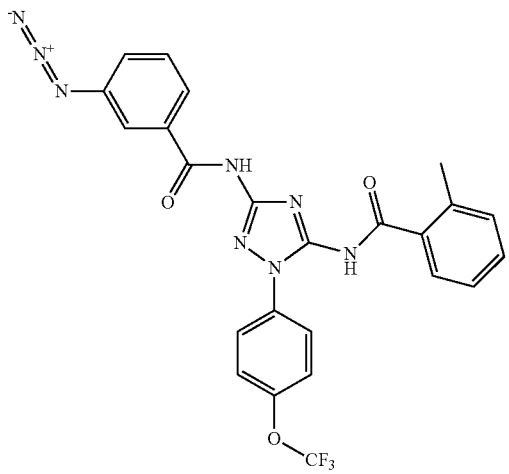 |

TABLE 1-continued

| Compd ID | Structure |
|---|---|
| 78 | 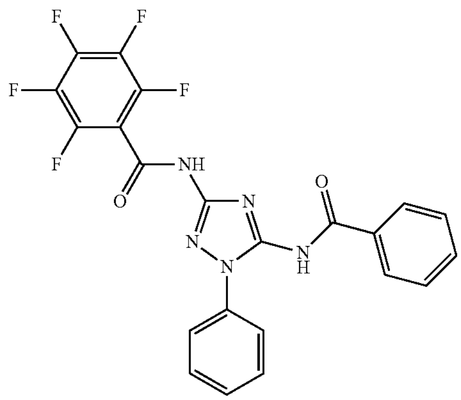 |
| 79 | 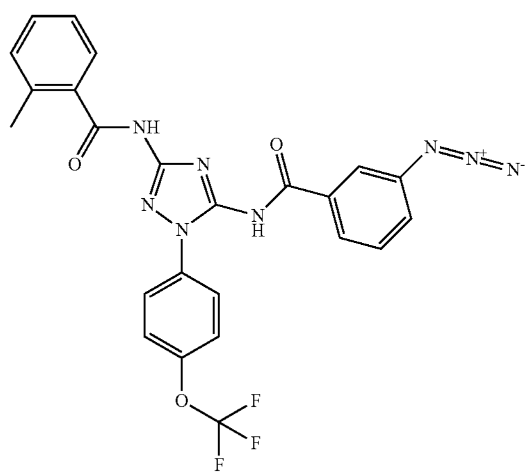 |
| 80 | 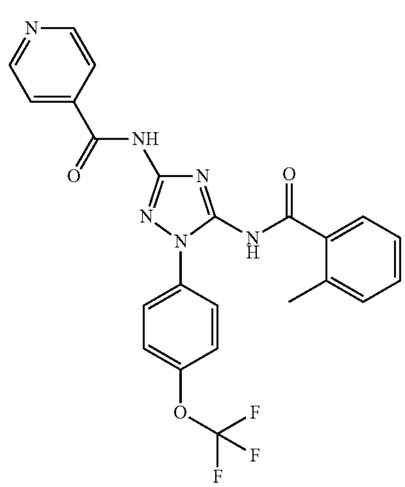 |

TABLE 1-continued

| Compd ID | Structure |
|---|---|
| 81 | *structure* |
| 82 | *structure* |
| 83 | *structure* |
| 84 | *structure* |

TABLE 1-continued

| Compd ID | Structure |
|---|---|
| 85 | *(structure)* |
| 86 | *(structure)* |
| 87 | *(structure)* |
| 88 | *(structure)* |

TABLE 1-continued
| Compd ID | Structure |
|---|---|
| 89 | 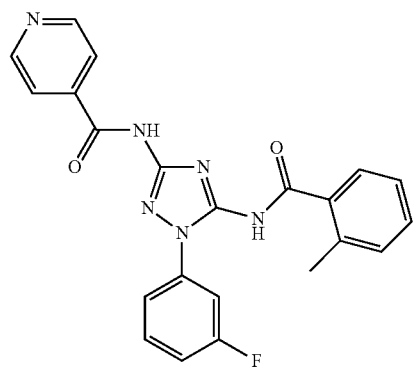 |
| 90 | 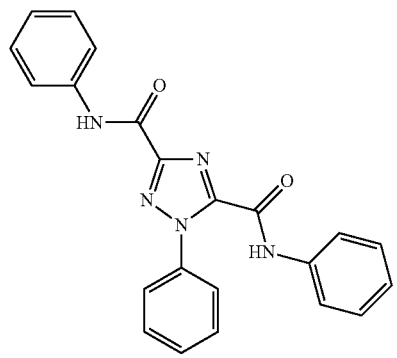 |
| 91 | 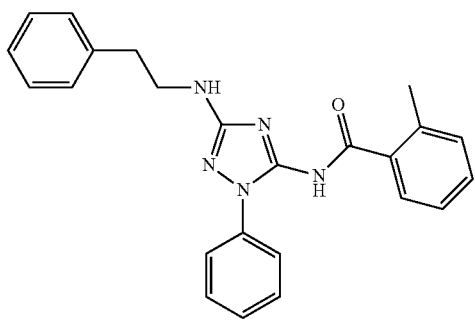 |
| 92 | 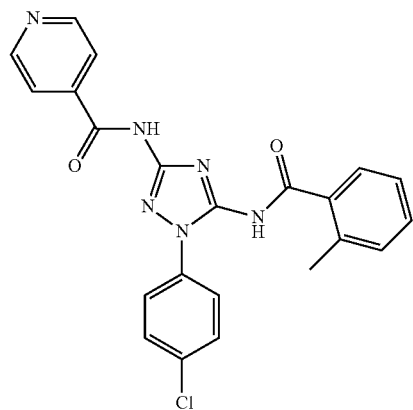 |

TABLE 1-continued
| Compd ID | Structure |
|---|---|
| 93 | 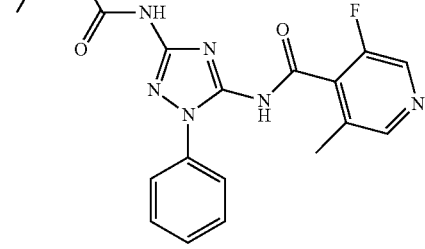 |
| 94 | 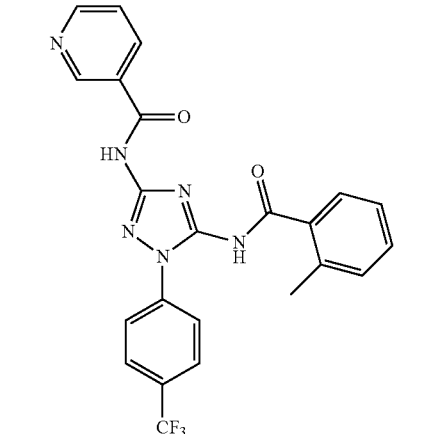 |
| 95 | 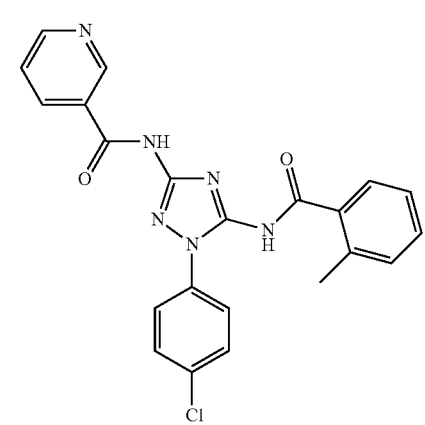 |
| 96 | 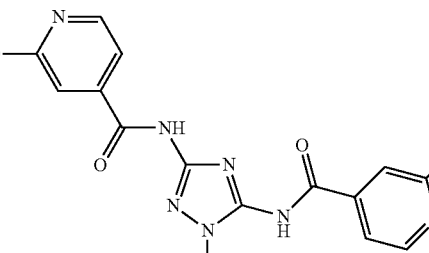 |

TABLE 1-continued
| Compd ID | Structure |
|---|---|
| 97 | 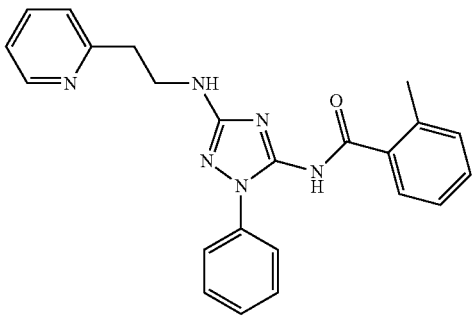 |
| 98 | 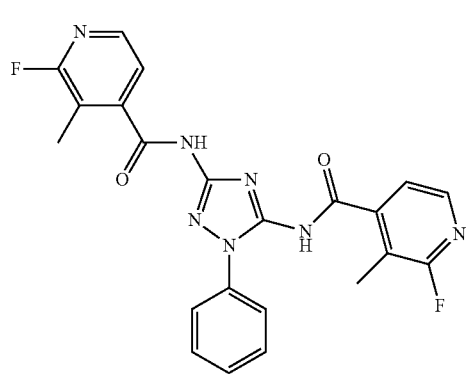 |
| 99 | 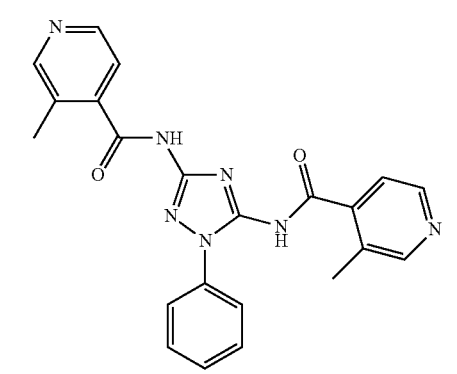 |
| 100 | 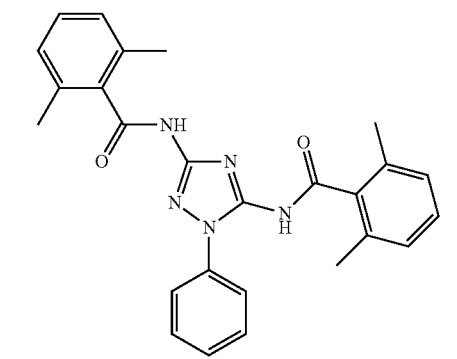 |

TABLE 1-continued

| Compd ID | Structure |
|---|---|
| 101 | 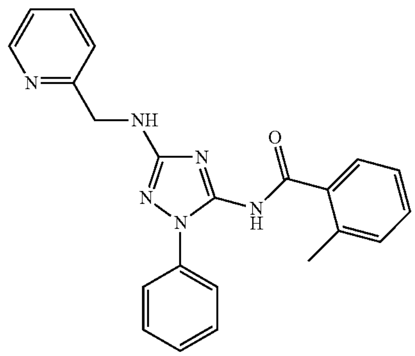 |
| 102 | 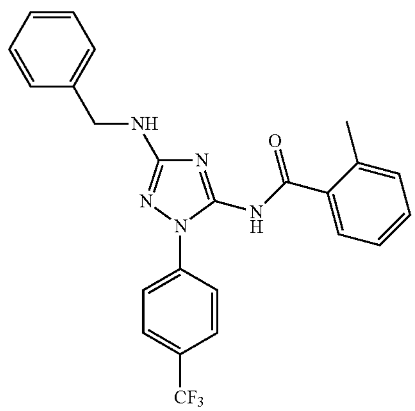 |
| 103 | 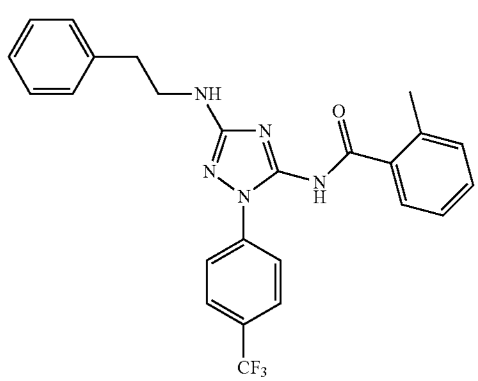 |
| 104 | 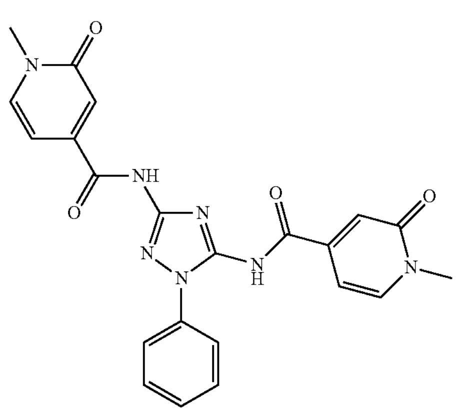 |

TABLE 1-continued
| Compd ID | Structure |
|---|---|
| 105 | 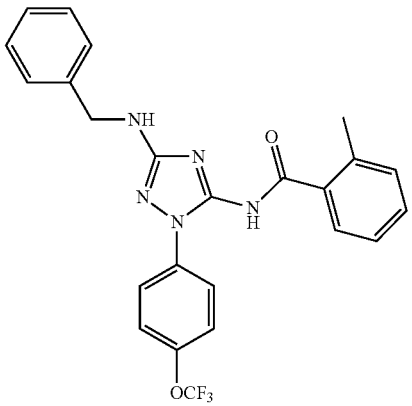 |
| 106 | 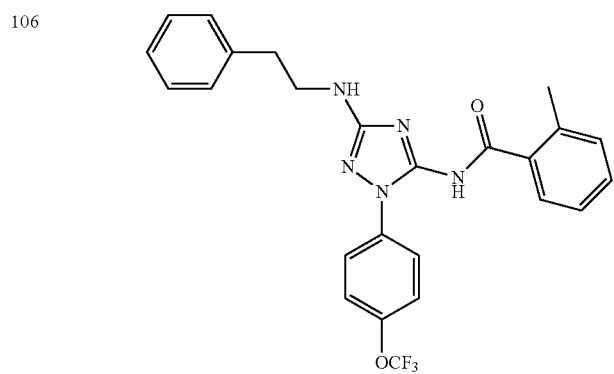 |
| 107 | 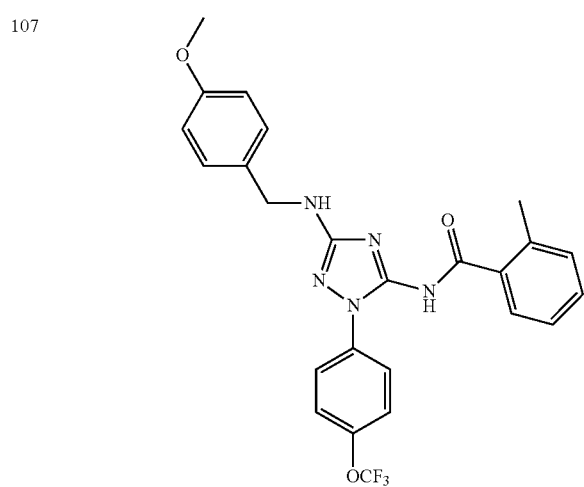 |

TABLE 1-continued
| Compd ID | Structure |
|---|---|
| 108 | 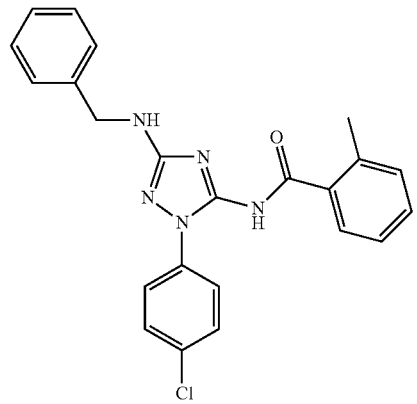 |
| 109 | 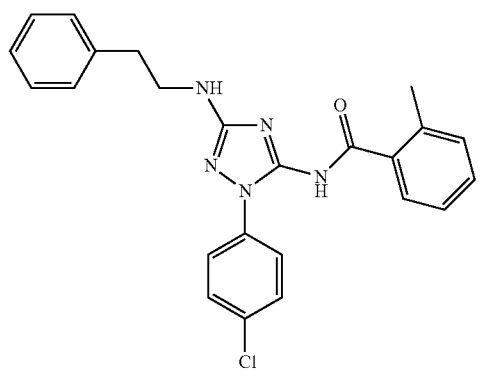 |
| 110 | 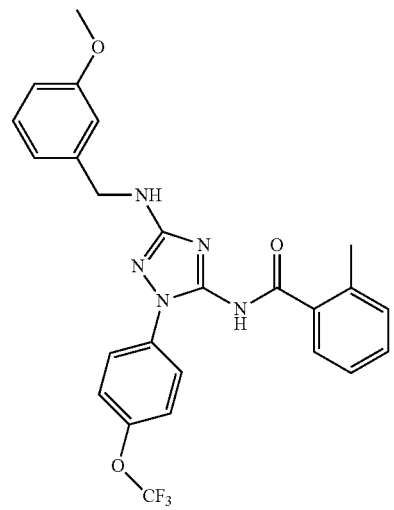 |

TABLE 1-continued
| Compd ID | Structure |
|---|---|
| 111 | 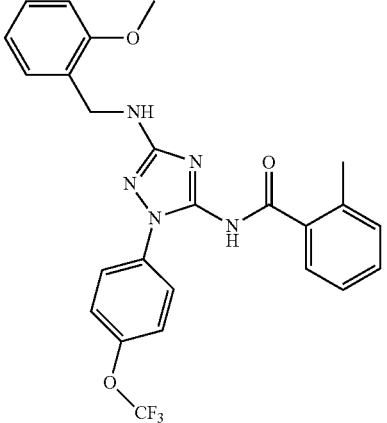 |
| 112 | 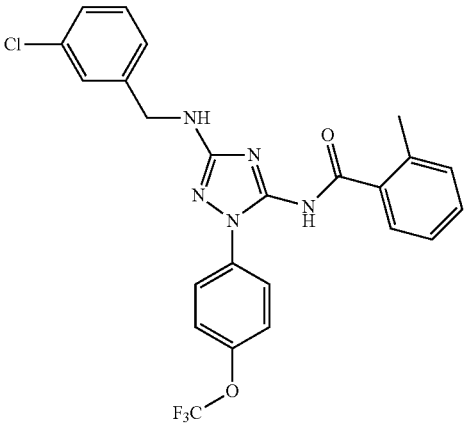 |
| 113 | 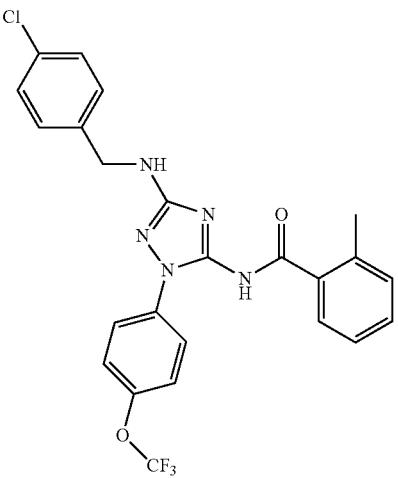 |

TABLE 1-continued

| Compd ID | Structure |
|---|---|
| 114 | (S)-2-methyl-N-(3-((1-phenylethyl)amino)-1-phenyl-1H-1,2,4-triazol-5-yl)benzamide |
| 115 | (R)-2-methyl-N-(3-((1-phenylethyl)amino)-1-phenyl-1H-1,2,4-triazol-5-yl)benzamide |
| 116 | N-(3-((2-chlorobenzyl)amino)-1-(4-(trifluoromethoxy)phenyl)-1H-1,2,4-triazol-5-yl)-2-methylbenzamide |
| 117 | 2-methyl-N-(3-((1-phenylethyl)amino)-1-(4-(trifluoromethoxy)phenyl)-1H-1,2,4-triazol-5-yl)benzamide |

TABLE 1-continued
| Compd ID | Structure |
|---|---|
| 118 | 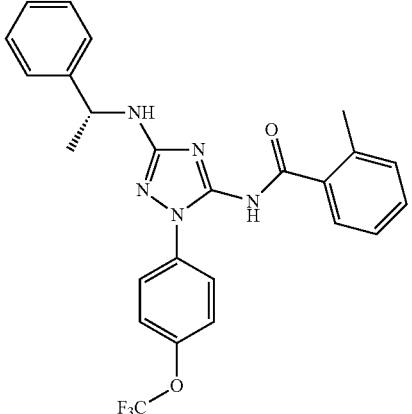 |
| 119 | 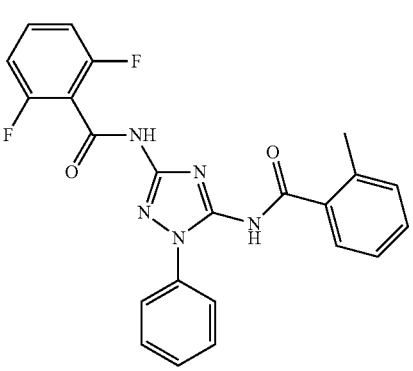 |
| 120 | 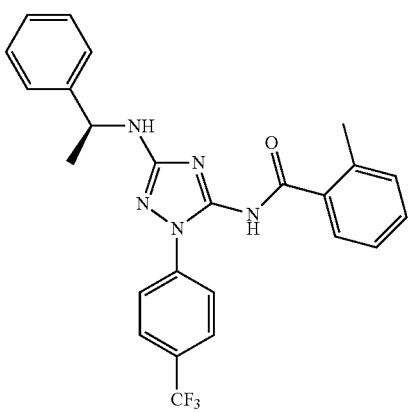 |
| 121 | 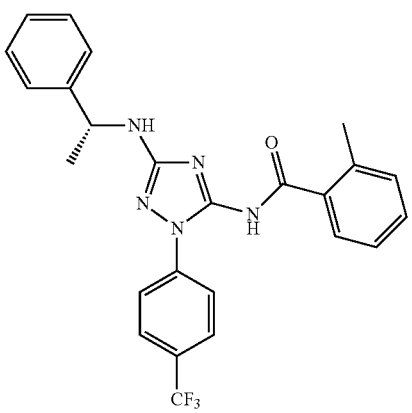 |

TABLE 1-continued
| Compd ID | Structure |
|---|---|
| 122 | 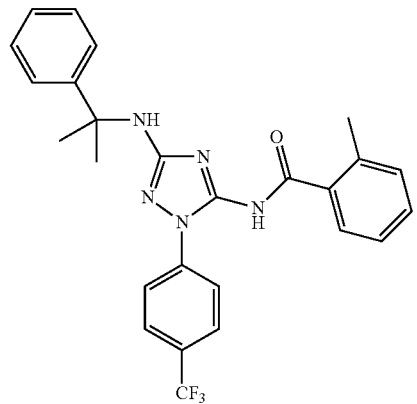 |
| 149 | 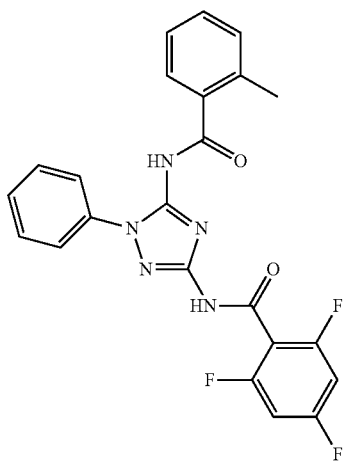 |
| 150 | 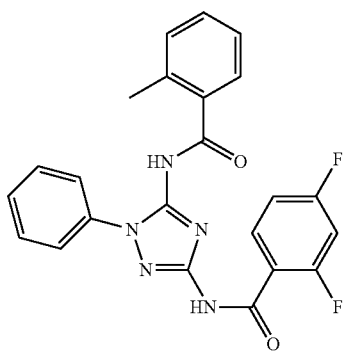 |

TABLE 1-continued

| Compd ID | Structure |
|---|---|
| 151 | 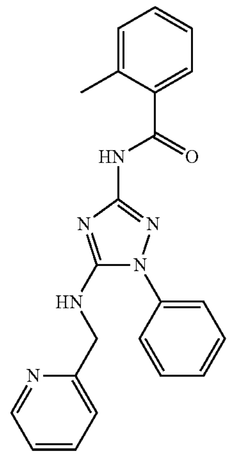 |
| 152 | 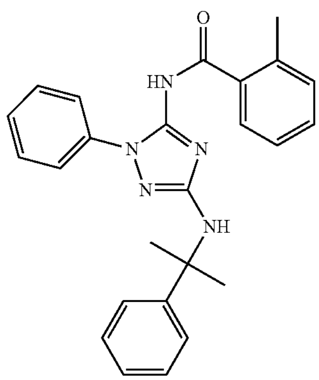 |
| 153 | 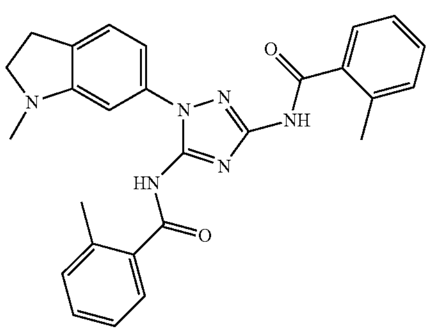 |

In one embodiment, the compound of formula (I) or (IA) is

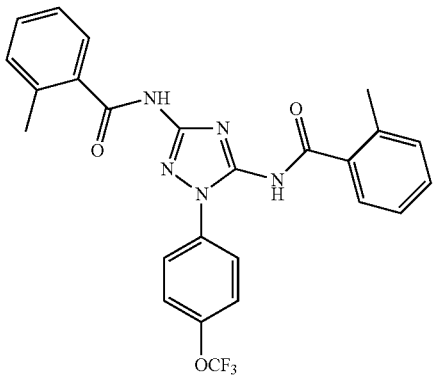

or a pharmaceutically acceptable salt thereof. In other embodiments, the compound of formula (I) or (IB) is

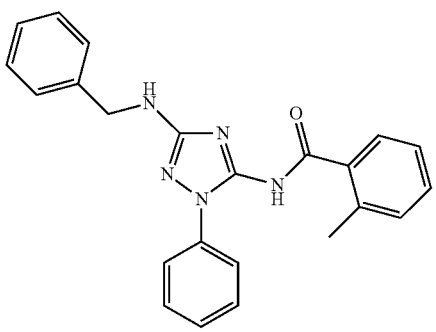

or a pharmaceutically acceptable salt thereof.

In one embodiment, the compound of the present disclosure is selected from Table 2, below, or a pharmaceutically acceptable salt or solvate thereof.

TABLE 2

| 147 | 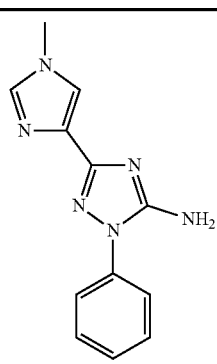 |
| --- | --- |
| 148 | 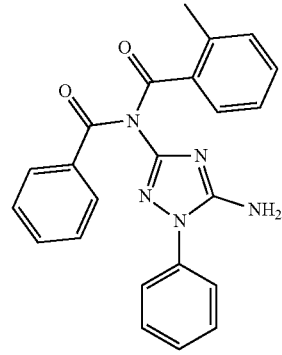 |

In one embodiment, the compound of formula (I), excludes compounds of Table A. In one embodiment, the compound of formula (I), (I'), (IA), (IB), (IB'), (IC), (ID), (IE), or (IF) excludes compounds of Table A.

In one embodiment, the present disclosure provides a pharmaceutical composition comprising a pharmaceutically acceptable carrier or a pharmaceutically acceptable excipient and a compound of any one of formula (I), (I'), (IA), (IB), (IB'), (IC), (ID), (IF), or (IF). In one embodiment, the pharmaceutical composition comprises

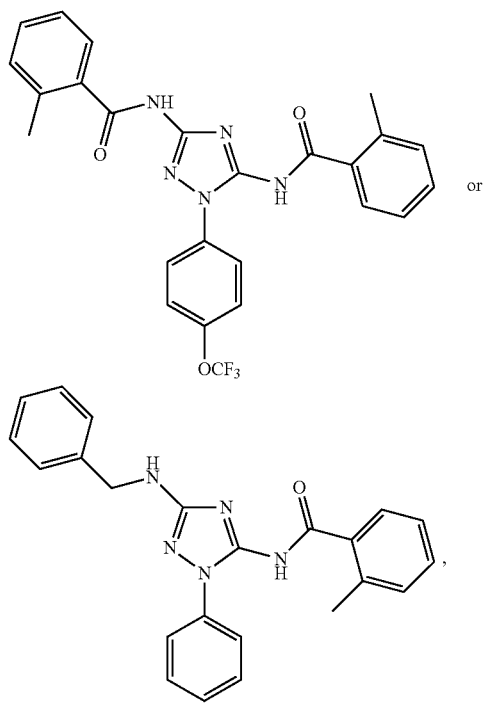

or a pharmaceutically acceptable salt thereof.

In one embodiment, the present disclosure provides a pharmaceutical composition comprising a pharmaceutically acceptable carrier or a pharmaceutically acceptable excipient and a compound of Table 2. In one embodiment, the present disclosure provides a pharmaceutical composition comprising a pharmaceutically acceptable carrier or a pharmaceutically acceptable excipient and

131

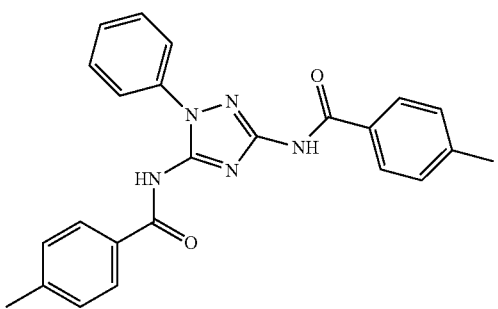

or a pharmaceutically acceptable salt thereof. In one embodiment of the pharmaceutical composition, the compounds of Table A are excluded.

In one embodiment, the present disclosure provides a pharmaceutical composition as disclosed herein comprises one additional therapeutically active agent.

In one embodiment, the present disclosure provides compounds comprising the structure of formula (II):

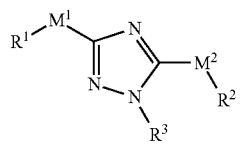
(II)

or a pharmaceutically acceptable salt or solvate thereof, wherein:

$M^1$ and $M^2$ are each independently selected from a bond, —$NR^4$—, or —$NR^4C(O)$—, —$C(O)NR^4$—;

$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl and heterocyclyl portion is optionally substituted with one or more $R^5$;

wherein at least one of $M^1$ and $M^2$ is a bond or —$NR^4$—;

wherein when $M^1$ is —$NR^4$—, then $R^1$ is cycloalkylalkyl, heterocyclylalkyl, arylalkyl, or heteroarylalkyl, wherein cycloalkyl, aryl, heteroaryl, and heterocyclyl portion is optionally substituted with one or more $R^5$;

wherein when $M^2$ is then $R^2$ is cycloalkylalkyl, heterocyclylalkyl, arylalkyl, or heteroarylalkyl, wherein cycloalkyl, acyl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;

$R^4$ is each independently alkyl, wherein each alkyl is optionally substituted with one or more $R^5$;

$R^5$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, or —$SR^6$;

132

$R^6$ is each independently alkyl, alkenyl, alkynyl, haloalkyl, haloalkenyl, haloalkynyl; or alternatively two $R^6$ on the same N atom can together form a 3-6 membered N-heterocyclyl; and $R^7$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, —$SR^6$, cycloalkyl, heterocyclyl, aryl, or heteroaryl, wherein each cycloalkyl, heterocyclyl, aryl, and heteroaryl is optionally substituted with one or more $R^5$;

wherein the compound is not N-benzyl-N-(5-(benzylamino)-1-phenyl-1H-1,2,4-triazol-3-yl)acetamide, N-(5-((2-chlorobenzyl)amino)-1-phenyl-1H-1,2,4-triazol-3-yl-2-fluorobenzamide and $N^3,N^5$-bis(4-methylbenzyl)-1-phenyl-1H-1,2,4-triazole-3,5-diamine.

In one embodiment of the compound of formula (II), at least one of -$M^1$-$R^1$ and -$M^2$-$R^2$ is —$NR^4$—($C_1$-$C_3$ alkylene)-cycloalkyl, —$NR^4$—($C_1$-$C_3$ alkylene)-heterocyclyl, —$NR^4$—($C_1$-$C_3$ alkylene)-aryl, or —$NR^4$—($C_1$-$C_3$ alkylene)-heteroaryl; wherein cycloalkyl, aryl, heteroaryl, and heterocyclyl is each optionally substituted with one or more $R^5$.

In one embodiment of the compound of formula (II), at least one of -$M^1$-$R^1$ and -$M^2$-$R^2$ is —$NR^4$—($C_1$-$C_3$ alkylene)-phenyl, or —$NR^4$—($C_1$-$C_3$ alkylene)-pyridyl, wherein phenyl and pyridyl is each optionally substituted with one or more $R^5$. In other embodiments, at least one of -$M^1$-$R^1$ and -$M^2$-$R^2$ is —$NR^4$—$CH_2$-phenyl, —$NR^4$—$CH_2CH_2$-phenyl, —$NR^4$—$CH_2$-pyridyl, —$NR^4$—$CH_2CH_2$-pyridyl,

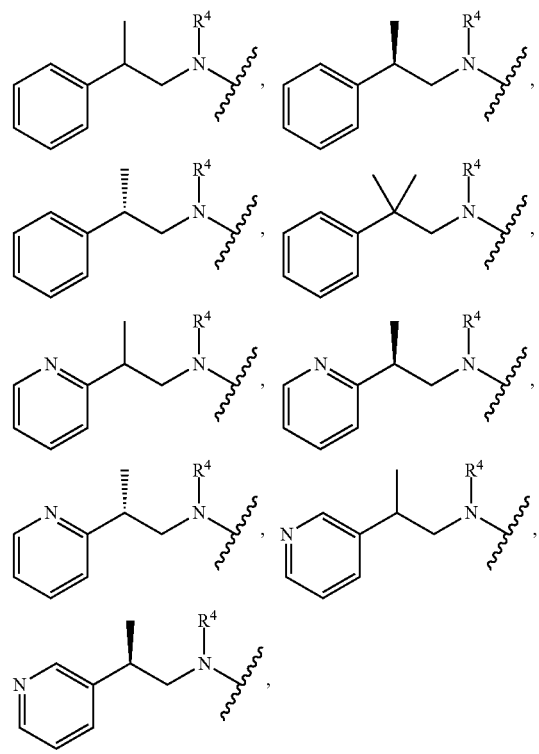

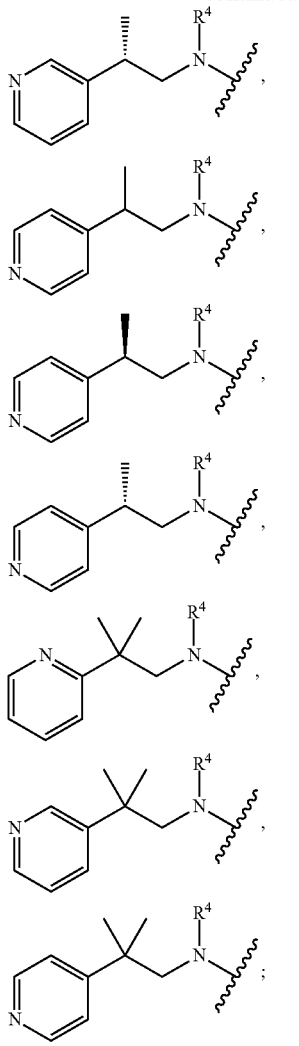
wherein phenyl and pyridyl is each optionally substituted with one or more $R^5$. In some embodiments, -$M^1$-$R^1$ and -$M^2$-$R^2$ are each selected from —$NR^4$—$CH_2$-phenyl, —$NR^4$—$CH_2CH_2$-phenyl, —$NR^4$—$CH_2$-pyridyl, —$NR^4$—$CH_2CH_2$-pyridyl,
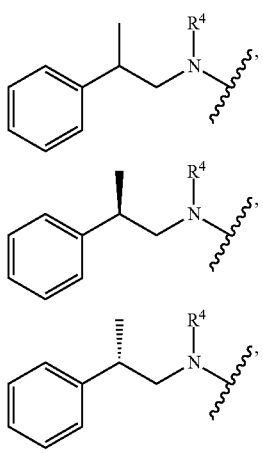
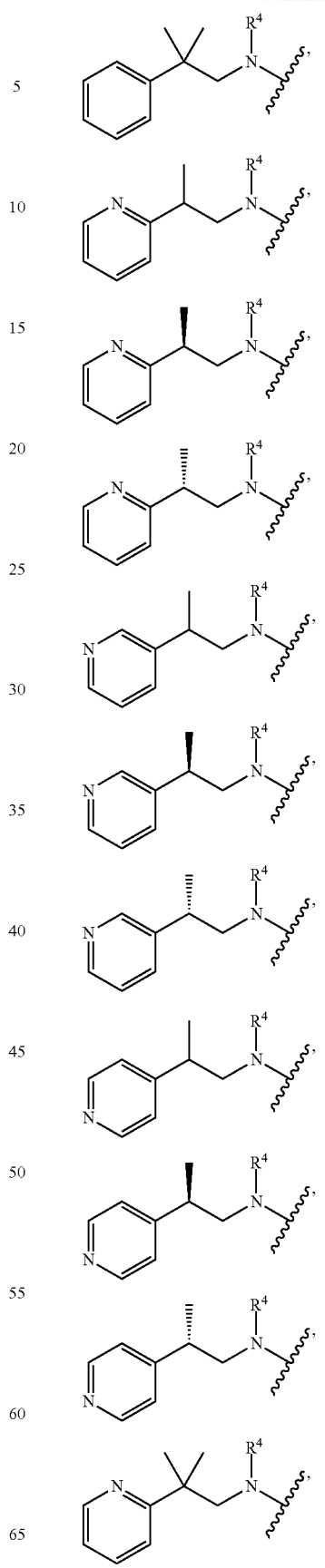

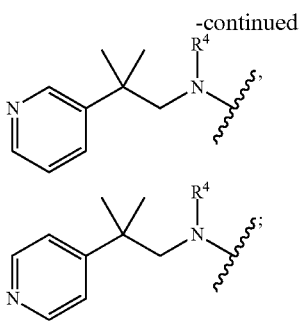

wherein phenyl and pyridyl is each optionally substituted with one or more R⁵.

In one embodiment of the compound of formula (II), -M¹-R¹ is —NR⁴C(O)R¹. In one embodiment of the compound of formula (II), -M²-R² is —NR⁴C(O)R².

In one embodiment of the compound of formula (II), R¹ and R² are each independently selected from phenyl or pyridyl, each optionally substituted with one or more R⁵.

In one embodiment of the compound of formula (II), one of M¹ and M² is a bond.

In one embodiment of the compound of formula (II), R¹ and R² are each independently selected from phenyl or 5-6 membered heteroaryl, each optionally substituted with one or more R⁵. In other embodiments, R¹ and R² are each independently selected from phenyl, azetidinyl, pyrrolidinyl, piperidinyl, imidazolyl, isoxazolyl, oxazolyl, thiazolyl, pyridyl, pyridazinyl, pyrazinyl, pyrimidinyl, pyridinoneor, or pyridine N-oxide, each optionally substituted with one or more R⁵.

In one embodiment of the compound of formula (II), M¹ is a bond and R¹ is pyridyl, optionally substituted with one or more R⁵.

In one embodiment of the compound of formula (II), M² is a bond and R² is pyridyl, optionally substituted with one or more R⁵.

In one embodiment of the compound of formula (II), M¹ is a bond and M² is —NR⁴— or —NR⁴C(O)—.

In one embodiment of the compound of formula (II), M² is a bond and M¹ is —NR⁴— or —NR⁴C(O)—.

In one embodiment of the compound of formula (II), R³ is phenyl, optionally substituted with one or more R⁷; and R⁷ is each independently I, Br, Cl, F, —CH₂F, —CHF₂, —CF₃, —OCF₃, —CN, —N₃, —OH, methyl, ethyl, propyl, —C≡CH; —CN, —NH₂, —NO₂, —N₃, —OH, —OCF₃, —OMe, —NMe₂, or —NEt₂.

In one embodiment of the compound of formula (II), R⁵ and R⁷ are each independently selected from I, Br, Cl, F, —CH₂F, —CHF₂, —CF₃, —OCF₃, —N₃, —CN, —OH, methyl, ethyl, propyl, —C≡CH; —CN, —NH₂, —NO₂, —N₃, —OH, —OCF₃, —OMe, —NMe₂, or —NEt₂.

In one embodiment of the compound of formula (II), R⁴ is each independently H or C₁-C₃.

In one embodiment, the compound of formula (II) has the structure of formula (IIA):

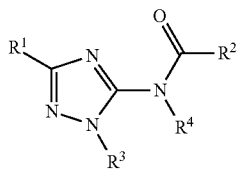

(IIA)

or a pharmaceutically acceptable salt or solvate thereof, wherein:

R¹ and R² are each independently selected from an cycloalkyl, aryl, biphenyl, heterocyclyl, or heteroaryl, each optionally substituted with one or more R⁵;

R³ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more R⁷;

R⁴ is each independently H, alkyl, wherein each alkyl is optionally substituted with one or more R⁵;

R⁵ is each independently I, Br, Cl, F, —CH₂F, —CHF₂, —CF₃, —CN, -alkyl-CN, —CONH₂, —CONHR⁶, —CONR⁶R⁶, —COOH, —NH₂, —NHR⁶, —NO₂, —NR⁶R⁶, —N₃, —OH, OR⁶, —COOR⁶, —OSO₃R⁶, oxo, R⁶, —SH; —SO₂R⁶, —SO₃H, —SO₃R⁶, or —SR⁶;

R⁶ is each independently alkyl, alkenyl, alkynyl, haloalkyl, haloalkenyl, haloalkynyl; or alternatively two R⁶ on the same N atom can together form a 3-6 membered N-heterocyclyl;

R⁷ is each independently I, Br, Cl, F, —CH₂F, —CHF₂, —CF₃, —OCF₃, —CN, -alkyl-CN, —CONH₂, —CONHR⁶, —CONR⁶R⁶, —COOH, —NH₂, —NHR⁶, —NO₂, —NR⁶R⁶, —N₃, —OH, OR⁶, —COOR⁶, —OSO₃R⁶, oxo, R⁶, —SH, —SO₂R⁶, —SO₃H, —SO₃R⁶, —SR⁶, cycloalkyl, heterocyclyl, aryl, or heteroaryl, wherein each cycloalkyl, heterocyclyl, acyl, and heteroaryl is optionally substituted with one or more R⁵.

In one embodiment of the compound of formula (IIA), R¹ is aryl, optionally substituted with one or more R⁵. In another embodiment, R¹ is phenyl, optionally substituted with one or more R⁵. In some embodiments, R¹ is 5-6 membered heteroaryl, optionally substituted with one or more R⁵. In other embodiments, R¹ is pyridyl, optionally substituted with one or more R⁵.

In one embodiment of the compound of formula (IIA), R² is phenyl optionally substituted with one or more R⁵. In some embodiments, R² is

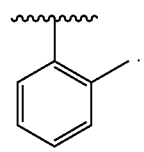

In one embodiment of the compound of formula (IIA), R³ is cycloalkyl, aryl, heterocyclyl, or heteroaryl, each optionally substituted with one or more R⁷. In some embodiments, R³ is phenyl optionally substituted with one or more R⁷.

In one embodiment of the compound of formula (IIA), R⁵ is I, Br, Cl, F, —CH₂F, —CHF₂, —CF₃, —C₁-C₆ alkyl, alknyl, —CN, —(C₁-C₃ alkylene)-CN, —NH₂, —NO₂, —N₃, —OH, —OCF₃, —OMe, —NMe₂, —NEt₂, or —C(O)O(C₁-C₆ alkyl).

In one embodiment of the compound of formula (IIA), R⁵ and R⁷ are each independently selected from I, Br, Cl, F, —CH₂F, —CHF₂, —CF₃, —OCF₃, —N₃, —CN, —OH, methyl, ethyl, propyl, —C≡CH; —CN, —NH₂, —NO₂, —N₃, —OH, —OCF₃, —OMe, —NMe₂, or —NEt₂.

In one embodiment, the compound of formula (II) and (IIA) excludes the compounds of Table C.

In one embodiment of the compound of formula (II) and (IIA), the compound is selected from Table 3A below, or a pharmaceutically acceptable salt or solvate thereof.

TABLE 3A

| 123 | [structure] |
| 124 | [structure] |
| 125 | [structure] |
| 126 | [structure] |

TABLE 3A-continued

| 127 | [structure] |
| 128 | [structure] |
| 129 | [structure] |
| 130 | [structure] |

TABLE 3A-continued
| | |
|---|---|
| 131 | 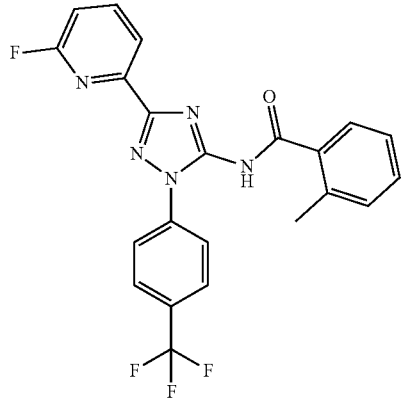 |
| 132 | 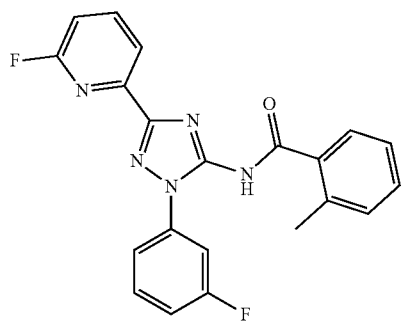 |
| 133 | 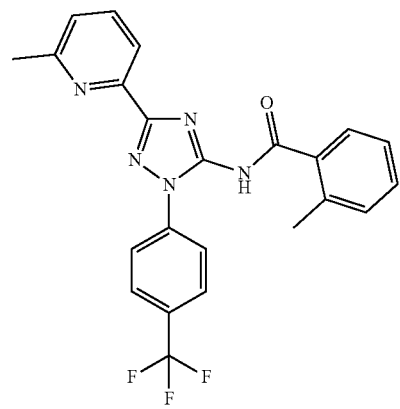 |
| 134 | 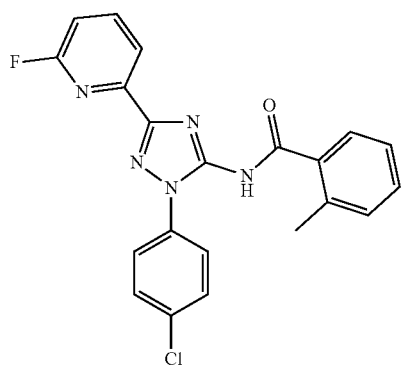 |
| 135 | 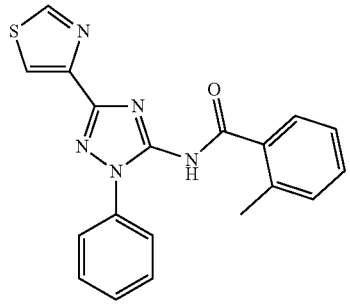 |
| 136 | 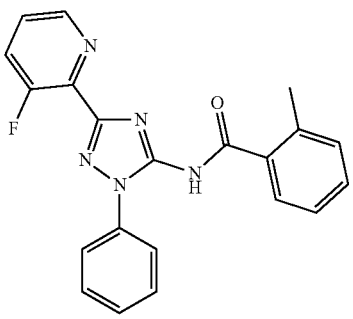 |
| 137 | 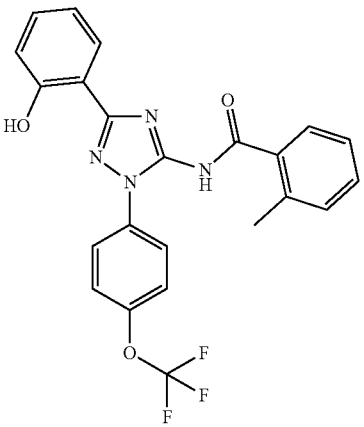 |
| 138 | 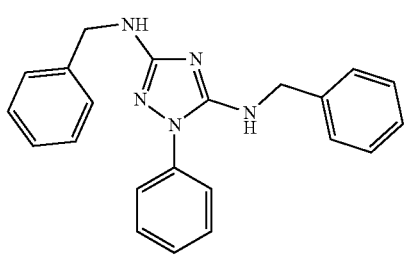 |

TABLE 3A-continued
139 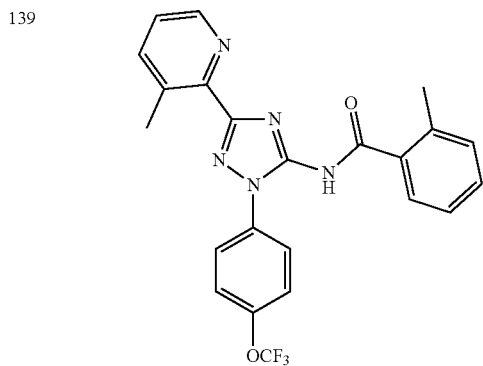
140 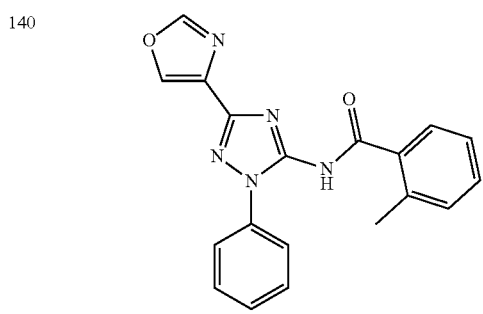
141 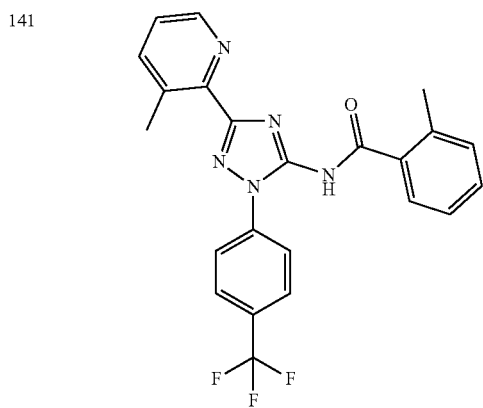
142 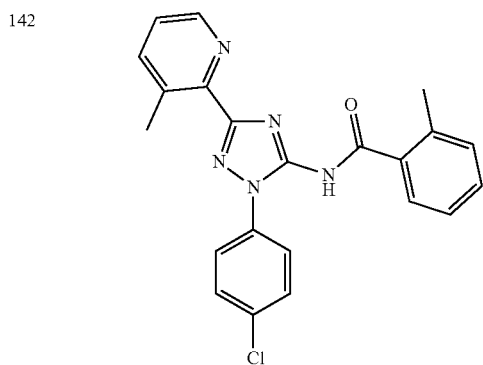
TABLE 3A-continued
143 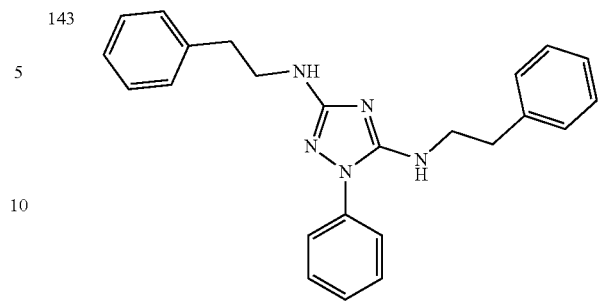
144 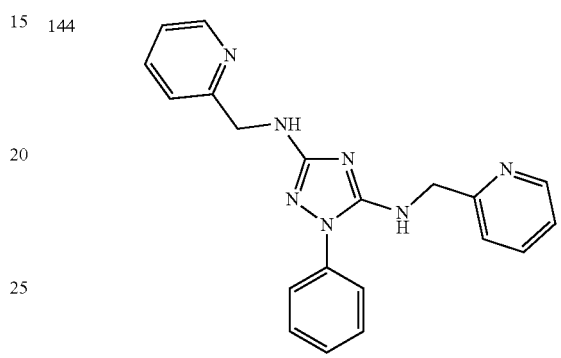
145 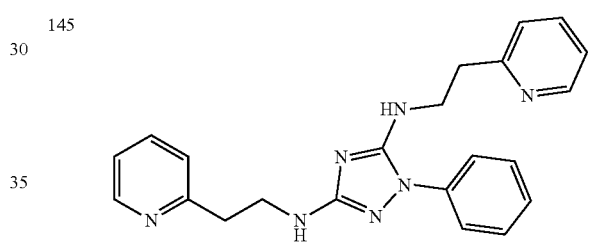
146 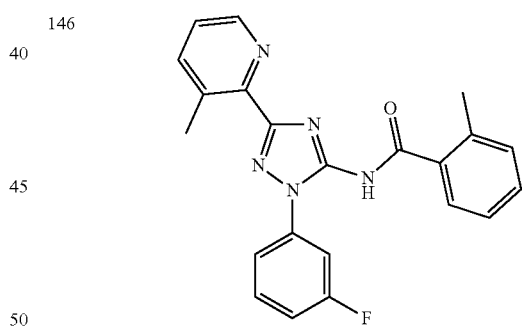
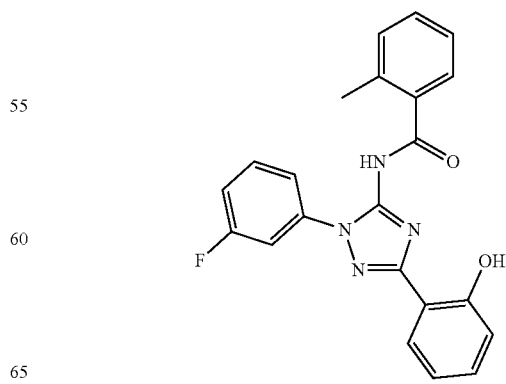

TABLE 3A-continued

154 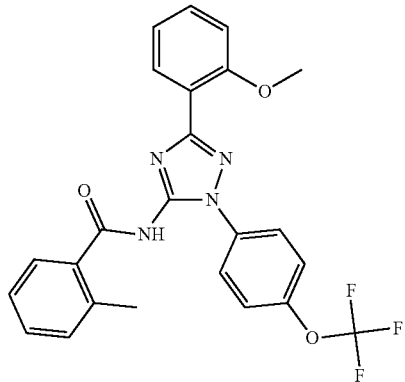

155 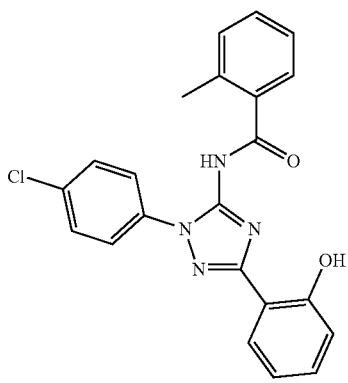

156 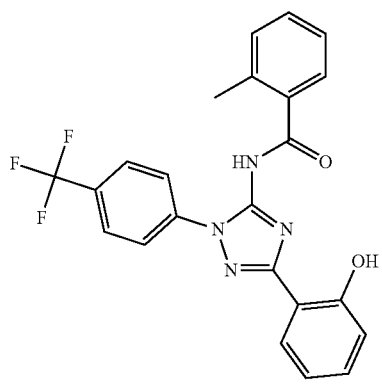

157 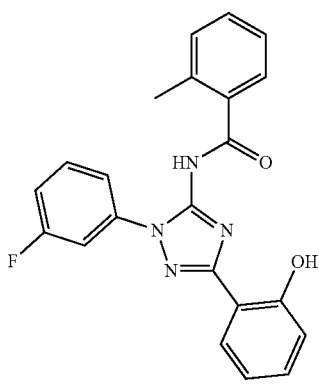

TABLE 3A-continued

158 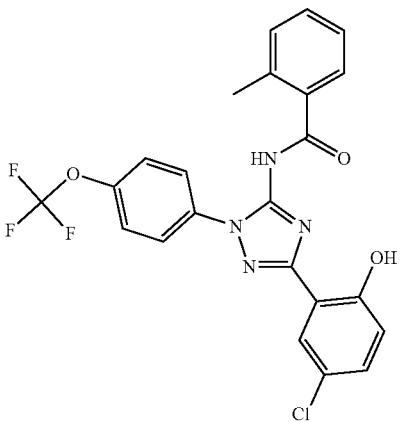

159 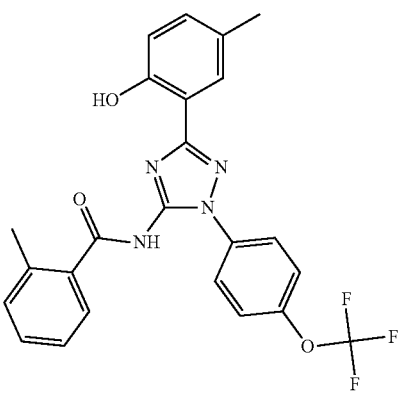

In one embodiment, the present disclosure provides compounds comprising the structure of formula (III):

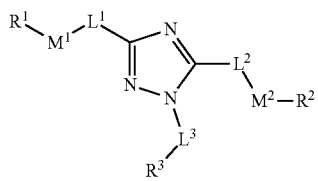

(III)

or a pharmaceutically acceptable salt or solvate thereof, wherein:

$L^1$, $L^2$ and $L^3$ are each independently selected from a bond, alkylene, or alkenylene;

$M^1$ and $M^2$ are each independently selected from —$NR^4$—, —$NR^4C(O)$—, —$N(C(O)R^1)$—, —$C(O)NR^4$—, —$NR^4C(O)NR^4$—, —$C(O)$—, —$C(=NR^4)$—, —$C(=NOR^4)$—, —$OC(O)$—, —$C(O)O$—, —$OC(O)O$—, —$OC(O)NR^4$—, —$NR^4C(O)O$—, —$S(O)_m$—, —$S(O)_mNR^4$—; or —$NR^4S(O)_m$—, provided that $M^1$ and $M^2$ are not both —$NR^4$—;

$R^1$ and $R^2$ are each independently selected from an alkyl, alkenyl, cycloalkyl, aryl, biphenyl; heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;

$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, heterocyclylalkyl, heteroaralkyl, heteroarylalkenyl, or heterowylalkynyl, wherein each cycloalkyl, aryl, heteroaryl, and heterocyclyl portion is optionally substituted with one or more $R^7$;

$R^4$ is each independently H, alkyl, wherein each alkyl is optionally substituted with one or more $R^5$;

$R^5$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —$COR^6$, —COOH, —$NH_2$, —$NHR^6$, —$NO_2$, —$NR^6R^6$, —$NR^6COR^6$, -(alkylene)$NR^6COR^6$, —$N^3$; —OH, $OR^6$, —$COOR^6$, —$OSO_3R^6$, oxo, $R^6$, —SH, —$SO_2R^6$, —$SO_3H$, —$SO_3R^6$, or —$SR^6$;

$R^6$ is each independently alkyl, alkenyl, alkynyl, haloalkyl, haloalkenyl, haloalkynyl; or alternatively two on the same N atom can together form a 3-6 membered N-heterocyclyl;

$R^7$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, —$SR^6$, cycloalkyl, heterocyclyl, aryl, or heteroaryl, wherein each cycloalkyl, heterocyclyl, aryl, and heteroaryl is optionally substituted with one or more $R^5$;

m is 0, 1, or 2; and wherein the compound is not N,N'-(1-phenyl-1H-1,2,4-triazole-3,5-diyl)dibenzamide, N-(3-benzamido-1-phenyl-1H-1,2,4-triazol-5-yl)furan-2-carboxamide, N-(5-cinnamamido-1-phenyl-1H-1,2,4-triazol-3-yl) benzamide, N-(1-phenyl-5-(phenylamino)-1H-1,2,4-triazol-3-yl)benzamide, 4-fluoro-N-(5-(4-methoxybenzamido)-1-phenyl-1H-1,2,4-triazol-3-yl) benzamide, N,N'-(1-phenyl-1H-1,2,4-triazole-3,5-diyl) bis(4-methylbenzamide), N-(5-((2-chlorobenzyl) amino)-1-phenyl-1H-1,2,4-triazol-3-yl)-2-fluorobenzamide, N-(3-benzamido-1-phenyl-1H-1,2,4-triazol-5-yl)-4-fluorobenzamide, N-(3-benzamido-1-phenyl-1H-1,2,4-triazol-5-yl)-4-nitrobenzamide, N-(3-benzamido-1-phenyl-1H-1,2,4-triazol-5-yl)-3-nitrobenzamide, and 4-((3-benzamido-1-phenyl-1H-1,2,4-triazol-5-yl)carbamoyl)benzoic acid.

In one embodiment, the compound of formula (III) has the structure of formula (IIIA):

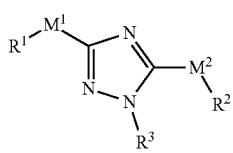

(IIIA)

or a pharmaceutically acceptable salt or solvate thereof, wherein:

$M^1$ and $M^2$ are each independently selected from —$NR^4$—, —$NR^4C(O)$— or —$C(O)NR^4$—, provided that $M^1$ and $M^2$ are not both —$NR^4$—;

$R^1$ and $R^2$ are each independently phenyl, optionally substituted with one or more $R^5$;

wherein at least one of $R^1$ or $R^2$ is substituted with —($C_1$-$C_6$ alkylene)NHCO($C_1$-$C_{10}$ alkyl) or —($C_1$-$C_6$ alkylene)N($C_1$-$C_3$ alkyl)CO($C_1$-$C_{10}$ alkyl);

$R^3$ is

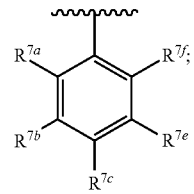

$R^4$ is each independently H or $C_1$-$C_3$ alkyl;

$R^5$ is each independently I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, —C(O)O($C_1$-$C_6$ alkyl), —CO($C_1$-$C_{10}$ alkyl), —NHCO($C_1$-$C_{10}$ alkyl), —N($C_1$-$C_3$ alkyl)CO($C_1$-$C_{10}$ alkyl), —($C_1$-$C_6$ alkylene)NHCO ($C_1$-$C_{10}$ alkyl) or —($C_1$-$C_6$ alkylene)N($C_1$-$C_3$ alkyl)CO ($C_1$-$C_{10}$ alkyl);

$R^{7a}$, $R^{7b}$, $R^{7e}$, and $R^{7e}$ is each independently H, I, Br, Cl, F, —$CH_2F$, —$CHF_2$, —$CF_3$, —$OCF_3$, —$N_3$, —CN, —OH, methyl, ethyl, propyl, $C_1$-$C_3$ haloalkyl, $C_1$-$C_3$ alkoxy, or $C_1$-$C_3$ haloalkoxy; and $R^{7c}$ is H, I, Br, Cl, F, —$CH_2F$, —$CHF_2$, —$CF_3$, —$OCF_3$, —$N_3$, —CN, —OH, $C_1$-$C_3$ alkyl, $C_1$-$C_3$ haloalkyl, $C_1$-$C_3$ alkoxy, $C_1$-$C_3$ haloalkoxy, 4-6 membered heterocyclyl, or 5-6 membered heteroaryl, wherein the heterocyclyl and heteroaryl is optionally substituted with one or more $R^5$.

In one embodiment, the compound of formula has the structure of formula (IIIB)

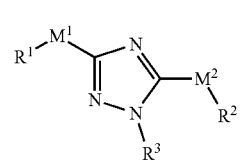

(IIIB)

or a pharmaceutically acceptable salt or solvate thereof, wherein:

$M^1$ and $M^2$ are each independently selected from —$NR^4$—, —$NR^4C(O)$— or —$C(O)NR^4$—, provided that $M^1$ and $M^2$ are not both —$NR^4$—;

$R^1$ and $R^2$ are each independently phenyl, optionally substituted with one or more $R^5$;

$R^3$ is phenyl, substituted with one or more $R^7$;

$R^4$ is each independently H or $C_1$-$C_3$ alkyl;

$R^5$ is each independently I, Br, Cl, F, —$CH_2F$, —$CHF_2$, —$CF_3$, —$C_1$-$C_6$ alkyl, alkynyl, —CN, —($C_1$-$C_3$ alkylene)-CN, —$NH_2$, —$NO_2$, —$N_3$, —OH, —$OCF_3$, —OMe, —$NMe_2$, —$NEt_2$, —C(O)O($C_1$-$C_6$ alkyl), —CO($C_1$-$C_{10}$ alkyl), —NHCO($C_1$-$C_{10}$ alkyl), —N($C_1$-$C_3$ alkyl)CO($C_1$-$C_{10}$ alkyl), —($C_1$-$C_6$ alkylene)NHCO ($C_1$-$C_{10}$ alkyl), or —($C_1$-$C_6$ alkylene)N($C_1$-$C_3$ alkyl) CO($C_1$-$C_{10}$ alkyl); and wherein at least one $R^7$ is heterocyclyl substituted with —CO($C_1$-$C_{10}$ alkyl) which is optionally further substituted with one or more $R^5$.

In some embodiment of the compounds of formula (III) and/or (IIIA), at least one of $R^1$ or $R^2$ is substituted with —($C_1$-$C_3$ alkylene)NHCO($C_1$-$C_8$ alkyl) or —($C_1$-$C_3$ alkylene)N($C_1$-$C_3$ alkyl)CO($C_1$-$C_8$ alkyl). In some embodiments, at least one of $R^1$ or $R^2$ is substituted with —$CH_2$NHCO($C_1$-$C_8$ alkyl) or —$CH_2$N($C_1$-$C_3$ alkyl)CO($C_1$-$C_8$ alkyl).

In some embodiment of the compounds of formula (III) and/or (III), $R^1$ is phenyl substituted with —($C_1$-$C_3$ alkylene)NHCO($C_1$-$C_8$ alkyl) or —($C_1$-$C_3$ alkylene)N($C_1$-$C_3$ alkyl)CO($C_1$-$C_8$ alkyl). In some embodiments, $R^1$ is phenyl substituted with —$CH_2$NHCO($C_1$-$C_8$ alkyl) or —$CH_2$N($C_1$-$C_3$ alkyl)CO($C_1$-$C_8$ alkyl). In some embodiments, $R^1$ is phenyl substituted with $CH_2$NHCO($C_4$-$C_8$ alkyl) or —$CH_2$N($C_1$-$C_3$ alkyl)CO($C_4$-$C_8$ alkyl).

In some embodiment of the compounds of formula (III) and/or (IIIA), $R^2$ is phenyl substituted with —($C_1$-$C_3$ alkylene)NHCO($C_1$-$C_8$ alkyl) or —($C_1$-$C_3$ alkylene)N($C_1$-$C_3$ alkyl)CO($C_1$-$C_8$ alkyl). In some embodiments, $R^2$ is phenyl substituted with —$CH_2$NHCO($C_1$-$C_8$ alkyl) or —$CH_2$N($C_1$-$C_3$ alkyl)CO($C_1$-$C_8$ alkyl). In some embodiments, $R^2$ is phenyl substituted with $CH_2$NHCO($C_4$-$C_8$ alkyl) or —$CH_2$N($C_1$-$C_3$ alkyl)CO($C_4$-$C_8$ alkyl).

In some embodiment of the compounds of formula (III) and/or (IIIA), $R^{7a}$, $R^{7b}$, $R^{7c}$, $R^{7e}$, and $R^{7c}$ is each independently H, I, Br, Cl, F, —$CH_2$F, —$CHF_2$, —$CF_3$, —$OCF_3$, —$N_3$, —CN, —OH, methyl, ethyl, propyl, —≡CH; —CN, —$NH_2$, —$NO_2$, —$N_3$, —OH, —$OCF_3$, —OMe, —$NMe_2$, or —$NEt_2$. In some embodiments, $R^{7a}$, $R^{7b}$, $R^{7e}$, and $R^{7e}$ is each independently H.

In some embodiment of the compounds of formula (III) and/or (IIIB), $R^3$ is phenyl, substituted with 6-membered heterocyclyl and wherein the 6-membered heterocyclyl is substituted with —CO($C_1$-$C_{10}$ alkyl). In one embodiment, $R^3$ is phenyl substituted with a $R^3$ is phenyl, substituted with 6-membered heterocyclyl comprising one or two heteroatoms selected from O, N, and S, and wherein the 6-membered heterocyclyl is substituted with —CO($C_1$-$C_{10}$ alkyl).

In some embodiment of the compounds of formula (III) and/or (IIIB), $R^3$ is phenyl substituted with a piperidine or a piperazine, wherein the piperidine or the piperazine is substituted with —CO($C_1$-$C_{10}$ alkyl). In one embodiment, $R^3$ is phenyl substituted with a piperidine or a piperazine, wherein the piperidine or the piperazine is substituted with —CO ($C_4$-$C_{10}$ alkyl).

In some embodiment of the compounds of formula (III) and/or (IIIB), $R^1$ and $R^2$ are each independently phenyl, optionally substituted with one or more substitutent selected from I, Br, Cl, F, —$CH_2$F, —$CHF_2$, —$CF_3$, —$OCF_3$, —CN, —OH, methyl, ethyl, propyl, —C≡CH; —CN, —$NH_2$, —$NO_2$, —$N_3$, —OH, —$OCF_3$, —OMe, —$NMe_2$, or —$NEt_2$.

In one embodiment, the compound of formula (III), excludes compounds of Table A. In one embodiment, the compound of formula (III), excludes compounds of Table B.

In some embodiments, various embodiments disclosed herein for formula (I), (I'), (IA), (IB), (IB'), (IC), (ID), (IE), and/or (IF) can be applied to the compounds of formula (III), (IIIA), and/or (IIIB).

In one embodiment of the compounds of formula (III), (IIIA), and/or (IIIB), the compound is selected from Table 3B below, or a pharmaceutically acceptable salt or solvate thereof.

TABLE 3B

160

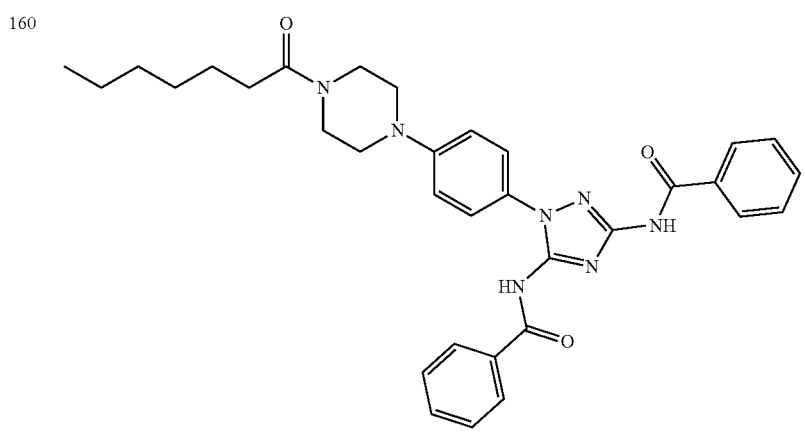

161

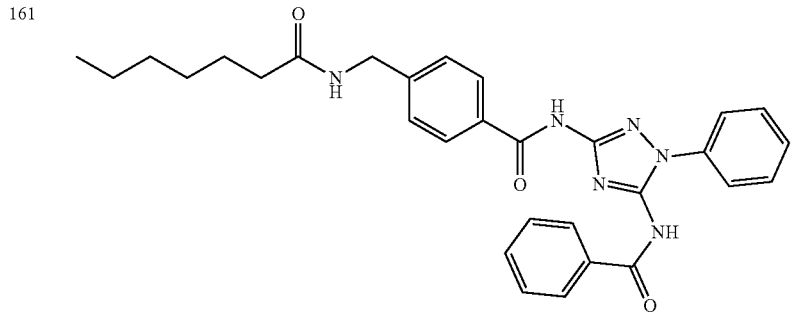

TABLE 3B-continued

162
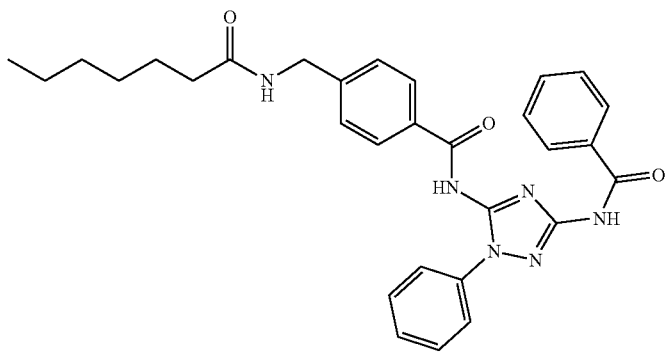

In one embodiment, the compound of the invention excludes compounds in Tables A-D. In some embodiments, the compound of formula (I), (III), (I'), (IA), (IB), (IB'), (IC), (ID), (IE), and (IF) excludes compounds in Table A. In some embodiments, the compound of formula (I), (III) (I'), (IA), (IB), (IB'), (IC), (ID), (IE), and (IF) excludes compounds in Table B. In other embodiments, the compound of formula (II) and (IIA) excludes compound of Table C. In other embodiments, the compound of formula (II) and (IIA) excludes compound of Table D.

TABLE A

B
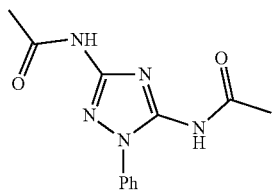

G
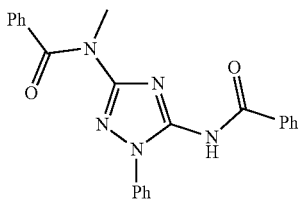

J
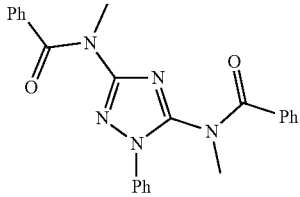

D
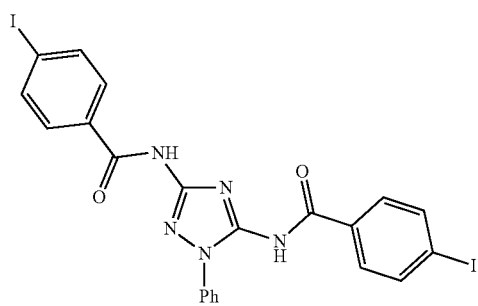

TABLE A-continued

E
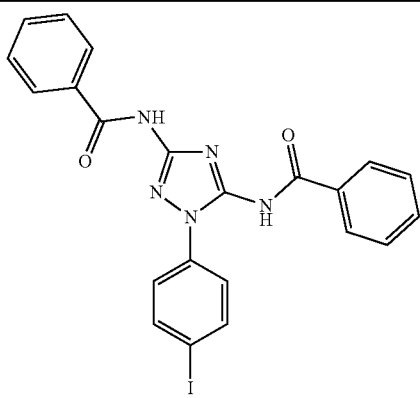

H
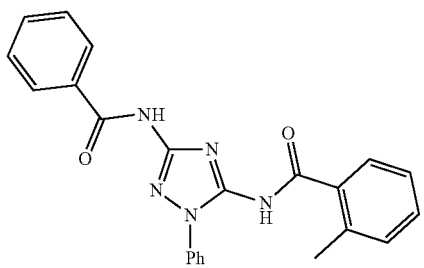

K
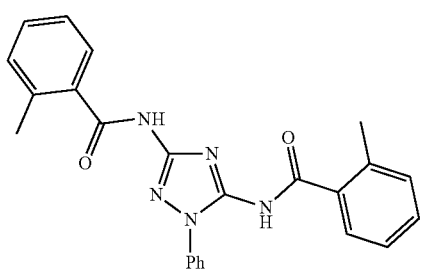

F

TABLE A-continued
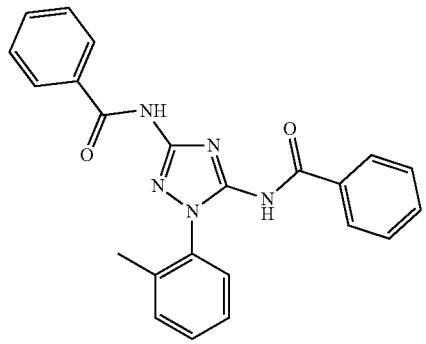   M
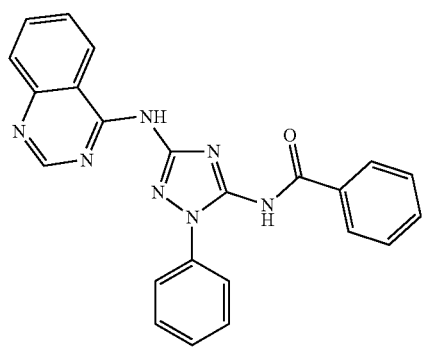   I
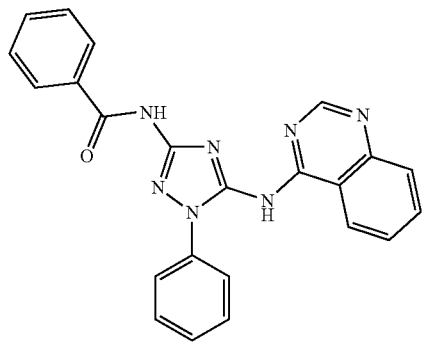   L
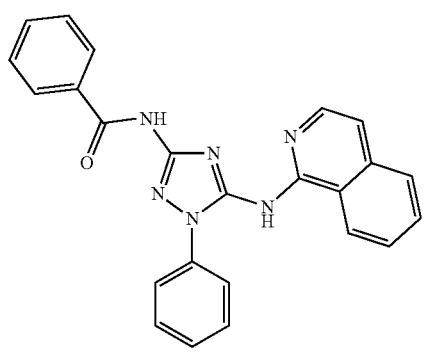   U
TABLE A-continued
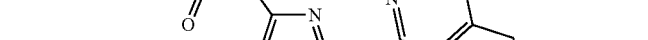   V
   W
   X
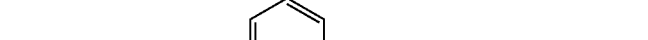   Z TABLE A-continued
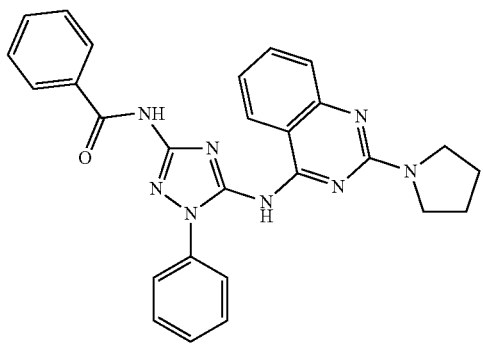
A1
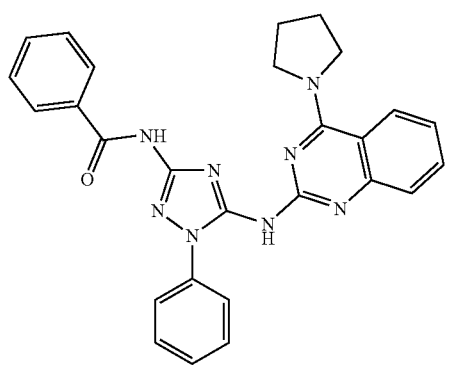
B1
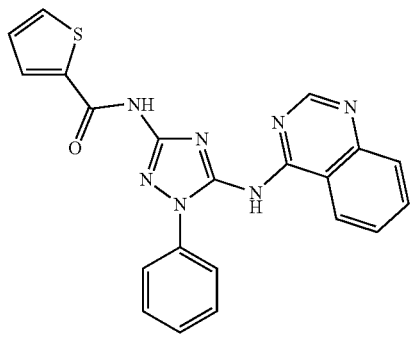
C1
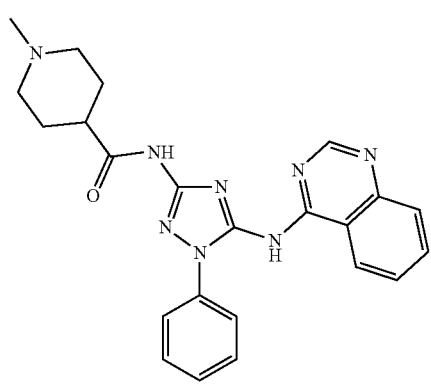
D1
TABLE A-continued
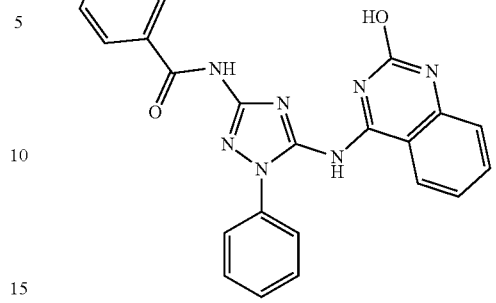
E1
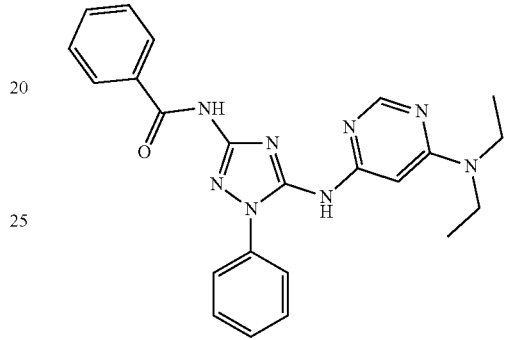
F1
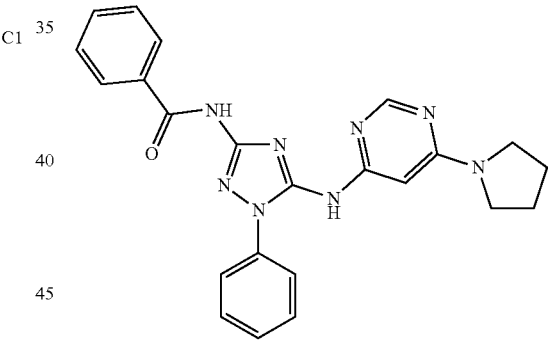
G1
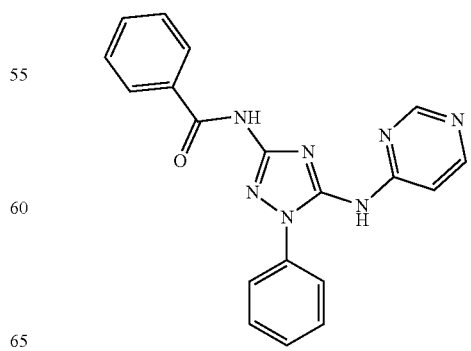
H1

TABLE A-continued
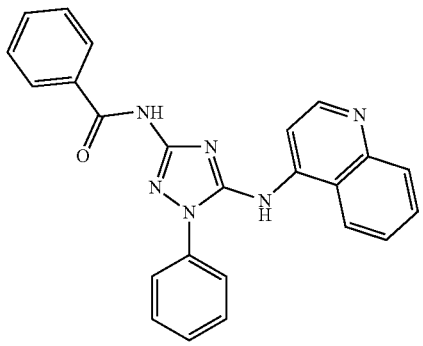 I1
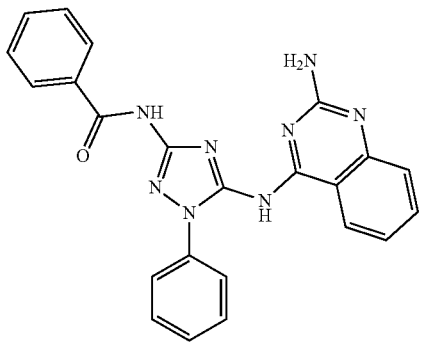 J1
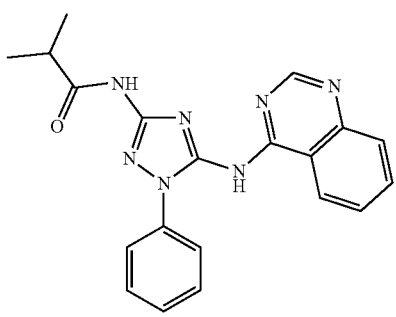 K1
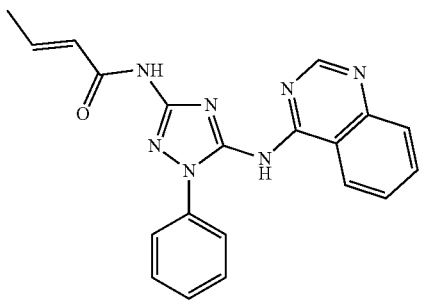 L1
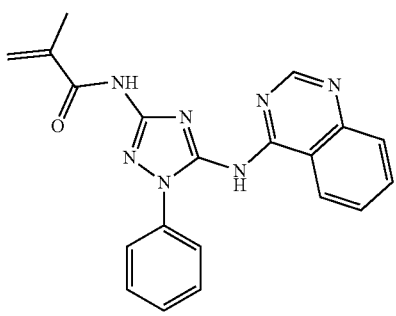 M1
TABLE A-continued
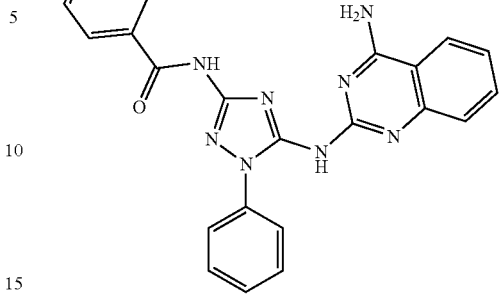 N1
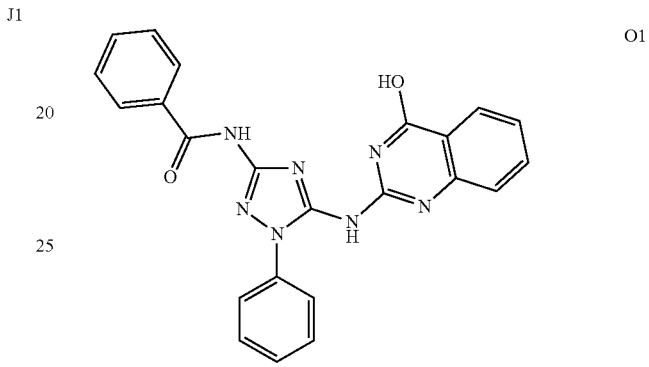 O1
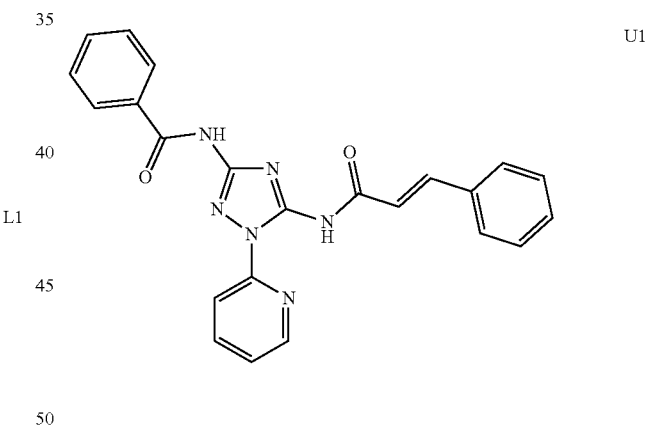 U1
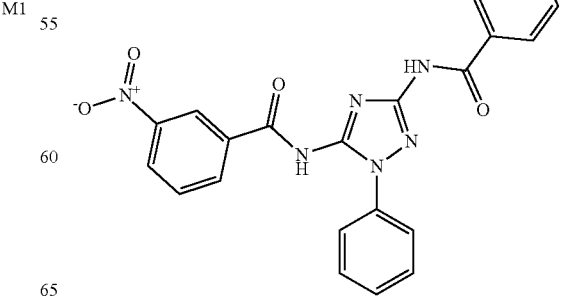 V1

TABLE A-continued
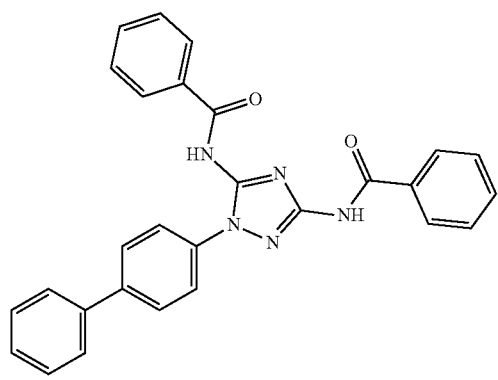
X1
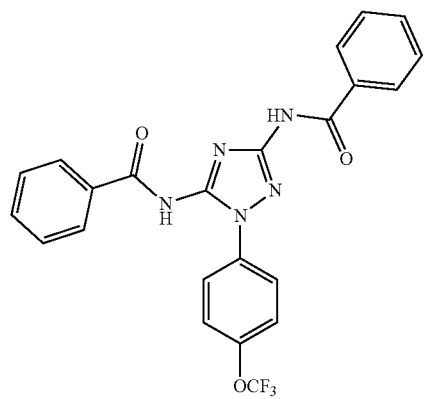
Z1
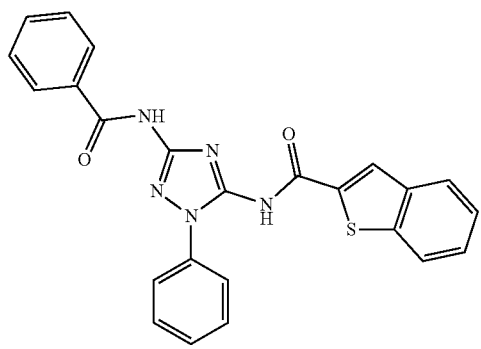
A2
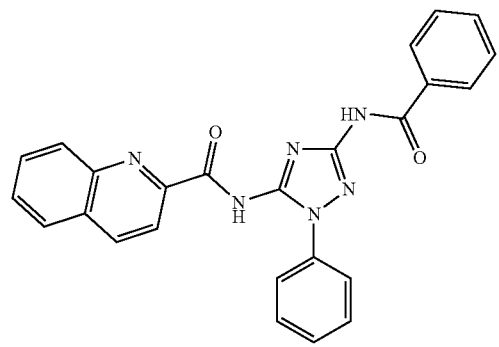
B2
TABLE A-continued
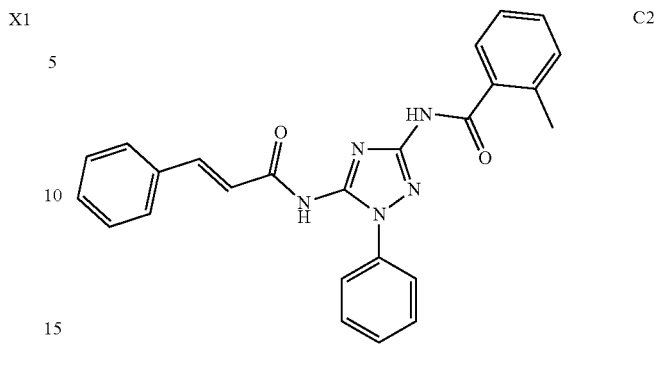
C2
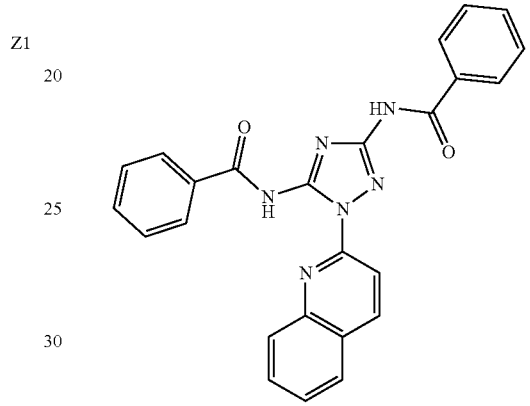
D2
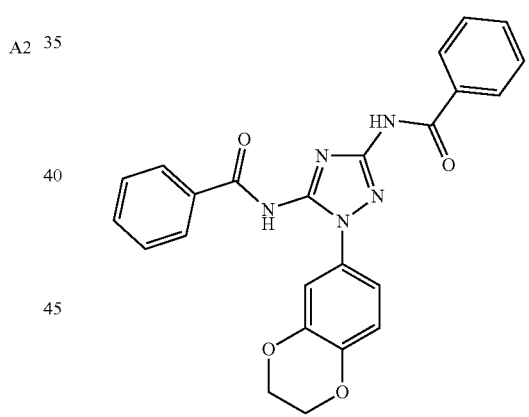
E2
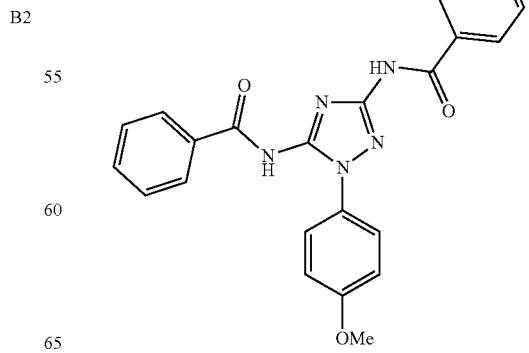
F2

TABLE A-continued
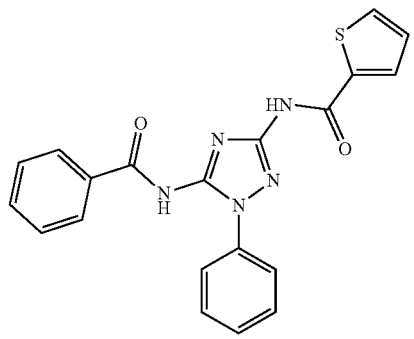
G2
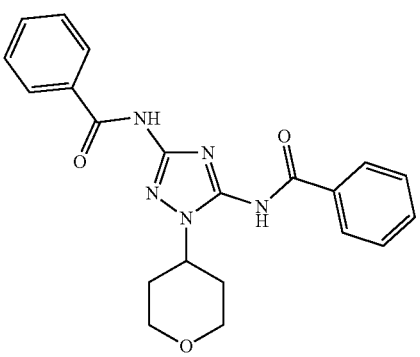
I2
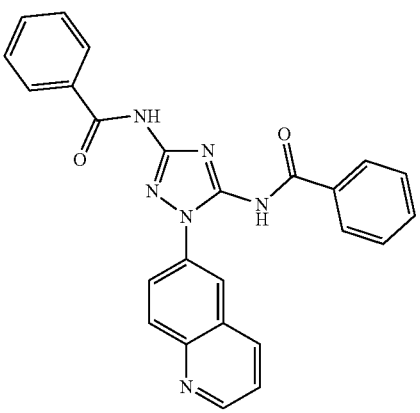
J2
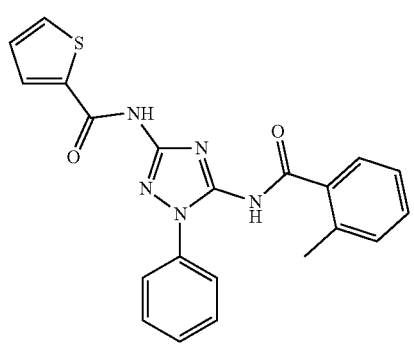
K2
TABLE A-continued
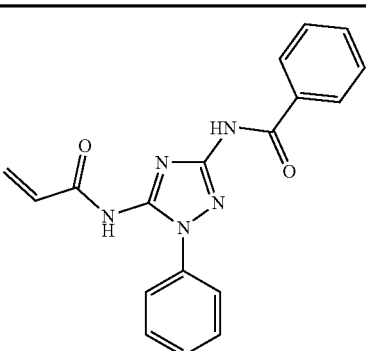
L2

TABLE A-continued
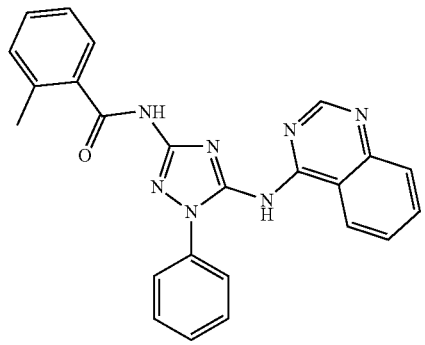
R2
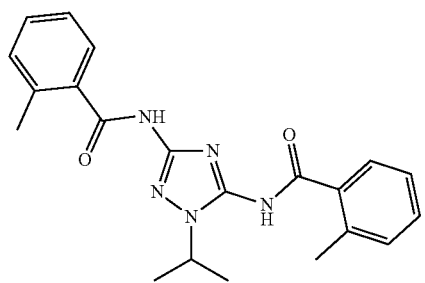
W2
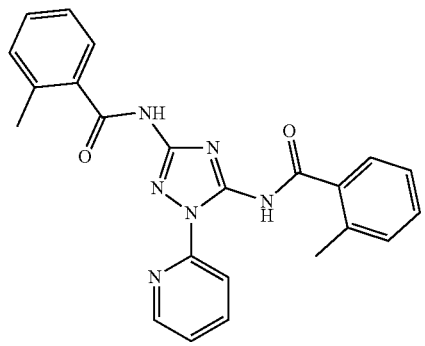
X2
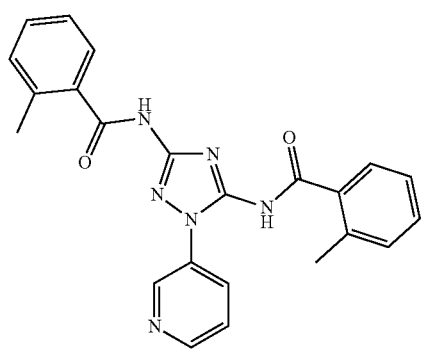
Y2
TABLE A-continued
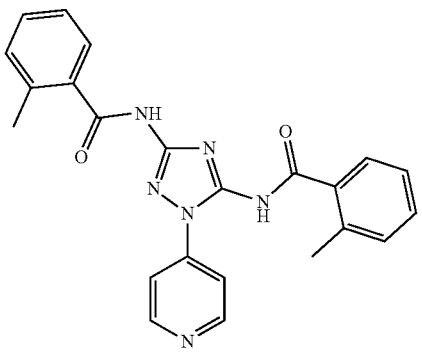
B3
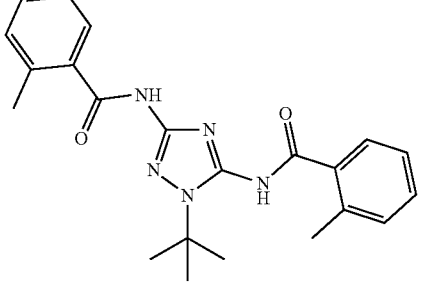
D3
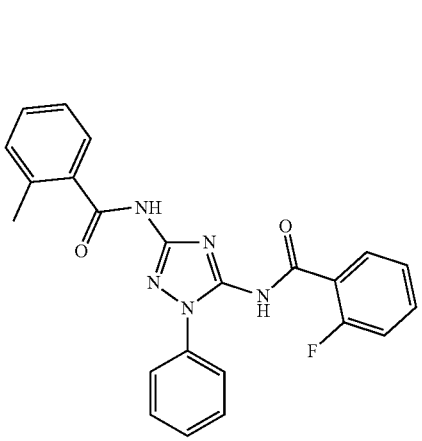
E3
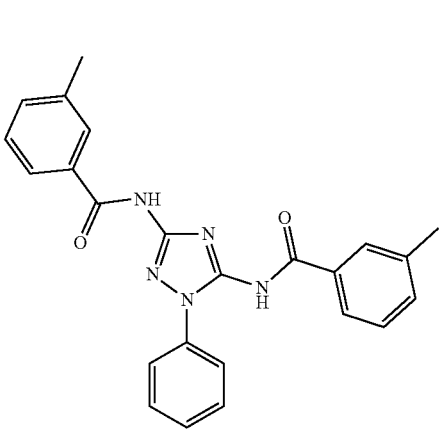
F3

TABLE A-continued
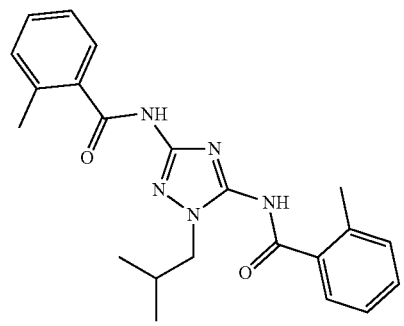
I3
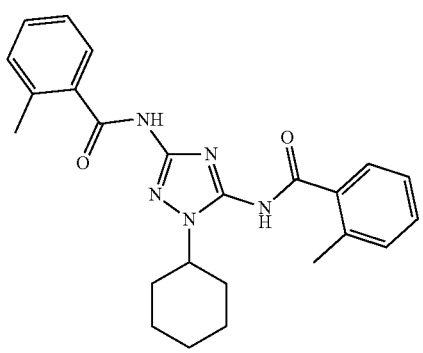
J3
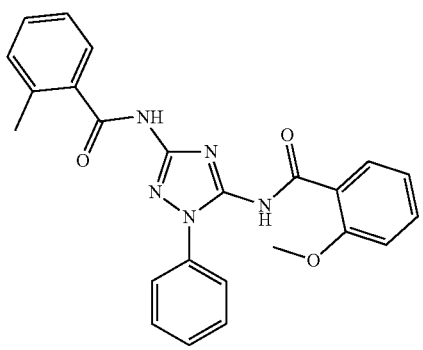
K3
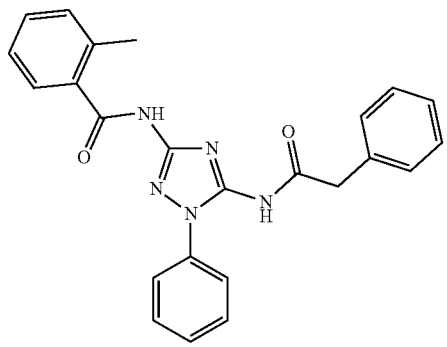
L3
TABLE A-continued
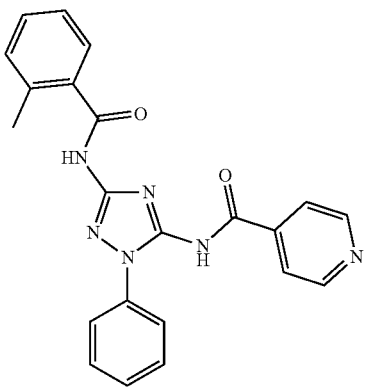
M3
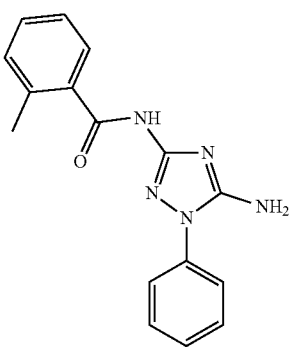
N3
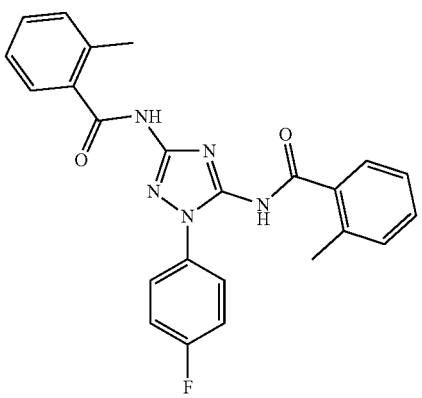
O3
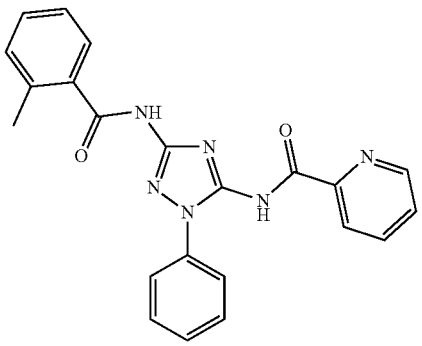
P3

TABLE A-continued
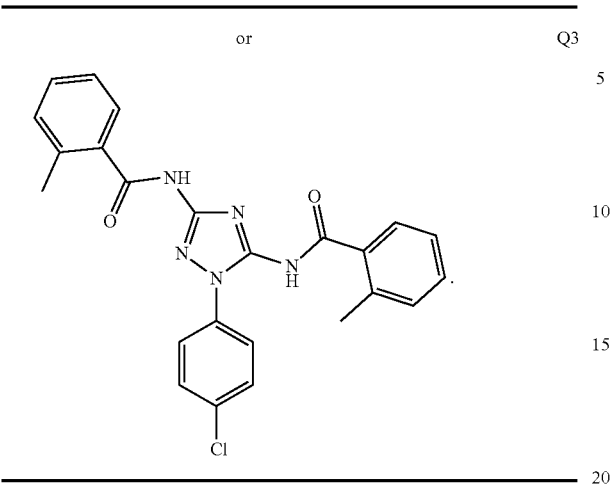
TABLE B
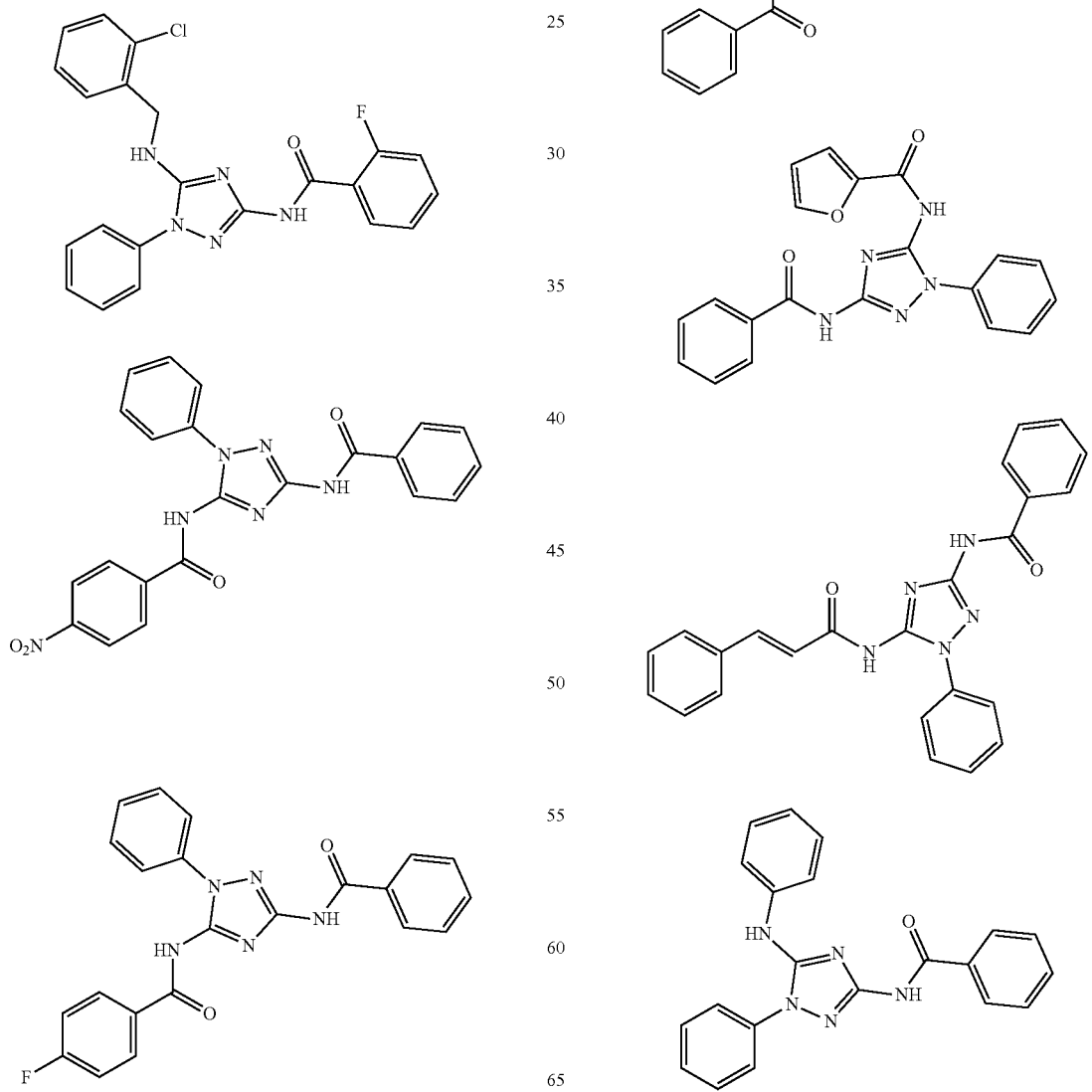

TABLE B-continued
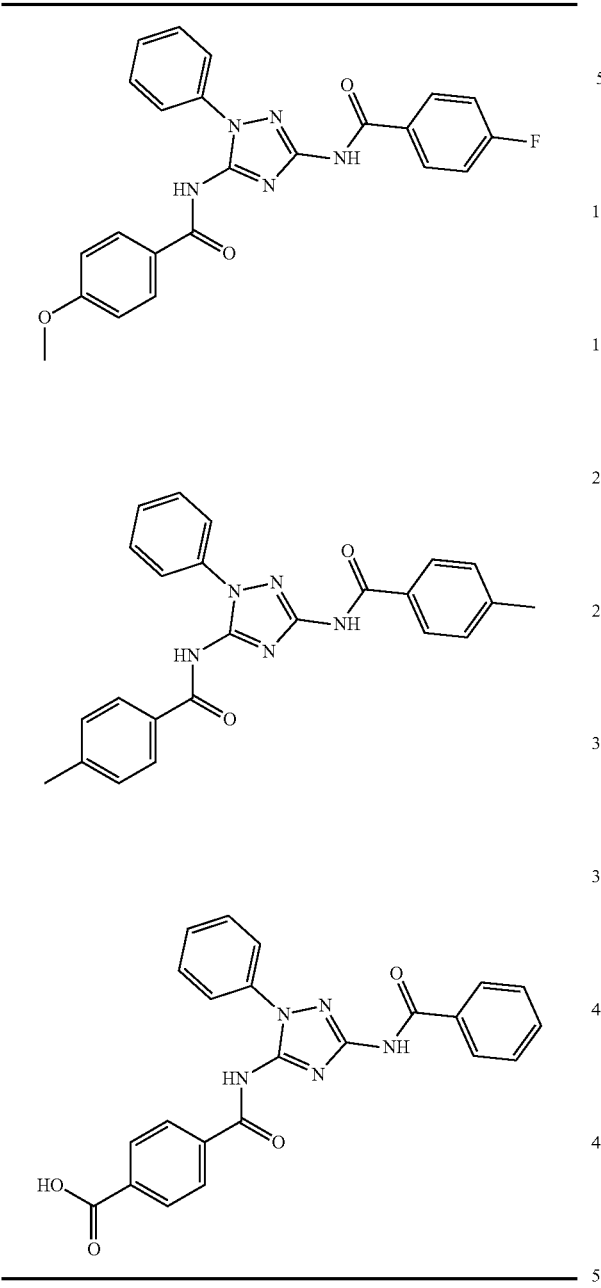
TABLE C
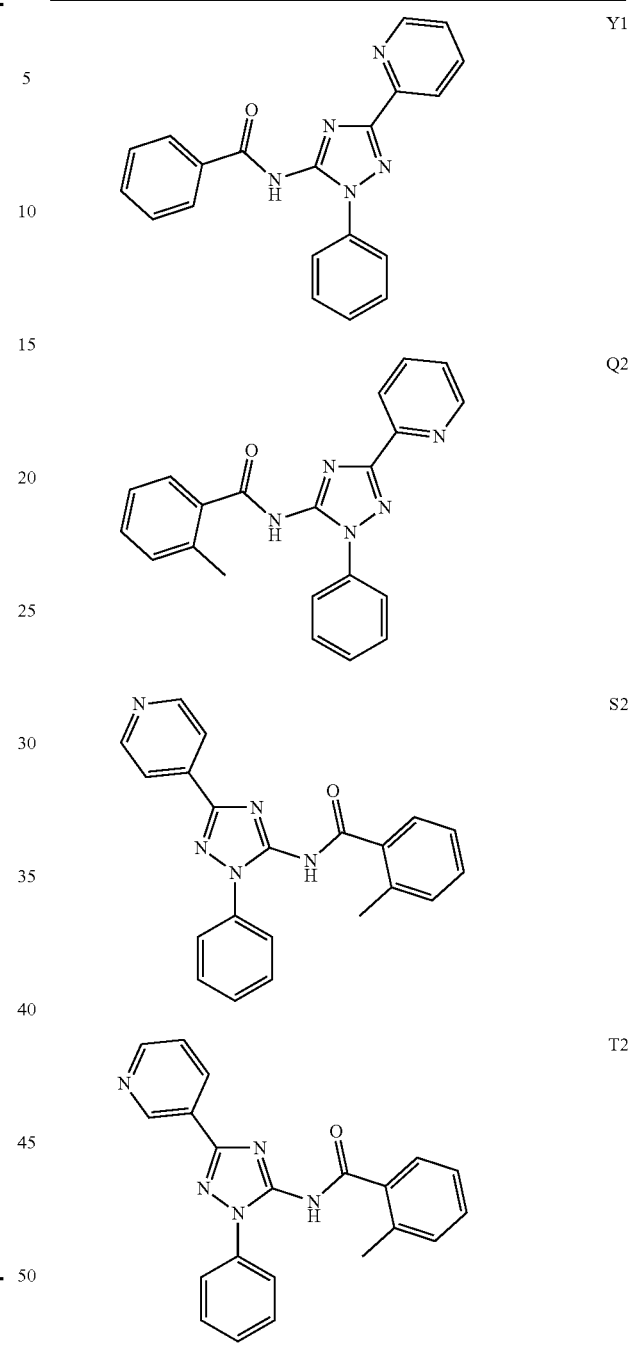

TABLE C-continued
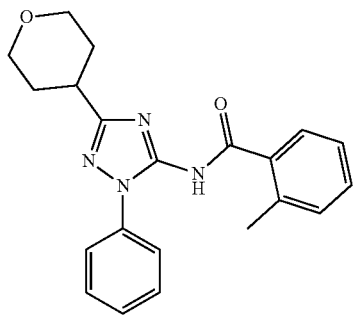
V2
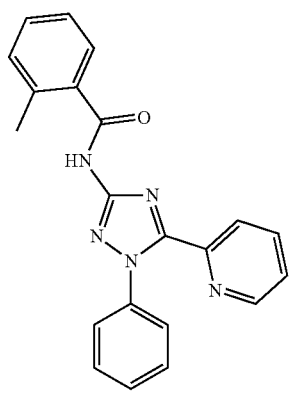
A3
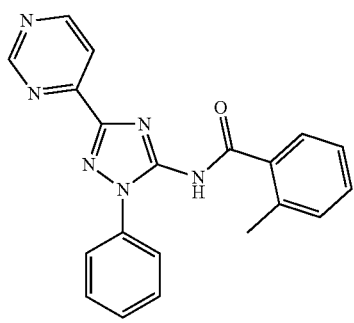
G3
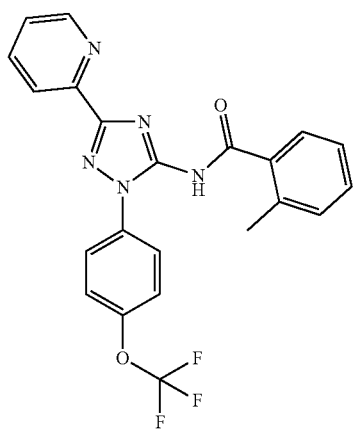
H3
TABLE C-continued
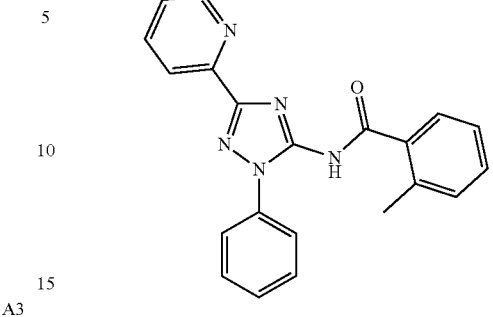
R3
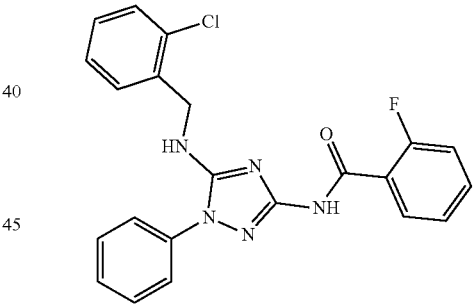
S3
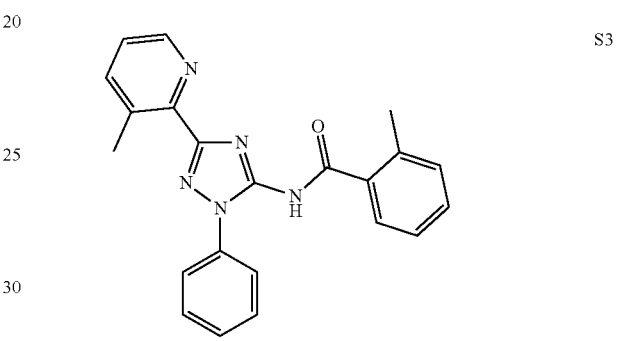
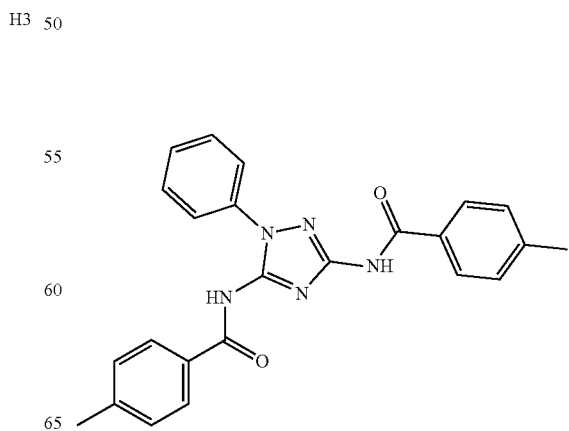

TABLE D

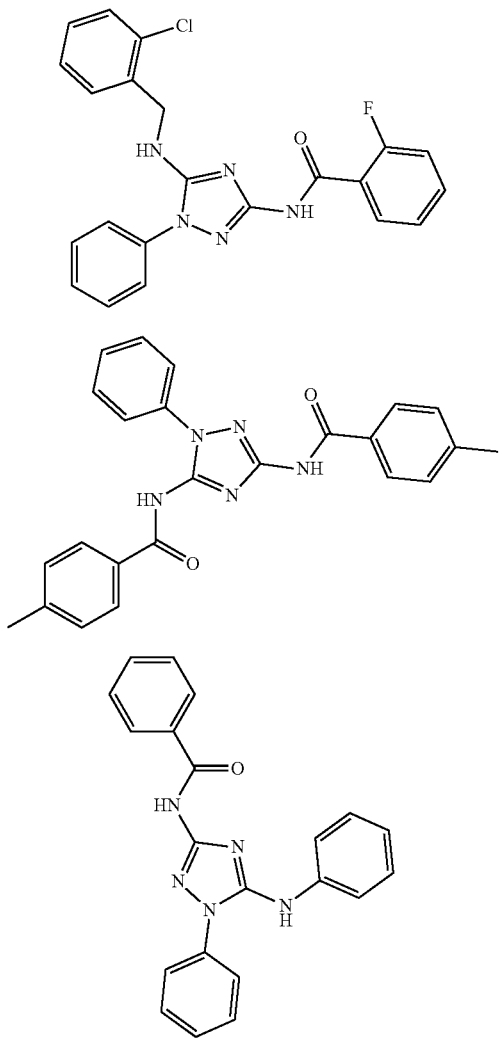

In another embodiment, the compounds described above may have particular functional characteristics. In one embodiment, the compound may have an oral bioavailability of about 10% to about 70% in a patient. In another embodiment, the compound may have an oral bioavailability of about 10% to about 50%. In another embodiment, the compound may have an oral bioavailability of about 10% to about 30%. In another embodiment, the compound may have an oral bioavailability greater than about 20%. In another embodiment, the compound may have an oral bioavailability in a patient with any of the ranges above when administered in the assay as in Example 6.

In another embodiment, when administered orally, the compound may have a Tmax of about 0.2 hrs to about 2 hrs in a patient. In another embodiment, the compound may have a Tmax of about 0.3 hrs to about 1 hr in a patient. In another embodiment, the compound may have a Tmax of about 0.4 hrs to about 0.6 hr in a patient. In another embodiment, the compound may have a Tmax in a patient with any of the ranges above when administered in the assay as in Example 6.

In another embodiment, when administered orally, the compound may have a Cmax of about 100 ng/mL to about 1,000 ng/mL in a patient. In another embodiment, when administered orally, the compound may have a Cmax of about 150 ng/mL to about 500 ng/mL in a patient. In another embodiment, when administered orally, the compound may have a Cmax of about 200 ng/mL to about 400 ng/mL in a patient. In another embodiment, the compound may have a Cmax in a patient with any of the ranges above when administered in the assay as in Example 6.

In another embodiment, the compound may have a half-life in human liver microsomes greater than about 100 minutes. In another embodiment, the compound may have a half-life in human liver microsomes greater than about 300 minutes. In another embodiment, the compound may have a half-life in human liver microsomes greater than about 500 minutes.

In another embodiment, the compound may have half-life in human liver microsomes of about 100 minutes to about 1,000 minutes. In another embodiment, the compound may have half-life in human liver microsomes of about 200 minutes to about 800 minutes. In another embodiment, the compound may have half-life in human liver microsomes of about 500 minutes to about 700 minutes.

In another embodiment, the compound may have a half-life in rat liver microsomes greater than about 100 minutes. In another embodiment, the compound may have a half-life in rat liver microsomes greater than about 300 minutes. In another embodiment, the compound may have a half-life in rat liver microsomes greater than about 500 minutes.

In another embodiment, the compound may have half-life in rat liver microsomes of about 100 minutes to about 1,000 minutes. In another embodiment, the compound may have half-life in rat liver microsomes of about 200 minutes to about 800 minutes. In another embodiment, the compound may have half-life in rat liver microsomes of about 500 minutes to about 700 minutes.

In a specific embodiment, the compound with any of the functional characteristics as described above may be a compound of formula (I), (I'), (IA), (IB), (IB'), (IC), (ID), (IE), (IF), (III), (IIIA), (IIIB), (II) and/or (IIA), or a pharmaceutically acceptable salt or solvate thereof. In a specific embodiment, the compound with the functional characteristics as described above may from Table 1, Table 2, Table 3A anchor Table 33.

Methods

Ubiquitination is crucial for a plethora of physiological processes, including cell survival and differentiation and innate and adaptive immunity. Proteins are built-up to cater for the structural and biochemical requirements of the cell and they are also broken-down in a highly-regulated process serving more purposes than just destruction and space management. Proteins have different half-lives, determined by the nature of the amino acids present at their N-termini. Some will be long-lived, while other will rapidly be degraded. Proteolysis not only enables the cell to dispose of misfolded or damaged proteins, but also to fine-tune the concentration of essential proteins within the cell, such as the proteins involved in the cell cycle. This rapid, highly specific degradation can be achieved through the addition of one to several ubiquitin molecules to a target protein. The process is called ubiquitination.

In recent years, considerable progress has been made in the understanding of the molecular action of ubiquitin in signaling pathways and how alterations in the ubiquitin system lead to the development of distinct human diseases. It has been shown that ubiquitination plays a role in the onset and progression of cancer, metabolic syndromes, neurodegenerative diseases, autoimmunity, inflammatory disorders, infection and muscle dystrophies (Popovic et al. *Nature Medicine* 20, 1242-1253 (2014)).

Ubiquitin-protein (E3) ligases are a large family of enzymes that select various proteins for ubiquitination. These ubiquitin ligases, called "Ub ligases" are known to have a role in various diseases and conditions, including but not limited to, cancer, inflammation and infectious diseases.

One specific Ub ligase is Parkin ligase. Parkin ligase is a component of a multiprotein "E3" ubiquitin ligase complex, which in turn is part of the ubiquitin-proteasome system that mediates the targeting of proteins for degradation. Although the specific function of Parkin ligase is not known, mutations in Parkin ligase are linked to various diseases, such as Parkinson's disease, cancer and mycobacterial infection. Parkin ligase is thus an attractive target for therapeutic intervention.

Further, there are various known methods for regulating ligases known in the art. Many ligases, particularly ligases involved in the Ubiquitin-Proteasome Pathway System (UPS), are known to have Zinc Finger (ZnF) domains that stabilize critical protein binding regions in that ligase.

ZnF domains coordinate zinc ions and this coordination stabilizes functional activity of the protein. The functional activity provided by proteins with ZnF domains can include the regulation of important cellular signaling pathways, such as recognizing ubiquitins, regulation of DNA, such as transcription and repair, and acting as cellular redox sensors. The binding of zinc to ZnF domains, or simply just regulating how zinc interacts with the ZnF domains, are essential to ligases involved in the UPS.

Parkin ligase is known to have one or more ZnF domains. The present disclosure focuses on two different strategies for modulating ZnF domains in Parkin ligase. One strategy of the present disclosure includes using chelating compounds that bind to the ZnF domains and thus disallowing the binding of zinc, or causing the dissociation of zinc, such as Zn, or $Zn^{2+}$, from the ZnF domain. Another strategy of the present disclosure includes using compounds that bind or react with a cysteine amino acid residue in the ZnF domain. One or more cysteine residues (and sometimes with the assistance of histidine residues) are essential in ZnF domains for binding to and/or coordinating to the zinc ion. The zinc ion (usually $Zn^{2+}$) can coordinate with multiple cysteine or histidine residues. The more cysteine residues there are in the domain, the more flexible is the ZnF domain, Ligases, such as Parkin ligase are thought to have multiple cysteine residues coordinated with zinc in their ZnF domains. This flexibility in the ZnF domains of Parkin ligase is thought to allow the domain to be reversible, and is thus is one possible mechanism for regulating Parkin ligase. For example, efforts directed to this approach are disclosed in U.S. patent application Ser. No. 14/961,285; U.S. Provisional Application No. 62/237,400; U.S. Provisional Application No. 62/222,008, and U.S. Provisional Application No. 62/087,972, all of which are hereby incorporated by reference in their entirety.

The present disclosure relates to the use of one or more agents or one or more compounds of formula (I), (I'), (IA), (IB), (IB'), (IC), (ID), (IE), and (IF), (III), (IIIA), and (IIIB), or (II) and (IIA), or a pharmaceutically acceptable salt or solvate thereof, which have electrophilic, chelation or both electrophilic and chelation properties that can interact with the zinc ion and/or the cysteine residue(s) in a Parkin ligase. In one embodiment, compounds of the present disclosure modulate Parkin ligase's activity. Specifically, without bound to any theory, it is believed that not allowing a zinc ion to coordinate in at least one of Parkin ligase's ZnF domains induces its activity. The present disclosure is thus directed to a method for activating or modulating Parkin ligase by the chelation of Zn followed by its removal from the ZnF domain, or through electrophilic attack at the cysteine amino acid(s) that holds the Zn in place.

Accordingly, in one embodiment of the present disclosure, a method of modulating or activating a Parkin ligase comprising administering to a subject in need thereof a therapeutically effective amount of one or more compounds of formula (I), (I'), (IA), (IB), (IB'), (IC), (ID), (IF), and (IF), (III), (IIIA), and (IIIB), or (II) and (IIA), or a pharmaceutically acceptable salt or solvate thereof, is disclosed. In another embodiment, a method of modulating or activating a Parkin ligase comprising administering to a subject in need thereof a therapeutically effective amount of one or more compounds of formula (I), (I'), (IA), (IB), (IB'), (IC), (II)), (IE), and (IF), (III), (IIIA), and (IIIB), or (II) and (IIA), or a pharmaceutically acceptable salt or solvate thereof, that disrupt at least one Parkin ligase zinc finger is disclosed. In another embodiment, a method of activating a Parkin ligase comprising administering to a subject two or more compounds that disrupt at least one Parkin ligase zinc finger is disclosed, wherein at least one of the compound is selected from a compound of formula (I), (I'), (IA), (IB), (IF), (IC), (ID), (IE), and (IF), (III), (IIIA), and (IIIB), or at) and (IIA), or a pharmaceutically acceptable salt or solvate thereof.

The present disclosure relates to the use of one or more agents or one or more compounds of formula (I), (I'), (IA), (IB), (IB'), (IC), (ID), (IE), and (IF), (III), (IIIA), and (IIIB), or (II) and (IIA), or a pharmaceutically acceptable salt or solvate thereof to promote parkin E3 ligase enzyme activity.

In a specific embodiment, the compounds of the present disclosure can be an electrophile or a chelator. In another embodiment, the compounds of the present disclosure can function as both an electrophile and as a chelator. For example, the compounds of the present disclosure can include multiple functional groups wherein at least one functional group has chelating properties and at least one other functional group has electrophilic properties.

In another specific embodiment, the compound useful for methods in modulating or activating Parkin ligase as disclosed herein is selected from Tables 1-3, or a pharmaceutically acceptable salt or solvate thereof.

In another embodiment, the compound of the present disclosure is useful in a method to increase the Parkin ligase reaction with the Activity-based Ubiquitin vinyl sulfone probe. See e.g., Example 2.

In another embodiment, the one or more compounds of the present disclosure can coordinate with a Zn ion, and/or bind or react with one or more cysteine residues. In a specific embodiment the Zn ion may be either a $Zn^+$ or a $Zn^{2+}$ ion. In another embodiment, the compound can coordinate to a Zn ion is a monodentate, bidentate, or tridentate ligand.

In another embodiment, the compound of the present disclosure can bind and/or react with a thiol group in more than one cysteine residues. In another embodiment, the compound can bind and/or react with a thiol group in two cysteine residues. In another embodiment, the compound can bind and/or react with a thiol group in three cysteine residues. In another embodiment, the compound can bind and/or react with a thiol group in four cysteine residues. In another specific embodiment, the compound can bind or react with one or more cysteine residues in one or more domains selected from the group consisting amino acids 141-225, amino acids 238-293, amino acids 313-377, and amino acids 418-449 of human Parkin ligase. See http://www.uniprot.org/uniprot/O60260.

The methods of the present disclosure also include activating auto-ubiquitinization of a Parkin ligase by administering to a subject in need thereof a therapeutically effective amount of one or more compounds of formula (I), (I'), (IA), (IB), (IB'), (IC), (ID), (IE), and (IF), (III), (IIIA), and (IIIB), or (II) and (IIA), or a pharmaceutically acceptable salt or solvate thereof.

In a specific embodiment, the one or more compounds of the present disclosure can disrupt at least one Parkin ligase zinc finger. For example, Phospho Ubiquitin (pUB), an endogenous cellular regulator of Parkin, can be added to Parkin ligase which can activate Parkin ligase and its auto-ubiquitinization. In one embodiment, one or more compounds can be administered to a subject in need thereof that acts synergistically with Phospho Ubiquitin (pUB) in activating the Parkin ligase. See, e.g., Example 3. In one embodiment, the one or more compounds that acts synergistically with pUB in activating the Parkin ligase is a compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof. In another embodiment, one or more compounds of the present disclosure can be administered with pUB to synergistically increase the activation of Parkin ligase and/or its auto-ubiquitinization.

In another specific embodiment, the activation of the Parkin ligase treats or reduces the incidence of one or more diseases or ailments selected from the group consisting of Alzheimer's Dementia, Parkinson's disease, Huntington Disease, Amyotrophic Lateral Sclerosis (ALS), Freidreich's ataxia, Spinocerebellar Ataxia, Multiple Systems Atrophy, PSP, Tauopathy, Diffuse Lewy Body Disease, Lewy Body dementia, any disorder characterized by abnormal accumulation of α-synuclein, disorders of the aging process, stroke, bacterial infection, viral infection, Mitochondrial related disease, mental retardation, deafness, blindness, diabetes, obesity, cardiovascular disease, multiple sclerosis, Sjogrens syndrome, lupus, glaucoma, including pseudoexfoliation glaucoma, Leber's Hereditary Optic Neuropathy, and rheumatoid arthritis.

In one embodiment, a method of treating Parkinson's disease is provided, comprising administering to a subject in need thereof a therapeutically effective amount of one or more compounds of formula (I), (I'), (IA), (IB), (IB'), (IC), (ID), (IE), and (IF), (III), (IIIA), and (IIIB), or (II) and (IIA), or a pharmaceutically acceptable salt or solvate thereof.

Without bound to any theory, loss of dopamine neurons are believe to lead to Parkinson's disease, which can be caused by damaged mitochondria. Damaged mitochondria leads to dopamine neuron loss across etiologies in Parkinson's Disease patients. In a normal dopamine neurons, Parkin is activated in response to damaged mitochondria leading to their removal via mitophagy (e.g., mitochondrial autophagy).

Park2 mutations are responsible for 50% of autosomal recessive early onset of Parkinson's, thus, without bound to any theory, Parkin enzyme is believed to play a key role in maintenance of dopamine neuron health. Accordingly, restoring Parkin function can delay or prevent dopamine neuron loss.

In some embodiments, the compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof delays or prevents dopamine neuron loss in a subject in need thereof, comprising administering a therapeutically effective amount of the compound to the subject. In some embodiments, the compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof restores dopamine neuronal balance in a subject in need thereof, comprising administering a therapeutically effective amount of the compound to the subject.

In some embodiments, the compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof slows the progression of Parkinson's Disease in a subject in need thereof, comprising administering a therapeutically effective amount of the compound to the subject. In some embodiments, the slowing of the progression is in genetic and sporadic Parkinson's Disease.

In some embodiments, the compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof promotes removal of damaged mitochondria in a subject in need thereof, comprising administering a therapeutically effective amount of the compound to the subject.

In some embodiments, the compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof enhances mitophagy in a subject in need thereof.

In a specific embodiment, the bacterial infection is *Mycobacterium* infection. In another specific embodiment the viral infection is HIV, Hepatitis B infection or Hepatitis C infection. Another embodiment of the present invention includes methods of treating and/or reducing the incidence of cancer, specifically comprising administering to a subject in need thereof a therapeutically effective amount of one or more compounds that disrupt at least one Parkin ligase zinc finger and induces Parkin ligase activity. In a specific embodiment, the activated Parkin ligase suppresses the growth of one or more tumors and/or prevents metastasis of one or more tumors.

In another embodiment the cancer may be selected from one or more of the group consisting of Acute Lymphoblastic Leukemia, Acute Myeloid Leukemia, Adrenocortical Carcinoma, AIDS-Related Cancers, Kaposi Sarcoma, Lymphoma, Anal Cancer, Appendix Cancer, Astrocytomas, Childhood Atypical Teratoid/Rhabdoid Tumor, Basal Cell Carcinoma, Skin Cancer (Nonmelanoma), Childhood Bile Duct Cancer, Extrahepatic Bladder Cancer, Bone Cancer, Ewing Sarcoma Family of Tumors, Osteosarcoma and Malignant Fibrous Histiocytoma, Brain Stem Glioma, Brain Tumors, Embryonal Tumors, Germ Cell Tumors, Craniopharyngioma, Ependymoma, Bronchial Tumors, Burkitt Lymphoma (Non-Hodgkin Lymphoma), Carcinoid Tumor, Gastrointestinal Carcinoma of Unknown Primary, Cardiac (Heart) Tumors, Lymphoma, Primary, Cervical Cancer, Childhood Cancers, Chordoma, Chronic Lymphocytic Leukemia, Chronic Myelogenous Leukemia, Chronic Myeloproliferative Neoplasms Colon Cancer, Colorectal Cancer, Cutaneous T-Cell Lymphoma, Ductal Carcinoma In Situ, Endometrial Cancer, Ependymoma Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Intraocular Melanoma, Retinoblastoma, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors, Extragonadal Cancer, Ovarian Cancer, Testicular Cancer, Gestational Trophoblastic Disease, Glioma, Brain Stein Cancer, Hairy Cell Leukemia, Head and Neck Cancer, Heart Cancer, Hepatocellular (Liver) Cancer. Histiocytosis, Langerhans Cell Cancer, Hodgkin Lymphoma, Hypopharyngeal Cancer, Intraocular Melanoma, Islet Cell Tumors, Pancreatic Neuroendocrine Tumors, Kaposi Sarcoma, Kidney Cancer, Renal Cell Cancer, Wilms Tumor and Other Childhood Kidney Tumors, Langerhans Cell Histiocytosis, Laryngeal Cancer, Leukemia, Chronic Lymphocytic Cancer, Chronic Myelogenous Cancer, Hairy Cell Cancer, Lip and Oral Cavity Cancer, Liver Cancer (Primary), Lobular Carcinoma In Situ (LCIS), Lung Cancer, Non-Small Cell Cancer, Small Cell Cancer, Lymphoma, Cutaneous T-Cell (Mycosis Fungoides and Sézary Syndrome), Hodgkin Cancer, Non-Hodgkin Cancer, Macroglobulinemia, Waldenström, Male Breast Cancer, Malignant Fibrous Histiocytoma of Bone and Osteosarcoma, Melanoma, Intraocular (Eye) Cancer, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia, Acute, Myeloma Multiple, Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Epithelial Cancer, Low Malignant Potential Tumor, Pancreatic Cancer, Pancreatic Neuroendocrine Tumors (Islet Cell Tumors), Papillomatosis, Paraganglioma, Parathyroid Cancer, Penile Cancer, Pharyngeal Cancer, Pheochromocytoma, Pituitary Tumor, Plasma Cell Neoplasirt/Multiple Myeloma, Pleuropulmonary Blastoma, Primary Central Nervous System Lymphoma, Rectal Cancer, Renal Cell (Kidney) Cancer, Retinoblastoma, Rhabdomyosarcoma, Salivary Gland Cancer, Sarcoma, Ewing Cancer, Kaposi Cancer, Osteosarcoma (Bone Cancer), Soft Tissue Cancer, Uterine Cancer, Sézary Syndrome, Skin Cancer, Childhood Melanoma, Merkel Cell Carcinoma, Nonmelanoma, Small Cell Lung Cancer, Small Intestine Cancer, Soft Tissue Sarcoma, Squamous Cell Carcinoma, Skin Cancer (Nonmelanoma), Childhood Squamous Neck Cancer with Occult Primary, Metastatic Cancer, Stomach (Gastric) Cancer, T-Cell Lymphoma, Cutaneous Cancer, Testicular Cancer, Throat Cancer, Thymoma and Thymic Carcinoma, Thyroid Cancer, Transitional Cell Cancer of the Renal Pelvis and Ureter, Unknown Primary, Carcinoma of Childhood, Unusual Cancers of Childhood, Urethral Cancer, Uterine Cancer, Endometrial Cancer, Uterine Sarcoma, Vaginal Cancer, Vulvar Cancer, Waldenström Macroglobulinemia, Wilms Tumor, and Women's Cancers.

In a specific embodiment, the cancer is glioblastoma, small cell lung carcinoma, breast cancer and/or prostate cancer. In another embodiment, the administration of the Parkin ligase suppresses one or more tumors in the subject.

In another specific embodiment, the compound eliminates damaged mitochondria, increases cell viability during cellular stress, decreases tumor transformation and/or mitigates alpha-synuclein in cells.

In another embodiment, the methods of the present disclosure include treating and/or reducing the incidence of Parkinson's disease, specifically by administering to a subject in need thereof a therapeutically effective amount of one or more compounds that disrupt at least one Parkin ligase zinc finger and induces Parkin ligase activity, wherein the compound can coordinate with a Zn ion and/or react with a thiol group in a cysteine(s). In one embodiment, the compound that disrupts at least one Parkin ligase zinc finger and includes Parkin ligase activity in the above mentioned method is selected from compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof. In another embodiment, the one or more compounds eliminate damaged mitochondria, increases cell viability during cellular stress and/or mitigates alpha-synuclein in cells. "Somatic Mutations of the Parkinson's disease-associated gene PARK2 in glioblastoma and other human malignancies" (*Nature Genetics* January 2010 42(1) 77-82). In one embodiment, the compound that eliminate damaged mitochondria, increase cell viability during cellular stress and/or mitigates alpha-synuclein in cells in the above mentioned method is a selected from compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof.

In another embodiment, the Parkin ligase activation alters ubiquitination. Specifically, the alteration of ubiquitination is caused by the ability of Parkin to modify a substrate protein by covalent attachment of Ubiquitin, a substrate protein being Parkin itself, or another protein such as Mitofusion 1 or 2, FBW7, or other publicly reported substrates of Parkin ligase.

Further embodiments of the present disclosure relate to methods of treating, preventing, or ameliorating one or more symptoms associated with neurological diseases or disorders including but not limited to Alzheimer's Dementia, Parkinson's disease, Huntington Disease, Amyotrophic Lateral Sclerosis (ALS), Freidreich's ataxia, Spinocerebellar Ataxia, Multiple Systems Atrophy, PSP, Tauopathy, Diffuse Lewy Body Disease, Lewy Body dementia, any disorder characterized by abnormal accumulation of α-synuclein, disorders of the aging process, and stroke.

Other embodiments of the present disclosure relate to methods of treating, preventing, or ameliorating one or more symptoms associated with but not limited to mental retardation, deafness, blindness, diabetes, obesity, cardiovascular disease, and autoimmune diseases such as multiple sclerosis, Sjogrens syndrome, lupus, glaucoma, including pseudoexfoliation glaucoma, Leber's Hereditary Optic Neuropathy, and rheumatoid arthritis.

Further embodiments of the present disclosure of the present invention relate to methods of treating, preventing, or ameliorating one or more symptoms associated with but not limited to Mitochondrial Related Diseases or Capsules as follows:

Alpers Disease
Barth Syndrome/LIC (Lethal Infantile Cardiomyopathy)
Beta-oxidation Defects
Carnitine-Acyl-Carnitine Deficiency
Carnitine Deficiency
Creatine Deficiency Syndromes
Co-Enzyme Q10 Deficiency
Complex I Deficiency
Complex II Deficiency
Complex III Deficiency
Complex IV Deficiency/COX Deficiency
Complex V Deficiency
CPEO
CPT I Deficiency
CPT II Deficiency
KSS
Lactic Acidosis
LBSL—Leukodystrohpy LCAD
LCHAD
Leigh Disease or Syndrome
Luft Disease
MAD/Glutaric Aciduria Type II
MCAD
MELAS
MERRF
MIRAS
Mitochondrial Cytopathy
Mitochondrial DNA Depletion
Mitochondrial Encephalopathy
Mitochondrial Myopathy
MNGIE
NARP
Pearson Syndrome
Pyruvate Carboxylase Deficiency
Pyruvate Dehydrogenase Deficiency
POLG Mutations
Respiratory Chain
SCAD
SCHAD
VLCAD.

In one embodiment, the methods of the present disclosure include treating and/or reducing the incidence of cancer, comprising administering to a subject in need thereof a therapeutically effective amount of a compound of formula (I), (I'), (IA), (IB), (IB'), (IC), (ID), (IE), and (IF), (III), (IIIA) and (IIIB), or (II) and (IIA), or a pharmaceutically acceptable salt or solvate thereof. The compound of the present disclosure can disrupts at least one Parkin ligase zinc finger and induces Parkin ligase activity, wherein the compound can coordinate with a zinc ion and/or bind or react with a cysteine. In a specific embodiment, the Parkin ligase suppresses the growth of one or more tumors and/or prevents metastasis of one or more tumors. In another embodiment, the compound of formula (I), (I'), (IA), (IB), (IB'), (IC), (ID), (IF), and (IF), (III), (IIIA), and (IIIB), or (II) and (IIA), or a pharmaceutically acceptable salt or solvate thereof eliminates damaged mitochondria, increases cell viability during cellular stress, decreases tumor transformation and/or mitigates alpha-synuclein in cells. In another embodiment, the cancer is glioblastoma, small cell lung carcinoma, breast cancer or prostate cancer. In another embodiment, the cancer is lymphoma. In another embodiment, the cancer is mantle cell lymphoma. In another embodiment, the cancer is colon cancer, lung cancer, and/or ovarian cancer.

In a specific embodiment, the methods of the present disclosure include treating and/or reducing the incidence of Parkinson's disease, comprising administering to a subject in need thereof a therapeutically effective amount of a compound of formula. (I), (I'), (IA), (IB), (IB'), (IC), (ID), (IE), and (IF), (III), (IIIA), and (IIIB), or (II) and (IIA), or a pharmaceutically acceptable salt or solvate thereof that disrupts at least one Parkin ligase zinc finger and induces Parkin ligase activity, wherein the compound can coordinate with a zinc ion and/or bind or react with a cysteine. In a specific embodiment, the compound of the present disclosure eliminates damaged mitochondria, increases cell viability during cellular stress and/or mitigates alpha-synuclein in cells.

In one embodiment, the methods of the present disclosure excludes administration of compounds disclosed in Table A or Table C.

Pharmaceutical Compositions and Formulations

The present disclosure also includes pharmaceutical compositions for modulating or activating a Parkin ligase in a subject. In one embodiment, a pharmaceutical composition comprises one or more compounds of formula (I), (I'), (IA), (IB), (IB'), (IC), (ID), (IE), and (IF), (III), (IIIA), and (IIIB), or (II) and (IIA), or a pharmaceutically acceptable salt or solvate thereof. In some embodiments, one or more compounds of formula (I), (I), (IA), (IB), (IB'), (IC), (ID), (IE), and (IF), (III), (IIIA), and (IIIB), or (II) and (IIA), or a pharmaceutically acceptable salt or solvate thereof, in a pharmaceutical composition as described herein disrupts at least one Parkin ligase zinc finger. In another embodiment, one or more compounds of formula (I), (I), (IA), (IB), (IB'), (IC), (ID), (IE), and (IF), (III), (IIIA), and (IIIB), or (II) and (IIA), or a pharmaceutically acceptable salt or solvate thereof, in a pharmaceutical composition as described herein coordinates with a Zn ion, and/or react with at least one thiol group in a cysteine.

In one embodiment of the present disclosure, a pharmaceutical composition comprises a therapeutically effective amounts of one or more compounds of formula (I), (I'), (IA), (IB), (IB'), (IC), (ID), (IE), and (IF), (III), (IIA), and (IIIB), or (II) and (IIA), or a pharmaceutically acceptable salt or solvate thereof.

In a specific embodiment, a pharmaceutical composition, as described herein, comprises one or more compounds selected from Table 1, or a pharmaceutically acceptable salt or solvate thereof. In one embodiment, a pharmaceutical composition as described herein comprise one or more compounds selected from Table 2, or a pharmaceutically acceptable salt or solvate thereof. In one embodiment, a pharmaceutical composition as described herein comprise one or more compounds selected from Table 3A, or a pharmaceutically acceptable salt or solvate thereof. In one embodiment, a pharmaceutical composition as described herein comprise one or more compounds selected from Table 3B, or a pharmaceutically acceptable salt or solvate thereof.

In one embodiment, a pharmaceutical composition described herein does not contain a compound disclosed in Table A or Table C.

In one embodiment, a pharmaceutical composition, as described herein, comprising one or more compounds of formula (I), (I'), (IA), (IB), (IB'), (IC), (ID), (IE), and (IF), (III), (IIIA), and (IIIB), or (II) and (IIA), or a pharmaceutically acceptable salt or solvate thereof, further comprises one or more additional therapeutically active agents. In one embodiment, one or more additional therapeutically active agents are selected from therapeutics useful for treating cancer, neurological disease, a disorder characterized by abnormal accumulation of α-synuclein, a disorder of an aging process, cardiovascular disease, bacterial infection, viral infection, mitochondrial related disease, mental retardation, deafness, blindness, diabetes, obesity, autoimmune disease, glaucoma, Leber's Hereditary Optic Neuropathy, and rheumatoid arthritis.

In a further embodiment of the present disclosure, a pharmaceutical composition comprising one or more compounds of formula (I), (I'), (IA), (IB), (IB'), (IC), (ID), (IE), and (IF), (III), (IIIA), and (IIIB), or (II) and (IIA), or a pharmaceutically acceptable salt or solvate thereof, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more compounds of formula (I), (II), (IA), (IB), (IB'), (IC), (ID), (IE), and (IF), (III), (IIIA), and (IIIB), or (II) and (IIA), or a pharmaceutically acceptable salt or solvate thereof, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a compound of formula (I), (I'), (IA), (IB), (IB'), (IC), (ID), (IE), and (IF), (III), (IIIA), and (IIIB), or (II) and (IIA), or a pharmaceutically acceptable salt or solvate thereof, as disclosed herein, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, poly vinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates EUDRAGIT®), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using compounds of formula (I), (I'), (IA), (IB), (IB'), (IC), (ID), (IE), and (IF), (III), (IIIA), and (IIIB), or (II) and (IIA), or a pharmaceutically acceptable salt or solvate thereof, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or poly oxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as guconic acid, lactic acid, citric acid or acetic acid, sodium guconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments; a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The agents or compounds, or pharmaceutically acceptable salts or derivatives thereof, are administered orally, nasally, transdermally, pulmonary, inhalationally, buccally, sublingually, intraperitoneally, subcutaneously, intramuscularly, intravenously, rectally, intrapleurally, intrathecally, intraportally, and parenterally. Alternatively or in addition, the route of administration is local, e.g., topical, intra-tumor and peri-tumor. In some embodiments, the compound is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichloratetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the compound of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more compounds of formula (I), (I'), (IA), (IB), (IB'), (IC), (ID), (IE), and (IF), (IIIA), and (IIIB), or (II) and (IIA), or a pharmaceutically acceptable salt or solvate thereof are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the amount of the compound of formula (I), (II), (IA), (IB), (IB'), (IC), (ID), (IE), and (IF), (III), (IIIA), and (IIIB), or (II) and (IIA), or a pharmaceutically acceptable salt or solvate thereof, or compounds disclosed in Tables 1, 2, 3A and/or 3B, or a pharmaceutically acceptable salt or solvate thereof, can be administered at about 0.001 mg/kg to about 100 mg/kg body weight (e.g., about 0.01 mg/kg to about 10 mg/kg or about 0.1 mg/kg to about 5 mg/kg).

The concentration of a disclosed compound in a pharmaceutically acceptable mixture will vary depending on several factors, including the dosage of the compound to be administered, the pharmacokinetic characteristics of the compound (s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the drug required to prevent, counter or arrest the progress of the condition.

The compounds or pharmaceutical compositions of the present disclosure may be manufactured and/or administered in single or multiple unit dose forms.

Having now generally described the invention, the same will be more readily understood through reference to the following examples, which are provided by way of illustration and are not intended to be limiting of the present invention.

EXAMPLES

Example 1: Identification of Parkin Activators

Assay Principle:

The assay based on the irreversible reaction of an Activity-Based Probe (ABP) with the active site cysteine in the enzyme. ABP consists of a ubiquitin moiety with an epitope tag (e.g. HA tag) at the N-terminus, and a reactive group at the C-terminus. The activity of Parkin-RBR (w/o the R0 inhibitory domain) is significantly higher than the activity of Parkin-R0RBR or the activity of full-length Parkin. The covalent attachment of ABP to Parkin can be monitored by Time Resolved Fluorescence Resonance Energy Transfer (TR-FRET)

Parkin-R0RBR, full-length Parkin→low TR-FRET signal (negative control)

Parkin RBR→high TR-FRET signal (positive control)

Compounds increasing the activity of Parkin-R0RBR or the activity of full-length—Parkin can be identified by an increase in TR-FRET signal.

Strategy: use of N-terminal His-SUMO tagged constructs of Parkin-R0RBR, full-length Parkin and Parkin-RBR. (from Evotec Slides; Based on Riley et al. 2013. Nat Common. 4:1982 & on information provided by E3x Bio; grant Application)

Constructs:

Full-length Parkin (1-465), R0RBR (141-465) and RBR (238-465) expression with N-terminal $His_6$-SUMO-tag (can potentially be removed during purification using SENP1 protease) in E. coli as described by Riley et al.

N-terminal $His_6$-tag enabling TR-FRET-assay→use of the purified protein that still have the N-terminal $His_6$-SUMO-tags on.

Small scale tests are conducted for all constructs to evaluate which construct, full-length Parkin or R0RBR, give better yield to facilitate an HTS-assay.

Phase 1: Protein Production

Initiate gene synthesis through third party for full-length Parkin with N-terminal $His_6$-SUMO, $His_6$-SUMO-R0RBR and $His_6$-SUMO-RBR, codon-optimized for expression in E. coli and subcloning into a suitable expression vector Small scale test expression evaluated by Western Blotting to estimate the yield of soluble protein Transform the RBR construct as well as either the full-length Parkin construct or the R0RBR construct into BL21 (DE3) and express as outlined in Riley et al., in the scale of 6-24L (depending on outcome of small scale test expression)

Purification of ~10 mg of the RBR construct as well as either the full-length Parkin construct or the R0RBR construct as described by Riley et al., i.e. IMAC, MonoQ and size exclusion.

Phase 2: Assay Development

Goals:

Set-up robust primary screening assays in 1,536-well assay plate format

Establish assays in 384-well format with a reasonable dynamic range (e.g. using Parkin +/− the R0 inhibitory domain)

Optimize assay (e.g. in terms of concentrations of assay components, buffer, additives, order of addition of reagents, and incubation temperature)

Run time course experiments to define optimal incubation times

Demonstrate assay robustness (goal: Z'>0.5)

Demonstrate readout stability

Test DMSO tolerance

Demonstrate specificity of the assay signal obtained using the Parkin RBR domain (w/o the R0 inhibitory domain) by titration of Lib (competing with ABP)

Transfer assay from 384- to final 1,536-well screening plate format; adapt the assay to the EVOscreen™ Mark III HTS platform If necessary, fine-tune the assay conditions in order to optimize assay robustness in this high density plate format (goal: Z'>0.5) and to demonstrate assay suitability for high-throughput screening (HTS)

Confirm stability of assay reagents under screening conditions over time

Demonstrate plate-to-plate and day-to-day assay robustness

Estimate and procure the amounts of all assay reagents required for screening and hit profiling.

Phase 3: Screening

Marker Library Screen (MLS):

Pre-screening of a diverse marker library of approximately 2.5 k representative lead-like compounds against the primary screening assay at two concentrations in triplicate Statistical analysis of the MLS and hit definition using the 3-sigma-method (plate-based, based on the scatter of compound-free DMSO wells)

Selection of the optimal compound concentration for primary screening Primary Screen (PS):

Screening of approximately 75,000 lead-like compounds against the primary screening assay at one uniform compound concentration (n=1); re-screening of compound plates that do not meet an agreed re-screen criterion (e.g. Z'>0.5)

Hit definition for the primary screen using the 3-sigma-method (plate-based, based on the scatter of compound-free DMSO wells)

Statistical analysis of the primary screen Primary Hit Compounds (Parkin activators) Hit Confirmation (HC):

Selection of a set of up to approximately 750 primary hits for Hit Confirmation

Cherry picking of the selected compounds and reformatting for testing

Retesting of the selected cpds against the primary screening assay at the compound screening concentration (n=3)

Statistical analysis of the Hit Confirmation campaign→Identification of confirmed small molecule Parkin activators.

Phase 4: HitProfiling (HP):

Selection of a set of up to approximately 250 confirmed hit compounds for Hit Profiling Cherry picking of the selected compounds and reformatting for concentration-response testing Concentration-response testing as 11-point compound dilution series against the primary screening assay (n=2)

Automated data fitting of the concentration response curves and calculation of the resulting $IC_{50}$ values LC/MS inspection of the hit compounds to confirm compound identity and purity Structure-activity relationship analysis (SAR) of the active hit compounds Confirmed & profiled small molecule Parkin activators.

Example 2: Activity-Based Probe Assay Using an Ubiquitin Vinyl Sulfone Probe

An Ubiquitin vinyl sulfone probe can be used that irreversibly binds to the active site cysteine of Parkin ligase. Covalent attachment of the probe to the Parkin can be monitored by TR-FRET. Candidate activator compounds can be identified by increasing the activity of Parkin ligase due to an increase in TR-FRET signal. Screening for activating compounds can be distinguished from the controls as follows:

100% activation signal=Heat activated Parkin+100 nM control activator in DMSO.

0% activation signal=Heat activated Parkin+DMSO only.

Parkin activators can be identified by an increase of the 0% activation signal TR-FRET signal.

Assay Conditions:

Materials:

Assay Plate: White 384 well plate (Corning 3572)

Enzyme: Parkin-His tagged 203 μM (10.5 mg/ml)

Probe: Ubiquitin vinyl-sulfone (HA-Ub-VS Boston Biochem U-212)

DMSO: DMSO (Sigma cat #D4540-100ML)

Reaction Buffer: 50 mM HEPES (pH 8.5), 150 mM NaCl, 0.01% Tween 20, 0.1% BSA

Detection Buffer: 50 mM HEPES (pH 8.5), 150 mM NaCl, 0.01% Tween 20, 0.1% BSA, 800 mM KF Detection Reagent A: 2.6 nM Anti-6HIS-Eu cryptate and 40 nM Anti-HA-XL665 in detection buffer Eu cryptate: Anti-6HIS-Eu cryptate (CisBio 61HISKLA)

XL665: Anti-HA-XL665 (CisBio 610HAXLA)

Enzyme Reaction (15 Min Pre Incubation Parkin with Activator Only)

Parkin: 40 nM

HA-Ub-VS Probe: 70 nM

Activator/DMSO: 2× Activator/2% DMSO

Reaction time: 60 minutes

Temperature: 22° C.

Total volume: 10 μl reaction

Detection Reaction

Take 10 ml of Enzyme Reaction above and add 10 μl detection Reagent A under the following conditions:

Reaction time: 60 minutes

Temperature: 22° C.

Total volume: 20 μl

Assay procedure (Using HP D-300 compound dispenser and Bravo for the operation):

1) Heat activate Parkin in reaction buffer (500 μl/1.5 ml tube: Eppendorf Thermomixer 5 minutes, 400 rpm at 58° C. and put on ice until needed).

2) Load assay plate wells with 4.8 μl 84.5 nM Parkin in reaction buffer by use of Bravo.

3) Deliver 0.2 μl 200× activator candidates in DMSO by use of HP D-300 compound dispenser. Highest 200× concentration=20 μm and then twofold dilutions.

4) Spin 1000 rpm, 2 minutes, at room temp.

5) Incubate plate for 15 minutes at room temp.

6) Add 5 μl 140 nM HA-Ub-VS Probe in reaction buffer by use of Bravo.

7) Spin 1000 rpm, 2 minutes, at room temp.

8) Incubate plate for 60 minutes at room temp.

9) Add 10 μl 2.6 nM Anti-6HIS-Eu cryptate and 40 nM Anti-IA-XL665 in detection buffer.

10) Spin 1000 rpm, 2 minutes, at room temp.
11) Incubate plate for 60 minutes at room temp.
12) Read plates on Perkin Elmer Envision instrument with the following parameters:
LANCE dual laser protocol loaded into the Envision® software
Top Mirror: LANCE/DELFIA Duel/Bias (Bar code 446)
Emission Filter: APC 665 EM (Bar code 205)
2nd Emission Filter: Europium 615 EM (Bar code 203)
Read 655 nm (channel 1) and 615 nm (channel 2) wavelengths on Envision®

Data Analysis: The Data can be read in CSV files. There are two tables in those CSV files, which are the values of 655 nm (channel 1) and 615 nm (channel 2) wavelengths respectively. The data is converted to an HTRF Ratio=(Channel 1/Channel 2)*10,000

The average of all the 0 µM controls (DMSO only) =BKGD (Background—0% activation). Subtract BKGD from each HTRF Ratio value=HTRF−BKGD. The average of all the 100 uM 100 nM control activator in DMSO controls=Max (100% activation). The following equation is then used to calculate % Activation for each well/candidate as follows:

% Activation=(HTRF−BKGD/Max)*100.

The % Activation of compound titration can then be used to find activation EC50 or highest % activation if less than 75% activation is seen for the candidate compound.

Graphpad Prism was used with Transform X values: X=Log(X) and nonlinear regression (dose-response-stimulation): Log(agonist) vs Response–variable slope (four parameters) with constrains set to Bottom=0 and Top=100.

The Activity-Based Probe Assay was performed with various compounds in Tables 1, 2, 3A and 3B. As shown in Table 4.

Compound F3 is

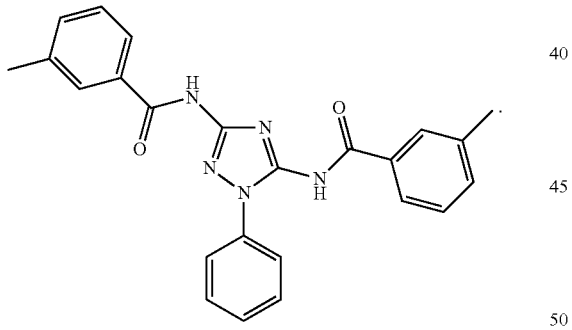

TABLE 4

| Probe Assay EC50 | |
|---|---|
| Compound ID | Probe Assay EC50 (µM) [Example 2] |
| 1 | 52.0 |
| 1 | >100 |
| 123 | 7.0 |
| 2 | 4.0 |
| 124 | 3.0 |
| 3 | 16.0 |
| 3 | >100 |
| 4 | 38.0 |
| 4 | 24.0 |

TABLE 4-continued

| Probe Assay EC50 | |
|---|---|
| Compound ID | Probe Assay EC50 (µM) [Example 2] |
| 5 | 3.0 |
| 125 | >100 |
| 6 | 2.0 |
| 7 | 12.0 |
| 147 | >100 |
| 8 | 4.0 |
| 9 | 32.0 |
| 10 | 30.0 |
| 11 | 2.0 |
| 12 | 1.0 |
| 12 | 3.0 |
| 13 | 7.0 |
| 14 | >100 |
| 15 | >100 |
| 16 | 3.0 |
| 17 | 10.0 |
| 18 | 1.0 |
| 18 | 3.0 |
| 19 | >100 |
| 20 | 2.0 |
| 21 | 5.0 |
| 22 | >100 |
| 23 | 10.0 |
| F3 | >100 |
| F3 | 4.0 |
| 148 | >100 |
| 24 | 3.0 |
| 25 | 0.9 |
| 25 | 2.0 |
| 25 | 2.0 |
| 26 | 6.0 |
| 27 | 3.0 |
| 28 | 22.0 |
| 29 | 2.0 |
| 30 | 3.0 |
| 31 | 4.0 |
| 32 | 9.0 |
| 33 | 3.0 |
| 34 | 2.0 |
| 35 | 3.0 |
| 36 | 3.0 |
| 36 | 4.0 |
| 37 | 4.0 |
| 38 | 5.0 |
| 39 | 4.0 |
| 40 | 1.0 |
| 41 | 2.0 |
| 42 | 1.0 |
| 42 | 3.0 |
| 42 | 3.0 |
| 43 | >100 |
| 44 | 3.0 |
| 45 | >100 |
| 46 | 6.0 |
| 47 | 16.0 |
| 48 | 2.0 |
| 49 | >100 |
| 50 | >100 |
| 50 | >100 |
| 50 | >100 |
| 51 | 84.0 |
| 52 | 61.0 |
| 53 | >100 |
| 54 | 10.0 |
| 55 | 12.0 |
| 56 | >100 |
| 57 | >100 |
| 58 | 7.0 |
| 59 | 3.0 |
| 60 | 0.3 |
| 60 | 0.1 |
| 60 | 0.6 |
| 60 | >100 |
| 60 | >100 |

TABLE 4-continued

Probe Assay EC50

| Compound ID | Probe Assay EC50 (μM) [Example 2] |
|---|---|
| 61 | 12.0 |
| 61 | 10.0 |
| 61 | 13.0 |
| 62 | 8.0 |
| 63 | 3.0 |
| 64 | 8.0 |
| 65 | 5.0 |
| 66 | 8.0 |
| 67 | >100 |
| 67 | 16.0 |
| 67 | 6.0 |
| 68 | 24.0 |
| 69 | 4.0 |
| 70 | 4.0 |
| 71 | 3.0 |
| 72 | 2.0 |
| 73 | 12.0 |
| 74 | 0.9 |
| 75 | 4.0 |
| 76 | 34.0 |
| 77 | 6.0 |
| 126 | 2.0 |
| 127 | 2.0 |
| 128 | 5.0 |
| 129 | 3.0 |
| 130 | 5.0 |
| 131 | 2.0 |
| 132 | 3.0 |
| 133 | 1.0 |
| 134 | 4.0 |
| 78 | 0.2 |
| 78 | 0.4 |
| 78 | 0.5 |
| 136 | >100 |
| 79 | 1.0 |
| 80 | 3.0 |
| 81 | 3.0 |
| 82 | 2.0 |
| 135 | >100 |
| 83 | >100 |
| 84 | 4.0 |
| 85 | 3.0 |
| 86 | 6.0 |
| 87 | 7.0 |
| 88 | 5.0 |
| 89 | 2.0 |
| 90 | >100 |
| 91 | 2.0 |
| 137 | 4.0 |
| 92 | 2.0 |
| 138 | >100 |
| 93 | >100 |
| 94 | 4.0 |
| 95 | 4.0 |
| 96 | 11.0 |
| 96 | 8.0 |
| 97 | 14.0 |
| 98 | 5.0 |
| 139 | 0.9 |
| 140 | >100 |
| 99 | 13.0 |
| 100 | 9.0 |
| 141 | 1.0 |
| 101 | 18.0 |
| 142 | 0.3 |
| 143 | >100 |
| 102 | 2.0 |
| 103 | 1.0 |
| 104 | >100 |
| 104 | >100 |
| 104 | 5.5 |
| 104 | 8.0 |
| 144 | >100 |
| 105 | 1.0 |
| 106 | >100 |
| 107 | 1.0 |
| 145 | >100 |
| 145 | >100 |
| 145 | >100 |
| 108 | 1.5 |
| 109 | 1.0 |
| 146 | 1.0 |
| 110 | 2.0 |
| 111 | 2.0 |
| 112 | 1.0 |
| 113 | 0.8 |
| 114 | 2.0 |
| 115 | 3.0 |
| 116 | 2.0 |
| 117 | 2.0 |
| 118 | 1.0 |
| 119 | 2.0 |
| 120 | 1.0 |
| 121 | NA |
| 122 | NA |

NA = not available

Example 3: Parkin pUB Auto-ubiquitinylation Assay

A Parkin pUB Auto-ubiquitinylation Assay is used to evaluate a compound's potency to activate Parkin's ability to Auto-ubiquitinylate itself.

The principle of this assay is that the E3 Ligase Parkin catalyzes the transfer of Ubiquitin to target proteins, but also has the ability to auto-ubiquitinylate itself. The phospho-Ubiquition (pub) added to the assay alters the Parkin to a state where small molecule activators can enable the Parkin to auto-ubiquitinylate though the E1-E2 cascade reaction. The use of a Eu cryptate Ubiquition and anti 6His-d2 that binds to the His tagged Parkin will give a signal when the Eu cryptate Ubiquition is auto-ubiquitinylate onto the Parkin which can be monitored by TR-FRET.

Similar to the Activity-based probe assay in Example 2, screening for activating compounds can be distinguished from the controls as follows:

100% activation signal=pUb activated Parkin+40 nM control activator in DMSO.

0% activation signal=pUb activated Parkin+DMSO only.

Parkin activators can be identified by an increase of the 0% activation signal TR-FRET signal.

Materials:
Assay Plate: White 384 well plate (Corning 3572)
Enzyme 1: E1 (Ubiquitin-activating enzyme/UBE1 Boston Biochem E-305)
Enzyme 2: E2 (UBcH7/Ube2L3 Boston Biochem E2-640)
Enzyme 3: Parkin-His tagged 203 μM (10.5 mg/ml)
pUb: Phospho-Ubiquitin (S65) (Boston Biochem U-102)
Eu Cryptate Reagent: Ubiquitin Eu (CisBio 61UBIKLA)
DMSO: DMSO (Sigma-34869-2.5L)
Reaction Buffer: 50 mM HEPES, 50 mM NaCl, 1 mM $MgCl_2$, 0.005% Tween 20, 0.1%
PF-127 (Fisher Scientific 50-310-494), pH 8.5
Detection Buffer: 50 mM HEPES, 50 mM NaCl, 800 mM KF, 5 mM EDTA, 0.005%

Tween 20, 0.1% PF-127, pH 8.5
Detection Reagent Z: 13.4 nM Anti-6His-d2 in detection buffer
d2 Reagent: Anti-6His-d2 (CisBio 61HISDLA)

Assay Conditions:
Enzyme Reaction (15 Min Pre-Incubation with Parkin, pUb and Activator Only)
Parkin: 196 nM
pUb: 196 nM
DMSO: 1% DMSO
E1: 5 nM
E2: 50 nM
Ubiquitin Eu: 8.8 nM
Reaction time: 120 minutes
Temperature: 22° C.
Total volume: 10 µl reaction
Detection Reaction
Take 10 µl of Enzyme Reaction above and add 10 µl detection Reagent Z under the following conditions:
Reaction time: 60 minutes
Temperature: 22° C.
Total volume: 20 µl Assay Procedure 1) Assay plate wells are loaded with 4.9 µl 400.0 nM Parkin, 400 nM pUb in reaction buffer by use of Eppendorf 12-channel pipette.
2) Deliver 0.1 µl 100× activator candidates in DMSO by use of Echo 555 compound dispenser. Highest 100× concentration=100 µm and then twofold dilutions. Add each compound and control in duplicate wells.
3) Spin 1000 rpm, 2 minutes, at room temp.
4) Incubate plate for 15 minutes at room temp.
5) Add 5 µl 10 nM E1, 100 nM E2, 17.6 nM Ubiquitin Eu and 2 mM ATP in Reaction Buffer by use of Eppendorf 12-channel pipette.
6) Spin 1000 rpm, 2 minutes, at room temp.
7) Incubate plate for 120 minutes at room temp.
8) Add 10 µl 13.4 nM anti his d2 in detection buffer by use of Eppendorf 12-channel pipette.
9) Spin 1000 rpm, 2 minutes, at room temp.
10) Incubate plate for 120 minutes at room temp.
11) Read plates on Perkin Elmer Envision instrument with the following parameters: LANCE dual laser protocol loaded into the Envision, software
Top Mirror: LANCE/DELFIA Duel/Bias (Bar code 446)
Emission Filter: APC 665 EM (Bar code 205)
2nd Emission Filter: Europium 615 EM (Bar code 203)
Read 655 nm (channel 1) and 615 nm (channel 2) wavelengths on Envision®

Data Analysis: The Data can be read in CSV files. There are two tables in those CSV files, which are the values of 655 nm (channel 1) and 615 nm (channel 2) wavelengths respectively. The data is converted to an HTRF Ratio=(Channel 1/Channel 2)*10,000

The average of all the 0 uM controls (DMSO only)=BKGD (Background–0% activation). Subtract BKGD from each HTRF Ratio value=HTRF–BKGD. The average of all the 100 uM control activator in DMSO controls=Max (100% activation). The following equation is then used to calculate % Activation for each well/candidate as follows: % Activation=(HTRF–BKGD/Max)*100.

The % Activation of compound titration can then be used to find activation EC50 or highest % activation if less than 75% activation is seen for the candidate compound.

XLFIT5 model 205 was applied for the data analysis. EC50 fit model (4 Parameter Logistic Model/Sigmoidal dose-Response Model); fit=(A+((B−A)(1+((C/x)^D)))); res=(y−fit). The parameters are:
A: Bottom
B: Top
C: Relative EC50
D: Hill Slope
Constrains set to Bottom=0 and Top=100.

This Parkin pUB auto-ubiquitinylation Assay is performed with various compounds in Tables 1, 2, 3A and/or 3B.

Example 4: Microsomal Stability Assay

Compounds were also tested for metabolic stability in both rat liver microsomes (RLM) and the compounds are tested for human liver microsomes (HLM) and their half-life is calculated (See Tables 5A and 5B). The assay was performed as follows. The total volume for each incubation was 250 µL. A 100 µM DMSO solution of compound (diluted from 10 mM stock solution) was spiked into 50 mM $KH_2PO_4$ (pH 7.4) buffer containing liver microsome at a concentration of 1.0 mg/mL. The reaction was initiated by the addition of 50 µL of 1 mM NADPH. The final concentration of each compound was 1 µM (1% DMSO). The positive controls, phenacetin for CYP1A2, diclofenac for CYP2C9, omeprazole for CYP2C19, dextromethorphan for CYP2D6 and midazolam for CYP3A4 were added to a separate tube with the final substrate concentrations of 1 µM (1% DMSO) for evaluating the enzyme activities in the liver microsomes. At 0, 15, 30 and 60 min, an aliquot of 15 µL reaction mixtures were removed and 200 µL of methanol (with internal standard of 25 ng/mL propranolol) was added to quench the reaction. The resulting mixture was centrifuged and supernatant was used for LC-MS/MS analysis.

The signals for each compound, or the metabolites for the probe substrates and the internal standard were integrated and the peak area ratios to internal standard were generated. Percent parent remaining at a specified timepoint was calculated based on the peak area ratios at time 0 (as 100%) for in vitro metabolic stability studies in liver microsome and hepatocyte. The observed rate constant ($k_{obs}$) for the metabolism of substrates was calculated by plotting the natural log of percentage substrate remaining versus time of incubation with the slope being $k_{obs}$. The half-life ($T_{1/2}$) was calculated according to the following equation:

$$T_{1/2} = 0.396/k_{obs}$$

TABLE 5A

Rat Liver Microsome Half-Life

| Compound ID | RLM $t_{1/2}$ (min) |
|---|---|
| 123 | 84.0 |
| 2 | 41.0 |
| 124 | 43.0 |
| 5 | 131.0 |
| 6 | 5.0 |
| 7 | 239.0 |
| 8 | 71.0 |
| 9 | 58.0 |
| 10 | 27.0 |
| 11 | 147.0 |
| 12 | 126.0 |
| 13 | 51.0 |
| 16 | 141.0 |

TABLE 5A-continued

Rat Liver Microsome Half-Life

| Compound ID | RLM $t_{1/2}$ (min) |
|---|---|
| 17 | 26.0 |
| 18 | 103.0 |
| 20 | 147.0 |
| 21 | 6.0 |
| 23 | 21.0 |
| 24 | 131.0 |
| 137 | 73 |
| 154 | 102 |
| 155 | 17.4 |
| 156 | 23.7 |
| 25 | 408.0 |
| 26 | 58.0 |
| 27 | 19.0 |
| 28 | 20.0 |
| 29 | 47.0 |
| 31 | 14.0 |
| 32 | 204.0 |
| 33 | 198.0 |
| 34 | 330.0 |
| 35 | 198.0 |
| 36 | 63.0 |
| 37 | 21.0 |
| 38 | 26.0 |
| 39 | 133.0 |
| 40 | >500 |
| 41 | 17.0 |
| 42 | 231.0 |
| 44 | 6.0 |
| 46 | 97.0 |
| 102 | 10 |
| 157 | 16.5 |
| 158 | 169 |
| 159 | 158 |

TABLE 5B

Human Liver Microsome Half-Life

| Compound ID | HLM $t_{1/2}$ (min) |
|---|---|
| 24 | 204.0 |
| 25 | 71.0 |
| 36 | 147.0 |
| 42 | >500 |
| 154 | 133 |
| 155 | 63.6 |
| 156 | 158 |
| 157 | 42 |
| 158 | 165 |
| 159 | 178 |

Example 5: In Vivo Cancer Xenograft Assay

Compound 42 was evaluated for in vivo therapeutic efficacy in the treatment of subcutaneous HCT-116 (colon cancer) xenograft model in nude mice.

Each mouse was inoculated subcutaneously at the flank region with either HCT-116 cells (1.0×106) in 0.1 ml of 1×PBS mixed with Matrigel (1:1) for tumor development and xenotransplantation.

Twenty (20) animals with approx 120-150 mm tumors are selected for HCT-116 follow up experiment and randomly placed into Groups 1, 2, 3, and 4, wherein Group 1 is for mice administered with a vehicle negative control; Group 2 is mice treated with Compound F at 25 mg/kg daily for up to 26 days; Group 3 is mice treated with 1 mg/kg of Compounds 42 daily for up to 26 days; and Group 4 is mice treated with 5 mg/kg of Compound 42 daily for up to 26 days. The vehicle with or without drug is administered to the mouse by intraperitoneal injection. The formulation with respective drug is as follows:

10% —DMA: N,N-Dimethyl acetamide

15% —Solutol HS 15: Macrogol 15 Hydroxy Stearate, Polyethylene glycol-15-hydroxystrerate; and 75%-20% aqueous HP-β-CD: Hydroxypropyl-beta-cyclodextrin

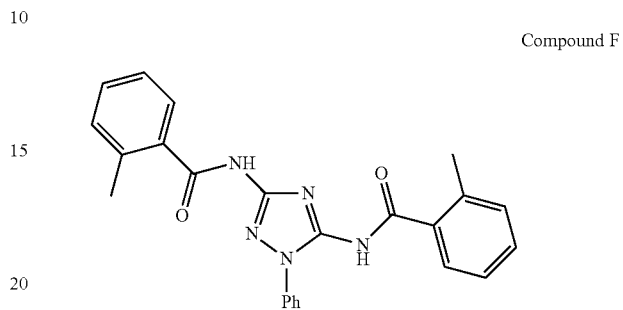

Compound F

Before grouping and treatment, all animals were weighed and the tumor volumes were confirmed (approx. 120-150 mm$^3$) using electronic caliper. Since the tumor volume can affect the effectiveness of any given treatment, mice were assigned into groups using randomized block design as following: First, the experimental animals were divided into homogeneous blocks based on their tumor volume. Secondly, within each block, randomization of experimental animals to different groups were conducted. By using randomized block design to assign experimental animals, we ensured that each animal had the same probability of being assigned to any given treatment groups and therefore systematic error was minimized.

After tumor cells were inoculated, the animals were checked daily for morbidity and mortality. At the time of routine monitoring, the animals were checked for any adverse effects of tumor growth and treatments on normal behavior such as mobility, visual estimation of food and water consumption, body weight gain/loss, eye/hair matting and any other abnormal effects. Death and observed clinical signs were recorded. Tumor volumes were measured every three days in two dimensions using an electronic caliper, and the volume data were expressed in mm$^3$ using the formula: V=0.5 a×b2 where a and b are the long and short diameters of the tumor, respectively. Tumor volume average is then recorded for each day for groups 1-4 until day 26.

FIG. 1 shows the xenograft study result for Compound 42. Compound 42 at 5 mg/kg reduced tumor size by greater than 50%.

Example 6: Cancer Cell Proliferation Assay

Measurement of the inhibitive effect of compounds on cancer cell proliferation was performed. Various cell lines were tested, including HCT-116 (colon); A549 (lung); TOV-21G (ovarian); Calu-6 (lung); and LS-174T (colon); and cell lines H1703 (Lung) and SKOV3 (ovarian); JEKO-1 (lymophoma); TOV-112D (ovarian) are tested. The assays were performed under the following conditions: Cells are harvested at a concentration of 4×10$^4$ cells/ml in media. Volumes of 100 μl/well of these cell suspensions were added to a 96 well plate using a multichannel pipette. Plates were gently agitated to ensure an even dispersion of cells over a given plate. Cells were then incubated at 37° C., 5% CO$_2$ overnight. Following this, 100 μl of compound at varying concentrations was added to wells in triplicate. Control wells are those with 100 µl media containing 0.33% DMSO added to cell suspension (this is the equivalent volume of DMSO found in the highest concentration of drug). Plates were then gently agitated, as above, and incubated at 37° C., 5% CO for 72 hrs (control wells have reached 80-90% confluency). Assessment of cell proliferation in the presence of the compound was determined by the acid phosphatase assay.

Figure 2:
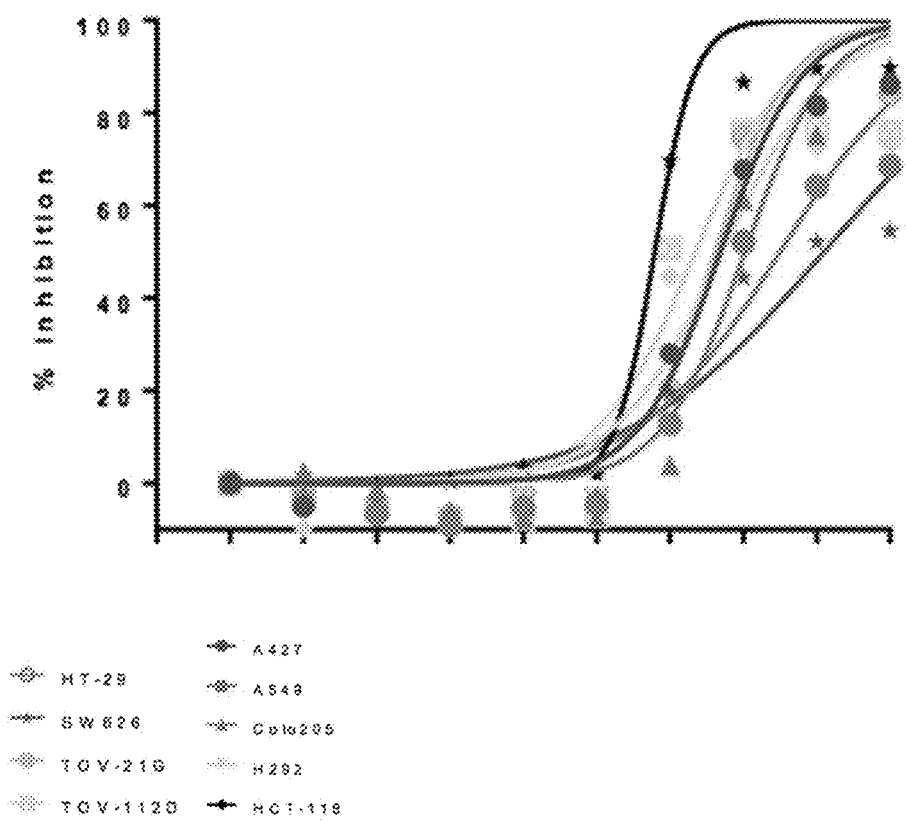
FIG. 2 shows the % inhibition of cancer cell line proliferation with Compound 42.

Following the incubation period of 72 hrs, media was removed from the plates. Each well on the plate was washed twice with 100 µl PBS. This was then removed and 100 µl of freshly prepared phosphatase substrate (10 mM p-nitrophenol phosphate in 0.1M sodium acetate, 0.1% triton X-100, pH 5.5) was added to each well. The plates were then incubated in the dark at 37° C. for 2 hours. Colour development was monitored during this time. The enzymatic reaction was stopped by the addition of 50 µl of 1N NaOH. The plate was read in a dual beam plate reader at 405 nm with a reference wavelength of 620 nm. The absorbance reading of the latter is subtracted from the former, and the effect of the drug on cell proliferation was then measured as a percentage against the control cells (DMSO), which is taken as 0% inhibition. Table 6A below shows $IC_{50}$ values on cancer cell proliferation including HCT-116 (colon); A549 (lung); TOV-21G (ovarian); Calu-6 (lung); and LS-174T (colon). Table 6B below shows $IC_{50}$ values on cancer cell proliferation including JEKO-1 (lymophoma) and TOV-112D (ovarian). FIG. 2 shows the % inhibition of cancer cell line proliferation with Compound 42. Table 6C shows $IC_{50}$ values corresponding to Compound 42's cell proliferation data shown in FIG. 2. Table 6D shows $IC_{50}$ values for Compound 42 tested in another set of cell proliferation assay with various cancer cell lines. Table 6E shows $IC_{50}$ values for Compound F and Compound 42 in a cell proliferation assay with various cancer cell lines.

TABLE 6A $IC_{50}$ Values of Various Compounds on Cancer Cell Line Proliferation

| Compound ID | HCT-116 IC50 (µM) | TOV-21G IC50 (µM) | A549 IC50 (µM) | Calu6 IC50 (µM) | LS-174T IC50 (µM) |
|---|---|---|---|---|---|
| 2 | 642 | 2.2 | 2.2 | N/A | N/A |
| 124 | N/A | 0.59 | 1.2 | 1.4 | N/A |
| 3 | N/A | 2.4 | N/A | N/A | N/A |
| 6 | N/A | 1.2 | N/A | N/A | N/A |
| 7 | N/A | >1 | N/A | N/A | N/A |
| 16 | N/A | 2.3 | 2.6 | N/A | N/A |
| 17 | N/A | >1 | N/A | N/A | N/A |
| 20 | N/A | >1 | N/A | N/A | >1 |
| 21 | N/A | 2.5 | 2.5 | >2.5 | >2.5 |
| 23 | N/A | 2.4 | >2.5 | >2.5 | >2.5 |
| F3 | 2 | 2.3 | 2.3 | N/A | N/A |
| 24 | N/A | 0.97 | 0.28 | 0.29 | 0.94 |
| 25 | 0.12 | <0.1 | 0.04 | 0.43 | <0.2 |
| 26 | N/A | 2.1 | 2.5 | N/A | >1 |
| 31 | N/A | 2.3 | 2.5 | N/A | >2.5 |
| 32 | N/A | >2.5 | >2.5 | N/A | >2.5 |
| 33 | N/A | >2.5 | >2.5 | N/A | n/a |
| 34 | N/A | 1.5 | 2.5 | N/A | 2.6 |
| 35 | N/A | 1.4 | 2.4 | N/A | 2.3 |
| 36 | N/A | 0.3 | 0.22 | 0.17 | 1.3 |
| 37 | N/A | 1.9 | 2.3 | N/A | 2.4 |
| 38 | N/A | 1.7 | 2.1 | 2.6 | 2.3 |
| 39 | N/A | 1.5 | 1.2 | 2.5 | 2.1 |
| 40 | N/A | >2.5 | N/A | N/A | >2.5 |
| 41 | N/A | >2.5 | 2.5 | N/A | 2.5 |
| 42 | 0.07 | 0.25 | 0.03 | 0.06 | 0.2 |
| 44 | N/A | 1.9 | 2 | >2.5 | 2.5 |
| 46 | N/A | 2.4 | 2.5 | N/A | 2.5 |

TABLE 6A-continued $IC_{50}$ Values of Various Compounds on Cancer Cell Line Proliferation

| Compound ID | HCT-116 IC50 (µM) | TOV-21G IC50 (µM) | A549 IC50 (µM) | Calu6 IC50 (µM) | LS-174T IC50 (µM) |
|---|---|---|---|---|---|
| 58 | N/A | 2.4 | 2.6 | N/A | N/A |
| 59 | 801 | 938 | 810 | N/A | N/A |
| 61 | 2.1 | 1.4 | N/A | N/A | N/A |
| 62 | 2.7 | N/A | 2 | N/A | N/A |
| 63 | 2.5 | N/A | N/A | N/A | N/A |
| 64 | 2.3 | 2.4 | 2.4 | N/A | 2.6 |
| 65 | 2.5 | 2.5 | N/A | N/A | N/A |
| 71 | 2.5 | N/A | 2.4 | N/A | N/A |
| 73 | 2.5 | N/A | 2.5 | N/A | N/A |
| 75 | 2.4 | N/A | 2.5 | N/A | 1 |
| 126 | 1.7 | 1.9 | 1.4 | N/A | 1 |
| 127 | 1.7 | 2.1 | 1.1 | N/A | 1.6 |
| 128 | 2.5 | 2.4 | 2.5 | N/A | N/A |
| 129 | 2.4 | 2 | 2.5 | N/A | N/A |
| 131 | 2.3 | 2.2 | 2.3 | N/A | N/A |
| 132 | 2.2 | 1.9 | 2.4 | N/A | N/A |
| 133 | 2.3 | 1.8 | 2.5 | N/A | N/A |
| 134 | 2.3 | 1.8 | 2.6 | N/A | N/A |
| 102 | 2.5 | >2.5 | >2.5 | N/A | N/A |
| 108 | >2.5 | >2.5 | >2.5 | N/A | N/A |
| 146 | 0.4 | 0.5 | 0.3 | N/A | N/A |
| 116 | >2.5 | >2.5 | >2.5 | N/A | N/A |
| 149 | >2.5 | >2.5 | N/A | N/A | N/A |
| 150 | >2.5 | >2.5 | N/A | N/A | N/A |
| 152 | >2.5 | N/A | N/A | N/A | N/A |
| 154 | >2.5 | N/A | N/A | N/A | N/A |
| 155 | 0.24 | N/A | N/A | N/A | N/A |
| 156 | 0.24 | N/A | N/A | N/A | N/A |
| 157 | 0.35 | N/A | N/A | N/A | N/A |
| 158 | 0.24 | N/A | N/A | N/A | N/A |
| 159 | 0.30 | N/A | N/A | N/A | N/A |

NA = not available

TABLE 6B

EC50 Values of Various Compounds on Cancer Cell Line Proliferation

| Compound ID | JEKO-1 IC50 (µM) | TOV-112D IC50 (µM) |
|---|---|---|
| 155 | 0.04 | 0.04 |
| 156 | 0.08 | 0.04 |
| 157 | 0.08 | 0.12 |
| 158 | 0.2 | 0.19 |
| 159 | 0.09 | 0.06 |

TABLE 6C

IC50 Values for Compound 42 on Various Cancer Cells

| Cell Line | IC50 (µM) |
|---|---|
| A427 (lung) | 0.15 |
| A549 (lung) | 65 |
| H292 (lung) | 0.16 |
| Colo205 (colon) | 0.2 |
| HCT-116 (colon) | 0.08 |
| HT-29 (colon) | 0.2 |
| SW626 (ovarian) | 0.3 |
| TOV-21G (ovarian) | 0.15 |
| TOV-112D (ovarian) | 0.13 |

TABLE 6D

EC50 Values for Compound 42 on Various Cancer Cells

| Cell Line | EC50 (nM) |
| --- | --- |
| Colon (HCT-116) | 87 |
| Lung (A549) | 72 |
| Mantle cell (Jeko-1) | 154 |
| Ovarian (A2780) | 58 |
| Ovarian (ES-2) | 42 |
| Ovarian (OAW2B) | 114 |
| Ovarian (OAW42) | 166 |
| Ovarian (SKOV3) | 376 |
| Ovarian (SW626) | 334 |
| Ovarian (TOV0112D) | 98 |
| Ovarian (TOV21G) | 74 |

TABLE 6E

IC50 Values for Compound F and Compound 42 on Various Cancer Cells

| | Cell Line | Compound F Proliferation IC50 (nM) | Compound 42 Proliferation IC50 (nM) |
| --- | --- | --- | --- |
| Ovarian | A2780 | 1300 | 84 |
| | ES-2 | Not Tested | 57 |
| | OAW28 | Not Tested | 140 |
| | OAW42 | >2500 | 166 |
| | OVCAR-3 | Not Tested | 140 |
| | TOV21G | 1500 | 109 |
| | TOV112D | 850 | 103 |
| CRC | HCT-116 | 1300 | 87 |
| Mantle Cell | Jeko-1 | >2500 | 154 |
| | Mino | 884 | 345 |

Example 7. Oral Bioavailability (PO) and Pharmacokinetics Assay

The pharmacokinetics and oral bioavailability of various compounds was evaluated following IV or PO administration to fasted male Sprague-Dawley mice (N=3/route/dose). Each compound was administered to fasted male Sprague-Dawley mice as a single dose of 1 mg/kg (IV) or 5 mg/kg (PO). For IV dosing, each compound was formulated in 10% DMA/15% Solutol/75% HPβ-CD (20%) as a 1 mg/mL solution for IV (3 mg/kg), for IP (5 mg/kg) and for PO (10 mg/kg) administrations.

Blood samples (0.250 mL) were collected into EDTA tubes then processed to generate plasma samples. Blood samples were collected at pre-dose, 0.083, 0.25, 0.5, 1, 2, 4, 8 and 24 hours post-dose administration. Plasma concentrations of each compound were determined using LC-MS/MS with a lower limit of quantitation of 1.0 ng/mL. The pharmacokinetic parameters were determined by non-compartmental methods using WinNonlin.

The pharmacokinetic parameters of each compound were determined by non-compartmental analysis (Model 201 for IV administration and Model 200 for PO administration) using WinNonlin Version 6.4 (Pharsight, Mountain View, Calif.). The area under the curve from the time of dosing to the last measurable concentration, $AUC_{(0-t)}$, was calculated by the linear trapezoidal rule. The area under the concentration-time curve extrapolated to infinity, $AUC_{(0-\infty)}$, was calculated as follows: $AUC_{(0-\infty)} = AUC_{(0-t)} + C_{last}/k$ Where $C_{last}$ is the last measurable concentration and k is the first order rate constant associated with the terminal elimination phase, estimated by linear regression of log concentration versus time. The half-life ($T_{1/2}$) of the terminal elimination phase was estimated based on the following equation: $T_{1/2} = 0.693/k$ K was determined based on at least three timepoints with $R^2 \geq 0.9$. Additional parameters were calculated as follows: $CL = Dose/AUC_{(0-\infty)}$ Where CL is the clearance of the compound of the disclosure in L/hr/kg, Dose is the administered dose in mg/kg. Mean residence time (MRT) was calculated as follows: $MRT = AUMC_{(0-\infty)}/AUC_{(0-\infty)}$ Where area under the first moment curve extrapolated to infinity ($AUMC_{(0-\infty)}$) was calculated as follows: $AUMC_{(0-\infty)} = AUMClast + tlast*Clast-k + Clast/k^2$ The steady state volume of distribution (Vss) was calculated as follows: $Vss = CL \times MRT$.

The oral bioavailability based on $AUC_{(0-t)}$ was calculated as follows: $F(\%) = AUC_{PO}/AUC_{IV} \times Dose_{IV}/Dose_{PO} \times 100$. For IV administration, the initial concentration, Co is reported and is an extrapolated value. For PO administration, the maximum concentration, Cmax is report and is an observed value.

Compound 42 had reasonable IV clearance and Vss of 1.3 L/kg with $T_{1/2}$ of 16 hours (Table 7). Compound 42 had lower systemic exposures following IP injection and oral administration with oral bioavailability of 21% after oral dosing (Table 7).

Figure 3:
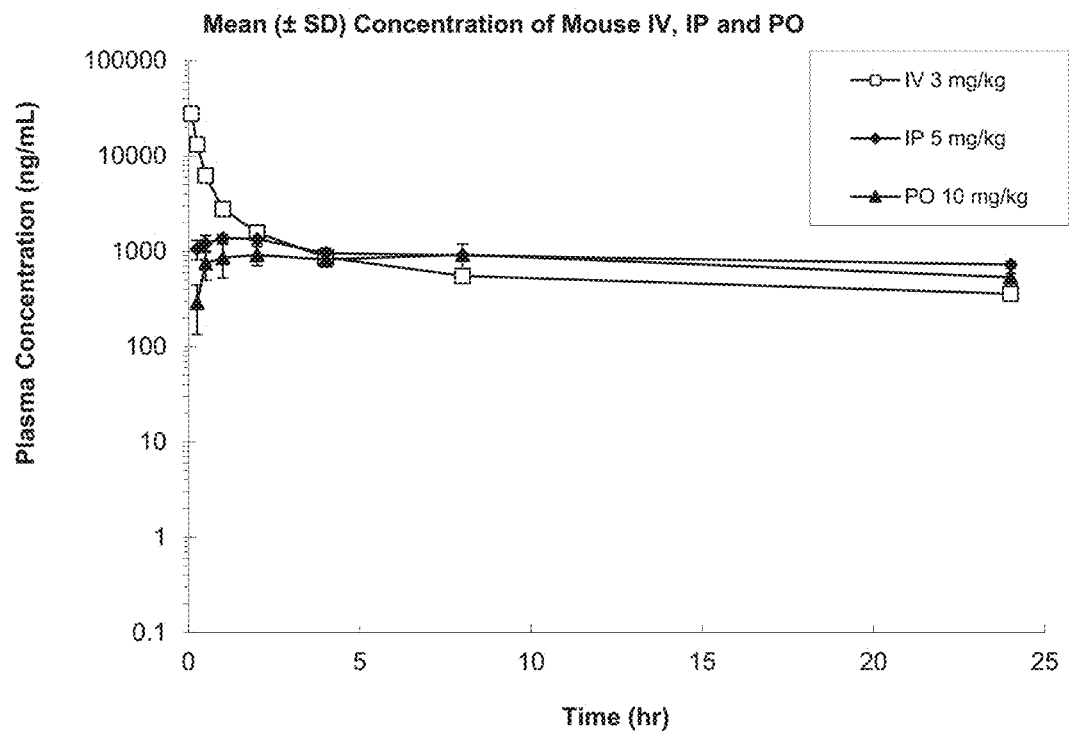
FIG. 3 shows mean plasma concentration of Compound 42 in mice after IV, IP, and PO administration.

The mean plasma concentration of Compound 42 in mice after IV, IP, and PO administration is shown in FIG. 3.

TABLE 7

Mouse intravenous (IV), intraperitoneal (IP) and oral (PO) bioavailability for Compound 42

| | Route (dose) | | |
| --- | --- | --- | --- |
| Formulation | IV bolus (3 mg/kg) 10% DMA/15% solutol/75% HP-b-CD (20%) | IP (5 mg/kg) | PO (10 mg/kg) |
| $C_0$ or $C_{max}$ (ng/mL) | 40499 | 1400 | 1057 |
| $T_{max}$ (hr) | NA | 1.33 | 3.67 |
| $T_{1/2}$ (hr) | 16.4 | 47.0 | 25.0 |
| $AUC_{0-t}$ (ng · hr/mL) | 25715 | 21543 | 18369 |
| Cl (mL/min/kg) | 1.49 | NA | NA |
| Vss (L/kg) | 1.32 | NA | NA |
| F (%) | NA | 50.3% | 21.4% |

Example 8. Mitophagy Cellular Assay

Figure 4:
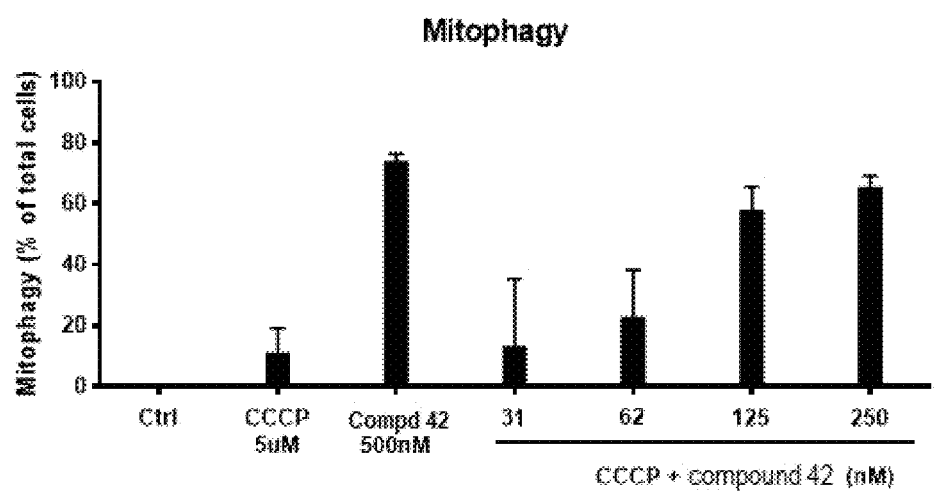
FIG. 4 shows mitophagy by Compound 42 treated with CCCP (carbonyl cyanide m-chlorophenyl hydrazine).

Mitophagy cellular assay was performed. FIG. 4 shows mitophagy was promoted by Compound 42 treated with CCCP (carbonyl cyanide m-chlorphenyl hydrazine). Without bound to any theory, functional Parkin initiates mitophagy in two steps: 1) Parkin with PINK1 identifies and isolates damaged mitochondria and 2) elimination of the damaged mitochondria. FIG. 4 shows that Compound 42 increases removal of damaged mictochondria.

The mitophagy cellular assay was performed as follows:
Cell Culture (YFP-Parkin Cells)

S-HeLa stably expressing a YFP-Parkin fusion protein were utilised in high content screening assays to assess Parkin-dependent endpoints. 4000 cells were seeded in each well of a 96 well plate (Perkin Elmer ViewPlate-96 F TC, cat. N. 6005182) and left to grow for 24 hours. Cells were then incubated with vehicle (DMSO) or increasing concentrations of compound (1, 2.5, 5, 10 μM) for 1 hour prior to adding 6 μM carbonyl cyanide m-chlorophenyl hydrazone (CCCP), each condition run in replicate of three. After 20 hours, the cells were processed for immunofluorescence.

Immunofluorescence

Samples were fixed in 4% PFA for 25 minutes RT and permeabilized with PBS 0.1% Triton-X100 for 3 minutes on ice, blocked with PBS 3% BSA, 0.3% Triton-X100 for 2 hours RT, followed by overnight incubation with primary antibody at 4° C. (0.5 µg/ml rabbit Tomm20 antibody FL-145; Santa Cruz Biotechnology) diluted in PBS 0.1% BSA, 0.3% Triton-X100. The secondary goat anti-rabbit antibody conjugated with DyLight 649 (Jackson ImmunoResearch) was applied for 1 hour at room temperature at a concentration of 2.8 µg/ml in conjunction with 1 µg/ml Hoechst33342. Cells were imaged using an Olympus Scan® automated microscope equipped with motorised stage and 20×APO planar objective. 18 images were acquired for each well using the following combination of excitation/emission filters: Hoechst33342 was excited through a 350/50 nm band pass filter and fluorescence intensity was collected through a 460/30 band pass filter. YFP was excited through a 500/20 nm band pass filter and fluorescence intensity was collected through a 540/35 band pass filter. DyLight 649 was excited through a 640/30 nm band pass filter and fluorescence intensity was collected through 700/75 band pass filter. Images were processed and analysed as described in the Image Analysis section.

Image Analysis

Images were processed and analyzed using Columbus HCS Analysis software (Version 2.5.0., PerkinElmer) as follows: Tomm20 fluorescence intensity was corrected using the parabola algorithm. Hoechst 33342 fluorescence was used to identify and count cells. Cells were segmented according to Tomm20 fluorescence intensity. Spot detection was optimized to recognize number and total cellular area of Tomm20 stained clusters (mitochondria). Tomm20 staining intensity, spot numbers and spot area were used to train a linear classifier algorithm that discriminated between Tomm20 positive (high intensity, spot numbers and spot area) and Tomm20 negative cells (low intensity, spot numbers and spot area). Bar graphs were generated reporting the number of Tomm20 negative cells expressed as percentage of total cells imaged for each well. Results were shown as mean±SD of 3 experiment performed in triplicate.

Statistical Analysis

Normalized data from the bar graphs were imported in Prism 7.0a (Graphpad™). The equation Y=Bottom+(Top−Bottom)/(1+10^((Log EC50−X)*HillSlope)) (log agonist vs. response−variable slope (4 parameters)) was applied to fit a non-linear curve to the dose response data and calculate $EC_{50}$ values.

Immunoblotting and Detection of Parkin Substrates

Hela YFP Parkin cells were cultured as described above, and $3 \times 10^5$ cells were plated in each well of a 6 well plate. 24 hours later, pre-incubated for one hour with 1% DMSO, 2.5, 5, or 10 µM compound (compound 42) in 1% DMSO and then treated with 6 µM CCCP with 2.5, 5, or 10 µM compound. As controls, cells were treated with DMSO and 6 µM CCCP alone. 4 hrs post treatment cells were washed three times with 1×PBS (3×5 min) and lysed with SDS lysis buffer (50 mM Tris/2% SDS/10% Glycerol). Cell lysates were sonicated for 15 secs, and protein quantification of cell lysates was determined by Thermo Scientific BCA assay.

Sample lysates were normalized for protein concentration and separated on 4%-12% pre-cast BOLT™ 15 well SDS-PAGE gels (Invitrogen) for 38 mins at 200V, and transferred to PVDF using iBLOT2 system (Life Technologies).

Processing of PVDF membranes for immune detection of Parkin substrates used specific antibodies to MFN2 (ab124773, Abcam. D2D10, Cell Signaling), VDAC (Anti-VDAC/Porin ab14734, Abcam), MitoNEET (16006-1-AP, Proteintech) and Parkin (P6248 PRK8, Sigma-Aldrich) followed by incubation in secondary antibody (Jackson ImmunoResearch HRP) and visualization of reaction by chemiluminesence (Fujifilm LAS-3000).

Example 9. Selectivity Screens and CYP Screen

Compound 42 was screened against 44 protein targets at 10 µM. The % inhibition shown in Table 8 indicates Compound 42's ability to displace radioligands. If the % inhibition is less than 50%, the test compounds is consider to have no effect. Thus, as shown in Table 8, Compound 42 demonstrated to have no effects against the 44 protein targets.

TABLE 8

% Inhibition of protein targets by Compound 42

| Assay | % Inhib |
| --- | --- |
| Ca2+ channel (L, dihydropyridine) | 45% |
| NA+ Channel (Site2) | 43% |
| PDE4D2 (h) | 35% |
| COX1(h) | 19% |
| alpha 1A (h) | 16% |
| dopamine transporter (h) | 13% |
| PDE3A (h) | 13% |
| 5-HT1A (h) | 10% |
| 5-HT transporter (h) | 10% |
| beta 2(h) | 9% |
| delta (DOP) (h) | 9% |
| NMDA | 8% |
| Lck kinase (h) | 8% |
| A2A(h) | 7% |
| mu (MOP) (h) | 6% |
| V1a (h) | 5% |
| MAO-A | 4% |
| M1 (h) | 4% |
| 5-HT2A (h) | 4% |
| GR (h) | 4% |
| kappa (KOP) | 3% |
| 5-HT1B | 1% |
| Potassium Channel hERG (human) | 1% |
| KV channel | 1% |
| norepinephrine transporter (h) | 1% |
| COX2(h) | 1% |
| acetylcholinesterase (h) | 1% |
| alpha 2A (h) | — |
| beta 1 (h) | — |
| BZD (central) | — |
| CB1 (h) | — |
| CB2 (h) | — |
| CCK1 (CCKA) (h) | — |
| D1 (h) | — |
| D2S (h) | — |
| ETA (h) | — |
| H1 (h) | — |
| H2 (h) | — |
| M2 (h) | — |
| M3 (h) | — |
| N neuronal alpha 4beta 2 (h) | — |
| 5-HT2B (h) | — |
| 5-HT3 (h) | — |
| AR (h) | — |

Compound 42 was also screened in a kinase panel assay. As shown in Table 9, Compound 42 does not inhibit CDK 4/6 or other kinases.

TABLE 9

| Kinases Screened | % Inhibition (10 μM) |
|---|---|
| ABL1 | 8 |
| AURKA (Aurora A) | 4 |
| CDK2/Cyclin A | 4 |
| CDK4/CyclinD1 | 12 |
| CDK4/CyclinD3 | 3 |
| CDK6/CyclinD1 | 0 |
| EGFR (ErbB1) | 8 |
| GSK3B (GSK3 beta) | 12 |
| MAPK1 (ERK2) | 4 |
| MAPK14 (p38 alpha) | 19 |
| MAPK3 (ERK1) | 1 |
| PAK4 | 5 |
| PIM1 | 5 |
| PLK1 | 4 |

% Inhibition of kinase targets by Compound 42

Lastly, Compound 42 was screened in a CYP inhibition assay. Compound 42 have no significant CYP inhibition activity for the 5 major CYP enzymes tested as shown in Table 10.

TABLE 10

% Inhibition of Various CYP by Compound 42

% Inhibition at 30 μM for Various CYP

| | 1A2 | 2C9 | 2C19 | 2D6 | 3A4 |
|---|---|---|---|---|---|
| Compound 42 | (16.2)* | 11.8 | 60.5 | 6.87 | (9.63)* |

*no inhibition

Representative Synthesis

Below examples demonstrate general methods in which one skilled in the art could use to synthesize the compounds of the disclosures. One skilled in the art would readily understand that below examples provide guidance for the synthesis and one skilled in the art would understand that by changing starting materials or intermediates, various asymmetric triazole compounds of the present disclosure can be obtained.

Example 10: Synthesis of N-[5-benzamido-1-(4-iodophenyl)-1,2,4-triazol-3-yl]benzamide (Compound E)

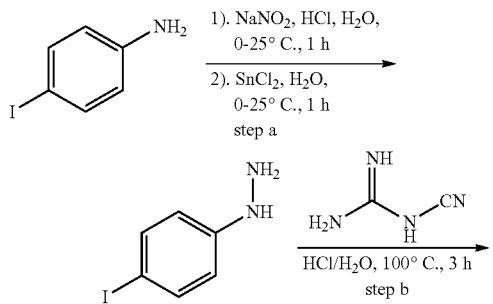

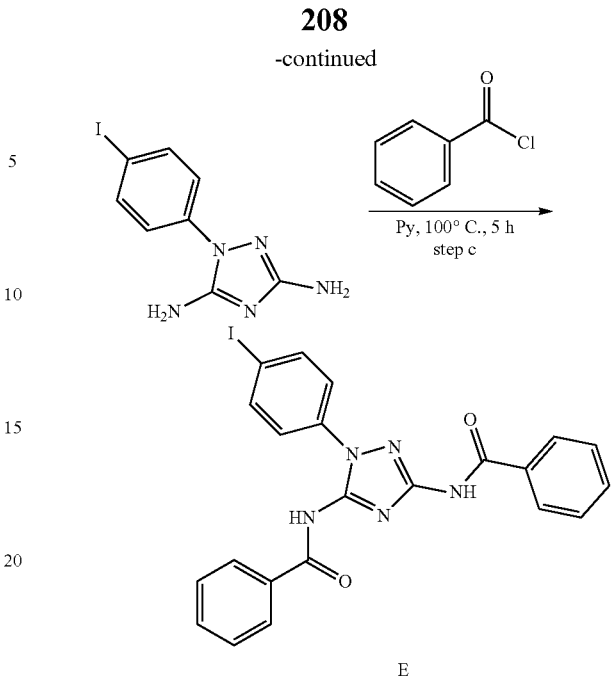

E

Step a: Synthesis of (4-iodophenyl)hydrazine

To a suspension of 4-iodoaniline (10.00 g, 45.66 mmol, 1.00 eq) in HCl (12 M, 30 mL) at 0° C. was added dropwise a solution of NaNO$_2$ (3.15 g, 45.66 mmol, 1.00 eq) in H$_2$O (15 mL), and the resulting mixture was stirred at 25° C. for 1 h. Then a solution of SnCl$_2$ (30.91 g, 136.98 mmol, 3.00 eq) in HCl (12 M, 20 mL) was added dropwise at 0° C. The reaction mixture was stirred at 25° C. for 1 h. TLC (DCM/MeOH=10:1) indicated the starting material was consumed completely and a new spot formed. The reaction mixture was filtered and the filter cake was dried under reduced pressure to afford (4-iodophenyl)hydrazine (9.50 g, HCl salt, crude) as a purplish red solid. $^1$H NMR (400 MHz, DMSO-d$_6$) δ ppm: 10.39 (br, 3H), 8.50 (br, 1H), 7.59 (d, J=8.8 Hz, 2H), 6.86 (d, J=8.8 Hz, 2H).

Step b: Synthesis of 1-(4-iodophenyl)-1,2,4-triazole-3,5-diamine

To a solution of (4-iodophenyl)hydrazine hydrochloride (6.50 g, 24.03 mmol, 1.00 eq) in H$_2$O (15 mL) was added 1-cyanoguanidine (2.02 g, 24.03 mmol, 1.00 eq) and HCl (12 M, 5 mL). The reaction mixture was stirred at 100° C. for 3 h. TLC (DCM/MeOH=8/1) indicated the starting material was consumed completely and new spots formed. The reaction was basified to pH=8 with aq. NaOH solution (40%, w/v). After removal of the solvent under vacuum, hexane (100 mL) was added and the resulting mixture was stirred at 25° C. for 15 min. The mixture was filtered and the filter cake was washed with DCM (150 mL). The solids were collected and dried in vacuo to afford 1-(4-iodophenyl)-1,2,4-triazole-3,5-diamine (1.00 g, crude) as a brown solid. LC-MS (ESI): m/z 301.8 (M+H)$^+$.

Step c: Synthesis of N-[5-benzamido-1-(4-iodophenyl)-1,2,4-triazol-3-yl]benzamide To a mixture of 1-(4-iodophenyl)-1,2,4-triazole-3,5-diamine (500 mg, 1.66 mmol, 1.00 eq) in pyridine (20 mL)

was added benzoyl chloride (934 mg, 6.64 mmol, 771.69 μL, 4.00 eq), then the mixture was stirred at 100° C. for 5 h. LC-MS indicated the desired product was detected. Ethyl acetate (60 mL) was added and the resulting mixture was washed with HCl (1 M, 40 mL×3). The organic layer was dried over anhydrous $Na_2SO_4$, concentrated to afford the crude product, which was purified by prep-HPLC (column: Phenomenex Synergi C18 150×25×10 μm; mobile phase: [water (0.05% HCl)-ACN]; B %: 50%-70%, 10.5 min) to afford N-[5-benzamido-1-(4-iodophenyl)-1,2,4-triazol-3-yl] benzamide (21.80 mg, 42.80 μmol, 3% yield, 99+% purity) as a white solid. $^1$H NMR (400 MHz, DMSO-$d_6$) δ ppm: 11.27 (br, 1H), 11.01 (br, 1H), 8.10-8.00 (m, 2H), 8.00-7.80 (m, 4H), 7.67-7.60 (m, 2H), 7.56-7.36 (m, 6H); $^{13}$C NMR (75 MHz, DMSO-$d_6$) δ ppm: 166.8, 165.8, 155.5, 146.1, 138.7, 137.2, 134.0, 133.3, 132.6, 129.2, 129.0, 128.4, 125.1, 94.6. LC-MS (ESI): m/z 510.0 (M+H)$^+$.

Example 11: Synthesis of 2-methyl-N-[5-[(2-methylbenzoyl)amino]-1-phenyl-1,2,4-triazol-3-yl]benzamide (Compound F)

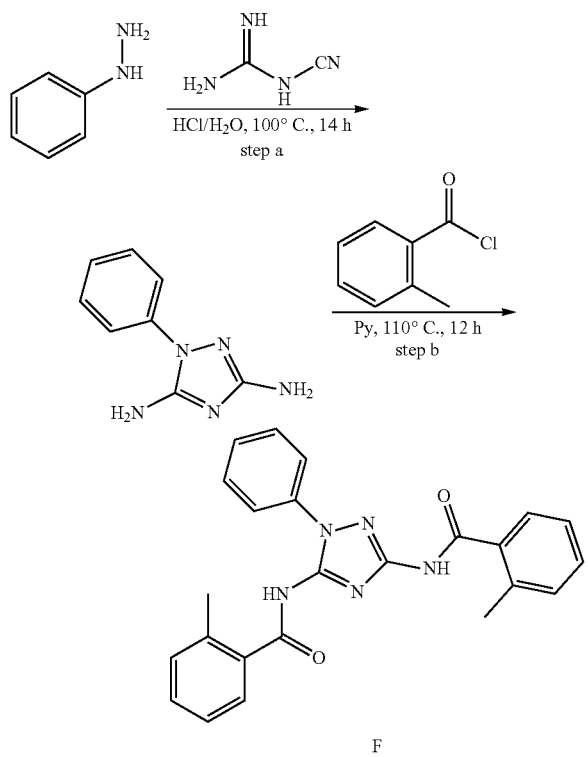

Step a: Synthesis of 1-phenyl-1,2,4-triazole-3,5-diamine

To a solution of 1-cyanoguanidine (10.00 g, 118.93 mmol, 1.00 eq) and phenylhydrazine (12.86 g, 118.93 mmol, 11.69 mL, 1.00 eq) in $H_2O$ (40 mL) was added hydrochloric acid (12 M in water, 8 mL). Then the reaction mixture was stirred at 100° C. for 14 h. The reaction mixture was basified pH to 8 with 40% sodium hydroxide aqueous solution. After removal of the solvent, the residue was slurried with hexane (150 mL) and followed by DCM (200 mL). The mixture was filtered and the filter cake was collected to give 1-phenyl-1,2,4-triazole-3,5-diamine (36.00 g, 197.27 mmol, 83% yield) as a yellow solid. $^1$H NMR (400 MHz, DMSO-$d_6$) δ 7.48-7.40 (m, 4H), 7.23-7.19 (m, 1H), 6.70 (brs, 2H), 6.23 (brs, 2H).

Step b: Synthesis of 2-methyl-N-[5-[(2-methylbenzoyl)amino]-1-phenyl-1,2,4-triazol-3-yl]benzamide To a solution of 1-phenyl-1,2,4-triazole-3,5-diamine (800 mg, 4.57 mmol, 1.00 eq) in pyridine (10 mL) was added 2-methylbenzoyl chloride (2.12 g, 13.70 mmol, 1.78 mL, 3.00 eq). The reaction mixture was heated to 110° C. and stirred for 12 h. LC-MS indicated the starting material was consumed completely and desired compound was detected. The reaction mixture was quenched by saturated aqueous $NH_4Cl$ (80 mL), and then extracted with ethyl acetate (100 mL×3). The organic layers were combined, washed with sat. $NH_4Cl$ (50 mL), and sat. brine (50 mL), then dried over anhydrous $Na_2SO_4$, filtered and concentrated under reduced pressure to give a residue, which was purified by column chromatography on silica gel (3-50% ethyl acetate/petroleum ether) to afford the crude product. It was further purified by prep-HPLC (column: Phenomenex Synergi C18 150×25×10 μm; mobile phase: [water (0.05% HCl)-ACN]; B %: 37%-57%, 10.5 min) to afford 2-methyl-N-[5-[(2-methylbenzoyl)amino]-1-phenyl-1,2,4-triazol-3-yl]benzamide (22.0 mg, 52.40 μmol, 98% purity) as a white solid. $^1$H NMR (400 MHz, $CD_3OD$) δ 7.61-7.54 (m, 2H), 7.52-7.50 (m, 4H), 7.42-7.39 (m, 3H), 7.31-7.25 (m, 4H), 2.48 (s, 3H), 2.29 (s, 3H); $^{13}$C NMR (100 MHz, $CD_3OD$) δ 169.9, 169.6, 154.1, 145.4, 136.7, 136.2, 130.8, 130.7, 129.2, 127.2, 127.1, 125.5, 125.5, 125.4, 18.4. LC-MS (ESI): m/z 412.1 (M+H)$^+$.

Example 12: Synthesis of 2-methyl-N-(3-(5-methylpyridin-2-yl)-1-phenyl-1H-1,2,4-triazol-5-yl)benzamide (Compound R3) and 2-methyl-N-(3-(3-methylpyridin-2-yl)-1-phenyl-1H-1,2,4-triazol-5-yl) benzamide (Compound S3)

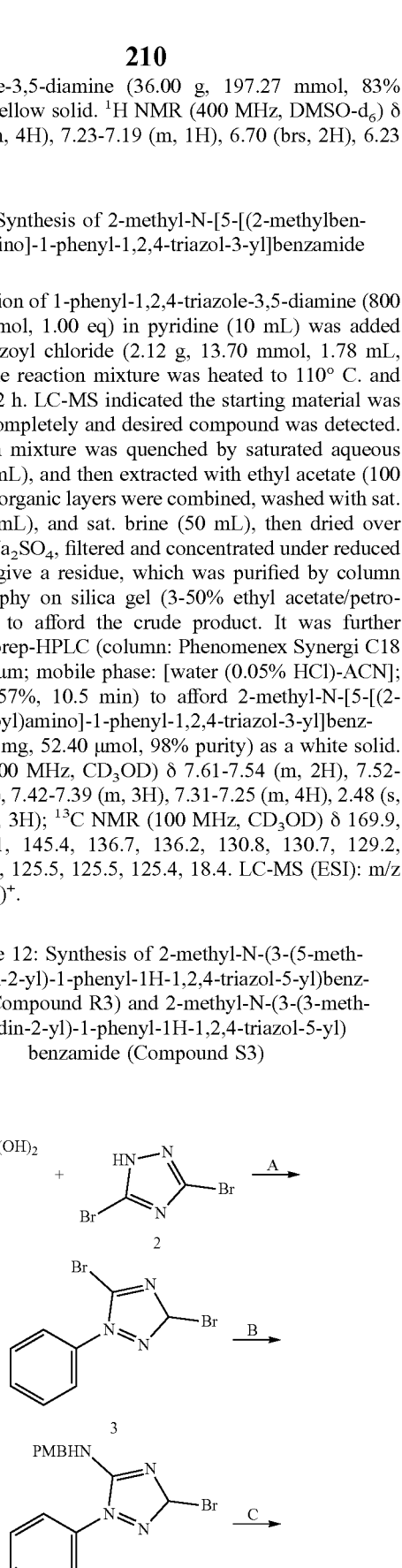

211
-continued

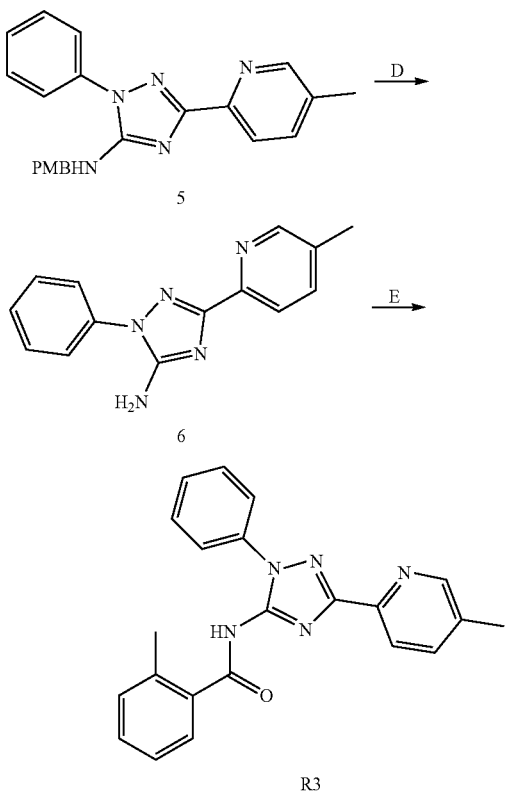

212
-continued

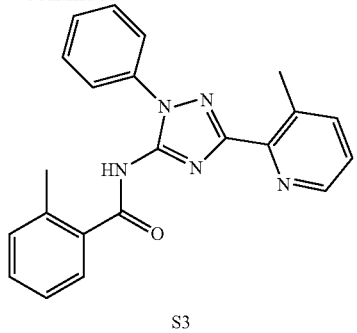

S3

Step A: Synthesis of 3,5-dibromo-1-phenyl-1H-1,2,4-triazole

Two batches of phenylboronic acid (13.5 g, 111 mmol, 1.0 eq), 3,5-dibromo-1H-1,2,4-triazole (25 g, 110 mmol, 1.0 eq), Cu(OAc)2 (30 g, 165 mmol, 1.5 eq), pyridine (26.5 g, 335 mmol, 27 mL, 3.0 eq) and 4 Å MS (5 g, 22.0 mmol) in toluene (250 mL) was degassed and purged with $O_2$ for three times, and then the mixture was stirred at 80° C. for 16 h under 02 atmosphere (15 psi). After completion of the reaction, the two batches of reaction mixture were mixed and filtered, then concentrated under reduced pressure to give a residue. The residue was purified by flash silica gel chromatography (ISCO®: 200 g SepaFlash@ Silica Flash Column, eluent of 0~10% ethyl acetate/petroleum ether gradient @ 80 mL/min) to give 36 g crude product with 67% purity. 2 g was used for next step directly. The remaining 34 g was diluted with DCM (200 mL) and washed with saturated aqueous NaHCO3 (100 mL×1), brine (100 mL), dried over anhydrous Na2SO4, filtered and concentrated under reduced pressure to give 3,5-dibromo-1-phenyl-1,2,4-triazole (29.2 g, 37% yield, 85% purity) as a light yellow solid. LC-MS (ESI): m/z (M+H) 303.9.

Step B: Synthesis of 3-bromo-N-(4-methoxybenzyl)-1-phenyl-1H-1,2,4-triazol-5-amine Two batches of 3,5-dibromo-1-phenyl-1,2,4-triazole (2 g, 5.61 mmol, 1.0 eq), (4-methoxyphenyl) methanamine (795 mg, 5.80 mmol, 0.75 mL, 1.0 eq) and K2CO3 (1.16 g, 8.42 mmol, 1.5 eq) in NMP (3 mL) was stirred at 150° C. for 1 h under microwave. TLC (petroleum ether/ethyl acetate=2:1) showed one main spot with desired product was detected for the two batches. The two batches of reaction mixture were combined, diluted with DCM (80 mL), washed with water (50 mL×3), saturated NaCl (50 mL), dried over $Na_2SO_4$, filtered and concentrated under reduced pressure. The residue was purified by flash silica gel chromatography (TLC: petroleum ether/ethyl acetate=5:1; ISCO®; 20 g SepaFlash® Silica Flash Column, eluent of 0~20% ethyl acetate/petroleum ether gradient @ 80 mL/min) to give 5-bromo-N-[(4-methoxyphenyl)methyl]-2-phenyl-1,2,4-triazol-3-amine (2.4 g, 58% yield, 97% purity) as light yellow oil. LC-MS (ESI): m/z (M+H) 359.1/361.1.

Step C: Synthesis of N-(4-methoxybenzyl)-3-(5-methylpyridin-2-yl)-1-phenyl-1H-1,2,4-triazol-5-amine A mixture of 5-bromo-N-[(4-methoxyphenyl)methyl]-2-phenyl-1,2,4-triazol-3-amine (500 mg, 1.35 mmol, 1.0 eq), tributyl-(5-methyl-2-pyridyl)stannane (500 mg, 1.31 mmol, 0.97 eq) and [2-(2-aminophenyl)phenyl]-chloro-palladium; dicyclohexyl-[2-(2,6-dimethoxyphenyl)phenyl]phosphane (100 mg, 139 µmol, 0.1 eq) in THF (20 mL) was degassed and purged with N2 for three times, and then the mixture was stirred at 90° C. for 16 h under N2. Most of start material remained. Then the reaction mixture was filtered and [2-(2-aminophenyl)phenyl]-chloro-palladium;dicyclohexyl-[2-(2,6-dimethoxyphenyl)phenyl]phosphane (100 mg, 139 µmol, 0.1 eq) was added to the mixture. The reaction mixture was stirred at 90° C. for 72 h. After being cooled to room temperature, the reaction mixture was quenched by addition of saturated aqueous KF (20 mL) and stirred at 15° C. for 1 h. Then the mixture was filtered and extracted with DCM (40 mL×3). The combined organic layers were dried over $Na_2SO_4$, filtered and concentrated under reduced pressure. The residue was purified by column chromatography ($SiO_2$, petroleum ether/ethyl acetate=10/1 to 2:1; DCM:MeOH=10:1) to give N-[(4-methoxyphenyl)methyl]-5-(5-methyl-2-pyridyl)-2-phenyl-1,2,4-triazol-3-amine (320 mg, 43% yield, 67% purity) as a yellow oil. LC-MS (ESI): m/z (M+H) 372.3.

Step D: Synthesis of 3-(5-methylpyridin-2-yl)-1-phenyl-1H-1,2,4-triazol-5-amine A mixture of N-[(4-methoxyphenyl)methyl]-5-(5-methyl-2-pyridyl)-2-phenyl-1,2,4-triazol-3-amine (320 mg, 577 µmol, 1 eq) in TFA (7.70 g, 67.5 mmol, 5 mL) was stirred at 50° C. for 2 h. After the reaction was completely, the reaction mixture was concentrated under reduced pressure to give a residue. The residue was purified by prep-HPLC (column: Luna C18 150×25 5 µm; mobile phase: [water (0.225% FA)-ACN]; B %: 15%-36%, 10 min) to give a crude product. The crude product was diluted with DCM (20 mL)/H2O (20 mL) and adjusted the pH to 10-12 with $NH_3.H_2O$. Then extracted with DCM (20 mL×3), the combined organic layers were dried over $Na_2SO_4$, filtered and concentrated under reduced pressure. The residue was purified by prep-TLC ($SiO_2$, DCM:MeOH=10:1) to give 5-(5-methyl-2-pyridyl)-2-phenyl-1,2,4-triazol-3-amine (70 mg, 48% yield) as a white solid. LC-MS (ESI): m/z (M+H) 252.0; 1H NMR (400 MHz, DMSO-d6) 8.46 (s, 1H), 7.88-7.86 (d, 1H), 7.69-7.67 (dd, 1H), 7.64-7.62 (d, 2H), 7.57-7.53 (t, 2H), 7.42-7.39 (t, 1H), 6.56 (s, 2H), 2.34 (s, 3H).

Step E: Synthesis of 2-methyl-N-(3-(5-methylpyridin-2-yl)-1-phenyl-1H-1,2,4-triazol-5-yl)benzamide (Compound R3)

To a solution of 5-(5-methyl-2-pyridyl)-2-phenyl-1,2,4-triazol-3-amine (70 mg, 279 µmol, 1.0 eq) and pyridine (68.6 mg, 867 µmol, 3.1 eq) in MeCN (9 mL) was added the solution of 2-methyl-benzoyl chloride (60 mg, 388 µmol, 50.4 uL, 1.4 eq) in MeCN (1 mL) drop-wise at 80° C. The mixture was stirred at 80° C. for 2 h. Only a few desired product was formed, then a solution of 2-methylbenzoyl chloride (90 mg, 582.17 µmol, 2.1 eq) in MeCN (1 mL) was added dropwise at 80° C. The mixture was stirred at 80° C. for 16 h. After being cooled to room temperature, the reaction mixture was adjusted pH to 11-12 by saturated aqueous LiOH and stirred at 15° C. for 16 h. The reaction mixture was extracted with DCM (30 mL). The organic layer was washed with saturated aqueous NaHCO3 (30 mL), brine (30 mL); dried over Na2SO4, filtered and concentrated under reduced pressure. The residue was purified by prep-HPLC (column: Phenomenex Synergi C18 150×25×10 µm; mobile phase: [water (0.05% HCl)-ACN]; B %: 32%-52%, 7.8 min) to give 2-methyl-N-[5-(5-methyl-2-pyridyl)-2-phenyl-1,2,4-triazol-3-yl]benzamide (45 mg, 80% yield, HCl salt) as a white solid.

LC-MS (ESI): m/z (M+H) 370.2; 1H NMR (400 MHz. DMSO-d6) 11.32 (s, 1H), 8.75-8.74 (m, 1H), 8.22-8.20 (d, 1H), 8.12-8.09 (dd, 1H), 7.84-7.82 (m, 2H), 7.64-7.60 (m, 2H), 7.53-7.51 (m, 2H), 7.45-7.40 (td, 1H), 7.33-7.28 (m, 2H), 2.46 (s, 3H), 2.20 (s, 3H). 13C NMR (75 MHz, DMSO-d6) 168.6, 156.9, 147.8, 146.79, 143.19, 141.8, 136.6, 136.3, 136.0, 134.0, 131.0, 130.8, 129.5, 129.2, 127.5, 125.8, 123.8, 122.3, 19.3, 17.9.

Step F: Synthesis of N-(4-methoxybenzyl)-3-(3-methylpyridin-2-yl)-1-phenyl-1H-1,2,4-triazol-5-amine A mixture of 5-bromo-N-[(4-methoxyphenyl)methyl]-2-phenyl-1,2,4-triazol-3-amine (600 mg, 1.62 mmol, 1.0 eq), tributyl-(3-methyl-2-pyridyl)stannane (500 mg, 1.31 mmol, 0.8 eq) and [2-(2-aminophenyl)phenyl]-chloro-palladium; dicyclohexyl-[2-(2,6-dimethoxyphenyl)phenyl]phosphane (100 mg, 139 µmol, 0.86 eq) in THF (20 mL) was degassed and purged with N2 for three times, and then the mixture was stirred at 90° C. for 60 h under N2. But most of start material remained, the mixture was filtered and [2-(2-aminophenyl)phenyl]-chloro-palladium;dicyclohexyl-[2-(2,6-dimethoxyphenyl)phenyl]phosphane (100 mg, 139 µmol, 0.86 eq) was added. The reaction mixture was stirred at 90° C. for additional 32 h in a tube. After being cooled to room temperature, the reaction mixture was quenched by addition of saturated aqueous KF (20 mL) and stirred at 15° C. for 30 min. Then the mixture was diluted with DCM (20 mL) and extracted with DCM (30 mL×3). The combined organic layers were dried over Na2SO4, filtered and concentrated under reduced pressure. The residue was purified by column chromatography (TLC: EtOAc; $SiO_2$, petroleum ether/ethyl acetate=5/1 to 2:1; DCM:MeOH=10:1) to give a crude product. The crude product was repurified by prep-TLC ($SiO_2$, EtOAc) to give N-[(4-methoxyphenyl)methyl]-5-(3-methyl-2-pyridyl)-2-phenyl-1,2,4-triazol-3-amine (110 mg, 11% yield, 61% purity) as yellow oil. LC-MS (ESI): m/z (M+H) 372.0.

Step G: Synthesis of 3-(3-methylpyridin-2-yl)-1-phenyl-1H-1,2,4-triazol-5-amine A mixture of N-[(4-methoxyphenyl)methyl]-5-(3-methyl-2-pyridyl)-2-phenyl-1,2,4-triazol-3-amine (110 mg, 181 µmol, 1.0 eq) in TFA (4.62 g, 40.5 mmol, 3 mL) was stirred at 50° C. for 2 h. After completion of the reaction, the reaction mixture was concentrated under reduced pressure. The residue was diluted with DCM (15 mL) and water (10 mL), and adjust pH to 9-10 by $K_2CO_3$ (solid). Then the resulting was extracted with DCM (15 mL×2), the combined organic layers were concentrated under reduced pressure. The residue was purified by prep-TLC (TLC: DCM: MeOH=10:1; $SiO_2$, DCM:MeOH=10:1) to give 5-(3-methyl-2-pyridyl)-2-phenyl-1,2,4-triazol-3-amine (55 mg, crude) as a white solid. LC-MS (ESI): m/z (M+H) 252.0.

Step H: Synthesis of 2-methyl-N-(3-(3-methylpyridin-2-yl)-1-phenyl-1H-1,2,4-triazol-5-yl)benzamide (Compound S3)

To a solution of 5-(3-methyl-2-pyridyl)-2-phenyl-1,2,4-triazol-3-amine (55 mg, 219 µmol, 1.0 eq), pyridine (98 mg, 1.24 mmol, 5.7 eq) and DMAP (26 mg, 213 µmol, 0.97 eq) in toluene (9 mL) was added the solution of 2-methylbenzoyl chloride (100 mg, 647 mol, 3.0 eq) in toluene (1 mL) dropwise at 80° C. Then the mixture was stirred at 80° C. for 2 h. The reaction mixture was concentrated under reduced pressure. The residue was dissolved in CH3CN (10 mL) and adjusted the pH to 11-12 by saturated aqueous LiOH and stirred at 15° C. for 16 h. The reaction mixture was extracted with DCM (30 mL). The organic layer was washed with saturated NaHCO$_3$ (30 mL), brine (30 mL×1), dried over Na2SO4, filtered and concentrated under reduced pressure. The residue was purified by prep-HPLC (column: Phenomenex Synergi C18 150×25×10 µm; mobile phase: [water (0.05% HCl)-ACN]; B %: 30%-45%, 7.8 min) to give 2-methyl-N-[5-(3-methyl-2-pyridyl)-2-phenyl-1,2,4-triazol-3-yl]benzamide (16.1 mg, 17.54% yield, HCl salt) as a white solid. LC-MS (ESI): m/z (M+H) 370.2; 1H NMR (400 MHz, DMSO-d6) 11.30 (s, 1H), 8.69-8.68 (d, 1H), 8.26-8.24 (d, 1H), 7.77-7.71 (m, 3H), 7.64-7.61 (m, 2H), 7.57-7.49 (m, 2H), 7.45-7.41 (td, 1H), 7.34-7.29 (m, 2H), 2.74 (s, 3H), 2.22 (s, 3H).

Example 13: Synthesis of N-(1-phenyl-3-(pyridin-2-yl)-1H-1,2,4-triazol-5-yl)benzamide (Compound Y1)

Step A:
To a mixture of pyridine-2-carbonitrile (10.0 g, 96.1 mmol) in i-PrOH (57.7 g, 960 mmol, 9.99 eq), NaOMe (155 mg, 2.87 mmol, 0.03 eq) was added at 0° C. Then the mixture was stirred at 20° C. for 4 hr. The mixture was concentrated under vacuum to give a residue. n-Hexane (50 mL) and AcOH (0.15 mL) was added to the residue. Then the solution was filtered and the filtrate was concentrated under vacuum to give isopropyl pyridine-2-carboximidate (crude, 2) as brown oil, which was used for the next step without further purification.

Step B:
A solution of NH$_2$CN (7.5 g, 178 mmol, 1.95 eq), sodium dihydrogen phosphate (42.0 g, 350 mmol, 3.83 eq) and Na$_2$HPO$_4$.12H$_2$O (32.0 g, 89.4 mmol, 0.98 eq) in H$_2$O (100 mL) was added isopropyl pyridine-2-carboximidate (15.0 g crude, 1.0 eq, 2). Then the mixture was stirred at 20° C. for 16 h. DCM (300 mL) was added to the reaction mixture. The organic layer was concentrated under vacuum. The residue was purified by flash chromatography (ISCO®: 220 g Sepa Flash® Silica Flash Column, eluent of 0-25% Ethyl acetate/Petroleum ether gradient at 100 mL/min; TLC (petroleum ether/ethyl acetate=5/1, R$_f$=0.24) to give isopropyl N-cyanopicolinimidate (10.0 g, 57% yield, 3) as a white solid. LC-MS (ESI): m/z (M+H) 190.1; $^1$H NMR (400 MHz, DMSO-d$_6$) 8.81-8.79 (m, 1H), 8.11-8.07 (dt, 1H), 7.95-7.93 (m, 1H), 7.74-7.71 (m, 1H), 5.34-5.28 (hept, 1H), 1.41-1.39 (d, 6H).

Step C:
A mixture of isopropyl N-cyanopicolinimidate (1.0 g, 5.29 mmol, 3) and phenylhydrazine (627 mg, 5.80 mmol, 1.1 eq) in MeOH (15 mL) was stirred at 80° C. for 16 h. After being cooled to room temperature, the reaction mixture was concentrated under reduced pressure. The residue was purified by column chromatography (TLC: petroleum ether/ethyl acetate=0/1, R$_f$=0.1) (SiO$_2$, petroleum ether/ethyl acetate=1/0, 5/1, 2/1, 0:1) to afford 2-phenyl-5-(2-pyridyl)-1,2,4-triazol-3-amine (900 mg, 70% yield, 4) as a brown solid. LC-MS (ESI): m/z (M+H) 238.1.

Step D:
To a mixture of 2-phenyl-5-(2-pyridyl)-1,2,4-triazol-3-amine (200 mg, 843 µmol, 1.0 eq, 4) and NaOH (180 mg, 4.50 mmol, 5.34 eq) in THF (2 mL) and H$_2$O (2 mL), benzoyl chloride (242 mg, 1.72 mmol, 2.04 eq) was added. Then the mixture was stirred at 20° C. for 20 h. The reaction mixture was adjusted to pH=7 by HCl (2 M in water, 2 mL). The mixture was concentrated under vacuum. The residue was purified by reversed phase column (HCl condition) to give N-[2-phenyl-5-(2-pyridyl)-1,2,4-triazol-3-yl]benzamide (70.1 mg, 21% yield, Compound Y1) as a white solid. LC-MS (ESI): m/z (M+H) 342.1; $^1$H NMR (400 MHz, DMSO-d6+D$_2$O) 8.83-8.82 (d, 1H), 8.44-8.41 (m, 2H), 7.97-7.95 (d, 2H), 7.89-7.86 (m, 1H), 7.74-7.72 (m, 2H), 7.64-7.60 (m, 1H), 7.55-7.50 (m, 4H), 7.48-7.44 (dd, 1H). $^{13}$C NMR (100 MHz, DMSO-d$_6$) 167.1, 156.7, 148.8, 146.8, 145.5, 142.9, 137.0, 133.3, 132.5, 130.0, 129.6, 129.1, 128.6, 126.6, 123.8, 123.5.

Example 14: Synthesis of N,N'-(1-(4-(trifluoromethoxy)phenyl)-1H-1,2,4-triazole-3,5-diyl)bis(2-methylbenzamide) (Compound 42)

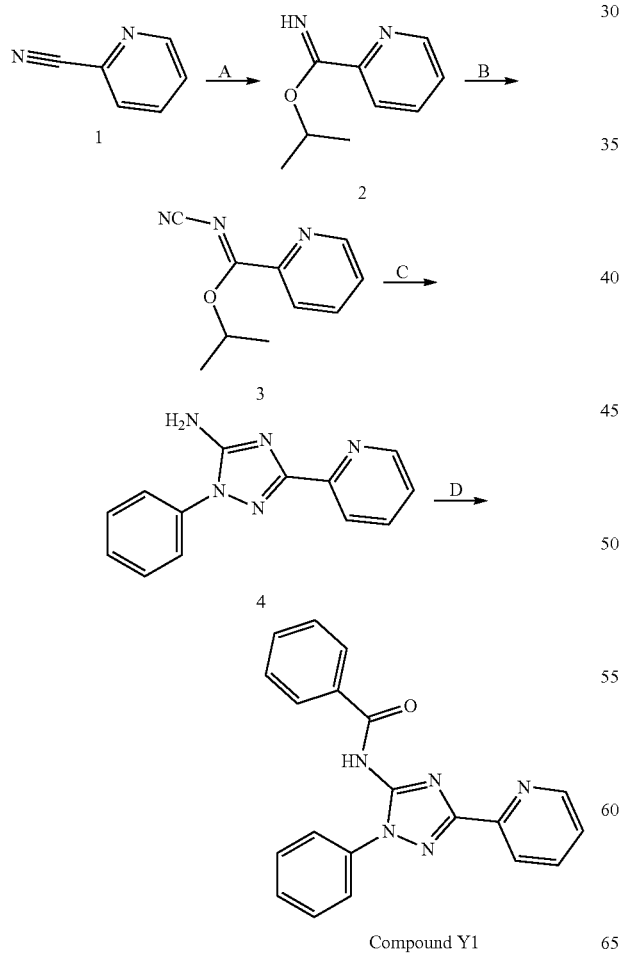

Compound Y1

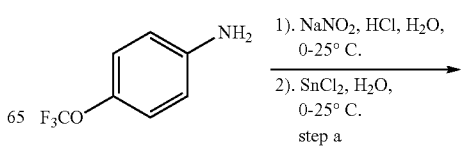

step a

-continued

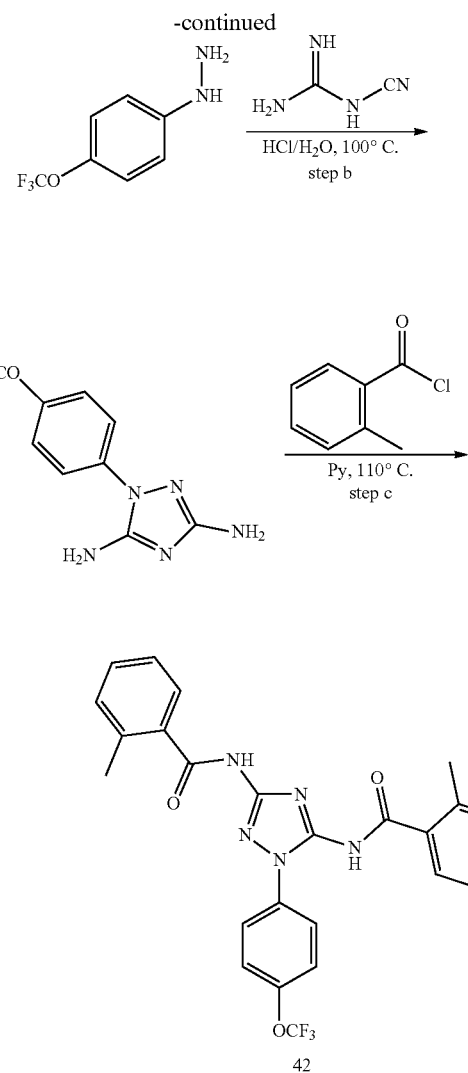
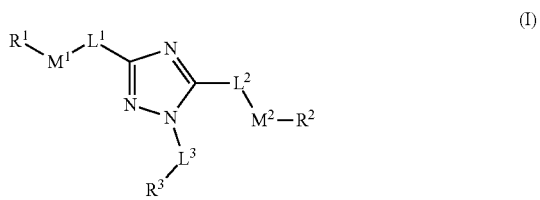

Compound 42 can be synthesized according to Examples 8 and 9. (4-(Trifluoromethoxy)phenyl)hydrazine can be prepared starting from 4-(trifluoromethoxy)aniline instead of 4-iodoaniline according to Example 10, step a. Compound 42 can then be prepared in two steps according to Example 11 starting with (4-(Trifluoromethoxy)phenyl)hydrazine instead of phenylhydrazine.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:
1. A compound of formula (I):

or a pharmaceutically acceptable salt thereof, wherein:
$L^1$, $L^2$ and $L^3$ are each independently selected from a bond, alkylene, or alkenylene;
$M^1$ and $M^2$ are each independently selected from —$NR^4$—, —$NR^4C(O)$—, —$N(C(O)R^1)$—, —$C(O)NR^4$—, —$NR^4C(O)NR^4$—, —$C(O)$—, —$C(=NR^4)$—, —$C(=NOR^4)$—, —$OC(O)$—, —$C(O)O$—, —$OC(O)O$—, —$OC(O)NR^4$—, —$NR^4C(O)O$—, —$S(O)_m$—, —$S(O)_mNR^4$—, or —$NR^4S(O)_m$—, provided that $M^1$ and $M^2$ are not both —$NR^4$—;
$R^1$ and $R^2$ are each independently selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^5$;
$R^3$ is selected from an alkyl, alkenyl, cycloalkyl, aryl, biphenyl, heterocyclyl heterocycloalkyl, heteroaryl, cycloalkylalkyl, arylalkyl, arylalkenyl, arylalkynyl, heterocyclylalkyl, heteroarylalkyl, heteroarylalkenyl, or heteroarylalkynyl, wherein each cycloalkyl, aryl, heteroaryl, and heterocyclyl portion is optionally substituted with one or more $R^7$;
$R^4$ is each independently H, or alkyl, wherein each alkyl is optionally substituted with one or more $R^5$;
$R^5$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, or —$SR^6$;
$R^6$ is each independently alkyl, alkenyl, alkynyl, haloalkyl, haloalkenyl, haloalkynyl; or alternatively two $R^6$ on the same N atom can together form a 3-6 membered N-heterocyclyl;
$R^7$ is each independently I, Br, Cl, F, —$CH_2F$, —$CHF_2$, —$CF_3$, —$OCF_3$, —CN, -alkyl-CN, —$CONH_2$, —$CONHR^6$, —$CONR^6R^6$, —COOH, —$NH_2$, —$NHR^6$, —$NO_2$, —$NR^6R^6$, —$N_3$, —OH, $OR^6$, —$COOR^6$, —$OSO_3R^6$, oxo, $R^6$, —SH, —$SO_2R^6$, —$SO_3H$, —$SO_3R^6$, —$SR^6$, cycloalkyl, heterocyclyl, aryl, or heteroaryl, wherein each cycloalkyl, heterocyclyl, aryl, and heteroaryl is optionally substituted with one or more $R^5$;
m is 0, 1, or 2; and
wherein the compound is not N,N'-(1-phenyl-1H-1,2,4-triazole-3,5-diyl)dibenzamide, N-(3-benzamido-1-phenyl-1H-1,2,4-triazol-5-yl)furan-2-carboxamide, N-(5-cinnamamido-1-phenyl-1H-1,2,4-triazol-3-yl) benzamide, N-(1-phenyl-5-(phenylamino)-1H-1,2,4-triazol-3-yl)benzamide, 4-fluoro-N-(5-(4- methoxybenzamido)-1-phenyl-1H-1,2,4-triazol-3-yl)
benzamide, N,N'-(1-phenyl-1H-1,2,4-triazole-3,5-diyl)
bis(4-methylbenzamide), N-(5-((2-chlorobenzyl)
amino)-1-phenyl-1H-1,2,4-triazol-3-yl)-2-
fluorobenzamide, N-(3-benzamido-1-phenyl-1H-1,2,4-
triazol-5-yl)-4-fluorobenzamide, N-(3-benzamido-1-
phenyl-1H-1,2,4-triazol-5-yl)-4-nitrobenzamide, N-(3-
benzamido-1-phenyl-1H-1,2,4-triazol-5-yl)-3-
nitrobenzamide, or 4-((3-benzamido-1-phenyl-1H-1,2,
4-triazol-5-yl)carbamoyl)benzoic acid.

2. The compound of claim 1, wherein the compound has the structure of formula (IA)

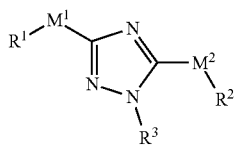

(IA)

or a pharmaceutically acceptable salt thereof, wherein:

$M^1$ and $M^2$ are each independently selected from —NR$^4$C(O)— or —C(O)NR$^4$—;

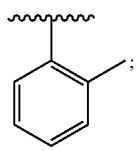

$R^1$ and $R^2$ are each independently

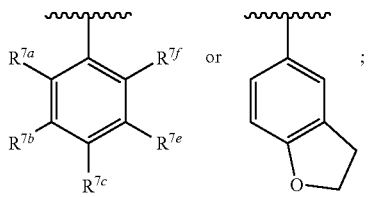

$R^3$ is selected from $R^4$ is each independently H or $C_1$-$C_3$ alkyl; and $R^{7a}$, $R^{7b}$, $R^{7e}$, and $R^{7f}$ is each independently H, I, Br, Cl, F, —CH$_2$F, —CHF$_2$, —CF$_3$, —OCF$_3$, —N$_3$, —CN, —OH, methyl, ethyl, propyl, $C_1$-$C_3$ haloalkyl, $C_1$-$C_3$ alkoxy, or $C_1$-$C_3$ haloalkoxy;

$R^7C$ is H, I, Br, Cl, F, —CH$_2$F, —CHF$_2$, —CF$_3$, —OCF$_3$, —N$_3$, —CN, —OH, $C_1$-$C_3$ alkyl, $C_1$-$C_3$ haloalkyl, $C_1$-$C_3$ alkoxy, $C_1$-$C_3$ haloalkoxy, 4-6 membered heterocyclyl, or 5-6 membered heteroaryl, wherein the heterocyclyl and heteroaryl is optionally substituted with one or more $R^5$;

$R^5$ is I, Br, Cl, F, —CH$_2$F, —CHF$_2$, —CF$_3$, —C$_1$-$C_6$ alkyl, alkynyl, —CN, —(C$_1$-$C_3$ alkylene)-CN, —NH$_2$, —NO$_2$, —N$_3$, —OH, —OCF$_3$, —OMe, —NMe$_2$, -NEt$_2$, or —C(O)O(C$_1$-$C_6$ alkyl);

wherein at least one of $R^{7a}$, $R^{7b}$, $R^{7c}$, $R^{7e}$, and $R^{7f}$ is not H.

3. The compound of claim 2, wherein $R^3$ is

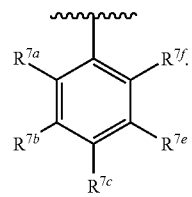

4. The compound of claim 3, wherein four of $R^{7a}$, $R^{7b}$, $R^{7c}$, $R^{7e}$, and $R^{7f}$ is H.

5. The compound of claim 3, wherein three of $R^{7a}$, $R^{7b}$, $R^{7c}$, $R^{7e}$, and $R^{7f}$ is H.

6. The compound of claim 2, wherein $R^{7a}$, $R^{7b}$, $R^{7c}$, $R^{7e}$, and $R^{7f}$ is each independently H, I, Br, Cl, F, —CHF$_2$, —CF$_3$, —OCF$_3$, —N$_3$, —CN, —OH, methyl, ethyl, propyl, —C≡CH; —CN, —NH$_2$, —NO$_2$, —N$_3$, —OH, —OMe, —NMe$_2$, or -NEt$_2$.

7. The compound of claim 2, wherein $R^3$ is

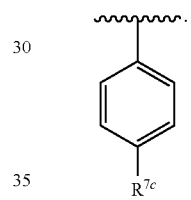

8. The compound of claim 7, wherein $R^{7c}$ is I, Br, —CH$_2$F, —CHF$_2$, —CF$_3$, methyl, ethyl, propyl, —C≡CH; —CN, —NH$_2$, —NO$_2$, —N$_3$, —OH, —OMe, —NMe$_2$, or -NEt$_2$.

9. The compound of claim 7, wherein $R^{7c}$ is I, Br, —CH$_2$F, —CHF$_2$, —CF$_3$, or OMe.

10. The compound of claim 1 having one of the following structures:

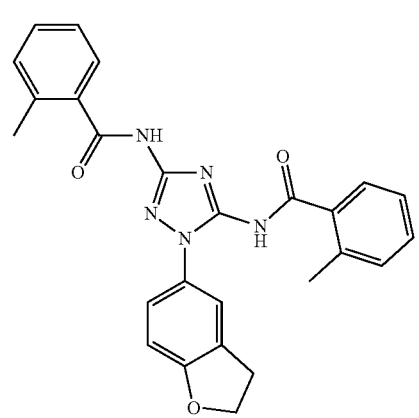

221
-continued
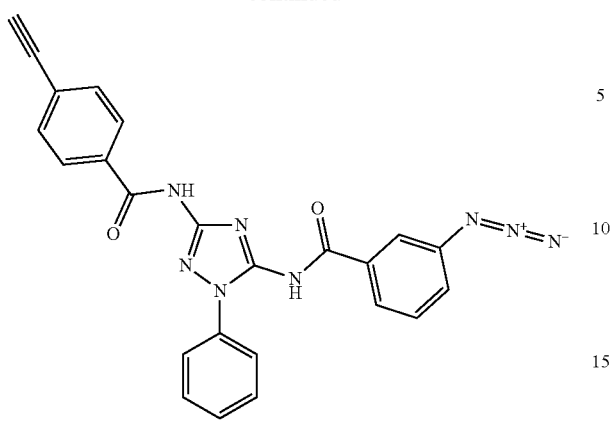
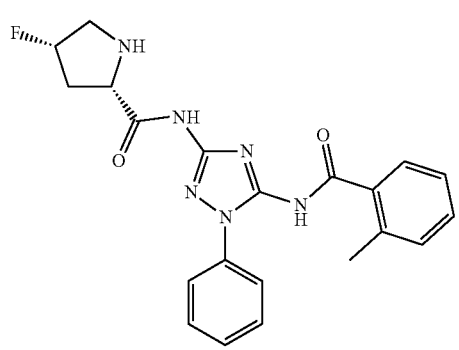
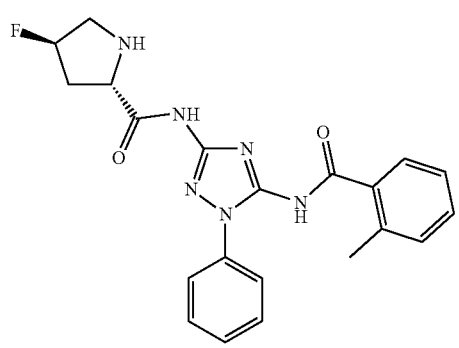
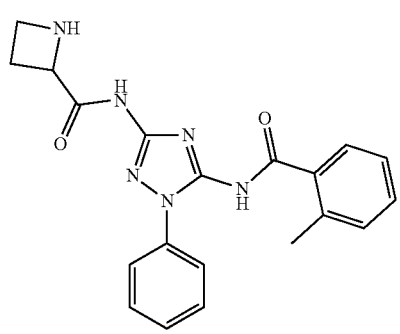
222
-continued
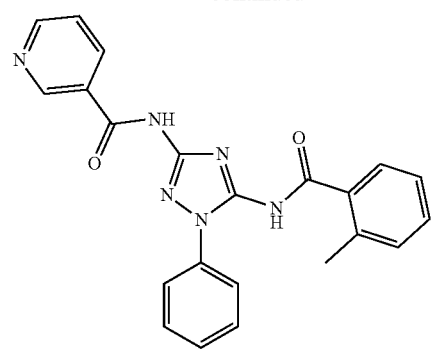
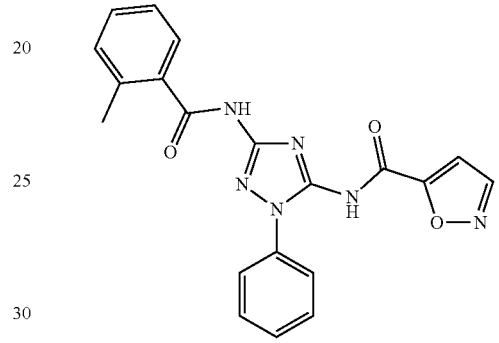
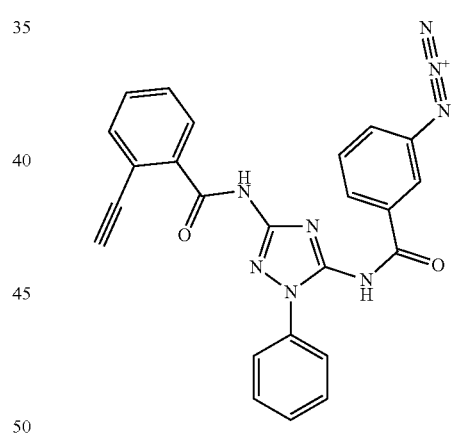
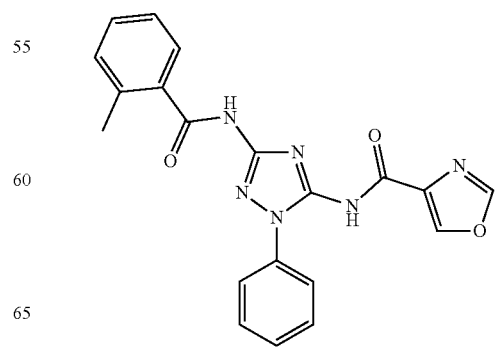

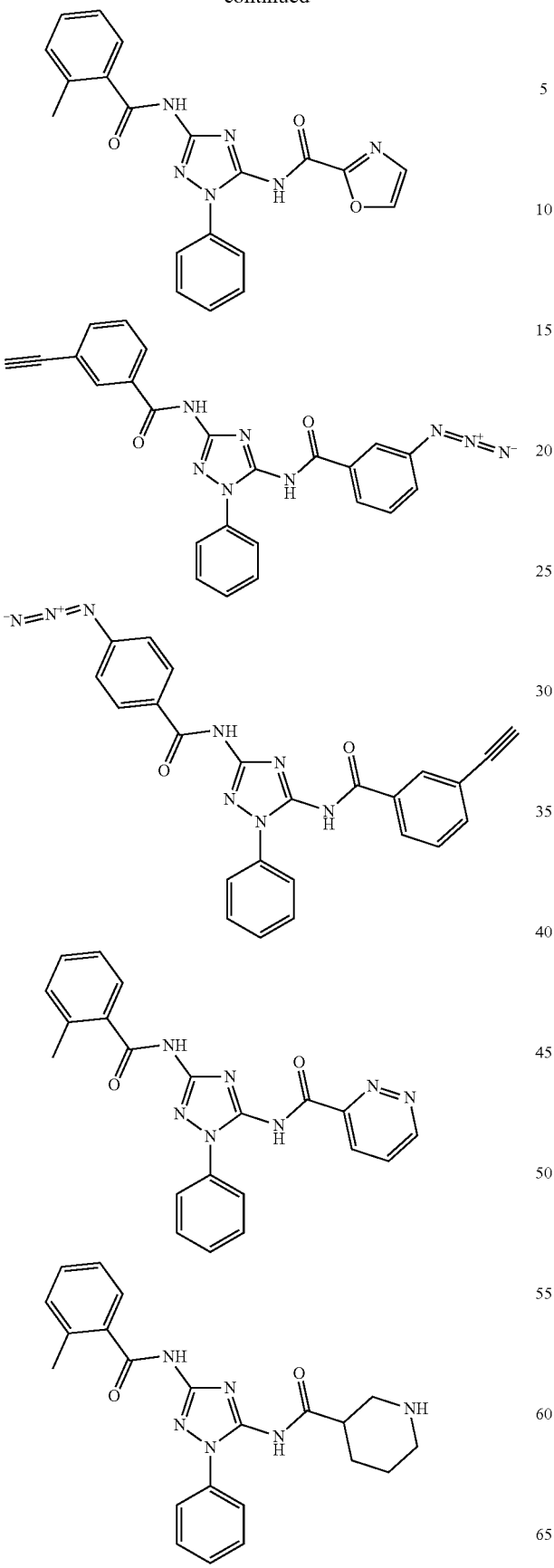
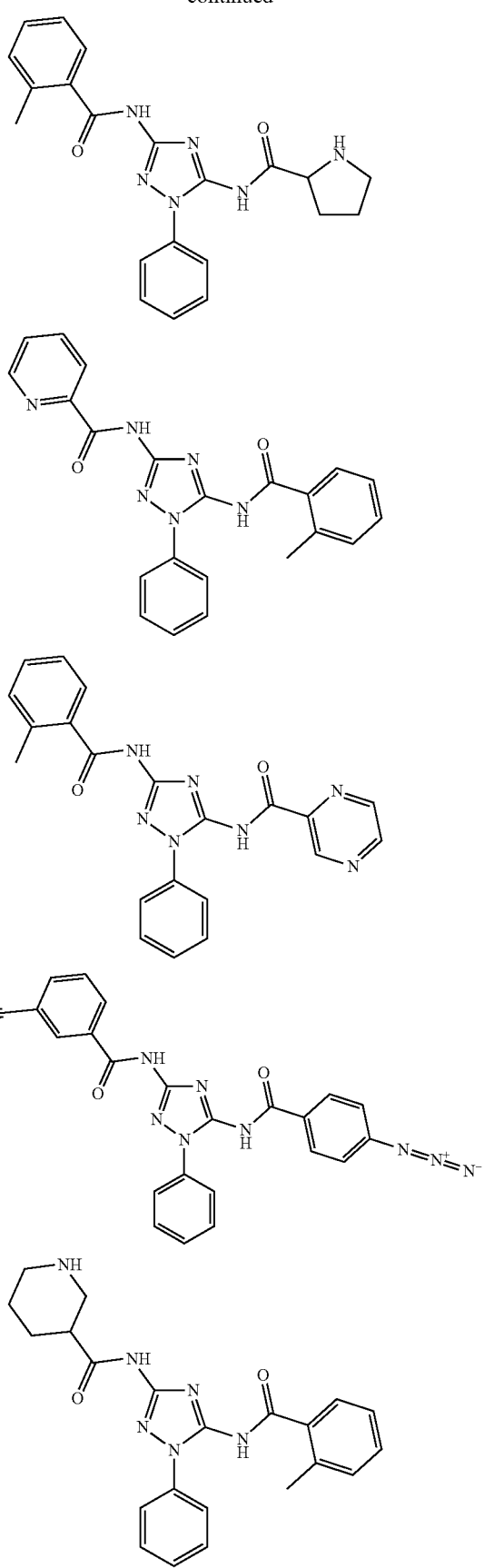

-continued
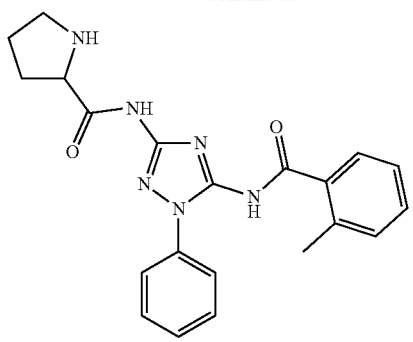
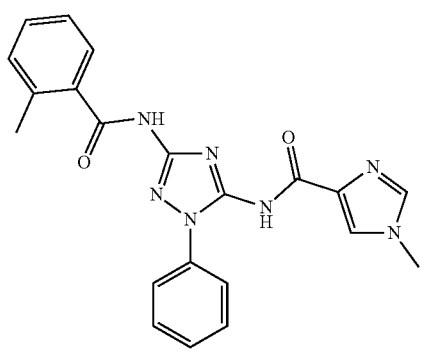
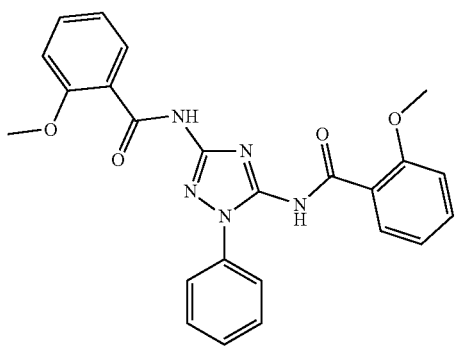
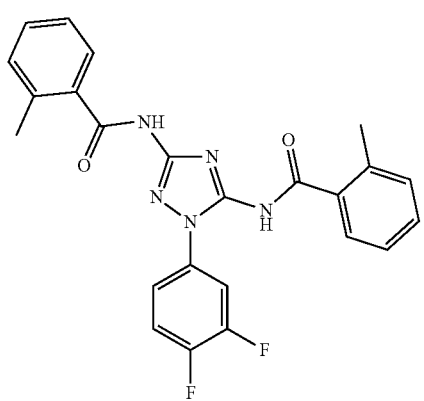
-continued
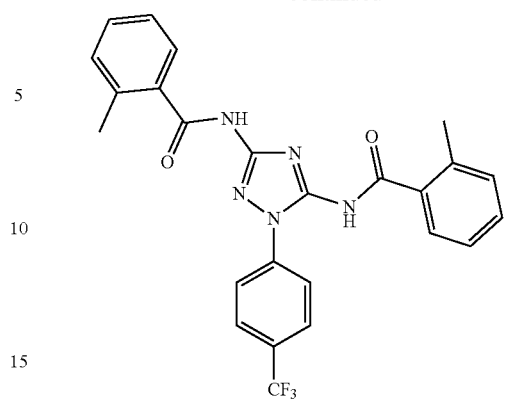
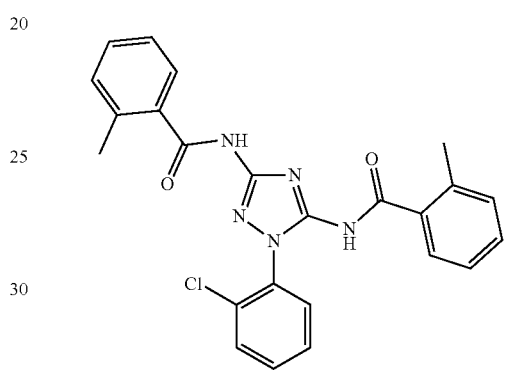
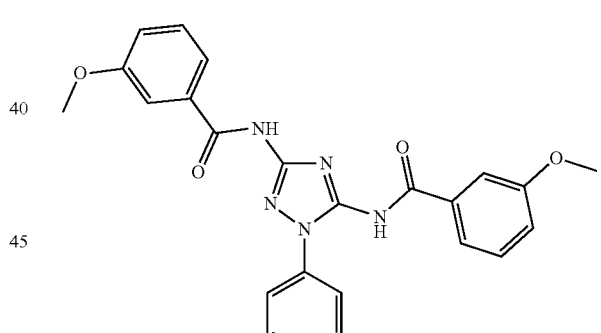

227
-continued
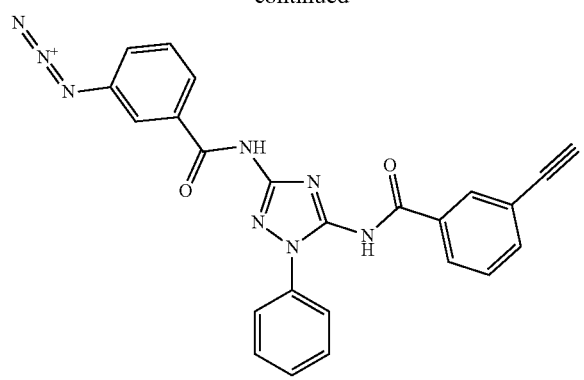
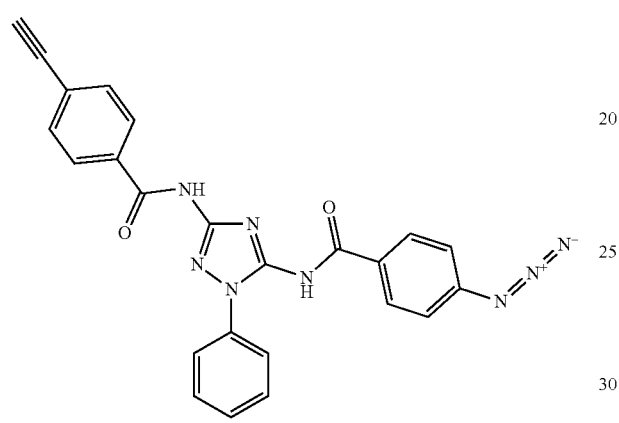
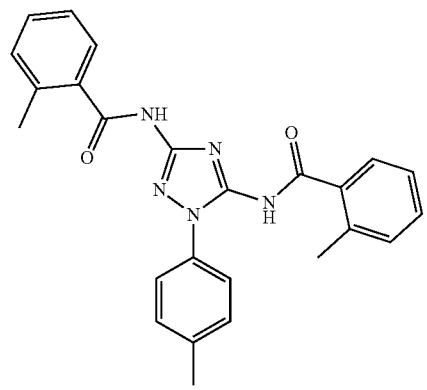
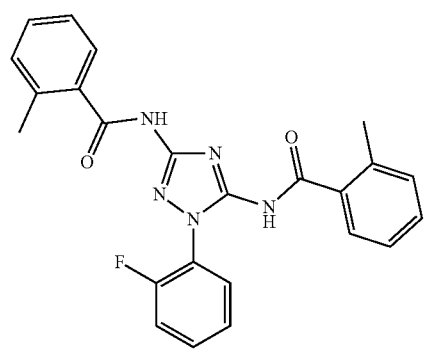
228
-continued
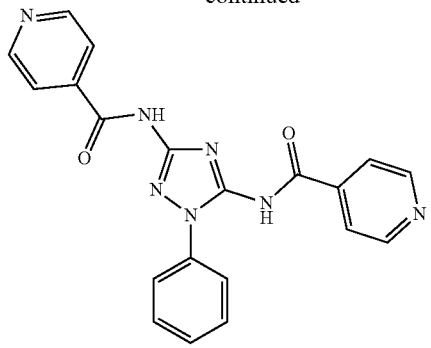
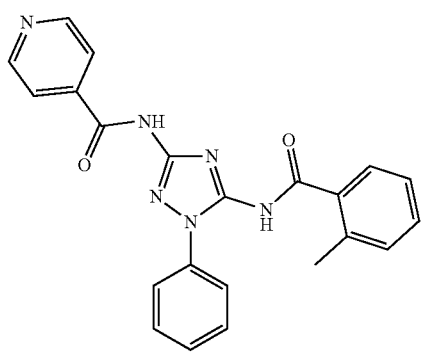
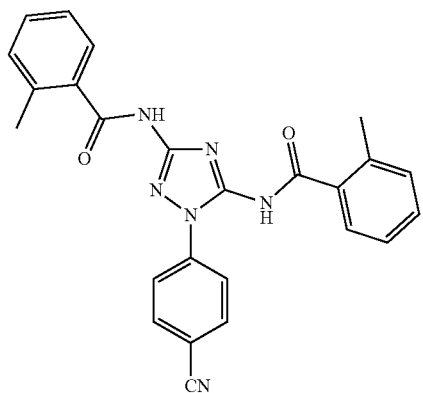
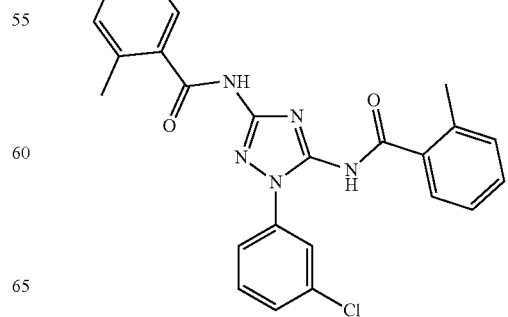

229
-continued
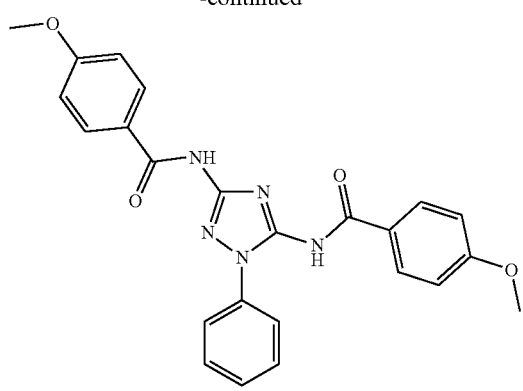
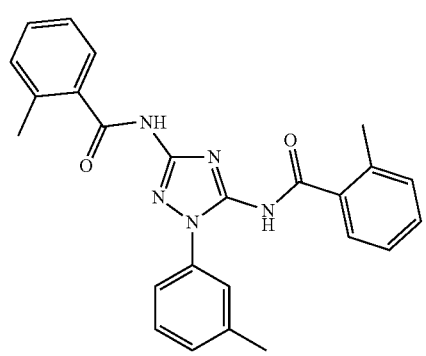
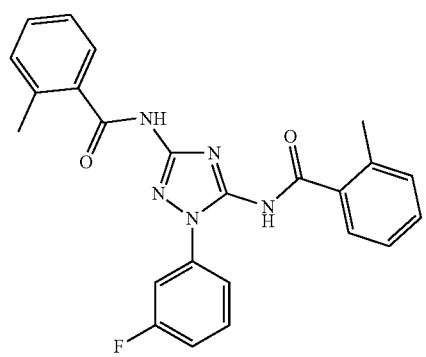
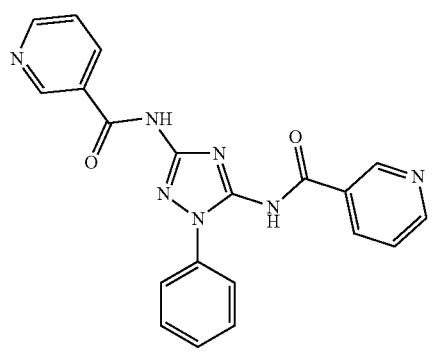
230
-continued
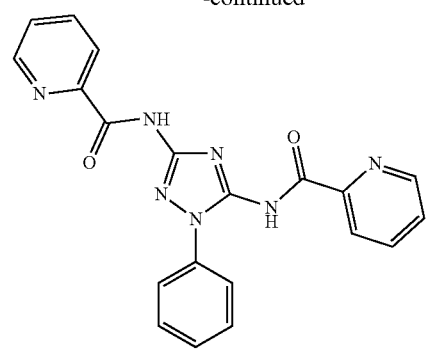
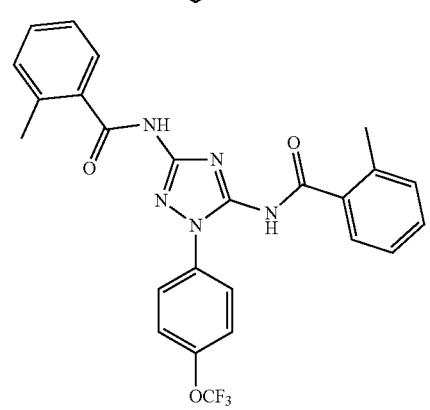
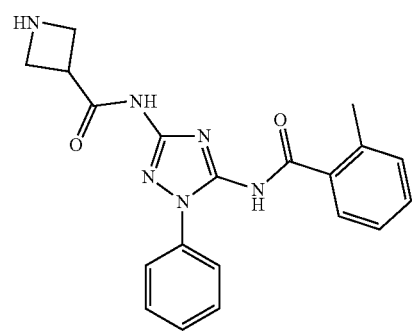
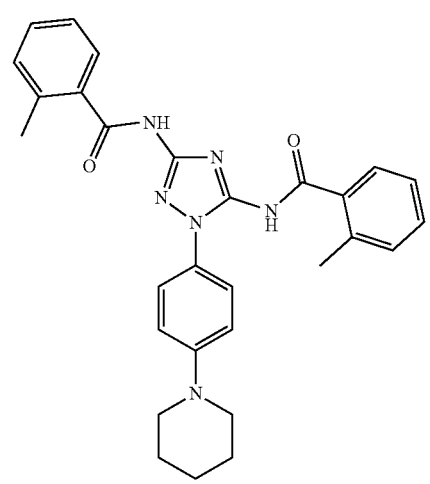

231
-continued
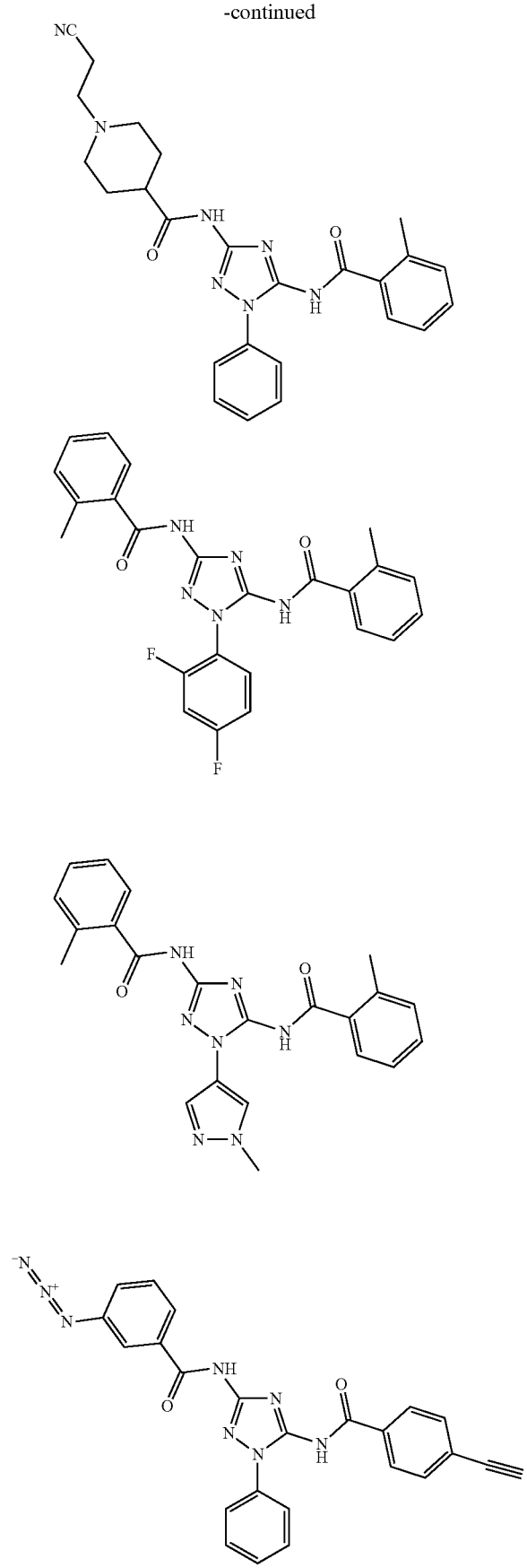
232
-continued
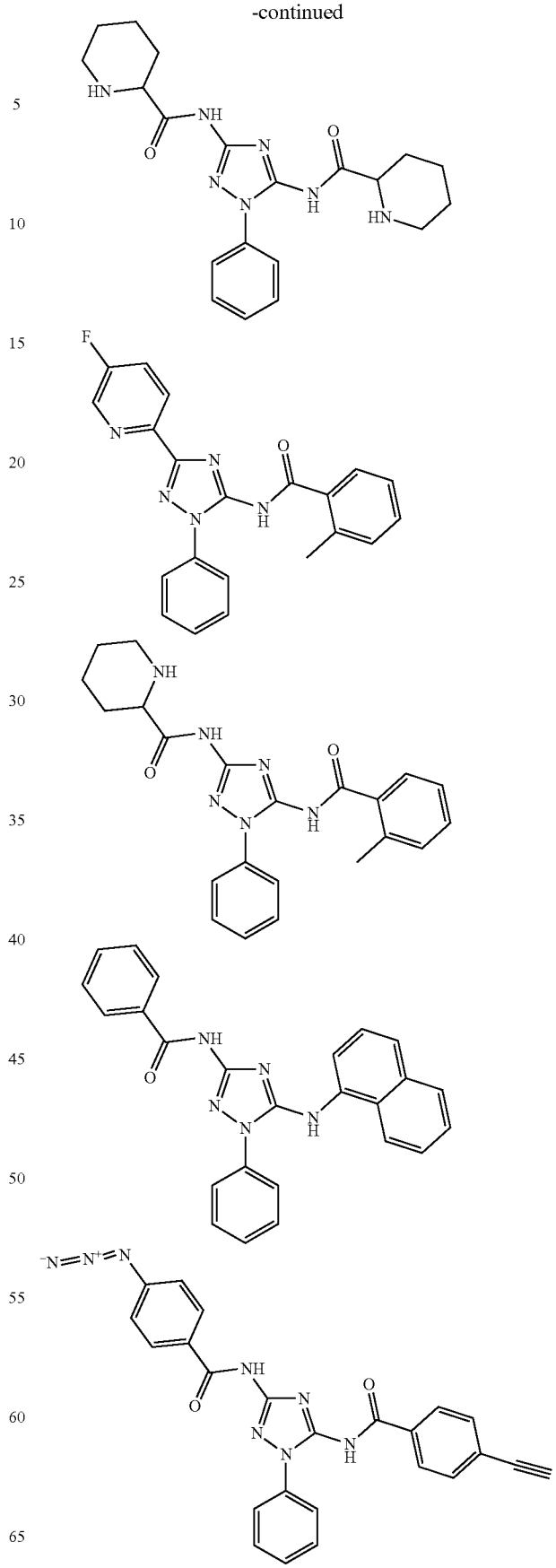

233
-continued
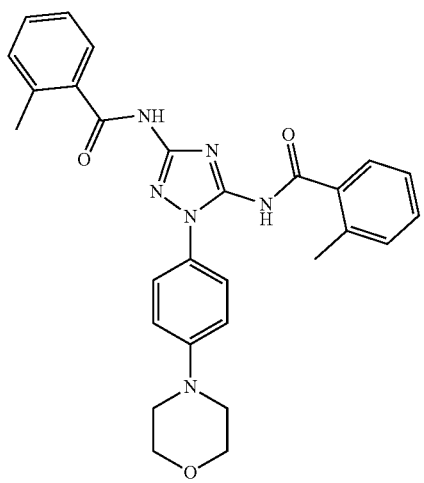
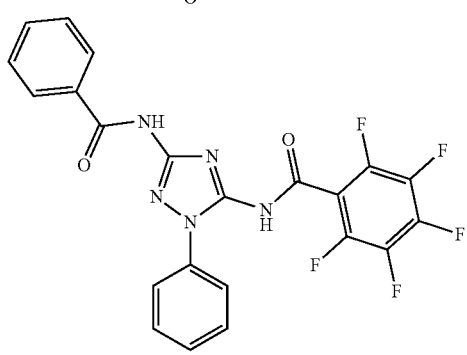
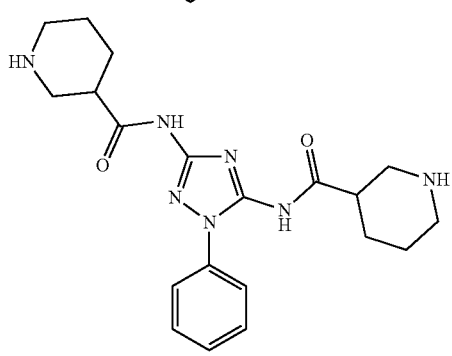
234
-continued
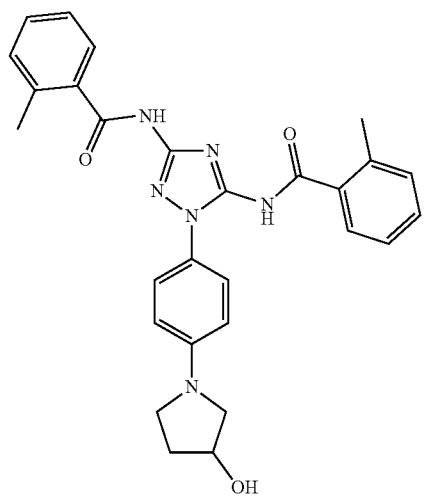
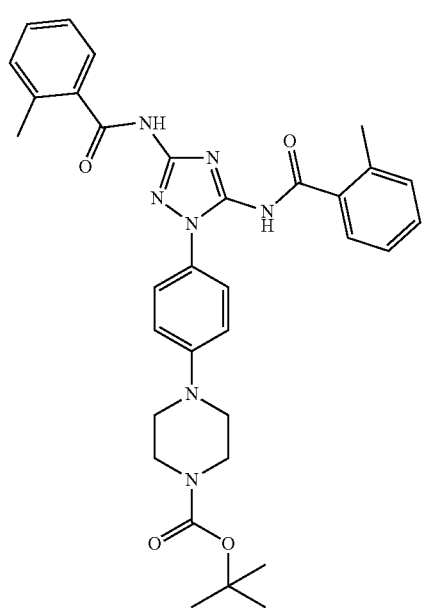
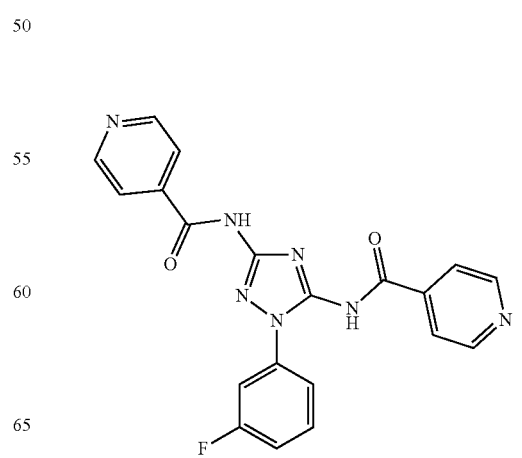

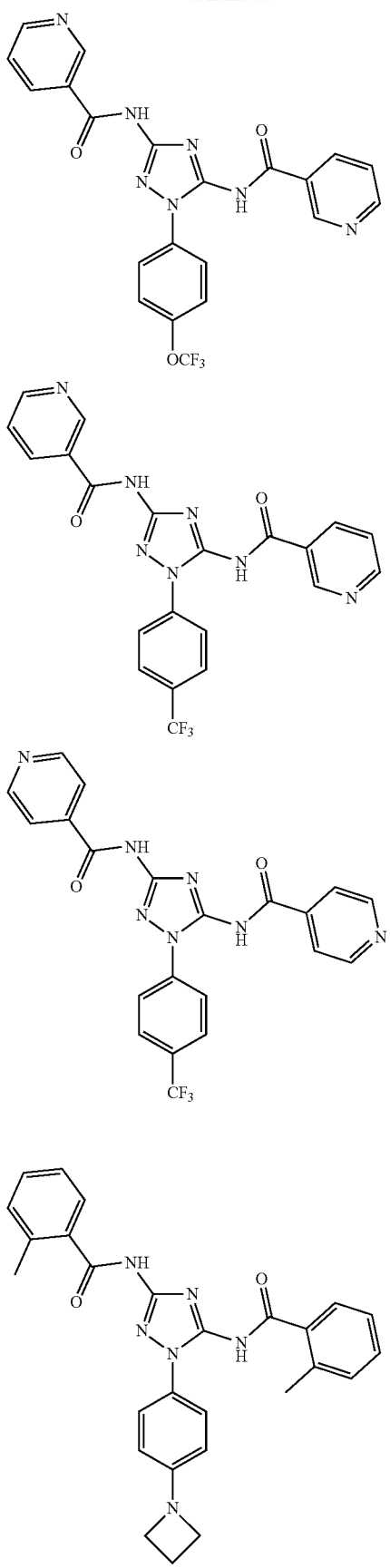
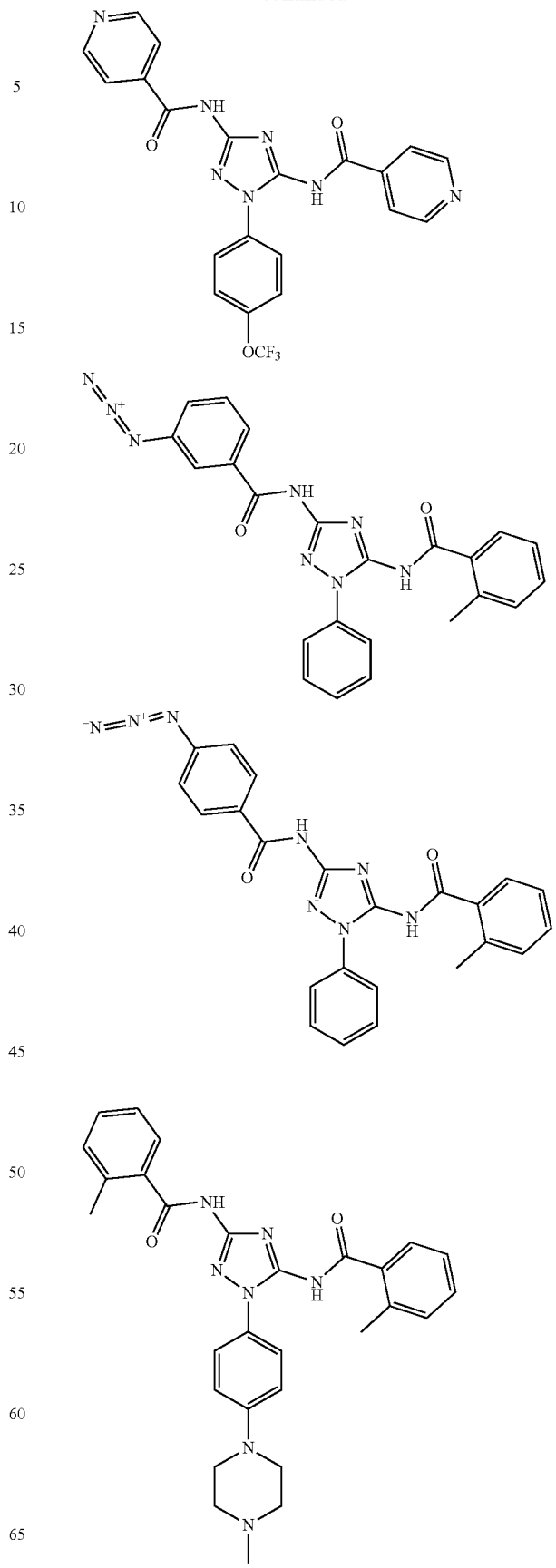

237
-continued
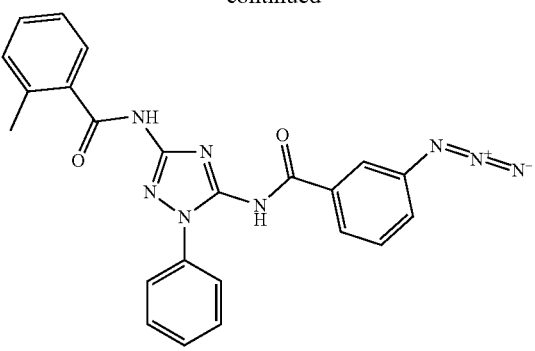
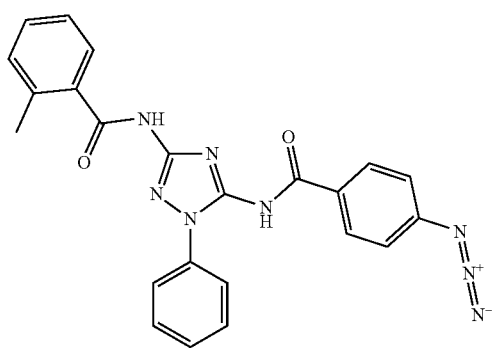
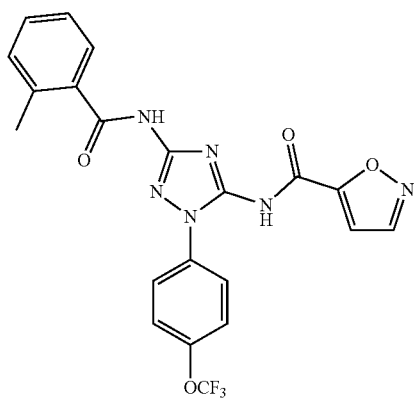
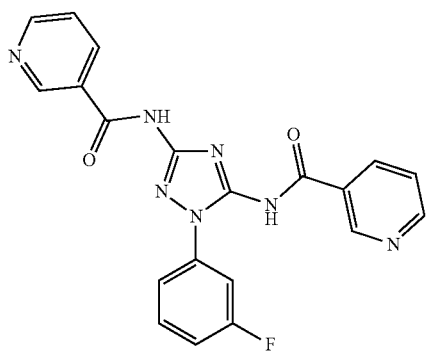
238
-continued
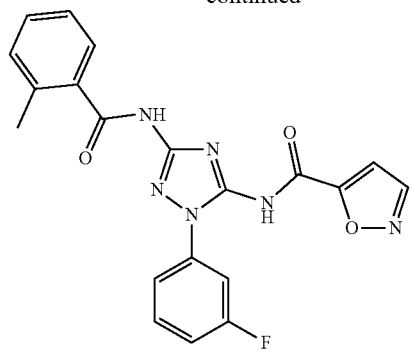
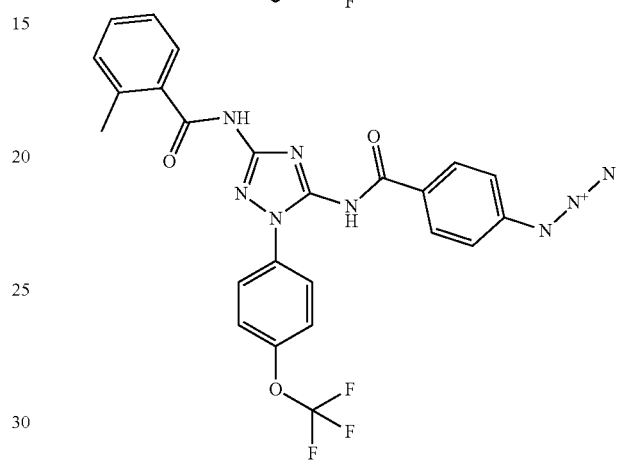
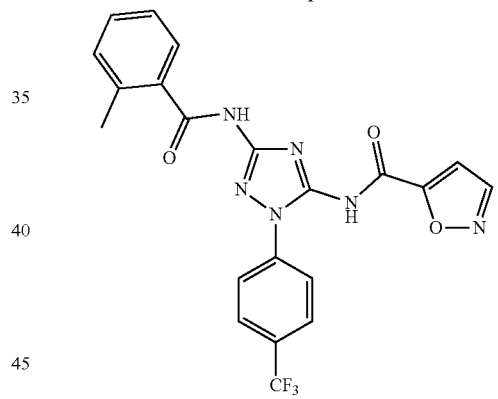
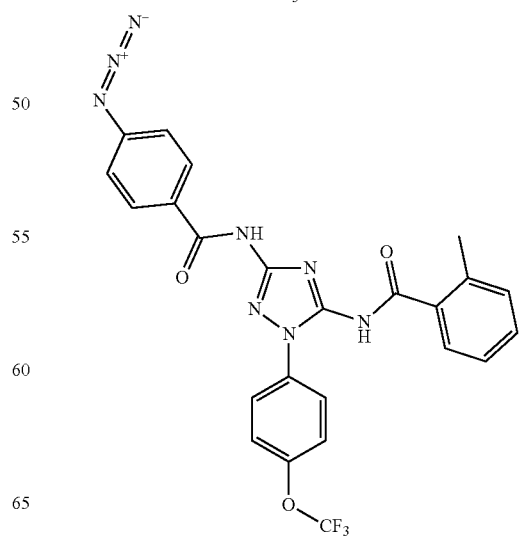

239
-continued
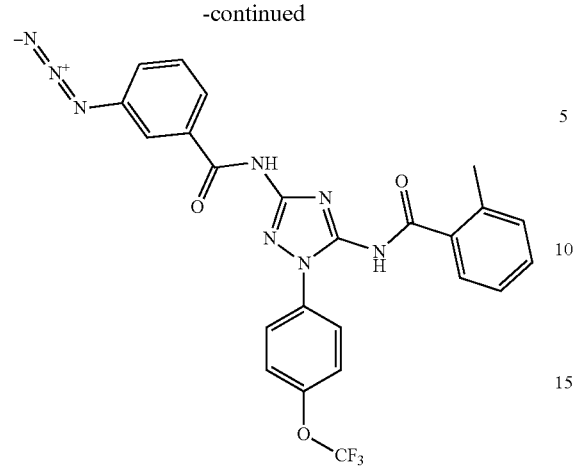
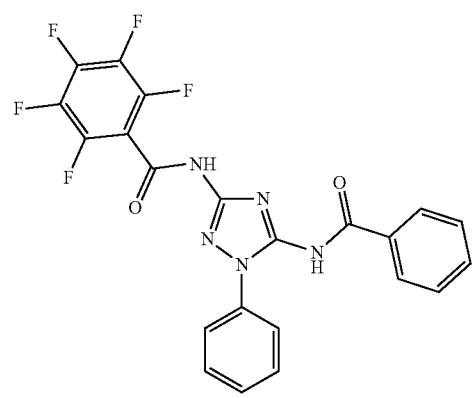
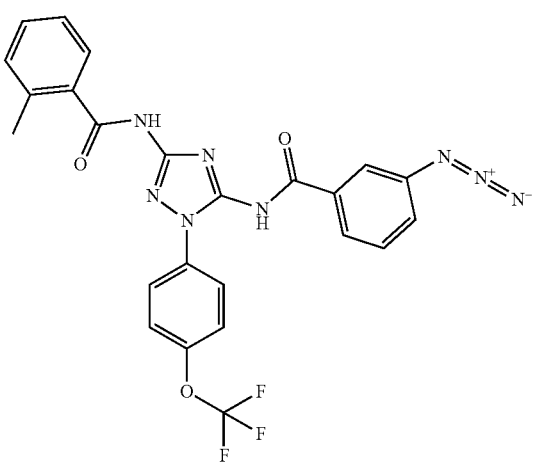
240
-continued
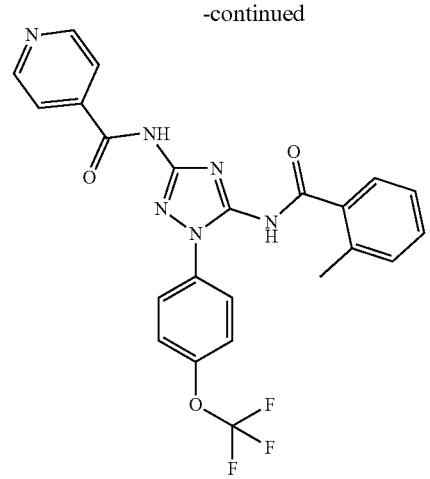
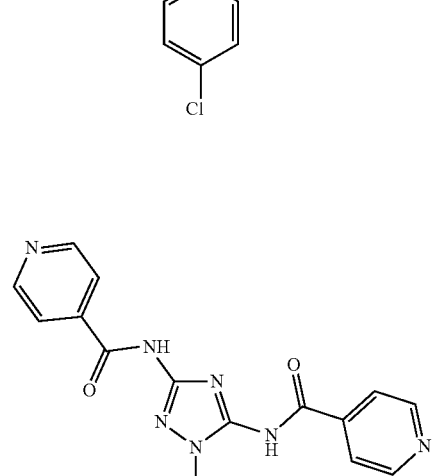
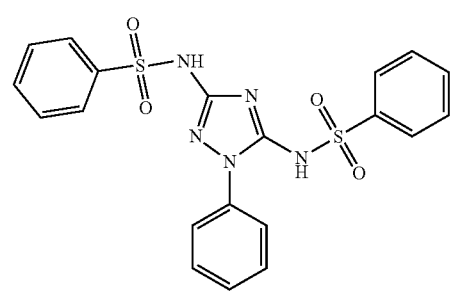

-continued
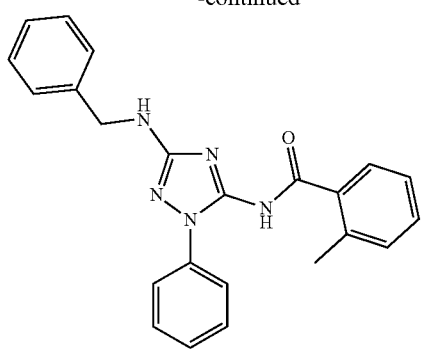
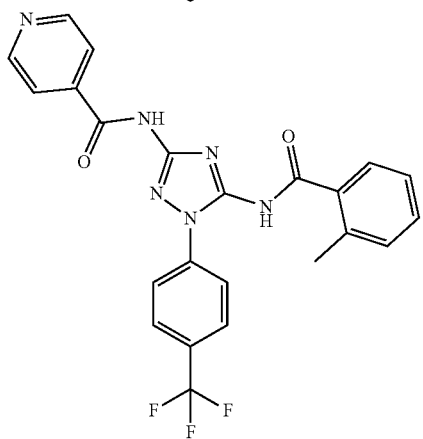
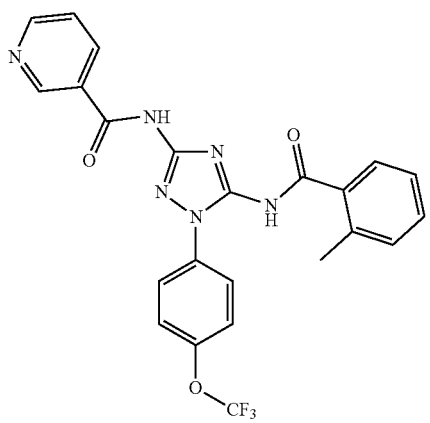
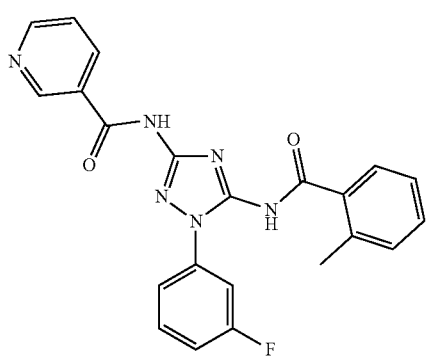
-continued
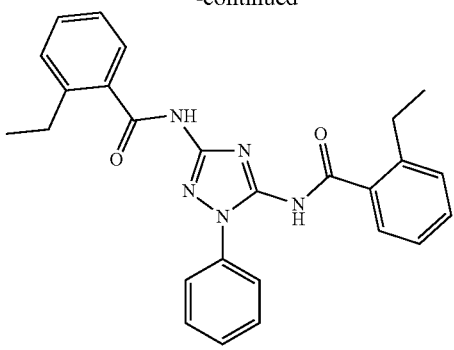
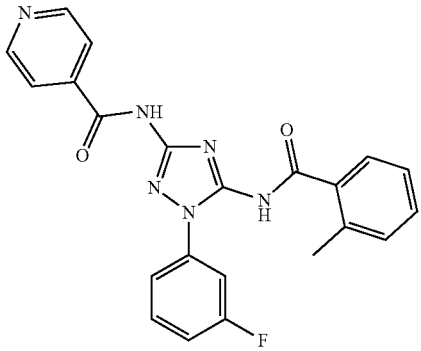
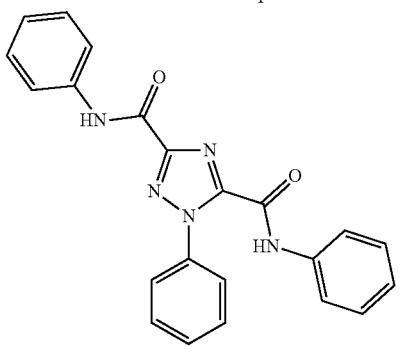
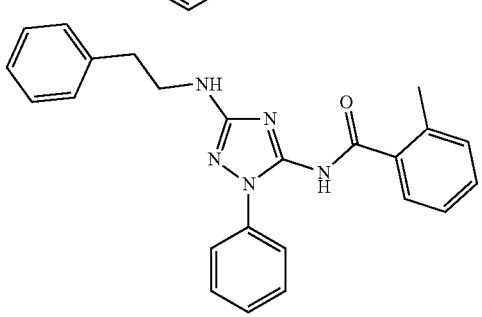
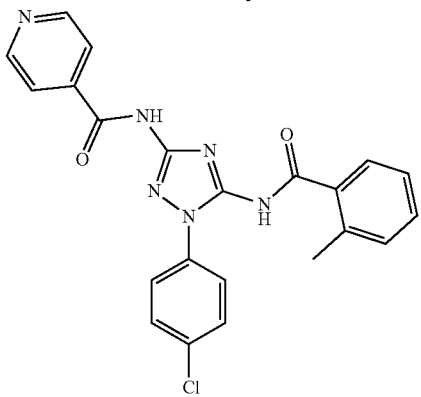

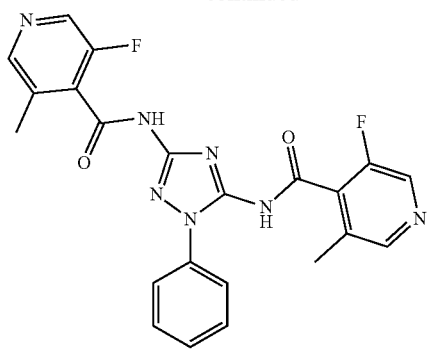
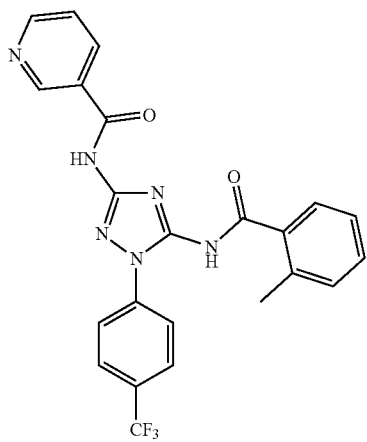
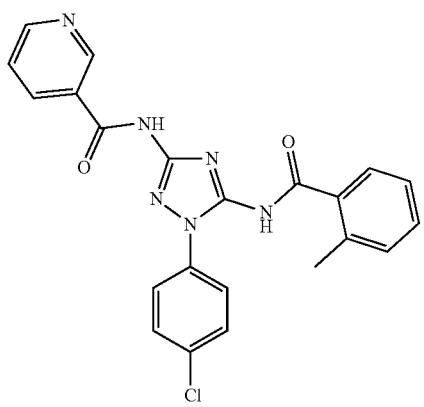
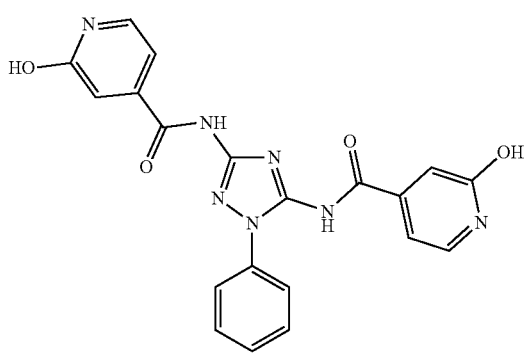
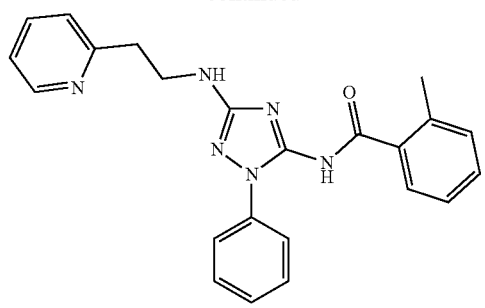
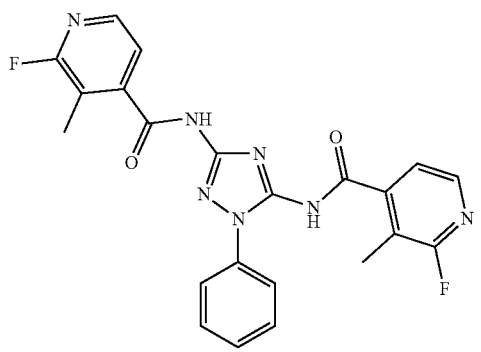
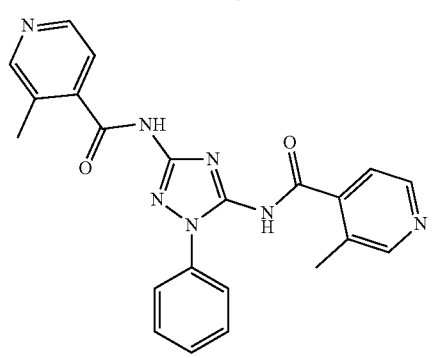
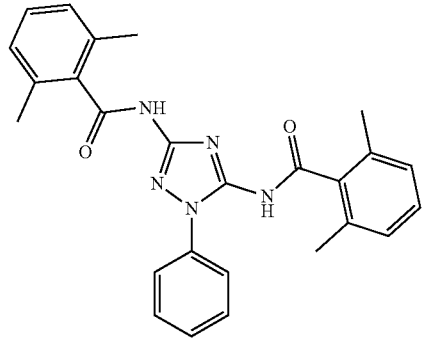
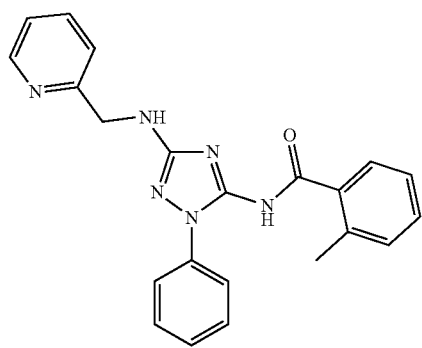

245
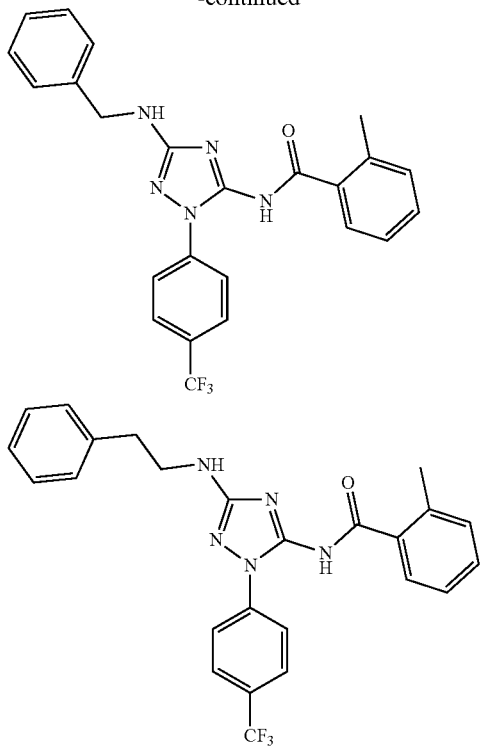
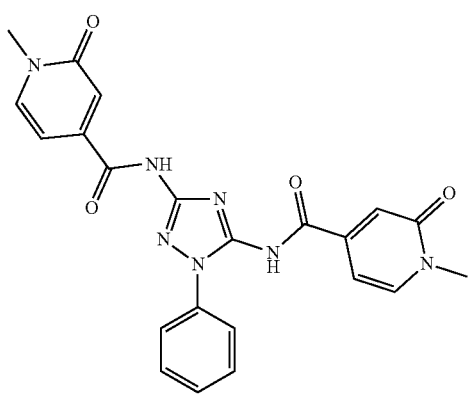
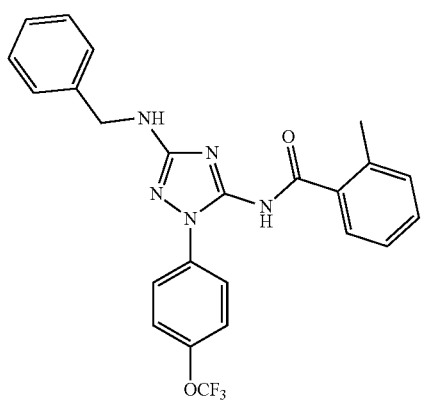
246
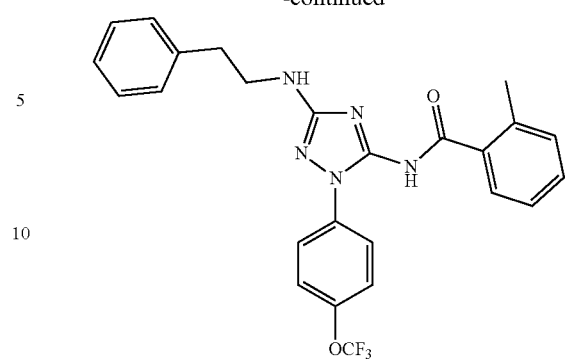
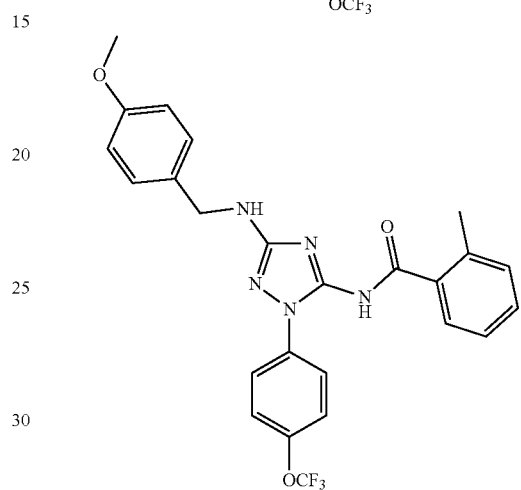
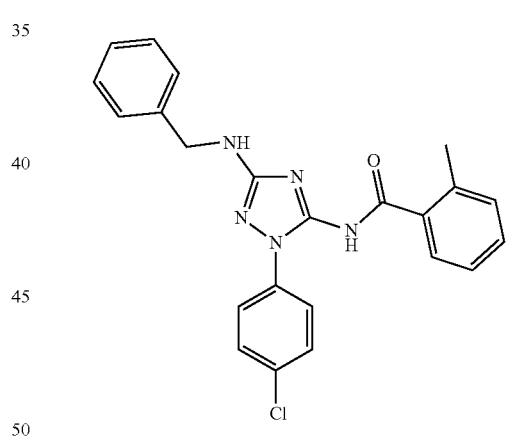
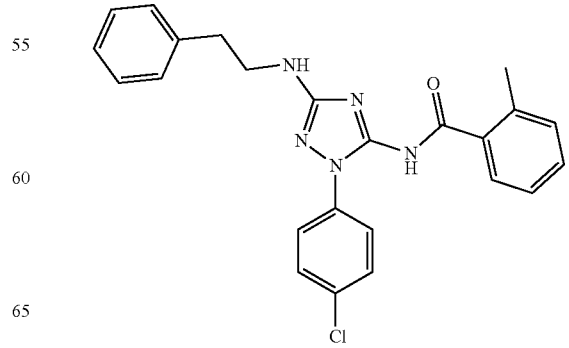

247
-continued
248
-continued
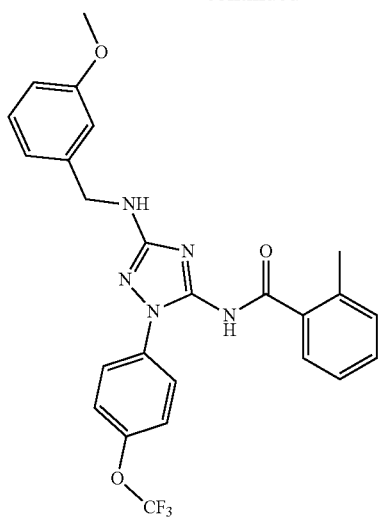
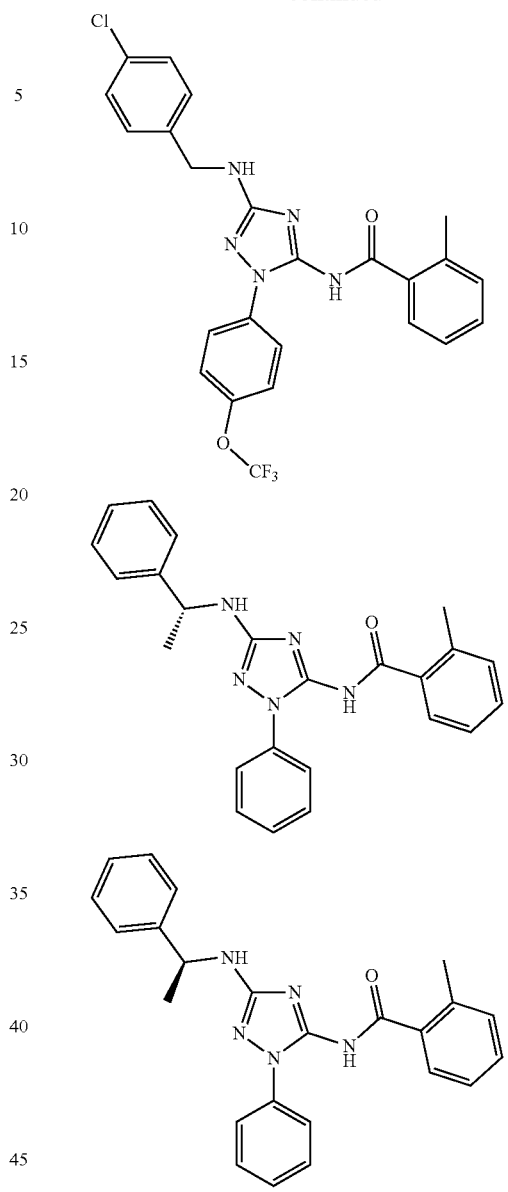
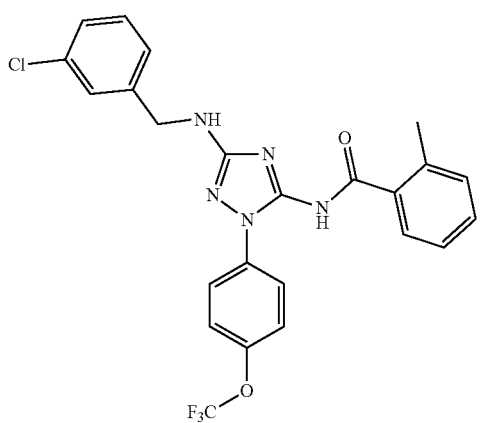

249
-continued
250
-continued
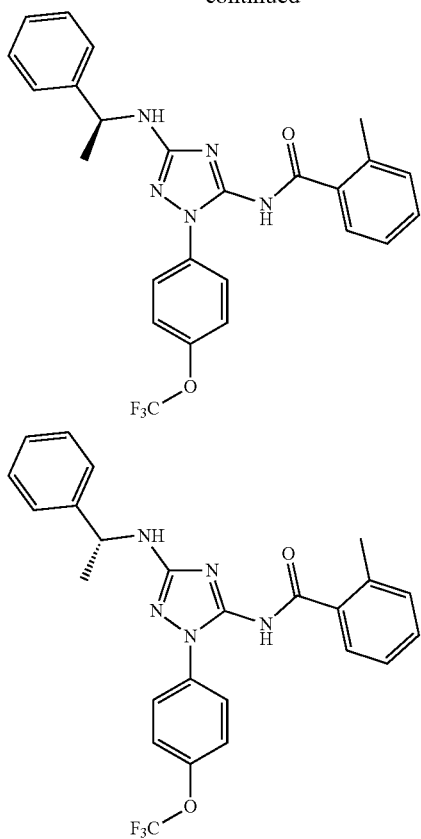
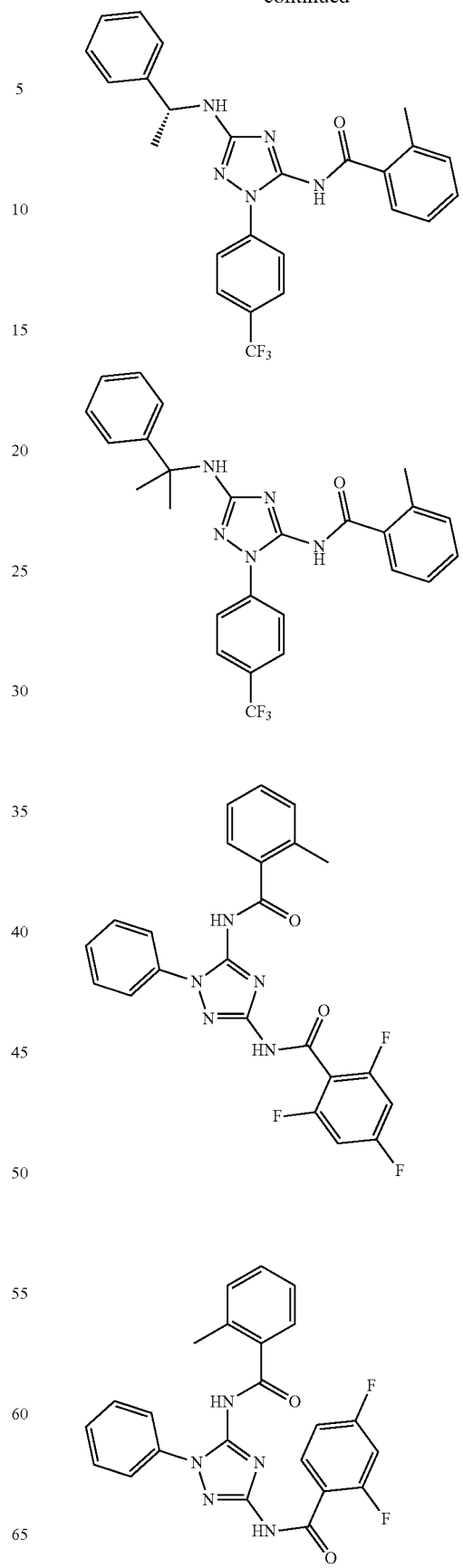

-continued

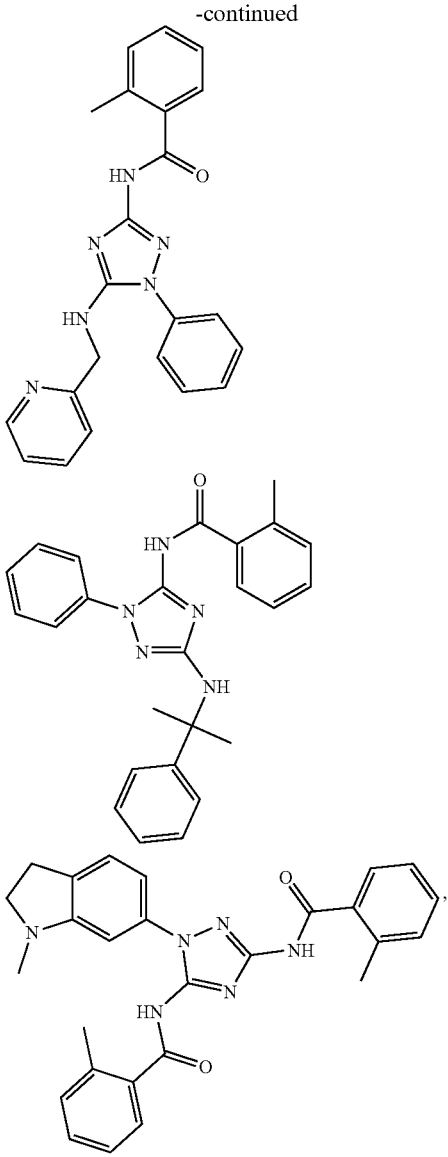

or a pharmaceutically acceptable salt thereof.

11. The compound of claim 1, having the following structure:

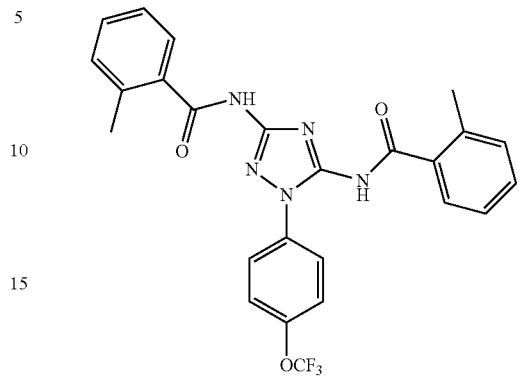

or a pharmaceutically acceptable salt thereof.

12. A pharmaceutical composition comprising a pharmaceutically acceptable carrier and a compound of claim 1.

13. The pharmaceutical composition of claim 12, wherein the compound has the following structure:

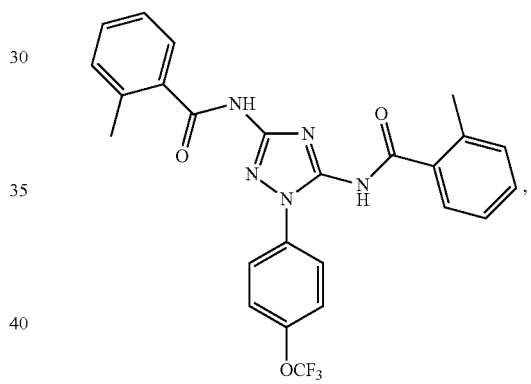

or a pharmaceutically acceptable salt thereof.

* * * * *